(12) United States Patent
Castro et al.

(10) Patent No.: US 10,130,373 B2
(45) Date of Patent: Nov. 20, 2018

(54) AUTOMATIC SURGICAL LIGATION CLIP APPLIER

(71) Applicant: Teleflex Medical Incorporated, Morrisville, NC (US)

(72) Inventors: Salvatore Castro, Raleigh, NC (US); Curtis Thornton, Pittsboro, NC (US); Lynn Willett, Raleigh, NC (US); Michael Ramsey, Raleigh, NC (US); Philip Schmidt, Roxboro, NC (US); Dan Monahan, Raleigh, NC (US); Adam Lehman, Northford, CT (US); Paul Whiting, Wake Forest, NC (US); Leland Ray Adams, Ansonia, CT (US); Alan Bachman, Milford, CT (US); Steven Morris, Cary, NC (US); Bradley J. Labarbera, Raleigh, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 211 days.

(21) Appl. No.: 15/018,565

(22) Filed: Feb. 8, 2016

(65) Prior Publication Data
US 2016/0151073 A1 Jun. 2, 2016

Related U.S. Application Data

(63) Continuation of application No. 13/618,215, filed on Sep. 14, 2012, now Pat. No. 9,271,737.
(Continued)

(51) Int. Cl.
*A61B 17/10* (2006.01)
*A61B 17/128* (2006.01)
(Continued)

(52) U.S. Cl.
CPC ........ *A61B 17/1285* (2013.01); *A61B 17/122* (2013.01); *A61B 17/128* (2013.01);
(Continued)

(58) Field of Classification Search
CPC . A61B 17/128; A61B 17/122; A61B 17/1285; A61B 2017/2936;
(Continued)

(56) References Cited

U.S. PATENT DOCUMENTS 2,277,139 A 3/1942 Niemand
2,968,041 A 1/1961 Skold
(Continued)

FOREIGN PATENT DOCUMENTS

EP 2361560 8/2011
JP 2004-500190 1/2004
(Continued)

OTHER PUBLICATIONS

Japanese Office Action dated Mar. 25, 2015, with English translation.
(Continued)

*Primary Examiner* — Amy R Weisberg
(74) *Attorney, Agent, or Firm* — Baker Hostetler LLP

(57) ABSTRACT

An applier for ligation clip is provided. The applier includes: an outer tube having mounting bosses; a pair of jaws pivotally connected to the mounting bosses, the jaws having actuating projections; a feed tube located in the outer tube and configured to move axially within the outer tube, the feed tube having actuating slots in which the actuating projections are located; a clip lock arm located in the outer tube and configured to move axially within the outer tube; and a clip advance arm located in the outer tube and configured to move axially within the outer tube, the clip advance arm having flexible pinchers at one end of the clip
(Continued)

advance arm. A method of applying a ligation clip is also disclosed.

19 Claims, 115 Drawing Sheets

Related U.S. Application Data

(60) Provisional application No. 61/535,166, filed on Sep. 15, 2011.

(51) Int. Cl.
 *A61B 17/122* (2006.01)
 *A61B 17/29* (2006.01)
 *A61B 17/064* (2006.01)
 *A61B 17/28* (2006.01)

(52) U.S. Cl.
 CPC ... *A61B 17/0643* (2013.01); *A61B 2017/2845* (2013.01); *A61B 2017/2912* (2013.01); *A61B 2017/2929* (2013.01); *A61B 2017/2936* (2013.01); *A61B 2017/2937* (2013.01)

(58) Field of Classification Search
 CPC .... A61B 2017/2929; A61B 2017/2912; A61B 17/0643; A61B 2017/2845; A61B 2017/2937
 USPC ......... 606/142–143, 227, 205, 207; 227/175.1–182.1; 600/104, 129
 See application file for complete search history.

(56) References Cited

U.S. PATENT DOCUMENTS

| | | | |
|---|---|---|---|
| 3,234,636 A * | 2/1966 | Brown ............... | A61B 17/0682 29/213.1 |
| 4,296,751 A | 10/1981 | Blake, III et al. | |
| 4,372,316 A | 2/1983 | Blake, III et al. | |
| 4,408,603 A | 10/1983 | Blake, III et al. | |
| 4,638,804 A * | 1/1987 | Jewusiak ............ | A61B 17/122 606/158 |
| 4,671,281 A | 6/1987 | Beroff et al. | |
| 4,722,466 A | 2/1988 | Hsu | |
| 5,084,057 A | 1/1992 | Green et al. | |
| 5,100,418 A | 3/1992 | Yoon et al. | |
| 5,100,420 A | 3/1992 | Green et al. | |
| 5,171,247 A | 12/1992 | Hughett et al. | |
| 5,171,249 A | 12/1992 | Stefanchik et al. | |
| 5,171,250 A | 12/1992 | Yoon | |
| 5,289,963 A | 3/1994 | McGarry et al. | |
| 5,300,081 A | 4/1994 | Young et al. | |
| 5,356,064 A | 10/1994 | Green et al. | |
| 5,366,458 A | 11/1994 | Korthoff et al. | |
| 5,366,459 A | 11/1994 | Yoon | |
| 5,395,381 A | 3/1995 | Green et al. | |
| 5,431,668 A | 7/1995 | Burbank et al. | |
| 5,437,680 A | 8/1995 | Yoon | |
| 5,447,513 A | 9/1995 | Davison et al. | |
| 5,456,401 A | 10/1995 | Green et al. | |
| 5,462,558 A | 10/1995 | Kolesa et al. | |
| 5,474,567 A | 12/1995 | Stefanchik et al. | |
| 5,474,732 A | 12/1995 | Korthoff et al. | |
| 5,478,003 A | 12/1995 | Green et al. | |
| 5,478,353 A | 12/1995 | Yoon | |
| 5,480,405 A | 1/1996 | Yoon | |
| 5,527,318 A | 6/1996 | McGarry | |
| 5,527,319 A | 6/1996 | Green et al. | |
| 5,542,949 A | 8/1996 | Yoon | |
| 5,545,167 A | 8/1996 | Lin | |
| 5,591,178 A | 1/1997 | Green et al. | |
| 5,593,414 A | 1/1997 | Shipp et al. | |
| 5,601,573 A | 2/1997 | Fogelberg et al. | |
| 5,601,574 A | 2/1997 | Stefanchik et al. | |
| 5,607,436 A | 3/1997 | Pratt et al. | |
| RE35,525 E | 6/1997 | Stefanchik et al. | |
| 5,643,291 A | 7/1997 | Pier et al. | |
| 5,645,551 A | 7/1997 | Green et al. | |
| 5,645,553 A | 7/1997 | Kolesa et al. | |
| 5,681,330 A | 10/1997 | Hughett et al. | |
| 5,695,502 A | 12/1997 | Pier et al. | |
| 5,700,270 A | 12/1997 | Peyser et al. | |
| 5,700,271 A | 12/1997 | Whitfield et al. | |
| 5,720,756 A | 2/1998 | Green et al. | |
| 5,725,537 A | 3/1998 | Green et al. | |
| 5,725,538 A | 3/1998 | Green et al. | |
| 5,755,726 A | 5/1998 | Pratt et al. | |
| 5,769,857 A | 6/1998 | Reztzov et al. | |
| 5,772,673 A | 6/1998 | Cuny et al. | |
| 5,779,718 A | 7/1998 | Green et al. | |
| 5,792,150 A | 8/1998 | Pratt et al. | |
| 5,833,696 A | 11/1998 | Whitfield et al. | |
| 5,833,700 A | 11/1998 | Fogelberg et al. | |
| 5,843,097 A | 12/1998 | Mayenberger et al. | |
| 5,921,997 A | 7/1999 | Fogelberg et al. | |
| 5,951,574 A | 9/1999 | Stefanchik et al. | |
| RE36,720 E | 5/2000 | Green et al. | |
| 6,258,105 B1 | 7/2001 | Hart et al. | |
| 6,273,253 B1 | 8/2001 | Forster et al. | |
| 6,273,898 B1 | 8/2001 | Kienzle et al. | |
| 6,277,131 B1 | 8/2001 | Kalikow | |
| 6,350,269 B1 | 2/2002 | Shipp et al. | |
| 6,599,298 B1 | 7/2003 | Forster et al. | |
| 6,652,539 B2 | 11/2003 | Shipp et al. | |
| 6,652,545 B2 | 11/2003 | Shipp et al. | |
| 6,743,240 B2 | 6/2004 | Smith et al. | |
| 6,824,548 B2 | 11/2004 | Smith et al. | |
| 6,843,794 B2 | 1/2005 | Sixto et al. | |
| 6,911,033 B2 | 6/2005 | De Guillebon et al. | |
| 7,070,602 B2 | 7/2006 | Smith et al. | |
| 7,090,685 B2 | 8/2006 | Kortenbach et al. | |
| 7,131,977 B2 | 11/2006 | Fowler | |
| 7,179,265 B2 | 2/2007 | Manetakis et al. | |
| 7,182,775 B2 | 2/2007 | Guillebon et al. | |
| 7,207,997 B2 | 4/2007 | Shipp et al. | |
| 7,211,092 B2 | 5/2007 | Hughett | |
| 7,223,272 B2 | 5/2007 | Francese et al. | |
| 7,261,724 B2 | 8/2007 | Molitor et al. | |
| 7,288,098 B2 | 10/2007 | Huitema et al. | |
| 7,297,149 B2 | 11/2007 | Vitali et al. | |
| 7,431,724 B2 | 10/2008 | Manetakis et al. | |
| 7,572,266 B2 | 8/2009 | Young et al. | |
| 7,582,095 B2 | 9/2009 | Shipp et al. | |
| 7,585,304 B2 | 9/2009 | Hughett | |
| 7,615,058 B2 | 11/2009 | Sixto et al. | |
| 7,637,917 B2 | 12/2009 | Whitfield et al. | |
| 7,686,820 B2 | 3/2010 | Huitema et al. | |
| 7,717,926 B2 | 5/2010 | Whitfield et al. | |
| 7,731,724 B2 | 6/2010 | Huitema et al. | |
| 7,740,641 B2 | 6/2010 | Huitema | |
| 7,819,886 B2 | 10/2010 | Whitfield et al. | |
| 7,905,890 B2 | 3/2011 | Whitfield et al. | |
| 8,038,686 B2 | 10/2011 | Huitema et al. | |
| 8,075,571 B2 | 12/2011 | Vitali et al. | |
| 8,097,004 B2 | 1/2012 | Wild | |
| 8,114,098 B2 | 2/2012 | Kimura et al. | |
| 8,216,257 B2 | 7/2012 | Huitema et al. | |
| 8,236,012 B2 | 8/2012 | Molitor et al. | |
| 8,246,634 B2 | 8/2012 | Huitema et al. | |
| 8,246,635 B2 | 8/2012 | Huitema | |
| 8,262,679 B2 | 9/2012 | Nguyen | |
| 8,267,944 B2 | 9/2012 | Sorrentino et al. | |
| 8,267,945 B2 | 9/2012 | Nguyen et al. | |
| 8,267,946 B2 | 9/2012 | Whitfield et al. | |
| 8,282,655 B2 | 10/2012 | Whitfield et al. | |
| 8,328,822 B2 | 12/2012 | Huitema et al. | |
| 8,357,171 B2 | 1/2013 | Whitfield et al. | |
| 8,403,945 B2 | 3/2013 | Whitfield et al. | |
| 2002/0068945 A1* | 6/2002 | Sixto, Jr. ............ | A61B 1/00073 606/142 |
| 2002/0068946 A1 | 6/2002 | Kortenbach et al. | |
| 2002/0198537 A1 | 12/2002 | Smith et al. | |

(56) References Cited

U.S. PATENT DOCUMENTS

| | | |
|---|---|---|
| 2002/0198539 A1* | 12/2002 | Sixto, Jr. .............. A61B 17/122 606/142 |
| 2003/0014060 A1 | 1/2003 | Wilson et al. |
| 2004/0097971 A1 | 5/2004 | Hughett |
| 2004/0193185 A1 | 9/2004 | McBrayer |
| 2004/0193186 A1 | 9/2004 | Kortenbach et al. |
| 2005/0049616 A1 | 3/2005 | Rivera et al. |
| 2005/0125010 A1* | 6/2005 | Smith ................. A61B 17/122 606/142 |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Smith et al. |
| 2005/0277956 A1 | 12/2005 | Francese et al. |
| 2006/0064117 A1 | 3/2006 | Aranyi et al. |
| 2006/0235444 A1 | 10/2006 | Huitema et al. |
| 2007/0049948 A1 | 3/2007 | Menn |
| 2007/0049949 A1 | 3/2007 | Manetakis |
| 2007/0049950 A1 | 3/2007 | Theroux et al. |
| 2007/0049951 A1 | 3/2007 | Menn et al. |
| 2007/0191868 A1 | 8/2007 | Theroux et al. |
| 2008/0004639 A1 | 1/2008 | Huitema et al. |
| 2008/0027465 A1 | 1/2008 | Vitali et al. |
| 2008/0207995 A1 | 8/2008 | Kortenbach et al. |
| 2008/0234703 A1 | 9/2008 | Cropper et al. |
| 2008/0243145 A1 | 10/2008 | Whitfield et al. |
| 2010/0057106 A1 | 3/2010 | Sorrentino et al. |
| 2011/0218556 A1 | 8/2011 | Nguyen et al. |
| 2011/0218555 A1 | 9/2011 | Huitema et al. |
| 2011/0224700 A1* | 9/2011 | Schmidt ............... A61B 17/122 606/151 |
| 2012/0116420 A1 | 5/2012 | Sorrentino et al. |

FOREIGN PATENT DOCUMENTS

| | | |
|---|---|---|
| JP | 2005-21587 | 1/2005 |
| JP | 2008-100071 | 5/2008 |
| WO | 91/09569 | 7/1991 |
| WO | 2011044039 | 4/2011 |

OTHER PUBLICATIONS

English translation of Japanese Office Action dated Sep. 16, 2015.
U.S. Office Action in U.S. Appl. No. 13/618,215 dated Dec. 12, 2014.
U.S. Notice of Allowance in U.S. Appl. No. 13/618,215 dated Jul. 27, 2015.
International Search Report and The Written Opinion dated Jan. 15, 2013 for PCT/US2012/055455.

* cited by examiner

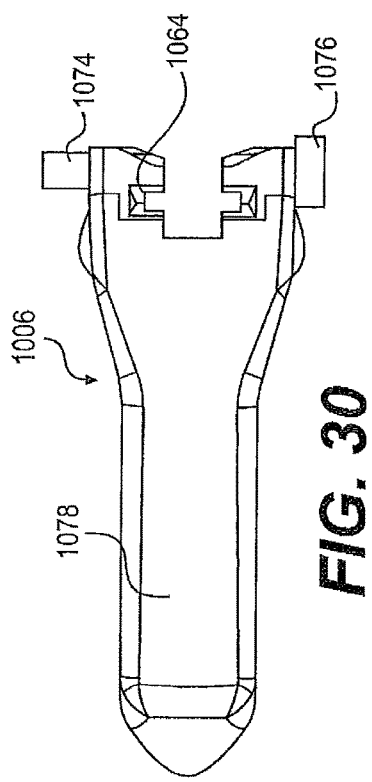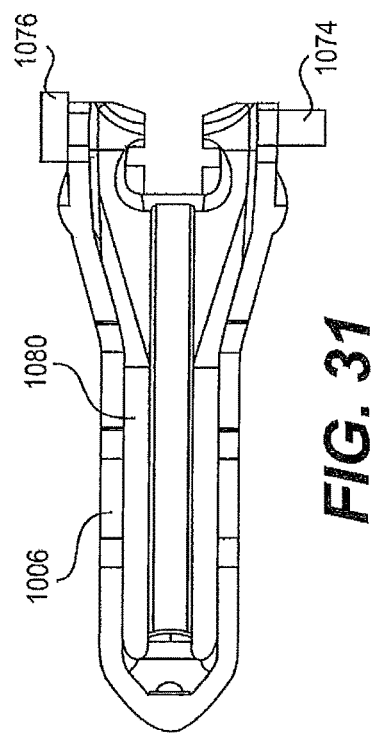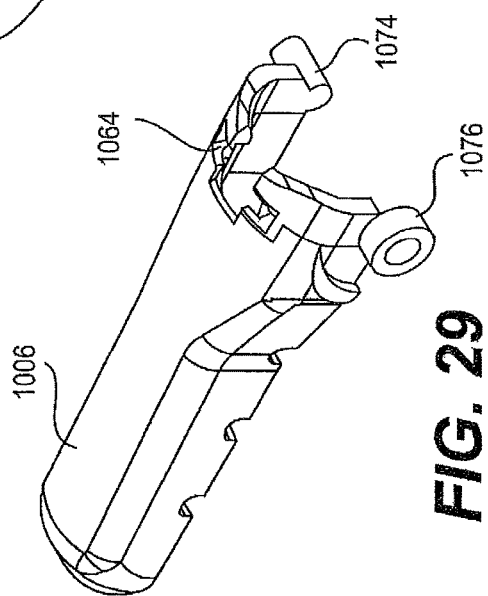

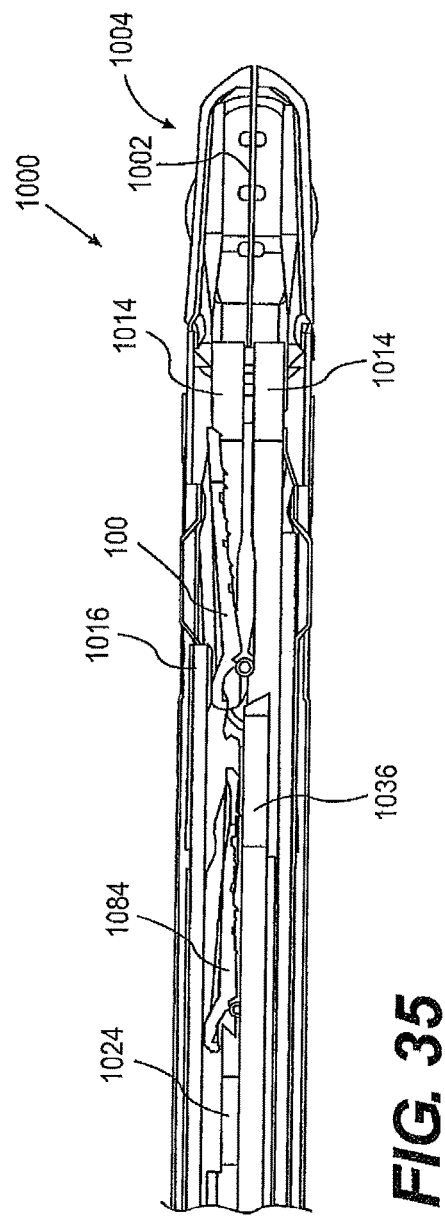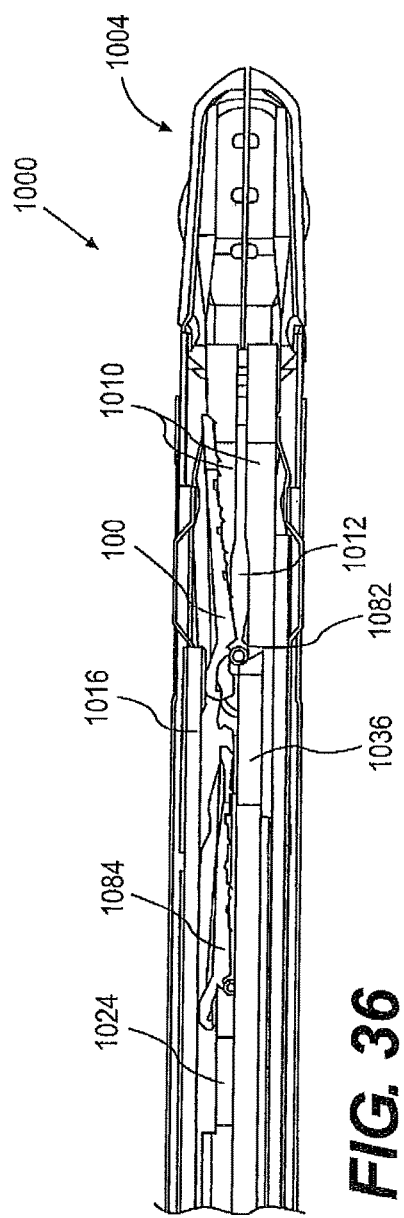

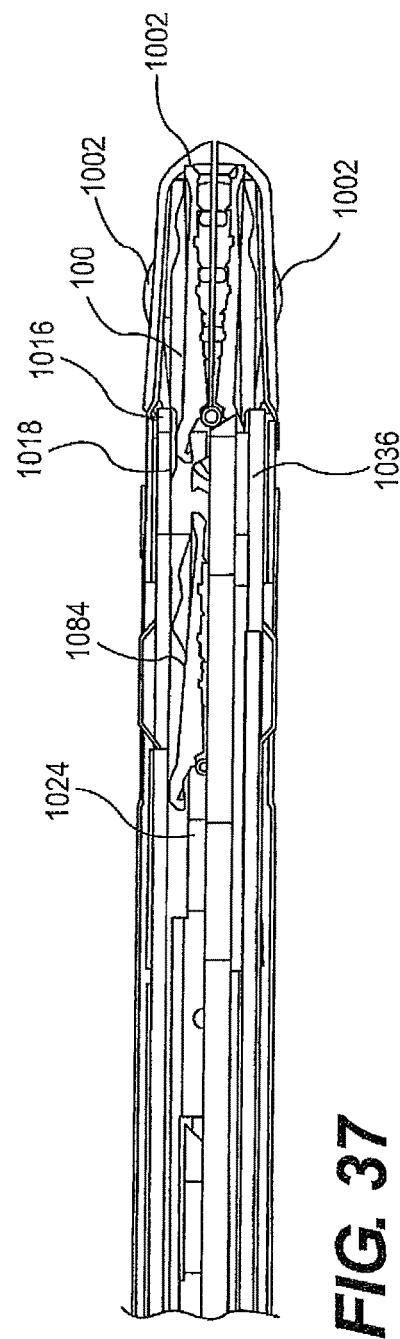
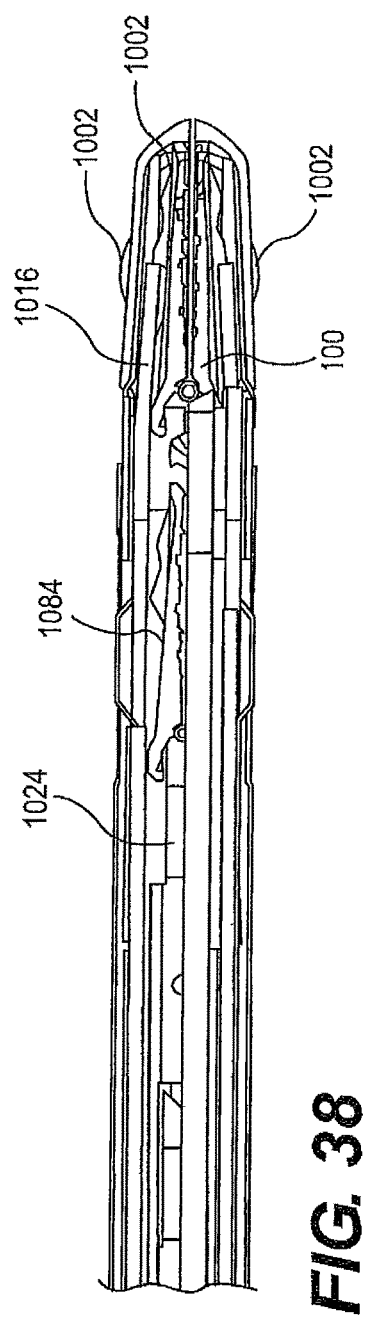

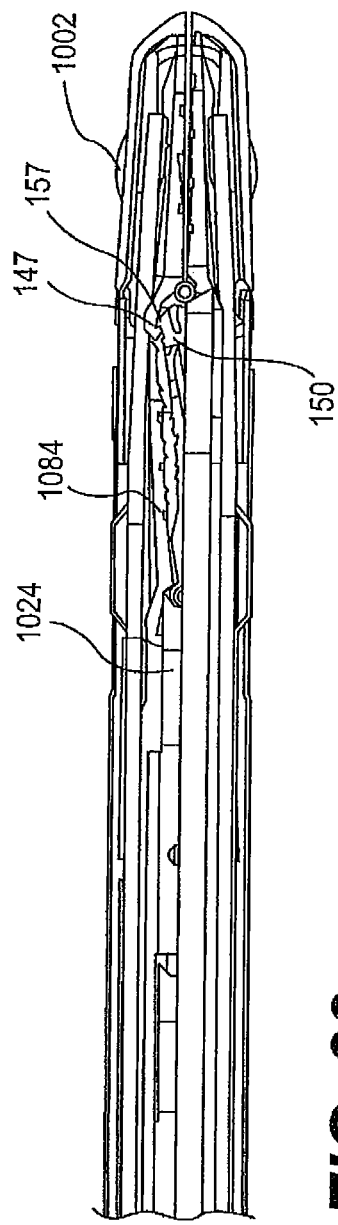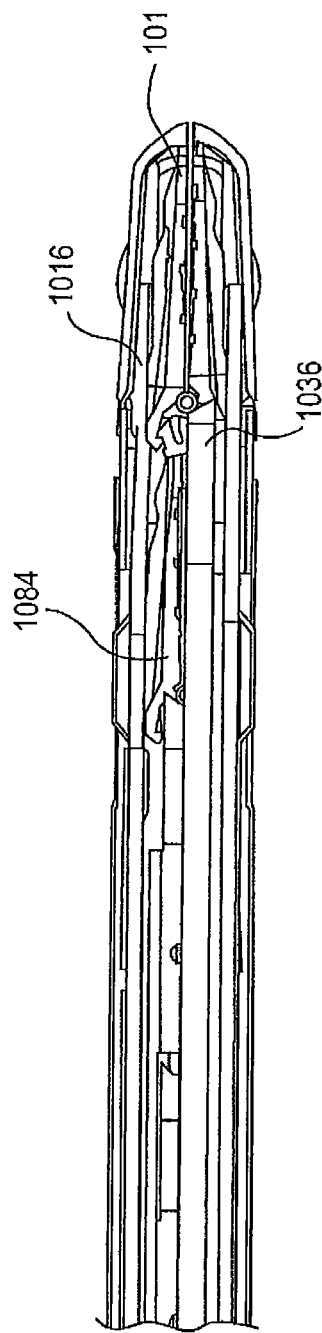
FIG. 39
FIG. 40

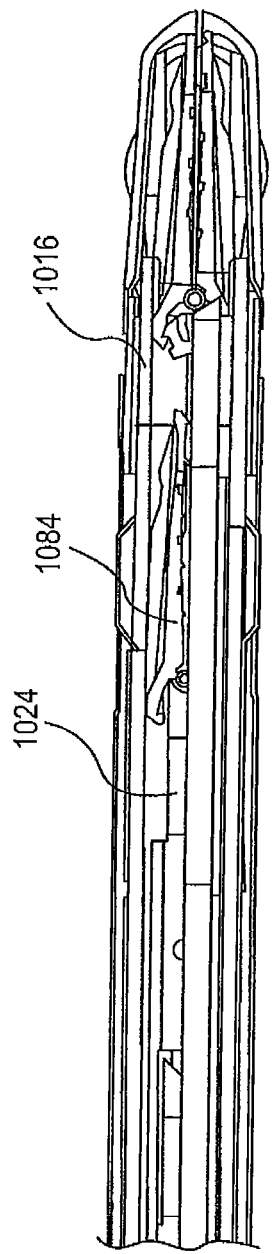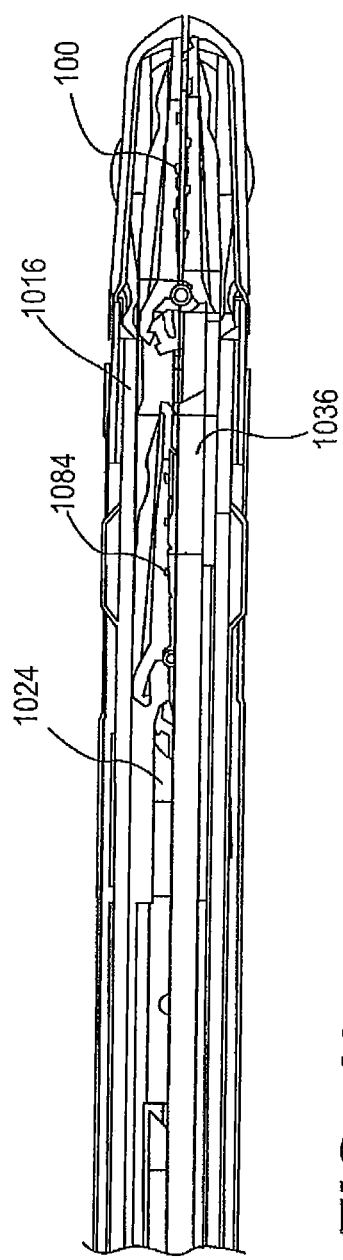
FIG. 41
FIG. 42

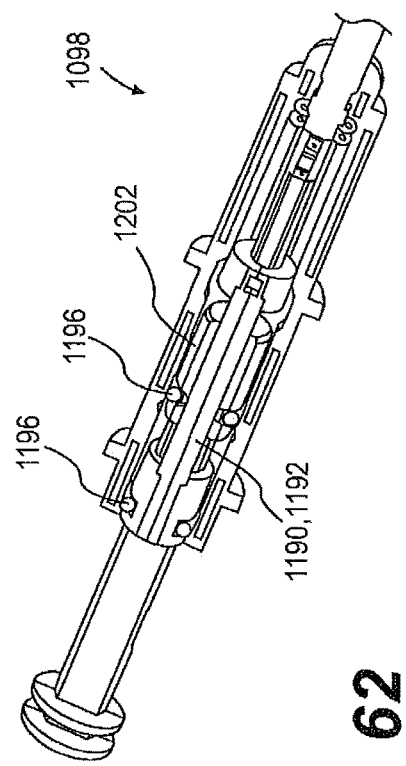
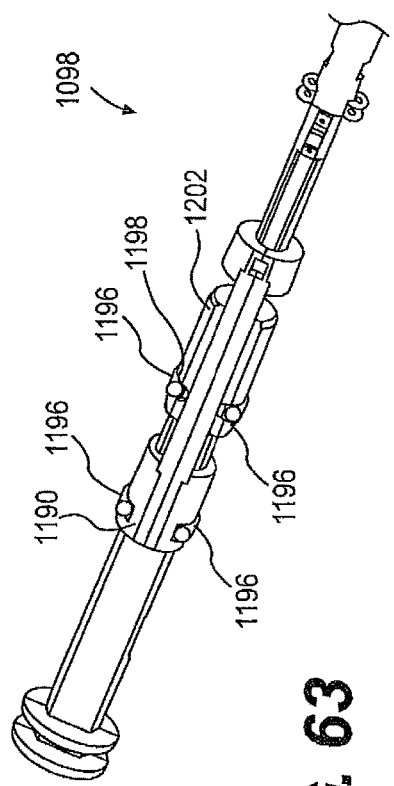
FIG. 62
FIG. 63

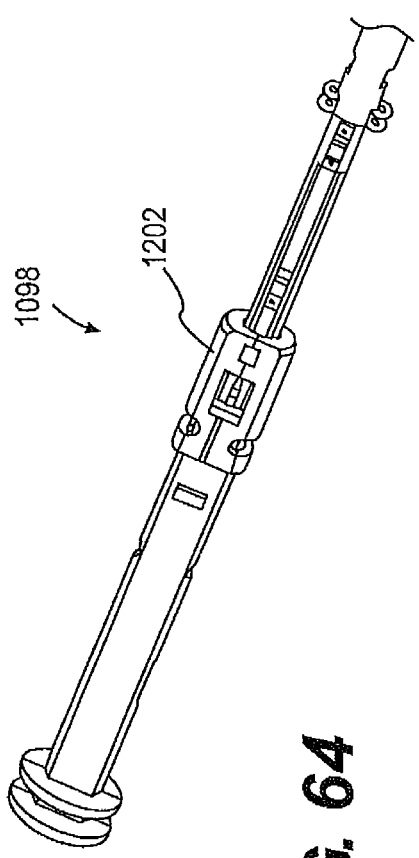
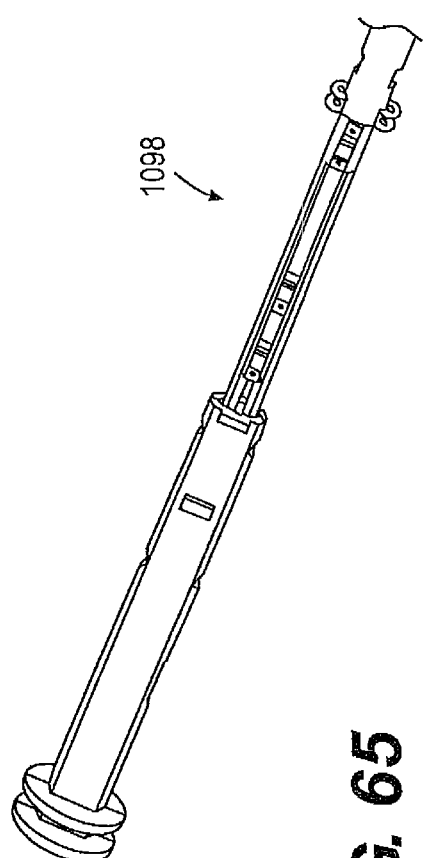
FIG. 64
FIG. 65

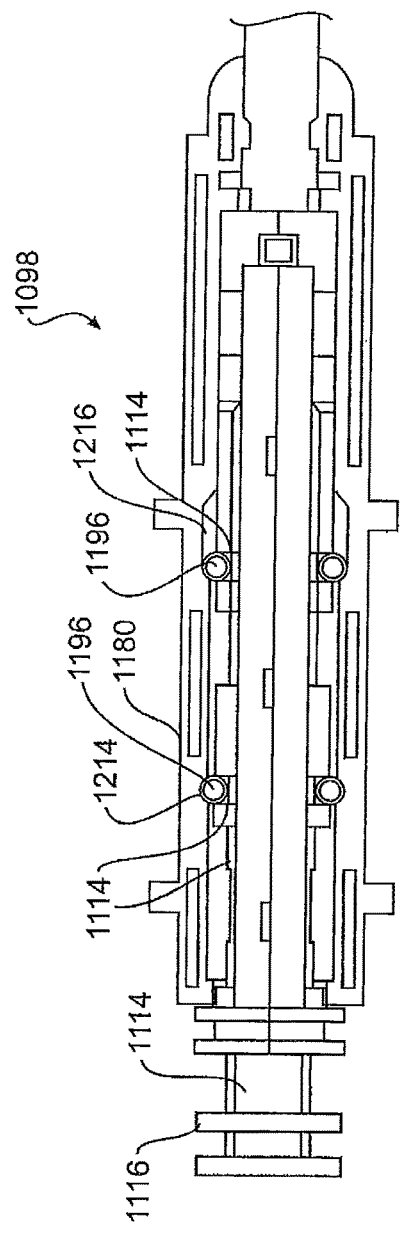
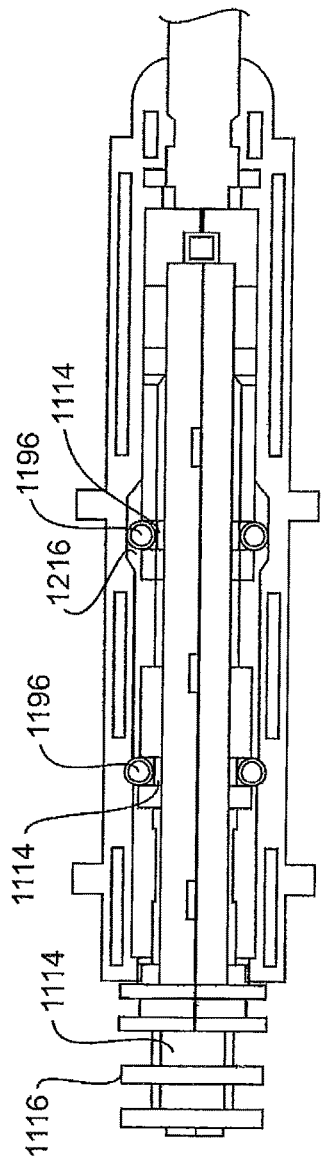
FIG. 71
FIG. 72

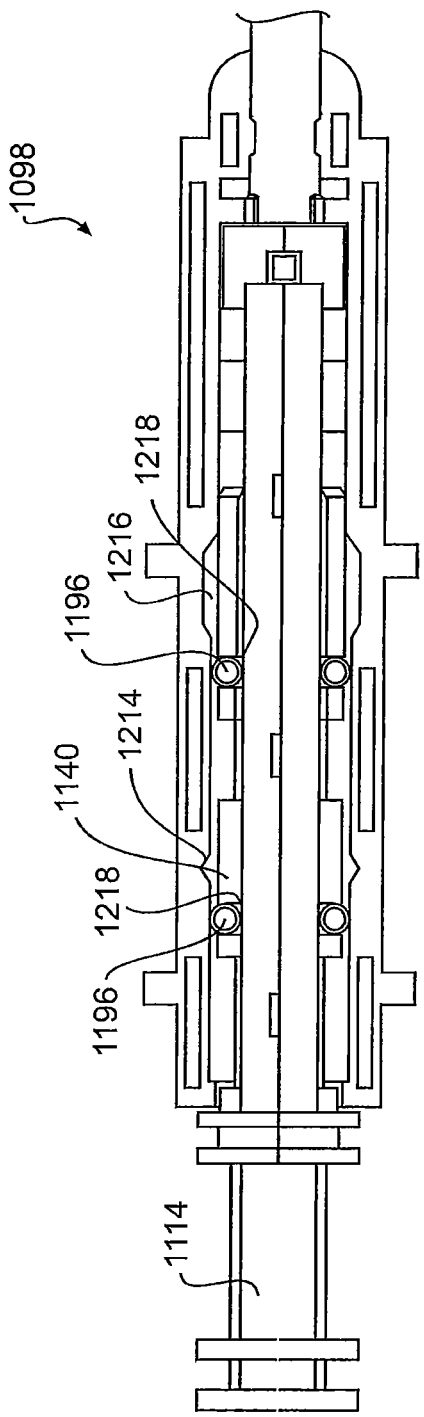
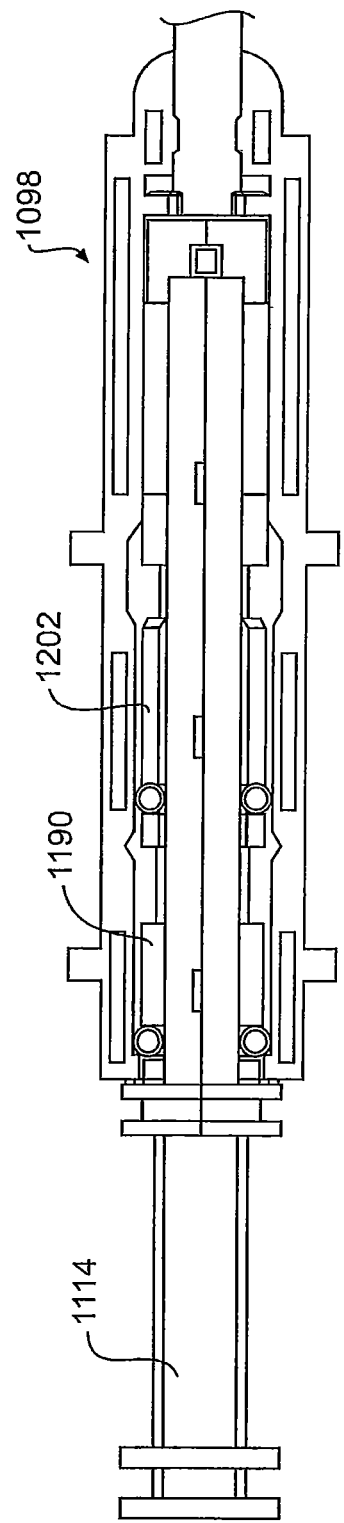

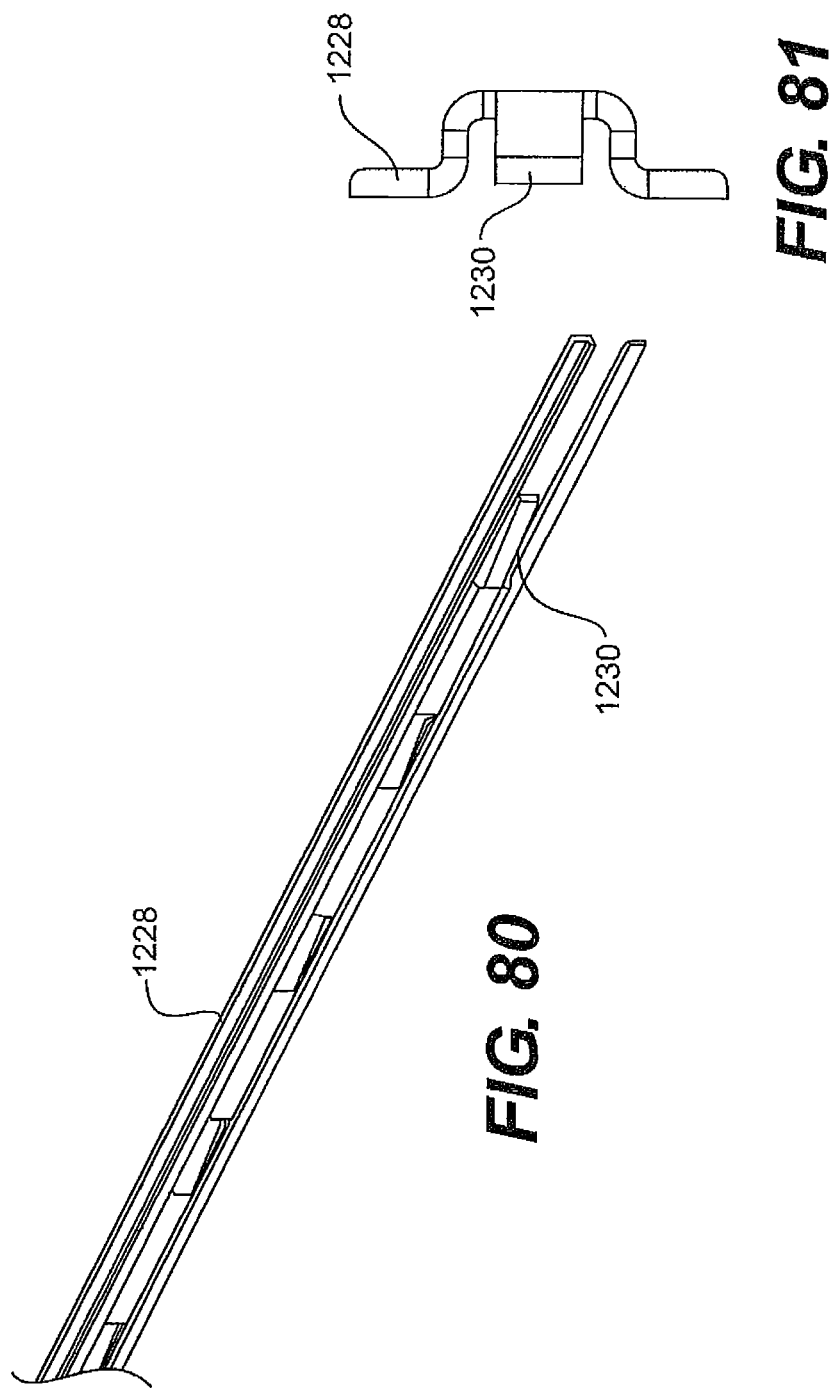

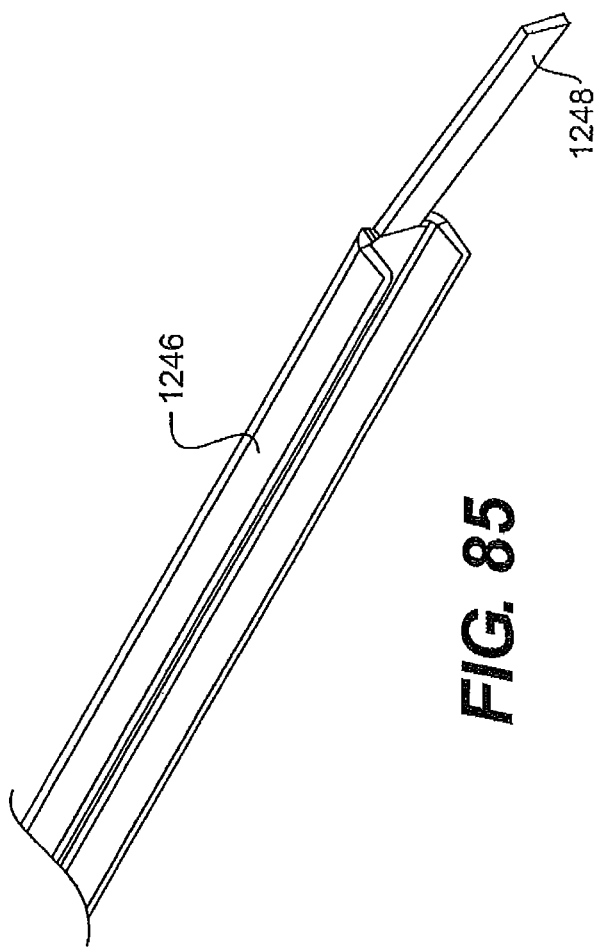

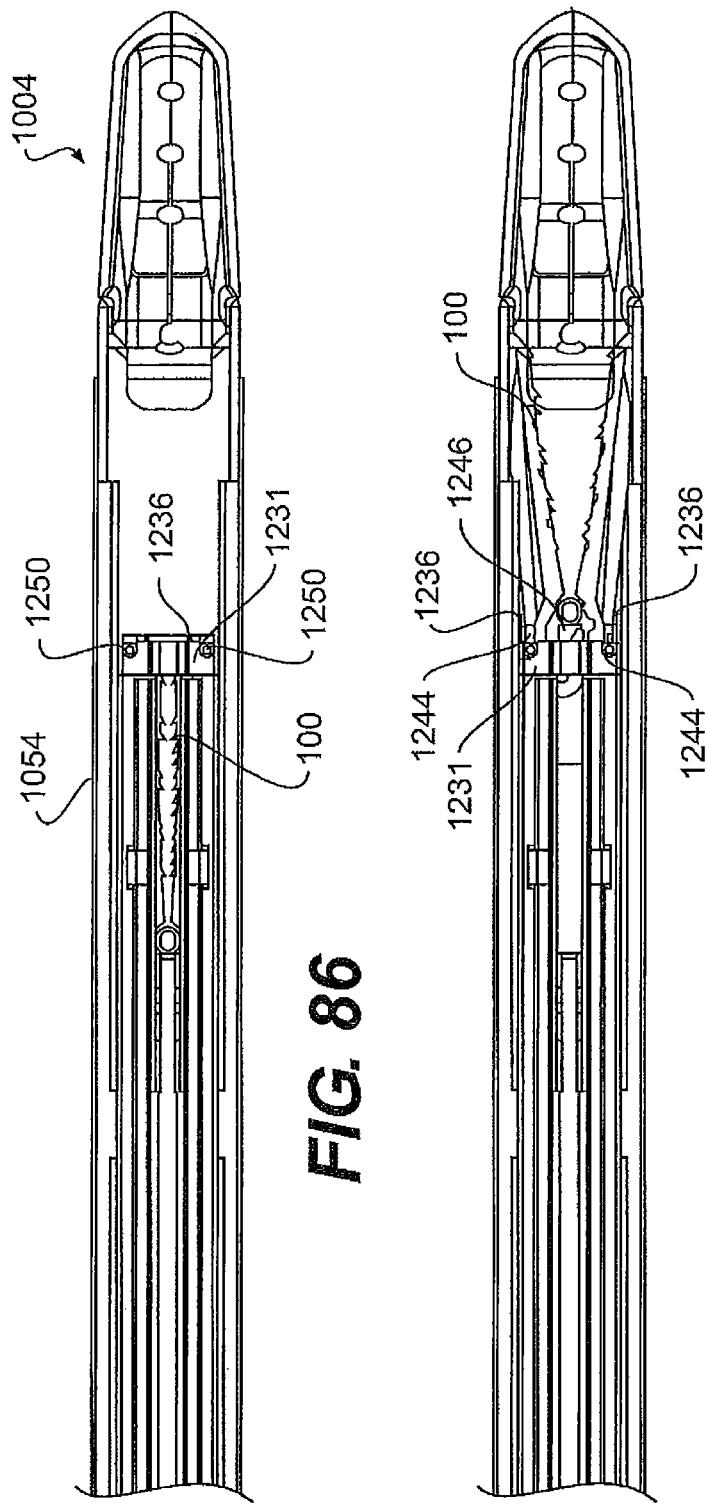

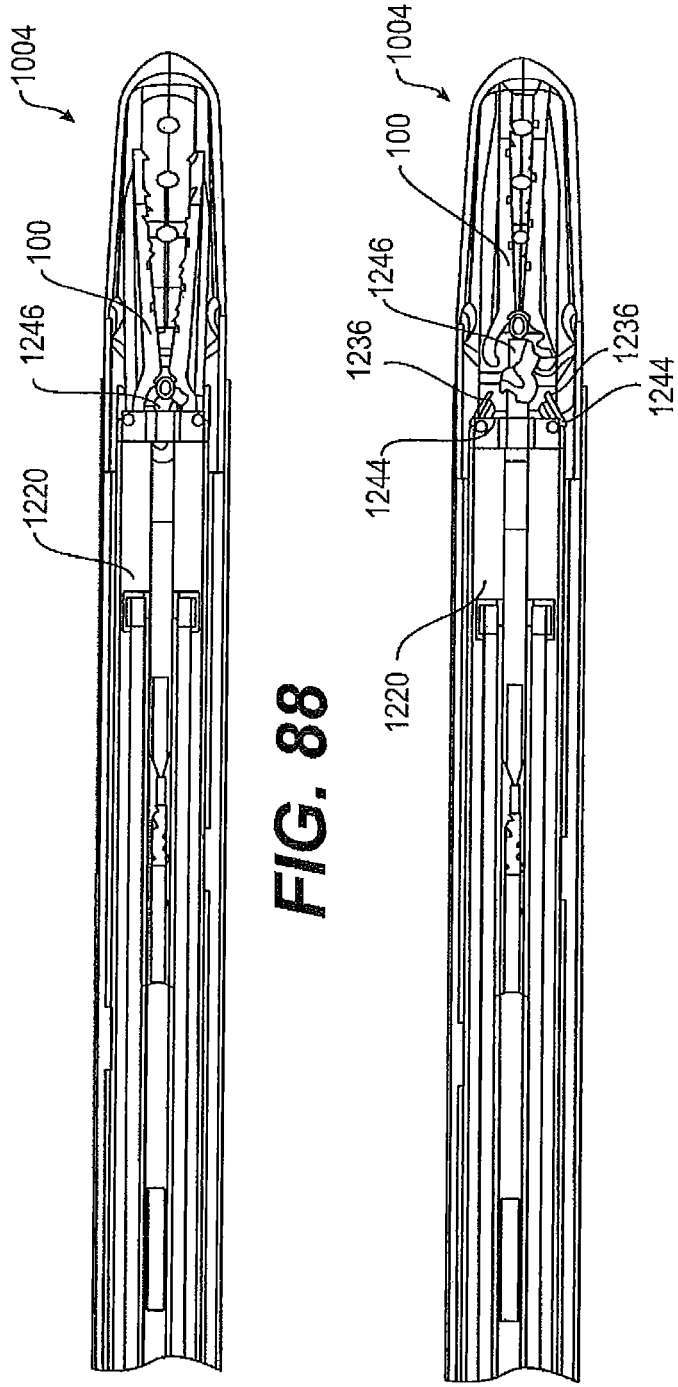

AUTOMATIC SURGICAL LIGATION CLIP APPLIER

CROSS-REFERENCE TO RELATED APPLICATIONS

This application is a Divisional Application of pending U.S. patent application Ser. No. 13/618,215, filed Sep. 14, 2012, which claims priority to provisional U.S. patent application entitled, Automatic Surgical Ligation Clip Applier, filed Sep. 15, 2011, having a Ser. No. 61/535,166, the disclosures of which are hereby incorporated by reference in their entirety.

FIELD OF THE INVENTION

The present invention relates to medical devices and, in particular, a device for applying surgical clips for ligation of vessels or tissue.

BACKGROUND

Many surgical procedures require vessels or other fluid ducts or tissue conduits and structures to be ligated during the surgical process, such as, for example, veins or arteries in the human body. For example, many surgical procedures require cutting blood vessels, and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. Generally, the clip is left in place after application to the tissue until hemostasis or occlusion occurs.

Ligating clips can be classified according to their geometric configuration (e.g., symmetric clips or asymmetric clips), and according to the material from which they are manufactured (e.g., metal clips or polymeric clips). Symmetric clips are generally "U" or "V" shaped and thus are substantially symmetrical about a central, longitudinal axis extending between the legs of the clip. Symmetric clips are usually constructed from metals such as stainless steel, titanium, tantalum, or alloys thereof. But, with the advent of high technology diagnostic techniques using computer tomography (CATSCAN) and magnetic resonance imaging (MRI), metallic clips have been found to interfere with the imaging techniques. To overcome such interference limitations, biocompatible polymers have been increasingly used for surgical clips.

Some well known polymeric clips are disclosed in U.S. Pat. No. 4,834,096 and U.S. Pat. No. 5,062,846. These plastic clips generally comprise a pair of curved legs joined at their proximal ends with an integral hinge or heel, and a closure or locking mechanism at their distal ends. Another example of a bio-compatible clip is shown in U.S. Pat. No. 4,671,281, which includes a mechanism to be actuated on a proximal end of the clip for causing the distally extending legs of the clip to converge. However this clip is: (i) rudimentary in construction, (ii) does not provide adequate clip closing or clamping strength, (iii) lacks any complex geometry which would adequately retain the clip in a closed position, and further (iv) is too unstable when closed to be safely applied over vessels. Examples of metal hemostatic clips are shown in U.S. Pat. No. 3,326,216 and U.S. Pat. No. 5,908,430.

In all of the known ligating clips however, there remains a need to improve the effectiveness of clamping about a vessel, while minimizing the damage to the vessel and surrounding tissue. For endoscopic surgical procedures, it is important to use tools and instruments that have the smallest, narrowest profile possible, such as the shafts of a tubular endoscope. Prior art polymeric and metal clips do not lend themselves to deployment through small diameter instrumentation, such as, for example, a ~5 mm endoscope. Known prior art clips can be very wide profile, especially when in the open position prior to closure and ligation, and thus require larger, wider endoscopic instruments and appliers for use in surgery. It is desirable therefore to provide for a surgical ligation clip that has the narrowest profile possible. It may also be desirable to allow for a clip to be opened again after initial closure, which is especially a problem with known surgical clips, such as metal hemostatic clips. Furthermore, prior art polymeric clips involve locking the distal ends of their legs together in order to clamp down on the vessel or structure being ligated. Such closure of a clip having locking parts at its distal end generally causes or requires dissection, removal, or clearance of additional surrounding tissue, in order to allow the clip's locking features to come together, and/or due to actuation of an applier tool surrounding or applied against the distal clip ends, requiring additional time during a surgical procedure and damage to tissue. In other cases, the user may choose not to prepare a path for the locking features and rely on the locking features penetrating through the tissue. In these cases, the locking feature may have difficulty penetrating the tissue or may have difficulty locking after it has penetrated the tissue. This technique may also result in unintended penetration of tissue or vessels.

Therefore it is desirable to provide a clip and a method and/or device for applying the clip which minimizes such dissection of tissue during application. It is further desirable to provide a clip which provides a proper, well-calibrated, reliable clamping force, such that the clip when closed is stable around the vessel ligated.

Accordingly, there is a need to provide an improved surgical ligating clip and a method and/or device for applying the clip, where the clip serves to reliably secure the tissue or vessel engaged by the clip, while robustly remaining attached to the vessel with a minimum level of damage to tissue.

SUMMARY OF THE INVENTION

The invention provides, in one or more embodiments, a surgical ligation clip and a device and/or a method of applying the clip to a vessel or tissue. The device may contain a plurality of clips and may apply a first clip to a vessel or tissue and advance a second clip contained in the applier to an applying position.

In another aspect of the invention, a method of applying a surgical ligation clip includes positioning the clip in an open position proximate an inner anatomical body vessel, the clip having first and second legs each extending along a longitudinal axis of the clip and having proximal and distal end portions with respect to said longitudinal axis, a clip hinge means joining the first and second legs at a point on their respective proximal end portions, the first and second legs each having inner clamping surface means between the clip hinge and the distal end portions of said first and second legs, the clamping surface means being apposed when the clip is in a fully closed position, and a locking means for biasing the legs closed extending proximal to the clip hinge means. An external force is applied substantially along the longitudinal axis to a proximal end portion of one of the legs which forms a portion of the locking means, to move a body formed as a first part of said locking means from a first position to a second position to provide an abutment force between a curved planar segment abutment portion of said body and a curved surface formed on a second part of said locking means disposed on the first leg to bias the clip in a closed position. The method may further include moving the clip through an instrument prior to positioning the clip proximate the vessel, and may also further include that a portion of the instrument opens the clip from a closed position to an open position.

The applier is an instrument used to deploy multiple proximal locking polymeric ligation clips, the number of clips within the applier is proportional to the length the distal end of the applier and the length of the clip. The automatic applier applies a single clip at a time with the ability to repeat the application multiple times without moving from the surgical site. The applier is an endoscopic instrument suitable for use in laparoscopic surgery applications.

The jaws of the applier will be able to actuate without disturbing the loaded clip. This allows the jaws to be used in the dissection and grasping of tissue around the vessel being ligated if necessary.

In one embodiment of the invention; the jaws of the applier will clamp over the vessel to flatten the section to be ligated. The clip is opened internally in the applier by a set of wedges. The clip is then positioned over the vessel and subsequently closed with actuation of the wedges and final pusher mechanisms. The clip is then closed with the wedges and a second clip, proximal to the first clip, engages the locking feature on the first clip and locks the clip to maintain the clamping pressure of the clip. The jaws then open allowing the ligated vessel and clip to clear the applier jaws. The internal components of the applier return to their start positions and the second clip becomes the first clip. This repeats until the applier is out of clips. The last clip is locked with a false clip that stays internal to the applier. When all clips have been delivered the false clip assists with the handle lockout which prevents the user from being able to use the ligation portion of the applier. The jaws continue to actuate.

In one embodiment of the invention; the jaws of the applier will clamp over the vessel to flatten the section to be ligated. The clip is pushed through a channel and into a set of doors with features on the underside that opens the clip. The clip is then positioned partially over the vessel with forward movement of the channel and clip advancers. The movement stops and the clip is advanced fully over the vessel with the clip advancers, at this time the clip is pushed out of the doors. The doors swing together and become the surface that is used to latch the clip. With the doors closed the channel continues forward and latches the clip. The jaws then open allowing the ligated vessel and clip to clear the applier jaws. The internal components of the applier return to their start positions and the second clip becomes the first clip. This repeats until the applier is out of clips.

Each of the distal end actuations are accomplished through the use of a proximal handle. The handle is made of a housing and rotation knob, which allow for a 360° continuous rotation of the distal end, separate triggers for jaw actuation and clip functions, and a multi-stage transmission that allows the distal end to be actuated in the proper sequence for effective clip delivery.

In one embodiment, the applier has a transmission that has at least two inputs. the inputs are manipulated by a jaw actuation trigger and a clip function or ligate trigger. The transmission is connected to clip advancers and the jaws of the applier and transform the trigger positions to articulations of the jaws and/or the clip advancers.

In one embodiment, a method of moving clips through an applier, attaching a clip to a vessel or tissue is provided.

In an embodiment, an applier for ligation clip is provided. The applier includes: an outer tube having mounting bosses; a pair of jaws pivotally connected to the mounting bosses, the jaws having actuating projections; a feed tube located in the outer tube and configured to move axially within the outer tube, the feed tube having actuating slots in which the actuating projections are located; a clip lock arm located in the outer tube and configured to move axially within the outer tube; and a clip advance arm located in the outer tube and configured to move axially within the outer tube, the clip advance arm having flexible pinchers at one end of the clip advance arm.

In an embodiment, a method of applying a ligation clip includes: sliding a feed tube forward thereby camming a projection on a jaw to move the jaw to an open position; sliding a clip arm forward thereby pushing a clip into the jaws;

sliding the feed tube rearward thereby camming the projection on the jaw to move the jaw to a closed position; and advancing a clip arm to a forward position to push a buttress on the clip into a buttress locking void thereby locking the clip and a closed position.

In an embodiment, an applier for ligation clip may include: an outer tube having mounting bosses; means for clamping pivotally connected to the mounting bosses, the means for clamping having actuating projections; means for opening and closing the means for clamping located in the outer tube and configured to move axially within the outer tube, the means for opening and closing the means for clamping having actuating slots in which the actuating projections are located; means for locking a clip in closed position located in the outer tube and configured to move axially within the outer tube; and means for advancing a clip located in the outer tube and configured to move axially within the outer tube.

There has thus been outlined, rather broadly, certain embodiments of the invention in order that the detailed description thereof herein may be better understood, and in order that the present contribution to the art may be better appreciated. There are additional embodiments and features of the invention that will be described below.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

BRIEF DESCRIPTION OF THE DRAWINGS

FIG. 12 is a perspective view from the top of the clip shown in FIG. 11a;

FIG. 13 is a side view of the clip shown in FIG. 11a;

FIGS. 29-31 shows jaws;

FIG. 35 shows jaws clamped on vessel;

FIG. 36 shows a start of ligation—wedges, primary & final pushers begin to move;

FIG. 37 shows an open clip advanced into jaws over vessel;

FIG. 38 shows wedges advance to close clip legs down on vessel;

FIG. 39 shows a second clip advanced into first clip rotating buttress and locking first clip;

FIG. 40 shows wedges begin to retract, feeder rails are together keeping the second from retracting;

FIG. 41 wedges continue to retract primary pusher and second clip retract;

FIG. 42 shows second clip stops in notch on feeder rails, wedges and primary pushers continue to retract final pusher begins to retract;

FIG. 62 show a jaw actuation links removed;

FIG. 63 shows a back outer shell removed;

FIG. 64 shows a final pusher latches and dowels removed;

FIG. 65 shows a primary pusher latches removed;

FIG. 71 shows input positions for wedges to advance to close first clip;

FIG. 72 shows input positions for a clip latch—primary pushers advance second clip to lock first clip;

FIG. 75 shows input positions for final pusher to retract other parts continue to retract;

FIG. 76 shows input positions when everything returns to start position-second clip is now the first clip;

FIG. 80 shows a walking beam pusher;

FIG. 81 shows a walking beam pusher;

FIG. 85 shows a clip advancer;
FIG. 86 shows a start position;
FIG. 87 shows a clip advancer pushes first clip through doors;
FIG. 88 shows a walking beam and clip advancers move forward to partially advance clip over vessel in jaws. The walking beam pusher stays stationary;
FIG. 89 shows the walking beam stops and the clip advancers push the clip the final distance.

DETAILED DESCRIPTION

Figure 1:
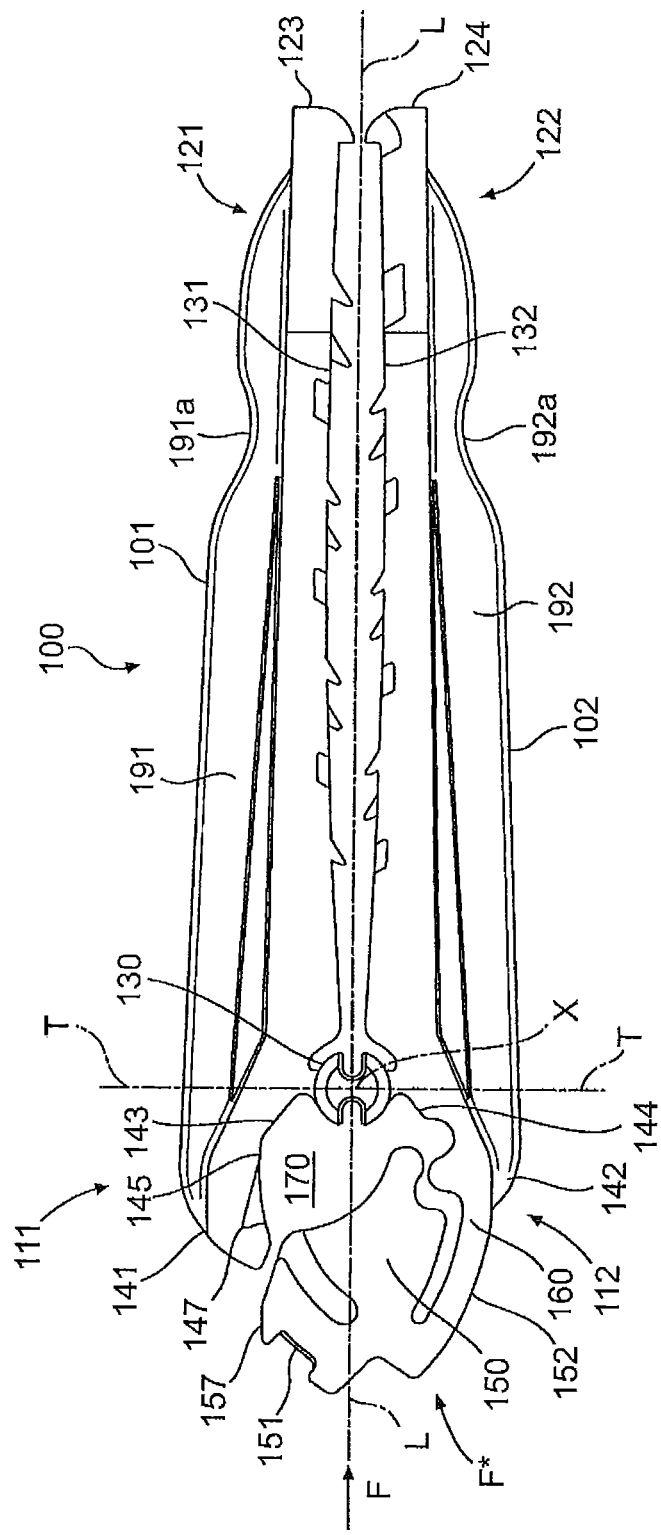
FIG. 1 shows a view of a first embodiment of a surgical ligation clip of the present invention.

The invention will now be described with reference to the drawing figures, in which like parts are referred to with like reference numerals throughout. Clips that may be used in accordance with some embodiments of the invention are described in U.S. provisional patent application No. 61/312,156, filed on Mar. 9, 2010, and U.S. non-provisional application Ser. No. 13/042,864, filed on Mar. 8, 2011 by Philip Schmidt, et al. the disclosures of which are both incorporated by reference in their entirety.

FIG. 1 shows a view of a first embodiment of a surgical ligation clip 100 in accordance with present invention. The clip 100 defines a longitudinal axis "L" along its longest dimension and includes a first leg 101 and a second leg 102 each extending along the longitudinal axis L and having proximal 111, 112 and distal 121, 122 end portions with respect to said longitudinal axis. As used herein, the term "proximal" shall refer to the portion of the clip referenced herein which is away from the tips of the clip which open, and "distal" shall refer to the portion of the clip at the tips which open, in accordance with the convention that the clip is inserted distal tip first through an instrument towards an anatomical body to be ligated, such that distal generally refers to the direction away from the user or applier of the surgical clip and proximal refers to the direction opposite to distal.

In clip 100, a clip hinge 130 joins the first and second legs 101, 102 at a point on their respective proximal end portions 111, 112, the first and second legs each having respective inner clamping surfaces 131, 132 between the clip hinge 130 and the distal ends 123, 124 of said first and second legs, the clamping surfaces being apposed when the clip is in a fully closed position. As used herein, the term "apposed" when used with regard to the inner clamping surfaces 131, 132 shall mean close to, or nearly in contact with each other, allowing for some small spacing therebetween or a concave radius of curvature for the clamping surfaces, such to allow for a clipped vessel to reside between such apposed surfaces, as is more fully illustrated herein and with respect to the drawing figures. The clip hinge 130 can include a bar or cylindrically shaped body or tube which defines a lateral pivot axis "P" (shown in FIGS. 2b and 2c) about which the legs 101 and 102 pivot as the clip moves from open to closed position and vice versa. A first jaw structure 141 on the first leg 101 extends proximal to a transverse axis "T" which is perpendicular to both the longitudinal axis L and lateral pivot axis P, all intersecting at a point "X" centered on the clip hinge 130, as shown in FIG. 1. As used throughout herein, the term "lateral" shall directionally mean orthogonal to both the directions of the longitudinal axis L and transverse axis T, and parallel to pivot axis P as shown in the figures. The first jaw structure 141 includes a first curved inner surface 143 extending from the clip hinge 130, the first curved inner surface 143 having a complex surface which is oriented at changing angles with respect to, but is generally facing towards, the longitudinal axis L, as shown in FIG. 1. The curved inner surface 143 is therefore substantially concave when viewed from the longitudinal axis (or plane spanning the longitudinal axis and pivot axis). As used herein, the term "substantially concave" shall mean a surface which is concave in overall curvature, but which may include one or more component areas which may have convex segments or protrusions, such as a notch surface or recess for mating thereto. A second jaw structure 142 is on the second leg 102 extending proximal to the transverse axis T and has a second curved inner surface 144 extending from the clip hinge 130. As used herein, the "curved inner surface" can include either a single smoothly curved surface segment, or a series of connected curved or straight planar segments, which, taken together, form an overall generally curving surface. As described herein, the surgical clip of the present invention provides that the jaws 141 and 142 are each substantially proximal to a transverse plane extending through transverse axis T and lateral pivot axis P, thus behind the clip hinge 130, thereby providing a means for actuating the clip legs 101 and 102 and biasing or locking the clip and its mating faces 131, 132 in a closed position, which biasing or locking means can be actuated and/or applied by acting only on the proximal end portions of the clip 100, without having to lock the distal ends 123, 124 to each other or use a clip applier tool which acts on said distal ends 123, 124, thereby obviating the need to dissect tissue around the distal end of the clip as in previously known surgical ligation clips.

As shown in FIG. 1, the means for biasing or locking the clip closed includes a wedge or buttress body 150 which extends from and is connected to the second jaw structure 142 by a first living hinge 160 at a proximal end of said second jaw structure 142, the buttress body 150 having an outer surface 151 at a proximal first end portion thereof, which is also disposed approximately as the proximal end of the clip 100 overall. The first and second jaw structures 141, 142 are spaced on opposite sides of the longitudinal axis L and define a locking space 170 there between. The wedge or buttress body 150 is pivotable about the living hinge 160 to move into the locking space 170 such that the outer surface 151 of the proximal first end portion of the buttress body 150 abuts against a proximal portion 145 of the curved inner surface 143 of the first jaw structure 141 to bias the clip in a closed position (as best shown in FIGS. 11a, and 12-14). Although the clip 100 is shown in FIG. 1 in a closed position, this is with the locking means of the first and second jaws 141, 142 and buttress body 150 being in the "unlocked" position as shown in FIGS. 1, 2a, and 3-7. Once the buttress body is in the "locked" position as shown in FIGS. 11a and 12-14, the first and second jaws 141, 142 are urged or spread apart (shown, as an example, by arrows "J1" and "J2" in FIGS. 13a and 14a) by action of surfaces of the wedge/buttress body 150 acting on portions of curved inner surfaces 143, 144, which act as moments about the clip hinge 130 and lateral pivot axis P to urge the legs 101, 102 and its inner clamping surfaces 131, 132 to become more closely apposed to each other, thereby providing additional clamping and closing force over a vessel around which the clip is applied.

A variety of means may be used to actuate the wedge or buttress body 150 from the unlocked position in FIG. 1 to the locked position shown in FIGS. 11a, 12-14. As shown in FIG. 1, an external force, shown, for example, as arrow "F" in FIG. 1, may be applied to a proximal end of the pivoting buttress body 150, in this example the external force F being substantially aligned with the longitudinal axis L. Alternatively, the external force applied may be at a small angle to the longitudinal axis L, such as, for example, a force shown by arrow "F*" shown in FIG. 1. In either case, the applied external force will create a moment about living hinge 160 to pivot the buttress body 150 into the locking space 170. The external force may be applied by an actuating rod or other structural means in an applier instrument, or may be another clip as fed through a multi-clip applier. As one example, the clip 100 may be inserted through an instrument having a bore or channel for receiving the clip 100, through which the clip 100 may travel distally for positioning near a vessel during a surgical procedure. The clip may be inserted in a legs closed position, but with the proximal locking means including buttress body 150 in open, unlocked position. Because the clip 100 can be inserted in such fashion in closed form, the clip forms a narrow profile and can fit in smaller sized surgical instruments, thereby allowing for smaller incisions and tissue dissection or damage during surgery. A rod or other actuating mechanism translating or moveable on the instrument inserting the clip, or a second instrument or second clip used in conjunction with the instrument used for inserting and positioning the clip in place, maybe used to lock the clip by application of an external force on the proximal end portion of the clip as discussed above.

Thus, a method of applying a surgical ligation clip on a vessel in accordance with an embodiment of the invention includes positioning a clip, such as, for example, clip 100, in an open position proximate a vessel, the clip having first and second legs each extending along a longitudinal axis of the clip and having proximal and distal end portions with respect to said longitudinal axis, a clip hinge means joining the first and second legs at a point on their respective proximal end portions, the first and second legs each having inner clamping surface means between the clip hinge and the distal end portions of said first and second legs, the clamping surface means being apposed when the clip is in a fully closed position. A locking means for biasing the legs closed may extend proximal to a transverse axis perpendicular to the longitudinal axis intersecting at a point centered on the clip hinge. The method includes applying an external force to a proximal end portion of the clip or of one of the legs which forms a portion of the locking means, to move a body formed as a first part of said locking means from a first position to a second position to provide an abutment force between said body and a surface formed on a second part of said locking means to bias the clip in a closed position. In the method, an instrument may be used, wherein, in moving the clip through the instrument prior to positioning the clip proximate a vessel, a portion of the instrument opens the clip from a closed position to an open position, such that the legs of the clip open for placement of the clip around a vessel. The locking means may then be applied to the proximal end portion of the clip to move and bias the legs closed and clamp the clip more fully over the vessel.

In FIG. 1, the clamping surfaces appear substantially parallel to each other, oriented, in the clip closed position, substantially or very close to parallel to a plane extending through the longitudinal axis L and lateral pivot axis P. However, in an embodiment of the invention, the inner clamping surfaces 131, 132 may be slightly curved concave when facing said surfaces, such that the surfaces bow away from the longitudinal axis L and straighten slightly when clamping force is applied by action of the locking mechanism of the buttress body 150 acting against jaws 141, 142. This allows for enhanced grasping and occlusion of vessels around which the clip 100 is applied, wherein the clamping force is spread more evenly across the clamping surface.

The living hinge 160 connecting the wedge or buttress body 150 to the second jaw 142 can be integral to the second jaw 142 such that the clip body of second leg 102 proximal to transverse axis T extends as a single unitary structure including the second jaw 142 and entire wedge or buttress body 150. Accordingly, in the wedge or buttress body 150, a lateral beam or curved body 152 connects the living hinge 160 to the rest of the buttress body 150, which beam 152 curves from the living hinge 160 (which is separated by a distance from the longitudinal axis L) towards the longitudinal axis L. As shown in FIG. 1 portions of wedge of buttress body 150 can be oriented on both sides of longitudinal axis L. The pivot axis of living hinge 160 extends in a lateral direction parallel the lateral pivot axis P of the main clip hinge 130.

Figure 12:
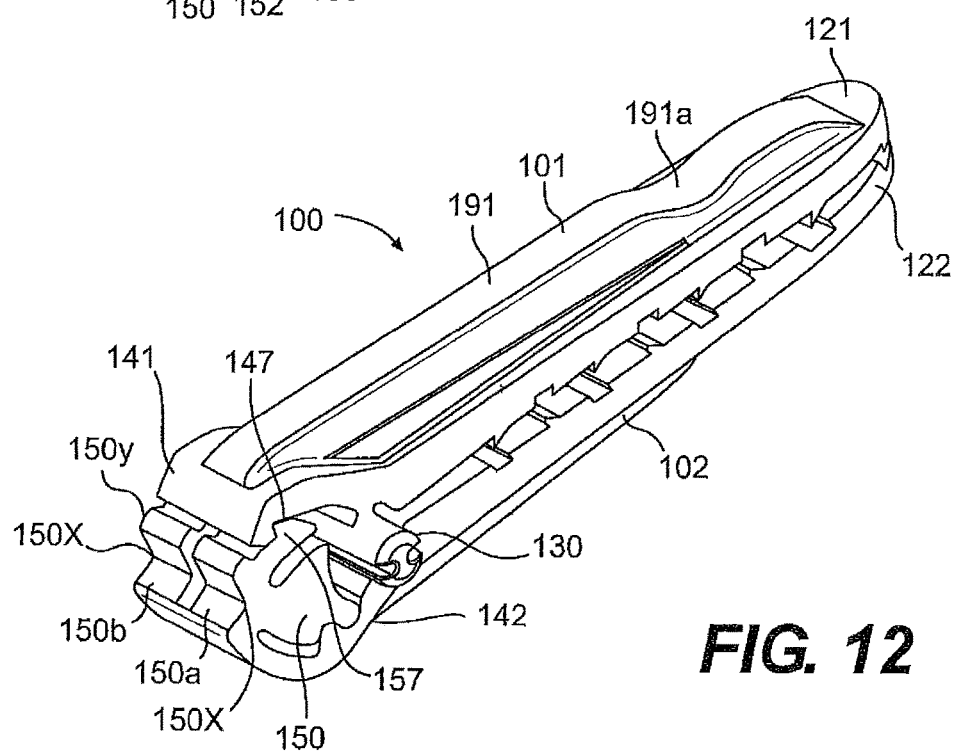
Figure 4:
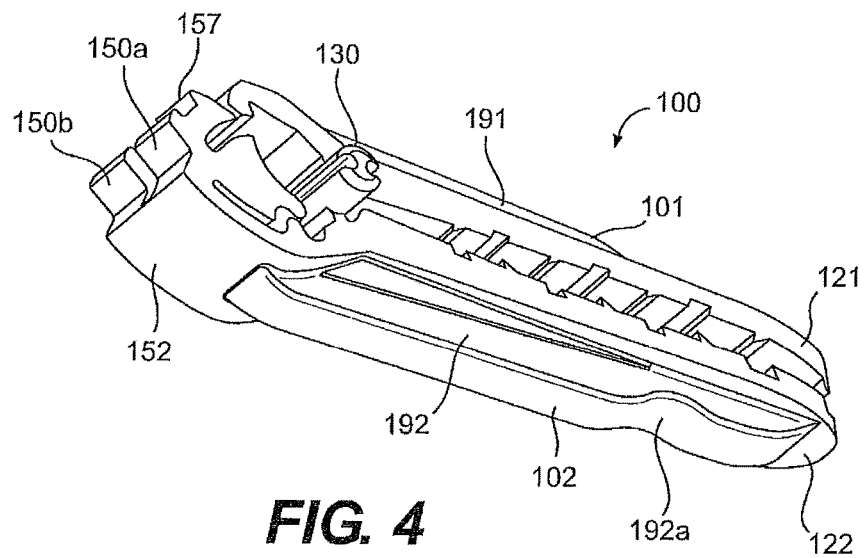
Figure 11C:
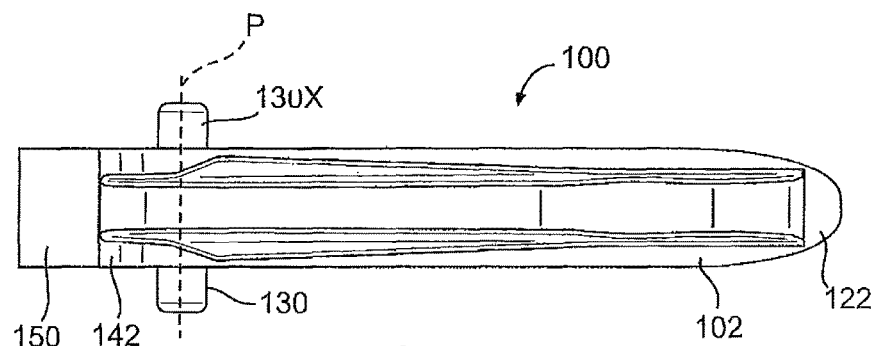
FIGS. 11a, 11b, and 11c show side, top, and bottom views respectively, of the clip shown in FIG. 1, with the proximal locking components in locked position.
Figure 11A:
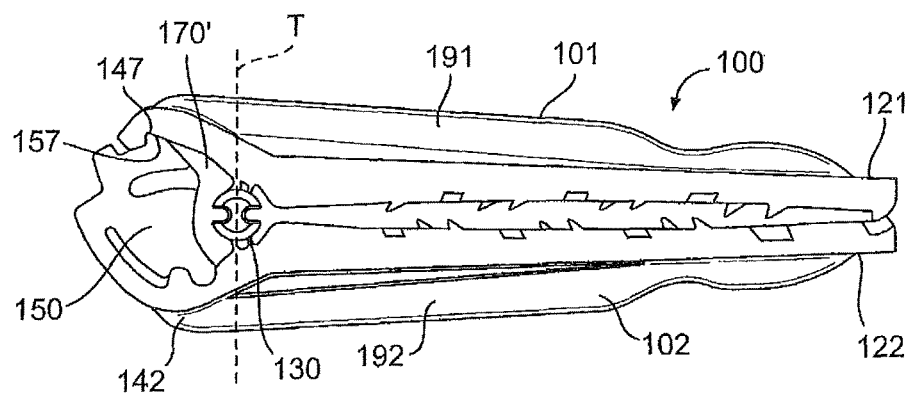
Figure 11B:
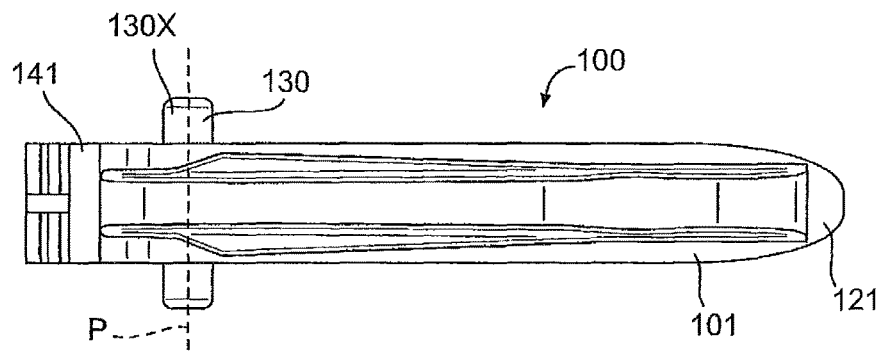
Figure 14A:
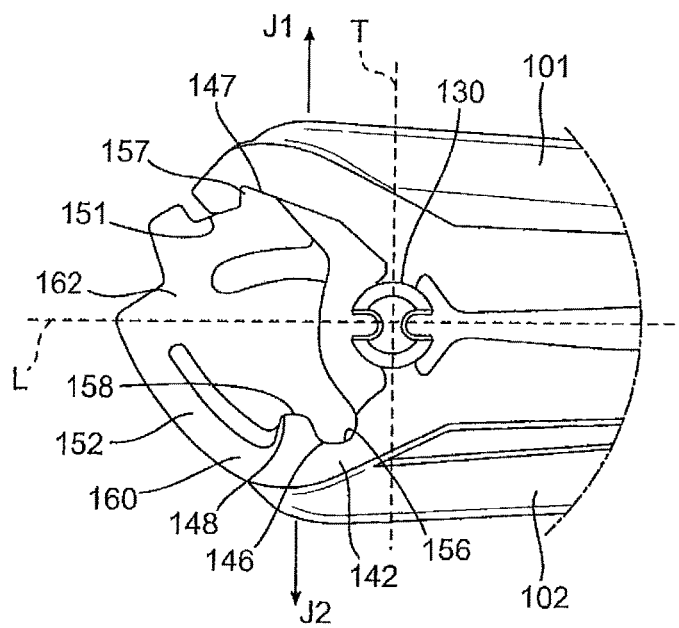
FIG. 14a is a close-up detail view of the portion of the clip shown in FIG. 14 in region "14a" therein.
Figure 14:
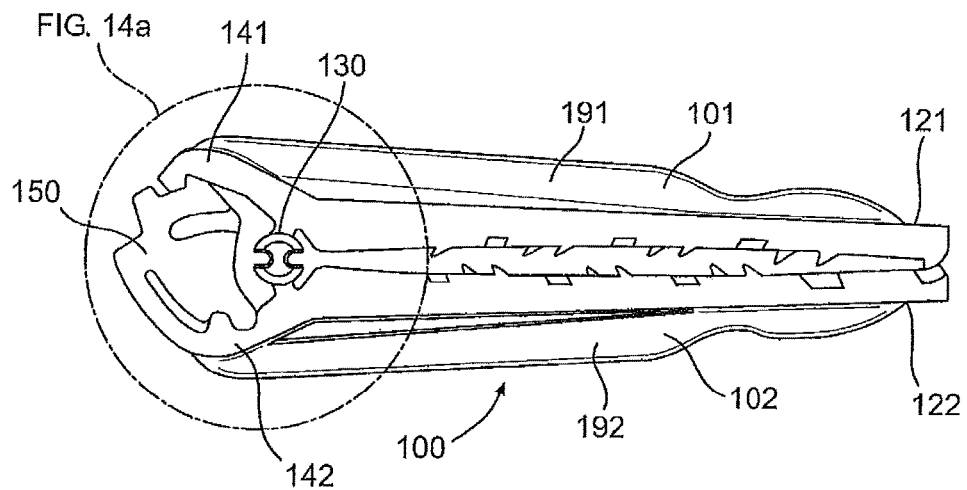
FIG. 14 is a side view of the clip shown in FIG. 11a from the side opposite to that shown in FIG. 13.

The present invention provides, in various embodiments, a locking mechanism cooperating between the buttress body 150 and another portion of the clip. In the clip 100 shown in FIG. 1, the proximal end portion 145 of the curved inner surface 143 of the first jaw structure 141 defines a notch 147 recessed from said curved inner surface 143, and the buttress body 150 defines a detent 157 formed on the outer surface thereof, the detent 157 mating with the notch 147 when the buttress body 150 is pivoted into the locking space 170 to bias the clip in the closed position, as best shown in FIGS. 11a, 12, and 14.

Figure 2A:
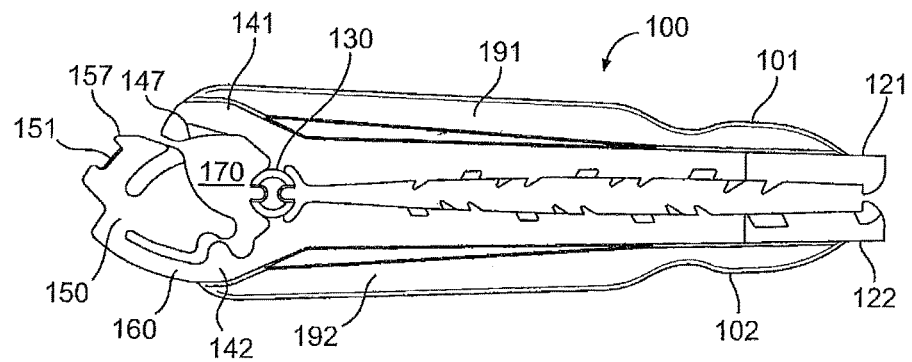
FIGS. 2a, 2b, and 2c show side, top, and bottom views respectively, of the clip shown in FIG. 1.
Figure 2B:
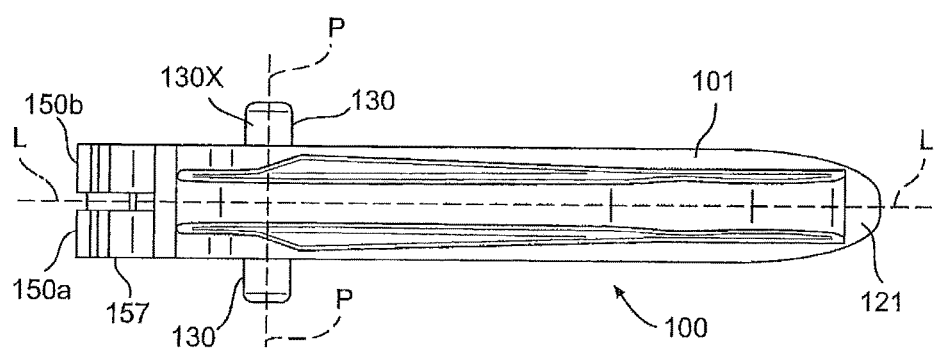
Figure 2C:
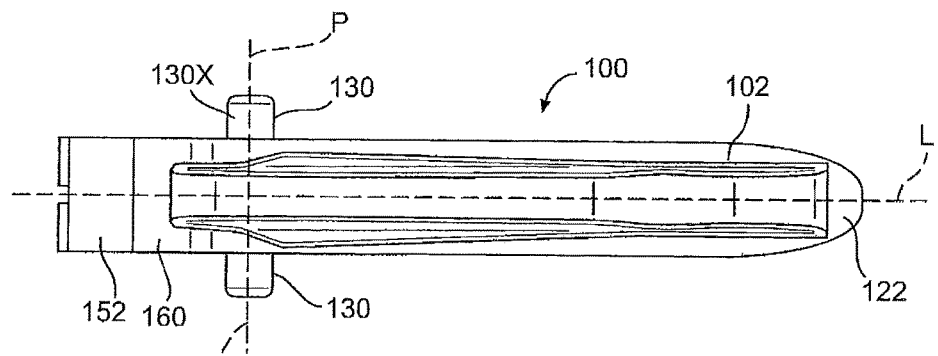
Figure 3:
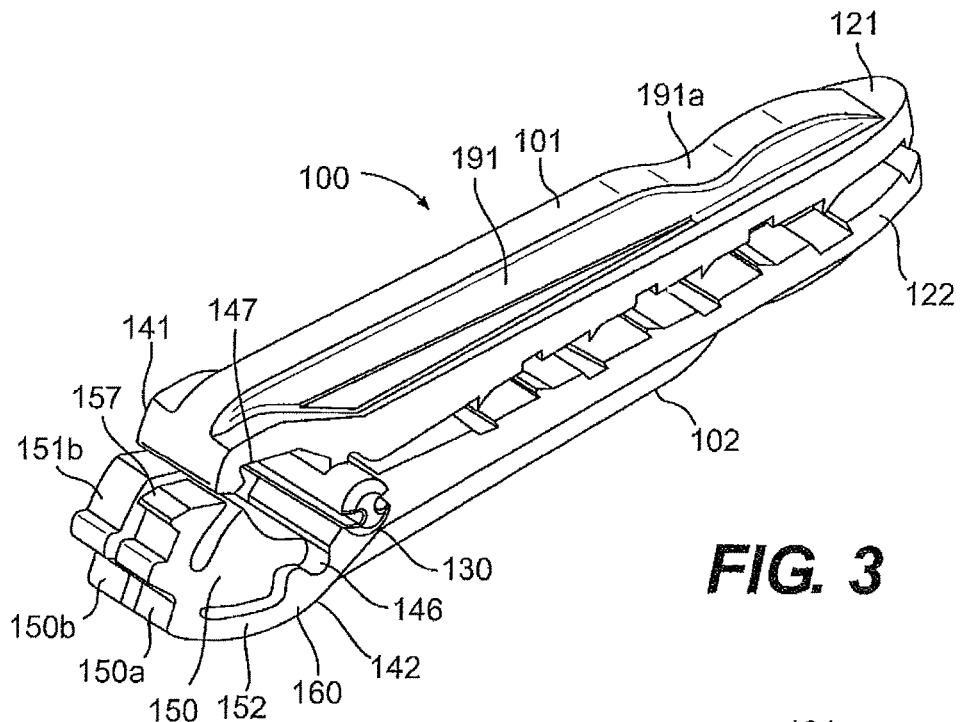
FIGS. 3 and 4 show perspective views of the clip shown in FIG. 1 from a first side.
Figure 7B:
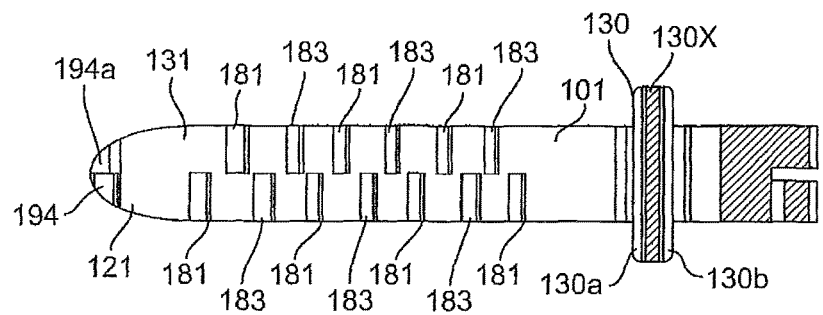
FIG. 7b is a sectional view of the clip shown in FIG. 7 taken along section C-C in the direction shown in FIG. 7.
Figure 7:
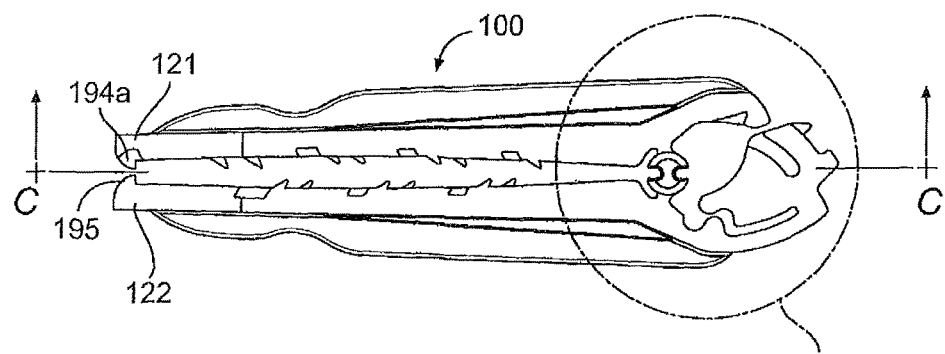
FIG. 7 is another side view of the clip shown in FIG. 1 from the opposite side to that shown in FIG. 6.
Figure 7A:
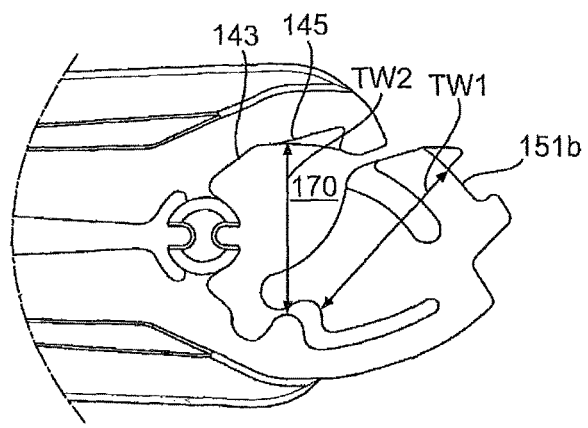
FIG. 7a is a close-up detail view of the portion of the clip shown in FIG. 7 in region "7a" therein.
Figure 8A:
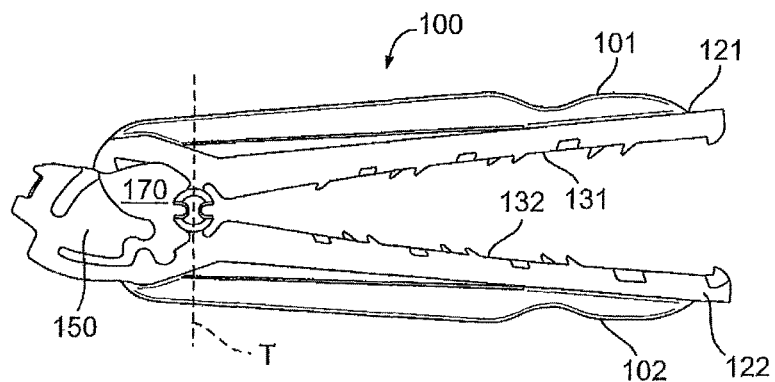
FIGS. 8a, 8b, and 8c, are side, top, and bottom views, respectively, of the clip shown in FIG. 1 in an open position.
Figure 8B:
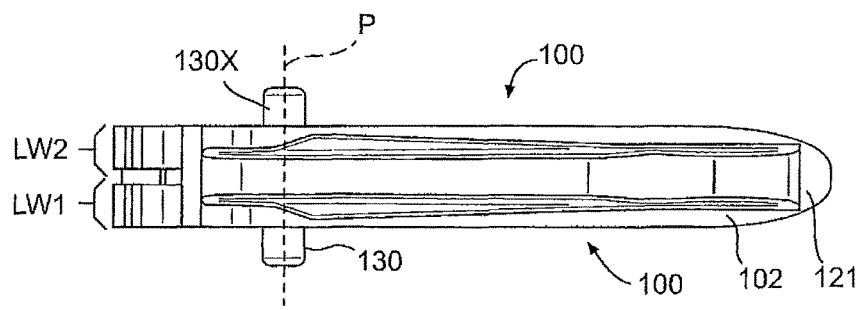
Figure 8C:
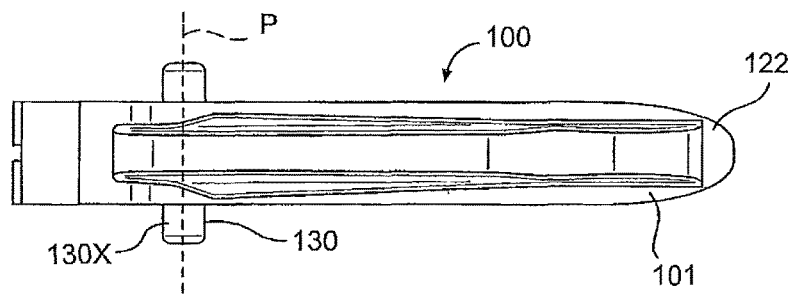
Figure 9:
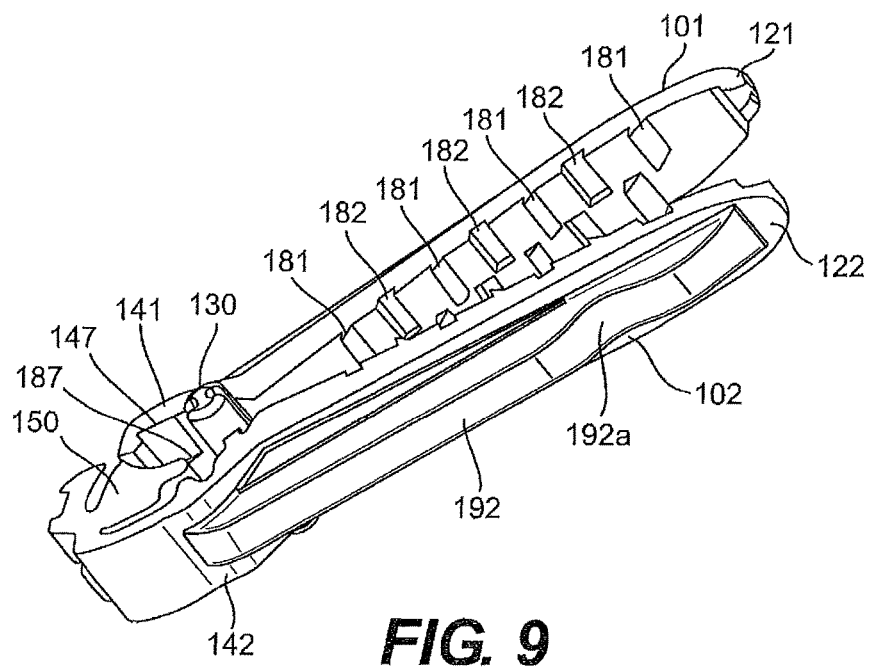
FIG. 9 is a perspective view from the bottom of the clip shown in FIG. 8a in the open position.
Figure 10:
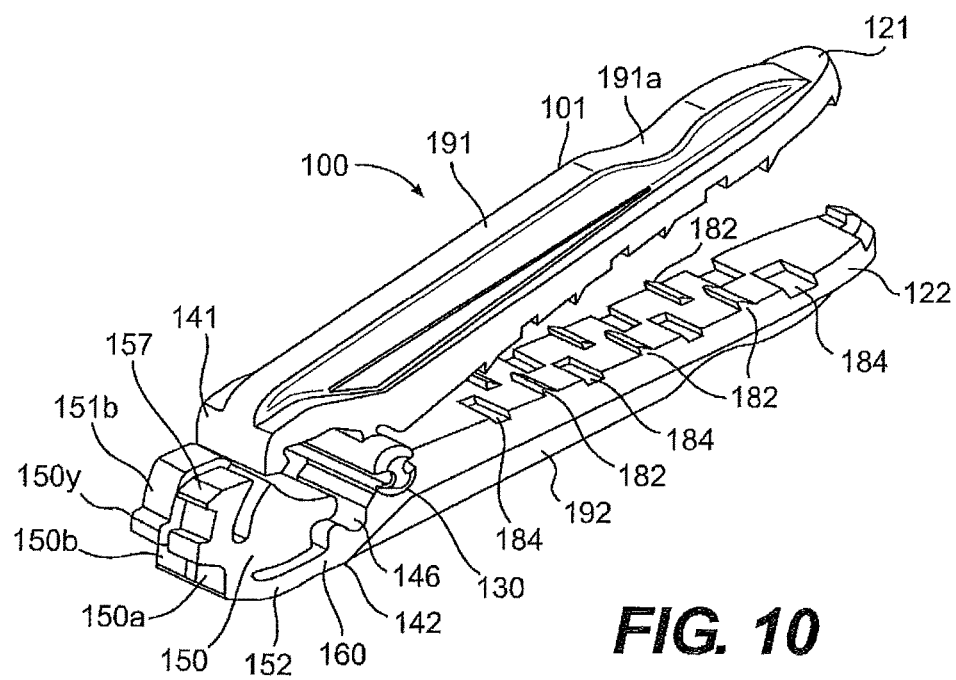
FIG. 10 is a perspective side view from the top of the clip shown in FIG. 8a in the open position.

FIGS. 2a, 2b, and 2c show side, top, and bottom views respectively, of the clip shown in FIG. 1. As shown in FIG. 2b, the wedge or buttress body 150 can be divided into two lateral sections or portions 150a and 150b, each on opposite sides of the longitudinal axis L as shown, and can form approximate lateral halves of the buttress body 150, with a possible space or small channel in-between. Lateral portion 150b of the buttress body 150 can have a width in a plane spanning the transverse and longitudinal axes sufficient to exceed a complementary width formed by the locking space 170 to create an interference fit between the proximal end portion 145 of the curved inner surface 143 of the first jaw structure 141 and the outer surfaces 151a, 151b on the proximal first end portion outer surface 151 of the buttress body 150, to bias the clip in a closed position. An example of the transverse width of said lateral portion 150b is shown as distance "TW1" in FIG. 7a, with complementary width "TW2" being formed by the locking space 170, it being understood that TW1 is slightly greater than TW2 in order to create the interference fit. In the embodiment as shown in FIGS. 1, 2b, and 7a, on lateral portion 150b there is no detent 157, and said lateral portion 150b of the buttress body is formed by a partial lateral width of the buttress body 150. Thus, as shown in FIG. 2b, the notch 147 and detent 157 are formed on corresponding partial lateral sections or slices of the buttress body 150 and first jaw structure 141, respectively, this lateral section 150a of buttress body 150 being on the opposite side thereof to the lateral section 150b. In this manner, the buttress body 150, once locked into place as shown in FIG. 12, is prevented from moving laterally from side to side since the notch 147 and detent 157 interlock only extends laterally partially across the clip, the detent 157 being limited in lateral movement by a shoulder 187 formed by a termination of the notch 147 laterally into the first jaw structure 141, as shown in FIG. 9. As shown in FIG. 8b, the lateral slice of buttress body 150 only extends for a lateral width LW1 which includes detent 157, which the lateral slice LW2 of buttress body 150 on the other side of the clip does not include the detent 157. In this manner, the proximal locking mechanism of the clip 100 is more stable in lateral directions, which is also useful for keeping all parts of the clip together in the event the living hinge 160 may break.

Figure 5:
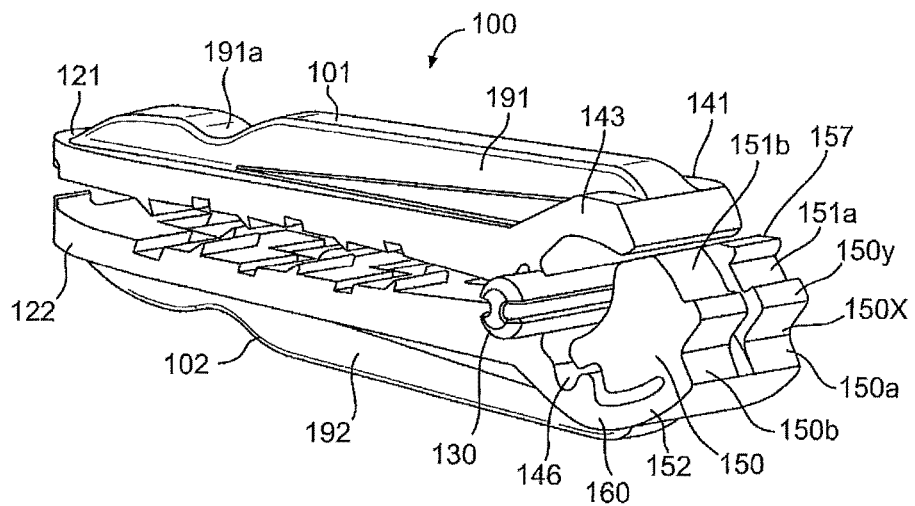
FIG. 5 shows a perspective view of the clip shown in FIG. 1 from the side opposite to that shown in FIGS. 3 and 4.

As best shown on FIG. 5, the outer surface 151 on proximal first end portion of buttress body 150 on a proximal end of the clip 100 defines one or more surfaces which form a curved planar segment abutment portion, which in the embodiment as shown includes curved planar segment abutment portions 151a and 151b. As used herein, the "curved planar segment abutment portion" formed by a surface may include a single curved surface segment or a series of curved or straight planar surface segments connected to one another which form an overall generally curved surface, each of the surface segments extending as a surface at least laterally. In the embodiment shown in FIG. 5, curved planar segment abutment portion 151a included planar and curved surface segments formed by the notch 157 and extends laterally for about one-half of the lateral width of clip 100, curved planar segment abutment portion 151b includes planar and curved surface segments which also extend laterally for about one-half of the lateral width of clip 100. Each of the curved planar segment abutment portions 151a and 151b on outer surface 151 forms a substantial abutment surface that pushes against complementary curved inner surfaces of jaw 141 to provide a stronger and more stable locking mechanism for clip 100. This is provided, at least in part, by the relatively larger and wider surface areas, lateral spans, and segmented surfaces with interlock and abut against each other to provide enhanced holding strength and stability, beyond what has been previously known or practiced in the field of surgical ligation clips.

Figure 6A:
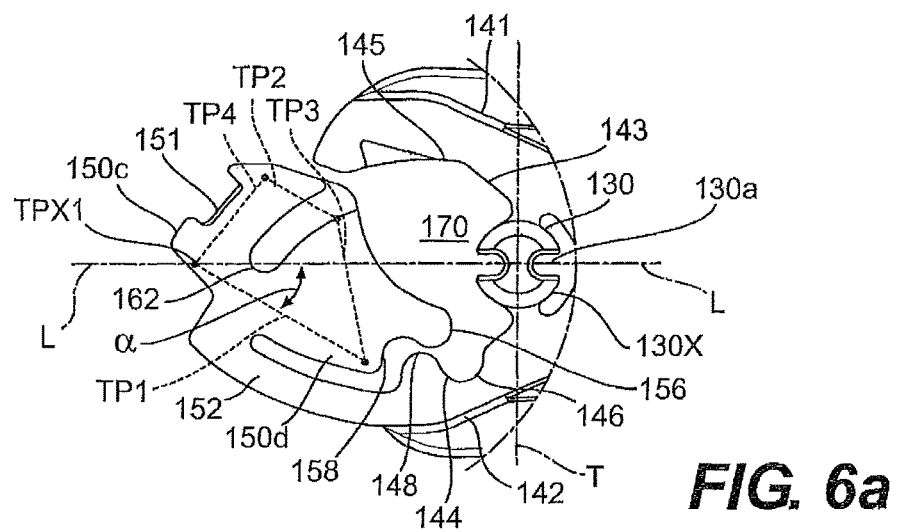
FIG. 6a is a close-up detail view of the portion of the clip shown in FIG. 6 in region "6a" therein.
Figure 6:
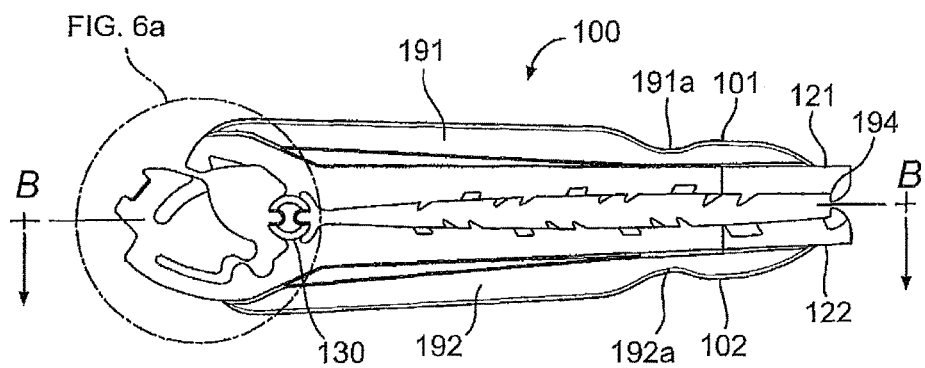
FIG. 6 is another side view of the clip shown in FIG. 1.
Figure 6B:
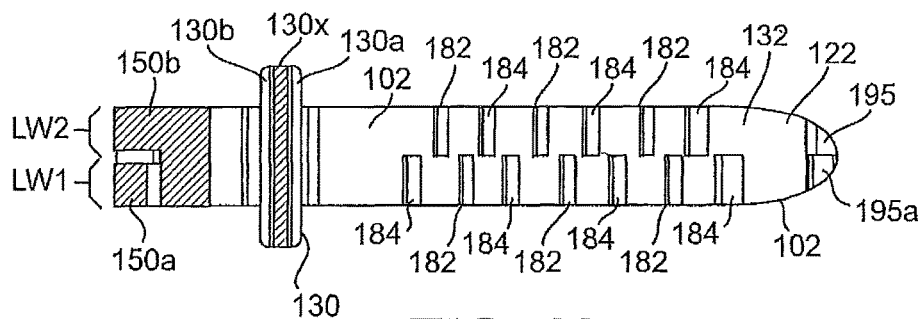
FIG. 6b is a sectional view of the clip shown in FIG. 6 taken along section B-B in the direction shown in FIG. 6.

As best shown in FIG. 6a, the second curved inner surface 144 on the second jaw structure 142 forms a first laterally spanning recessed groove 146 separated from the clip hinge 130 and a first laterally spanning ball-shaped or rounded protruding surface 148 proximal to said recessed groove 146, and a distal second end portion of the buttress body 150 forms a second laterally spanning recessed groove 158 and a second laterally spanning ball-shaped or rounded protruding surface 156 distal to said second recessed groove which are shaped complementary to the first rounded surface 148 and first recessed groove 146, respectively, so as to mate in abutment when the buttress body 150 is pivoted into the locking space 170 to further stabilize and bias the clip in a closed position. The first recessed groove 146, first rounded surface 148, second recessed groove 158, and second rounded surface 156 may extend laterally all the way across the lateral width of the buttress body 150, such that the first rounded surface 148 and second rounded surface 156 are not spherically shaped but rather form an extended, laterally-spanning, rounded, semi-cylindrical surface which can mate in corresponding semi-cylindrical shaped grooves formed by first recessed groove 146 and second recessed groove 158.

As shown in FIG. 6a, the buttress body 150 can further define a second living hinge 162 extending laterally between the proximal first end portion 150c of buttress body 150 and a distal second end portion 150d, wherein the proximal first end portion 150c including outer surface 151 further pivots about said second living hinge 162 when the buttress body 150 moves into the locking space 170, allowing the outer surface 151 of the proximal first end portion 150c of the buttress body to flex towards the longitudinal axis L prior to abutment against the curved inner surface 143 of the first jaw structure 141.

As best shown in FIGS. 5 and 12, the outer surface of the proximal end of the buttress body 150, or clip 100 itself, defines a V- or L-shaped laterally spanning notch 150x on the proximal end of the clip 100 and further defines a laterally spanning flange 150y extending from said notch 150x adjacent to the curved planar segment abutment portions 151a and 151b. Each of notch 150x and flange 150y may be divided into two lateral sections or components divided by a small space or channel there between as they are disposed on the lateral sectional halves 150a and 150b of the buttress body 150. The notch 150x provides a receiving space for the tip of an instrument, pushing or actuating rod, or another clip, so as to enable a more stable actuation of the buttress body 150 into locking space 170 to lock the clip 100. The flange 150y may act to limit the movement of buttress body 150 once fully inserted into locked position inside space 170, and also further stabilizes the locking mechanism for the clip 100.

Figure 13:
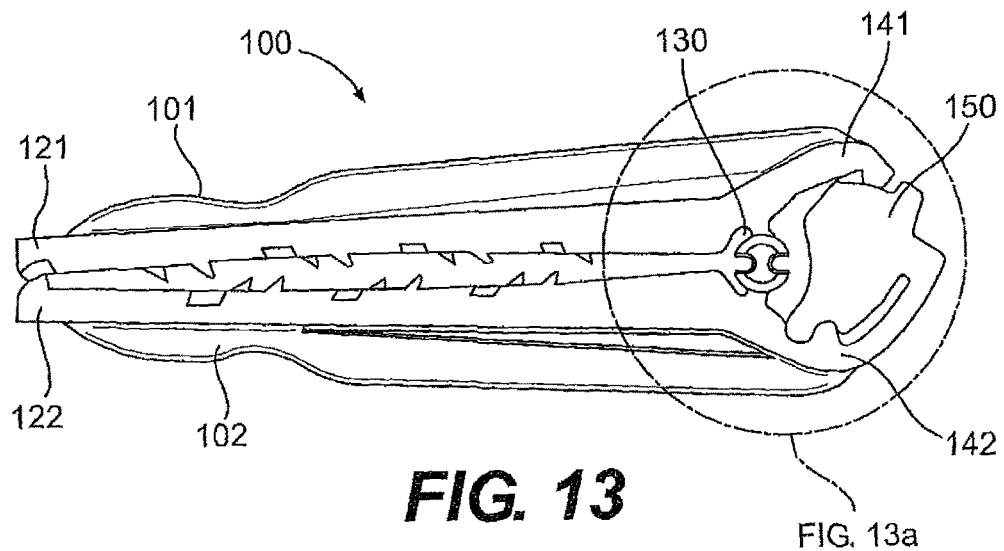
Figure 13A:
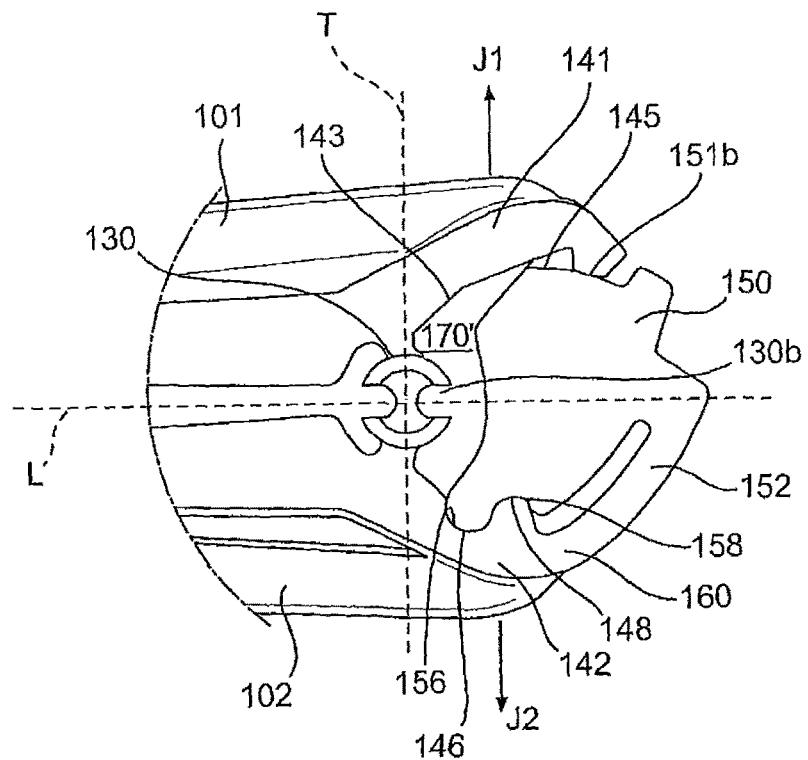
FIG. 13a is a close-up detail view of the portion of the clip shown in FIG. 13 in region "13a" therein.

In the embodiment shown in FIGS. 1-15, the buttress body may occupy a majority of a volume defined by locking space 170 when it is moved into clip locked position so as to bias the legs 101, 102 in a closed position. The volume defined by the locking space is limited by the lateral width of the clip legs 101, 102 near the hinge 130 and the jaws 141 and 142. As shown in FIG. 13a, the remaining locking space 170' between jaws 141 and 142, once the clip is locked by movement of the buttress body 150 into space 170, is less than half the volume of the locking space 170 as shown in FIG. 6a. The presence of a bulky body like buttress body 150 which occupies the majority of the volume or space between proximal extending jaws 141 and 142 when the clip 100 is in the locked position further provides a greater strength and stability to the locking of said clip.

In the embodiment shown in FIGS. 1-15, and as shown in FIG. 6a, the buttress body 150 can be characterized in one way as having a core mass which has, in a transverse plane spanning the longitudinal and transverse axes, a cross-section which approximately spans a trapezoidal shape, having rounded curved sides extending from the sides TP1, TP2, TP3, TP4 of the trapezoid. Side TP1 defines the longest side and one of the parallel sides of the trapezoid, while side TP2 defines the shorter parallel side. Side TP3 defines the longer and more distal of the non-parallel sides, while side TP4 defines the shorter and more proximal non-parallel side. Side TP1 is therefore connected to sides TP3 and TP4. When the clip is in the unlocked position as shown in FIG. 6a, and the buttress body 150 is fully extended away from the clip hinge 130 out in the most proximal position, the vertex TPX1 of sides TP1 and TP4 lies approximately on or near the longitudinal axis L, and side TP1 makes an angle α below the longitudinal axis, towards proximal jaw 142, such angle α being, in one embodiment, approximately 30 degrees. As shown in FIG. 6a, the rounded laterally-spanning protuberance 156 extends substantially from side TP3.

The clip hinge 130 can also be a resilient hinge providing additional biasing force to maintain the inner clamping surfaces 131, 132 of the legs towards a closed position. A span of each leg extending from the clip hinge 130 to its respective distal tip 123, 124, can be, in one embodiment of the present invention, at least 75% to 80% of an overall length of the clip. As shown in FIGS. 2b and 2c, the clip hinge 130 can define lateral bosses which extend laterally from the side surfaces of the clip legs, defining a bossed width or span which is greater than the clip width.

In the embodiment shown in FIGS. 1-15, the clip hinge 130 is formed as a laterally extending bar 130x integrally formed with the first and second legs 101, 102, each leg being resiliently coupled to first and second transverse sides of said bar, the bar 130x further defining laterally spanning grooves 130a and 130b on longitudinally distal and proximal sides of the bar, respectively. These grooves 130a and 130b further enable the clip 100 to flex as pivoting about the lateral axis of hinge 130, and further provide a resilient pivoting moment or force about said hinge.

Furthermore, in the embodiment shown in FIGS. 1-15, flanges 191 and 192 extend longitudinally across respective outer surfaces of each of the first and second legs 101, 102 which are on opposite sides to the inner clamping surfaces 131, 132 of each respective leg, the flange 191 of the first leg 101 extending from the first jaw structure 141 to the distal end portion 121 of the first leg 101, the flange 192 of the second leg 102 extending from the second jaw structure 142 to the distal end portion 122 of the second leg 102. Each of the flanges 191, 192 defines a transverse indentation 191a, 192a proximate the distal end portions 121, 122 of the legs 101, 102. The flanges 191 and 192 provide a rigidity to legs 101 and 102, respectively, such that said legs do not easily bend. Transverse indentations 191a and 192a provide a means for a clip applier to better actuate or grip the legs 101, 102.

Figure 19:
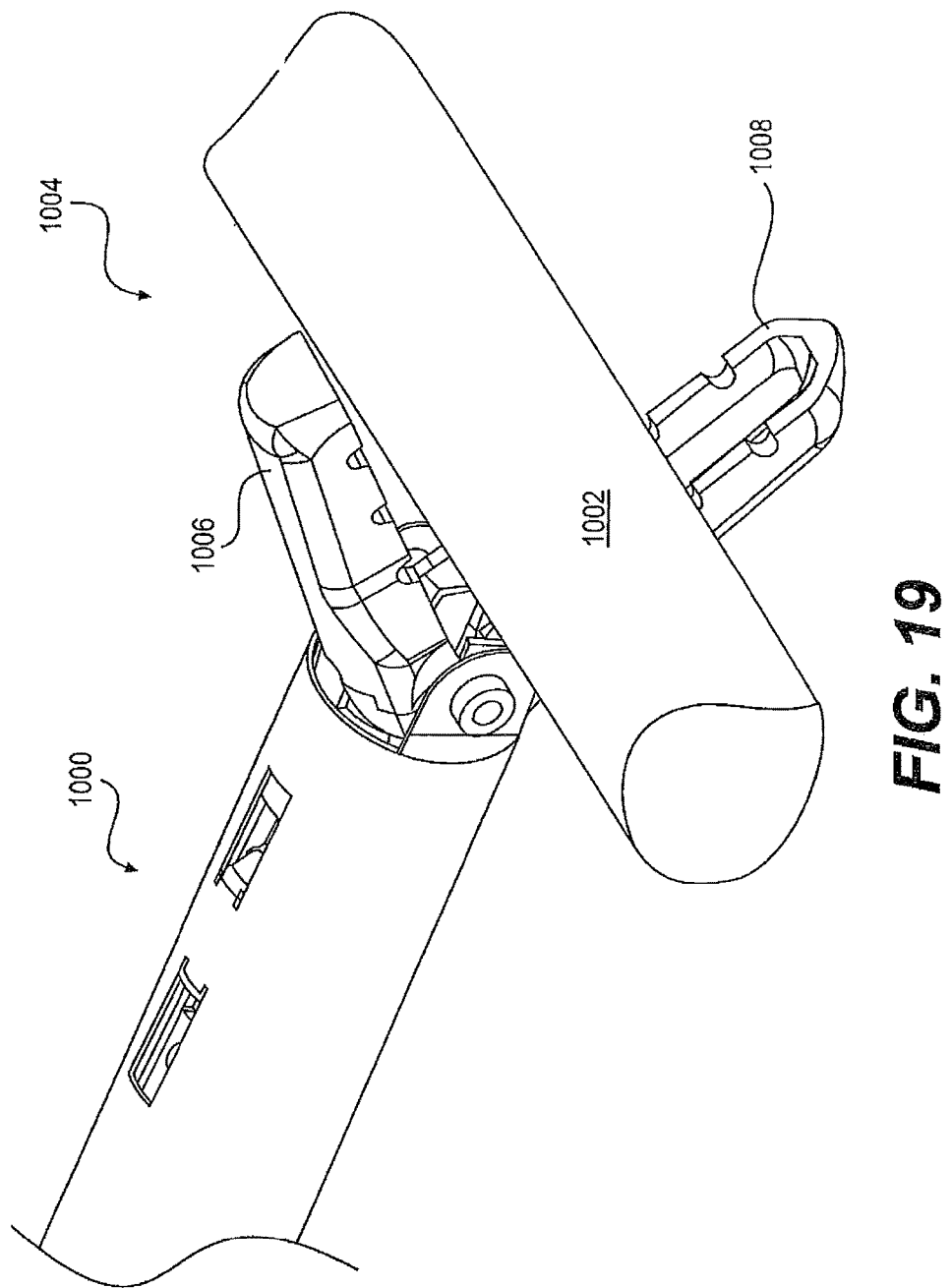
FIG. 19 shows an applier approach to vessel.
Figure 20:
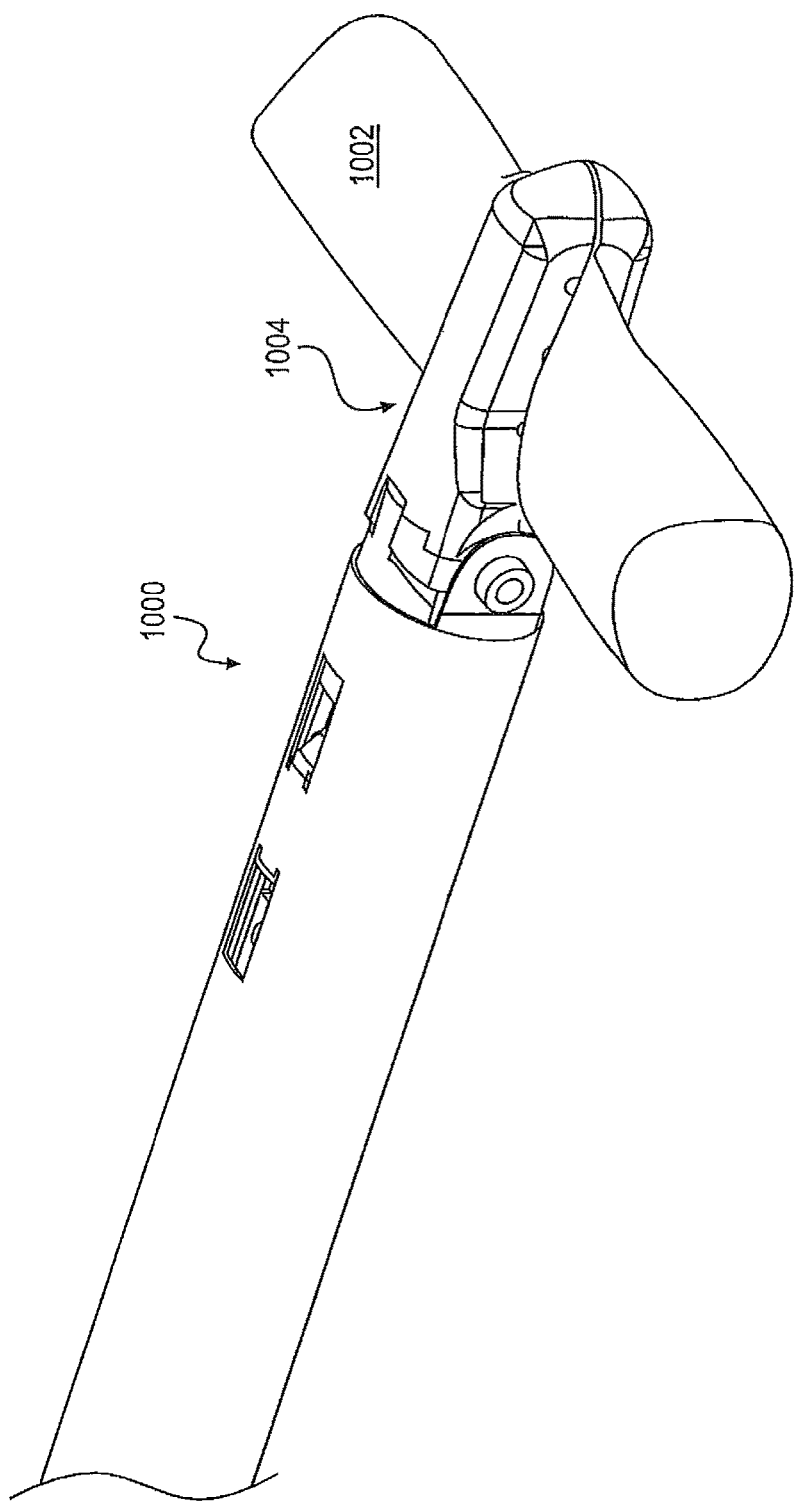
FIG. 20 shows an applier clamped on vessel.

The clip 100 further includes serrations, ridges, or teeth 181, 182 on the inner clamping surfaces 131 and 132, respectively, as shown in FIGS. 6b and 7b, and 9, 10, and 15a. The teeth or ridges 181, 182 provide additional grasping means to better attach and clamp the clip 100 onto a vessel when closed. The teeth or ridges 181, 182 are disposed to fit into complementarily arranged grooves 183 and 184 on the clamping surfaces 131 and 132, respectively. The teeth 181, 182 may have a slanted orientation, extending proximally, so as to better grip tissue. As best shown in FIGS. 6-6a and 7-7a, a pair of distal hook elements 194 and 195 may be disposed on the absolute distal tips of legs 101 and 102, respectively, each hook 194 and 195 offset laterally with respect to each other to form a scissor-like configuration, such that each hook 194 and 195 fit into corresponding recesses 195a and 194a, respectively, on the distal tips of legs 102 and 101, respectively. This mechanism provides means to further grip and contain tissue with the space between the clamping surfaces 131, 132 when the clip 100 is applied to body vessel, as illustrated in FIGS. 19 and 20.

Figure 15:
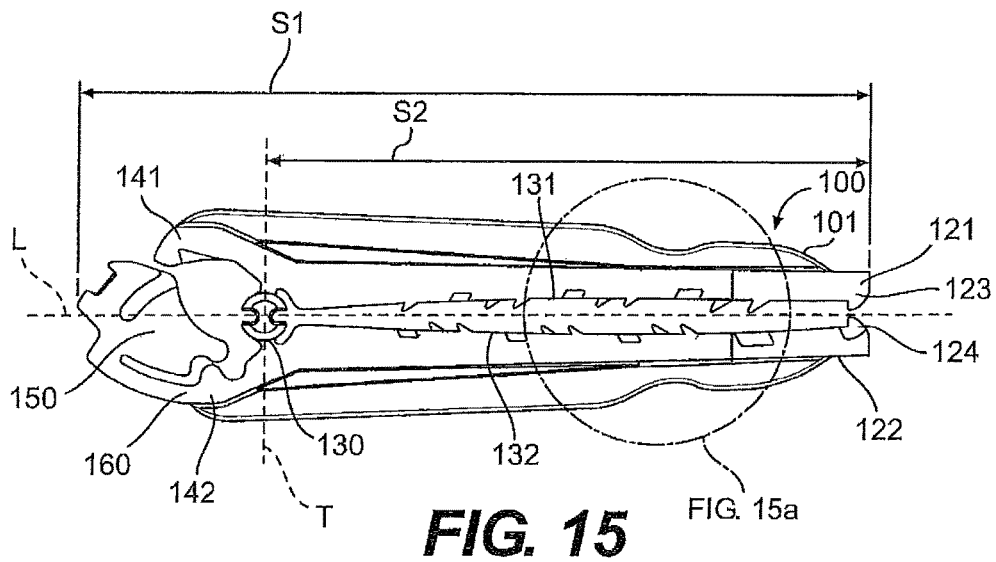
FIG. 15 is a view of the clip shown in FIG. 1.
Figure 15A:
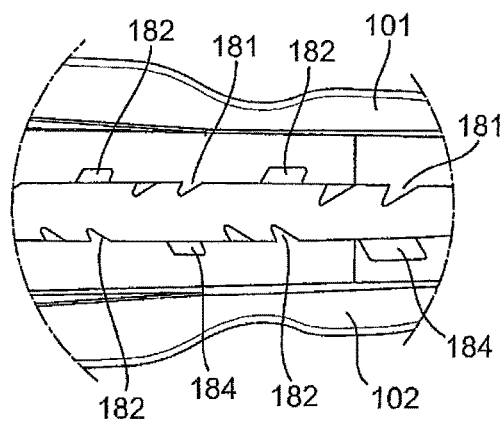
FIG. 15a is a close-up detail view of the portion of the clip shown in FIG. 15 in region "15a" therein.

The clip 100 may be in a range of sizes. As shown in FIG. 15, an overall length "S1" of the clip 100 may be approximately 0.50 inches; the length "S2", between the intersection of transverse axis T and longitudinal axis L centered at clip hinge 130 and the distal tip of the clip, may be approximately 0.40 inches, and the radius of curvature of the inner mating or clamping surfaces 131, 132 of the legs 101, 102 may be approximately 3.0 inches. Such sizes and dimensions are given as an example, and it is understood that the clip may, in one or more embodiments of the invention, vary in size ranging from approximately 0.15 to 0.80 inches in overall longitudinal length, and from approximately 0.03 to 0.15 inches in lateral width. As one embodiment of the invention, the illustration of clip 100 in FIG. 15 is shown as a scaled magnification of actual size, and shows all the parts of the clip 100 in actual proportion to each other.

The instrumentation used to deploy the clips discussed herein may include a manually loaded device that can apply a single clip at a time, or an automatically fed, multi-clip applier. Both appliers can be endoscopic instruments suitable for use in laparoscopic surgery applications. In both cases the applier will clamp over the vessel to flatten the section to be ligated. The clip will then be opened, positioned over the vessel and closed. Once closed, a mechanism will engage the locking feature on the proximal end of the clips disclosed herein, to the to maintain the clamping pressure of the clip. A manual applier will load/apply a single clip at a time. An automatic applier will be able to load/apply multiple clips before the instrument has to be removed from the surgical site. The sequence of clip application is as follows:

1. The clip is presented in the partially closed condition.
2. A device, such as a set of applier jaws clamps down on the vessel or tissue to be ligated or clamped. The applier jaws have a channel down the center that is just large enough to allow the clip to fit in the channel.
3. The clip is opened by pressing the proximal legs together lightly.

4. The clip is advanced over the vessel or tissue that is clamped within the jaws of the applier (the clip traveling in the channel area of the applier jaws).
5. Once fully advanced, the proximal legs are released and the clip springs back to the partially closed condition.
6. The proximal locking mechanisms discussed for the clip embodiments disclosed herein are actuated or pressed, causing the legs or 'clamping section' of the clips to close tightly on the vessel or tissue.

The various embodiments of the clips disclosed herein therefore can start in an as-molded state; can be opened further to better encapsulate the vessel; and can then be closed further (into a 3rd state). This process of opening and closing the clip can be repeated as needed, prior to locking. When closed and locked, the clip provides an active clamping force which can also squeeze the vessel, which is beneficial if the vessel necroses and/or shrinks over time.

The various embodiments of the surgical clips of the present invention are preferably made of one or more polymer materials, such as, by example, acetyl homopolymer, but could also be made of a variety of other materials, including one or more metals, or a combination of metal and polymer or plastic. In selecting the material(s) used, the radiopacity of the clip can be "tuned" to a desirable level, or can be tuned to be radiopaque.

The various embodiments of surgical clips of the present invention are an improvement over the known polymeric surgical ligation clips, as well as standard metal clips. Among the resulting advantages of the surgical clip of the invention as disclosed herein are: the ability to deliver a larger clip through a smaller endoscopic instrument; the ability to place a clip on a vessel just like a prior art malleable and deformable metal clip, with no need for added dissection or cleaning around the vessel, but with greater retention force than metal clips, which results in a reduced risk of clips slipping off the vessels. The greater clip locking stability and clip retention force is accomplished by the locking feature applying an active biasing or clamping force as discussed above, versus the passive clamping action created by plastic deformation of malleable metal clips.

The following several paragraphs provide a brief description of several embodiments and refer to the FIGS. Later below a more in-depth description is provided and refers to not only the FIGS. but also specific reference characters.

The litigation clip applier can be split into three main sections for discussion. They are the distal end or shaft, the multistage transmission, and the handle.

One embodiment of the distal portion of the applier is made up of 12 parts. Two feeder rails, see FIG. 21, two wedges, see FIG. 22, two primary pushers see FIG. 23, two final pushers, see FIG. 24, inner and outer tubes, see FIGS. 25 and 26, and two jaws, see FIG. 31. When assembled the inner and outer tubes are concentric and both attach to the jaws. The outer tube has tabs with holes that the jaws fit into and rotate about. The inner tube connects to the jaws in a pocket that provides the cam surface to open and close the jaws, see FIGS. 27 and 28. The inner tube acts as a push pull link to actuate the jaws, see FIGS. 19 and 20 for jaw actuation. The two feeder rails are assembled so that they make pockets to hold the clips, the number of clips to be held is determined by the ratio of the overall length of the applier and the size of the clip. The rails are spring loaded together and spread apart when the bosses on the clips pass through to the next pocket. The primary pushers ride on the sides of the feeder rails, the primary pusher has spring fingers that are spaced equidistant to match the pockets in the feed rail. When advanced they push the entire stack of clips forward to the next pocket in the feed rails. They also provide the push that allows the second clip to lock the first clip. The final pushers ride outside of the primary pushers and are what advanced the first clip over a vessel in the jaws of the applier. The final pushers also hold the first clip in place while the wedges retract. The wedges are just inside the feeder rails and are spring loaded together at the ends to open the first clip as it is advanced forward. The wedges also move forward into the jaws to cam the legs of the clip closed after it has fully advanced. The spring load for the wedges is provided by spring tabs in the outer tube that push down on the wedges. There is also a false clip that has two purposes, the first is to lock the last clip and the second is to pull on the cable that triggers the low clip indicator and last clip lockout. The false clip is advanced down the distal portion of the applier the same way the stack of clips is advanced. For actuation of the parts and clip advance/lock, see FIGS. 32-44.

The proximal end of the applier, or applier handle, is made up of many parts that provide a user interface portion of the applier. Each of the distal end actuations are accomplished through the use of the proximal handle. The handle has a two piece outer shell which stages the internal actuating components and provides a bearing surface for a multi stage transmission to allow 360° continuous rotation of the distal end. There is a two piece rotation knob clamped onto the distal portion of the multi stage transmission which is shaped to facilitate the 360° continuous rotation of the distal end, see FIGS. 46-48.

Figure 50:
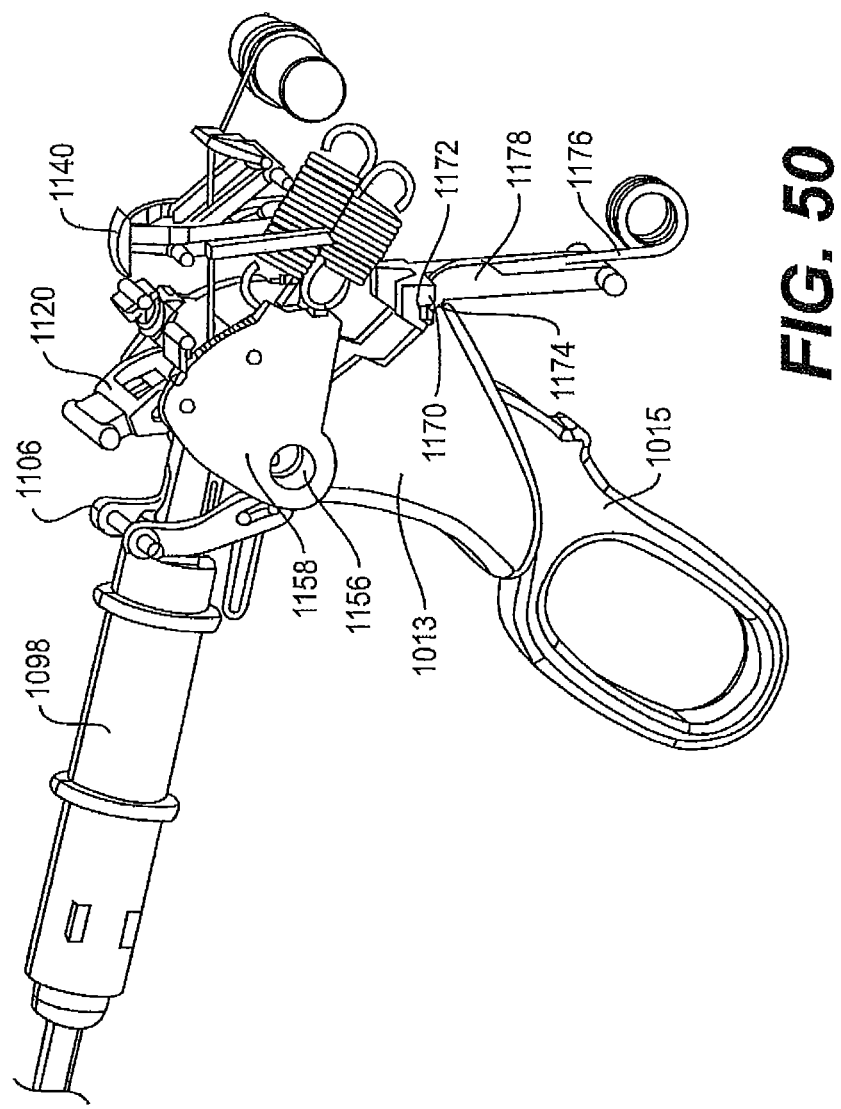
FIG. 50 shows triggers and mechanisms.

In one embodiment of the handle there are two triggers, both triggers rotate around the same center point, see FIG. 50. The lower trigger actuates the jaws and the upper trigger actuates the clip delivery sequence. The lower trigger is attached to the multistage transmission through two mirrored linkages which have features that allow the trigger to lock down when the jaws are closed. This feature is an over center cam. The linkages also have an inner profile which allows them to drive the section of the multistage transmission that actuates the jaws while allowing the 360° continuous rotation. The return stroke of the lower trigger is accomplished through a return spring attached to a cable that wraps around the front of the trigger and based on a pin at the proximal side of the handle. There is an interlock on the upper trigger that locks the upper trigger until the lower trigger is pulled and locked down to ensure a clip is not prematurely delivered. The upper trigger is attached to the multistage transmission through a linkage which has and inner profile that drives the section of the multistage transmission that actuates the clip delivery mechanisms and also allows the 360° continuous rotation. The return stoke of the upper trigger is accomplished through a return spring attached to the back side of the trigger and based on a pin at the proximal side of the handle. For both the actuation and return strokes there is a one way pawl that limits the direction of the upper trigger until a full stroke is completed. There is also a low clip indication/last clip lockout that is actuated when the false clip moves down shaft. As the clips get low the cable pulls off of the drum. At the end of the cable is a crimped on ball that starts to pull on the lockout latch which begins to move the lockout lever. The top of the lockout lever has an indicator that shows through a window in the handle outer shells indicating low clips in one color and then indicates no clips left in another. When there are no clips left the lockout lever engages the ligate trigger and locks the trigger in place. The jaw trigger still functions see FIG. 50 for triggers and actuating components.

In a second embodiment of the handle, the trigger functions are reversed so that the upper trigger actuates the jaws and the lower trigger actuates the clip delivery mechanisms.

Figure 49:
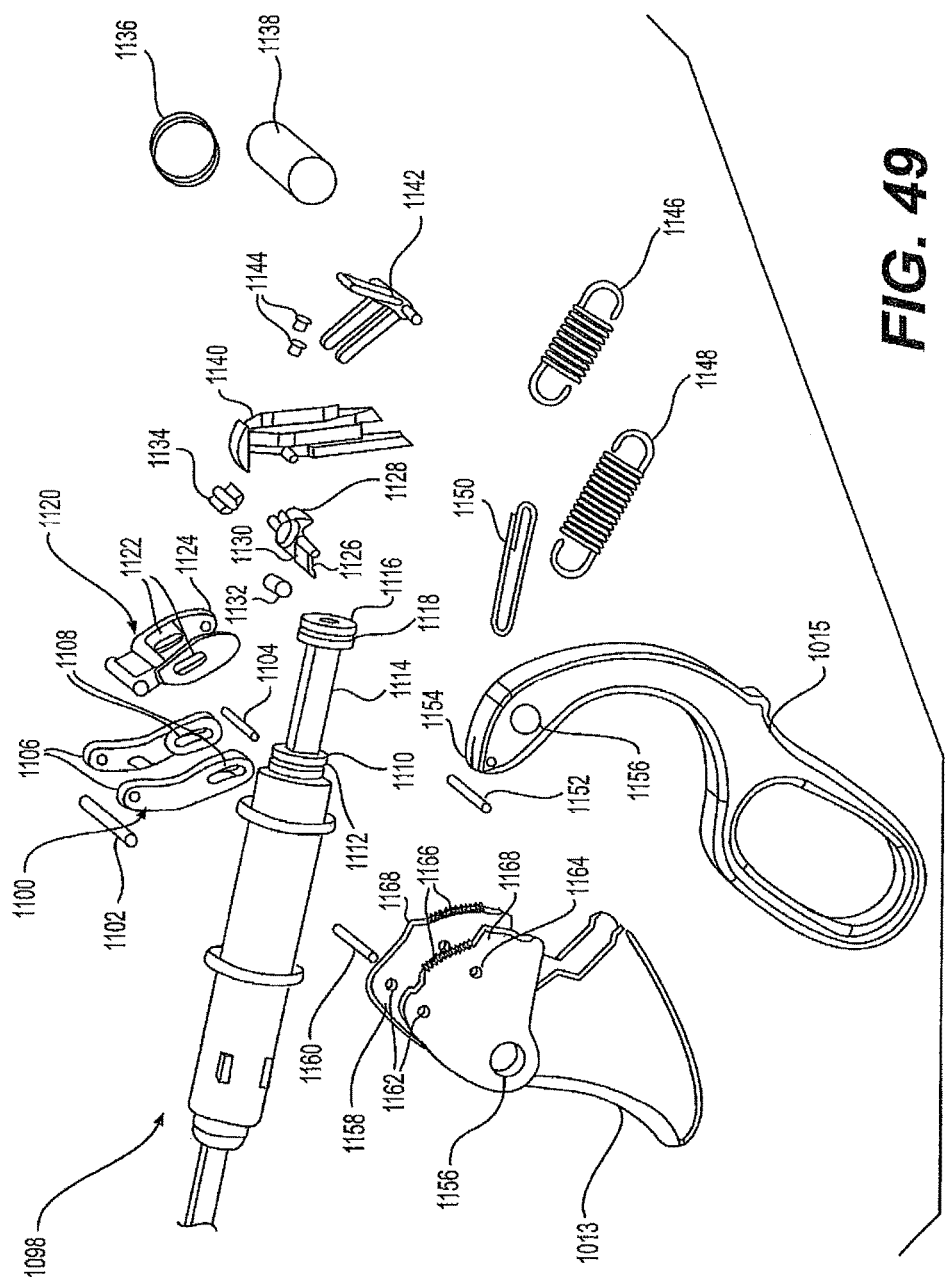
FIG. 49 shows internal handle components.

The distal portion of the applier is connected to the handle through the multi stage transmission, see FIGS. 49 and 50. One embodiment of the transmission is made up of a two piece outer shell which acts as the bearing to allow the rotation of the distal end. Internal to the shell are features that guide the internal components during the actuation sequences of the applier. There are two jaw links that connect to the inner tube of the distal end and provide the grove for the inner features of the lower trigger linkages. The jaw links snap together and ride on the internal surface of the transmission shell. The area between the jaw links is open to allow for additional transmission pails. There are two center spindles that snap together and attach to the wedges, the outer surfaces provide a guide for the final pusher latch and the primary pusher latch. The final pusher latch and the primary pusher latch move over the center spindles and are guided in slots on the outer shell of the transmission. Small pins move in and out of groves in the two pieces and the outer shell to achieve the appropriate timing for the clip delivery mechanisms in the shaft, see FIGS. 59-66 for the transmission assembly and FIGS. 67-76 for actuation sequence.

Figure 97:
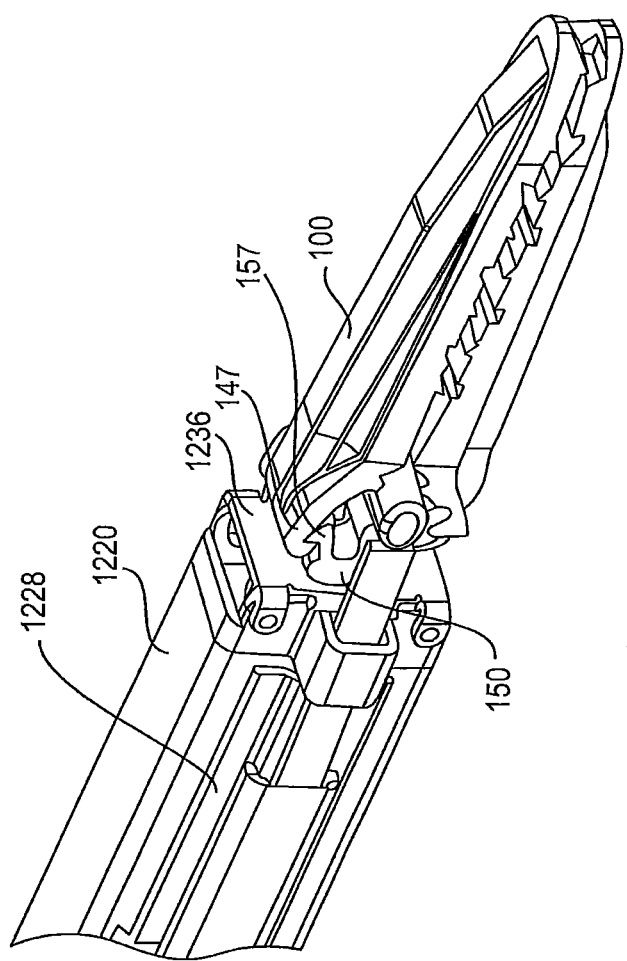
FIG. 97 shows a clip latched.
Figure 98:
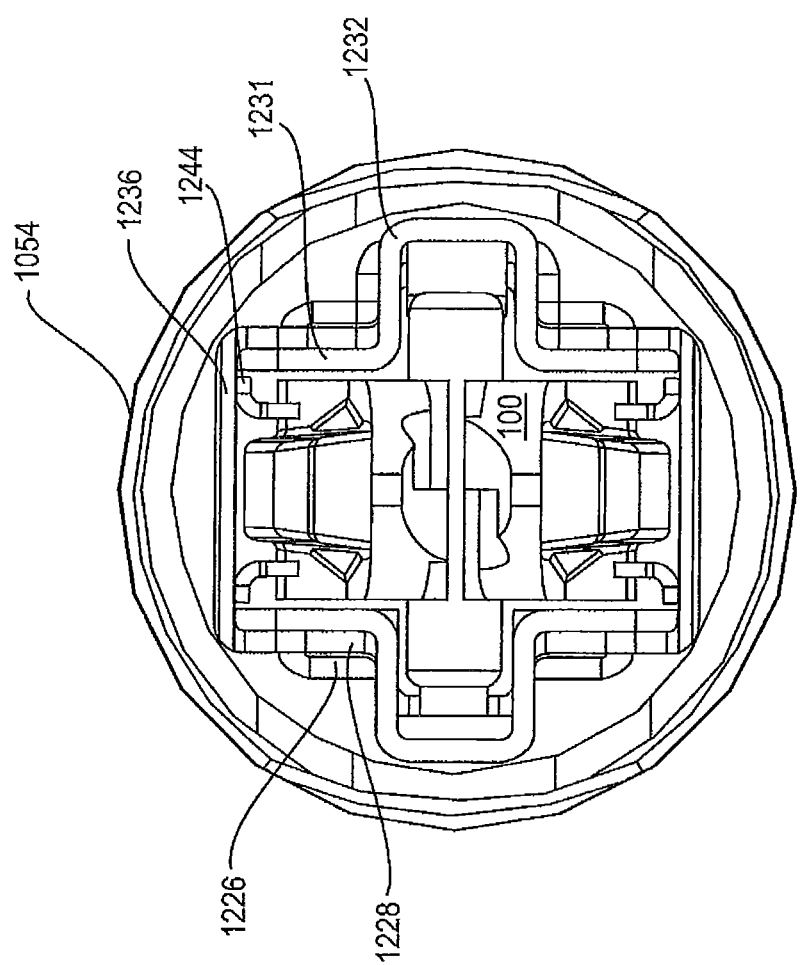
FIG. 98 shows a cross section end view with punch doors opened.
Figure 99:
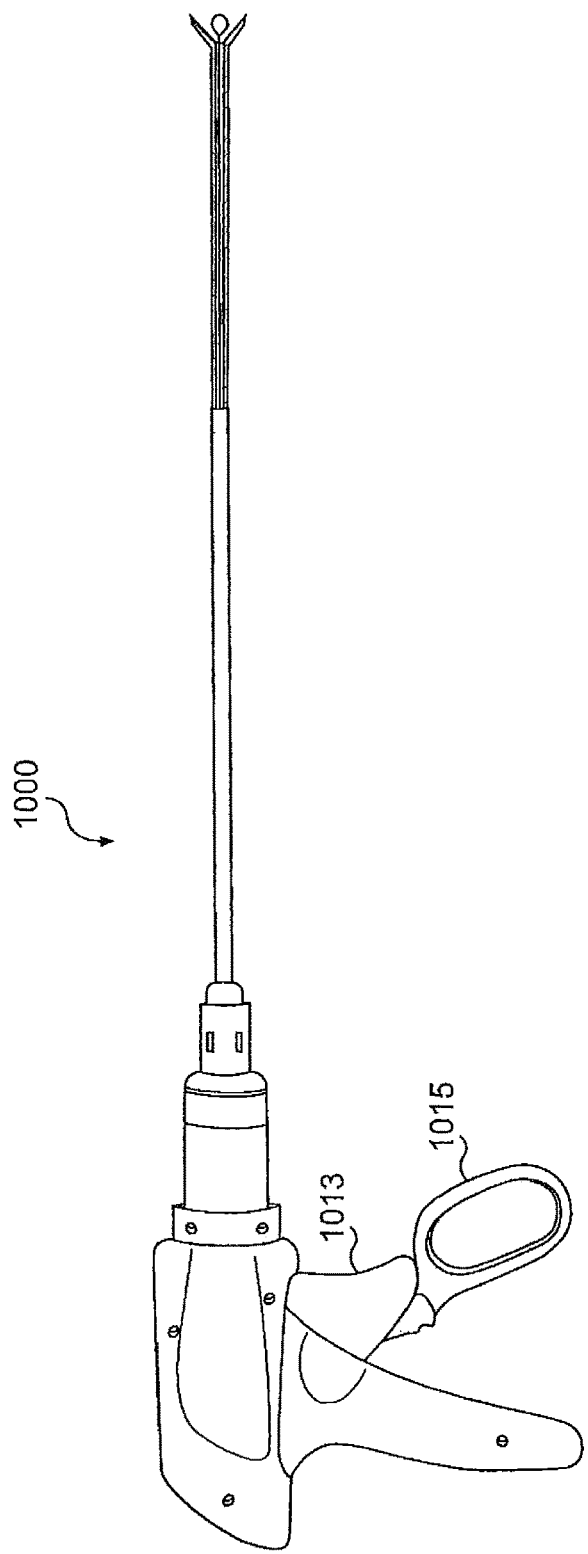
FIGS. 99-108 shows a side view of an applier.
Figure 100:
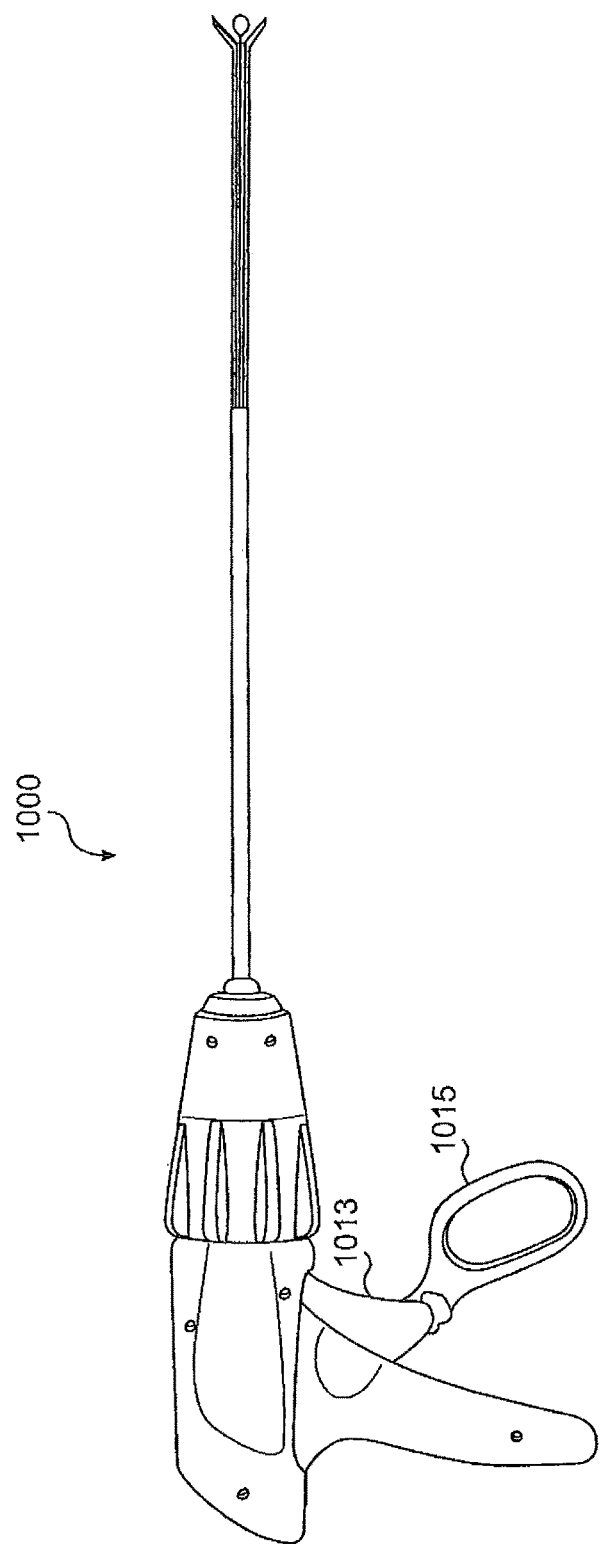
Figure 101:
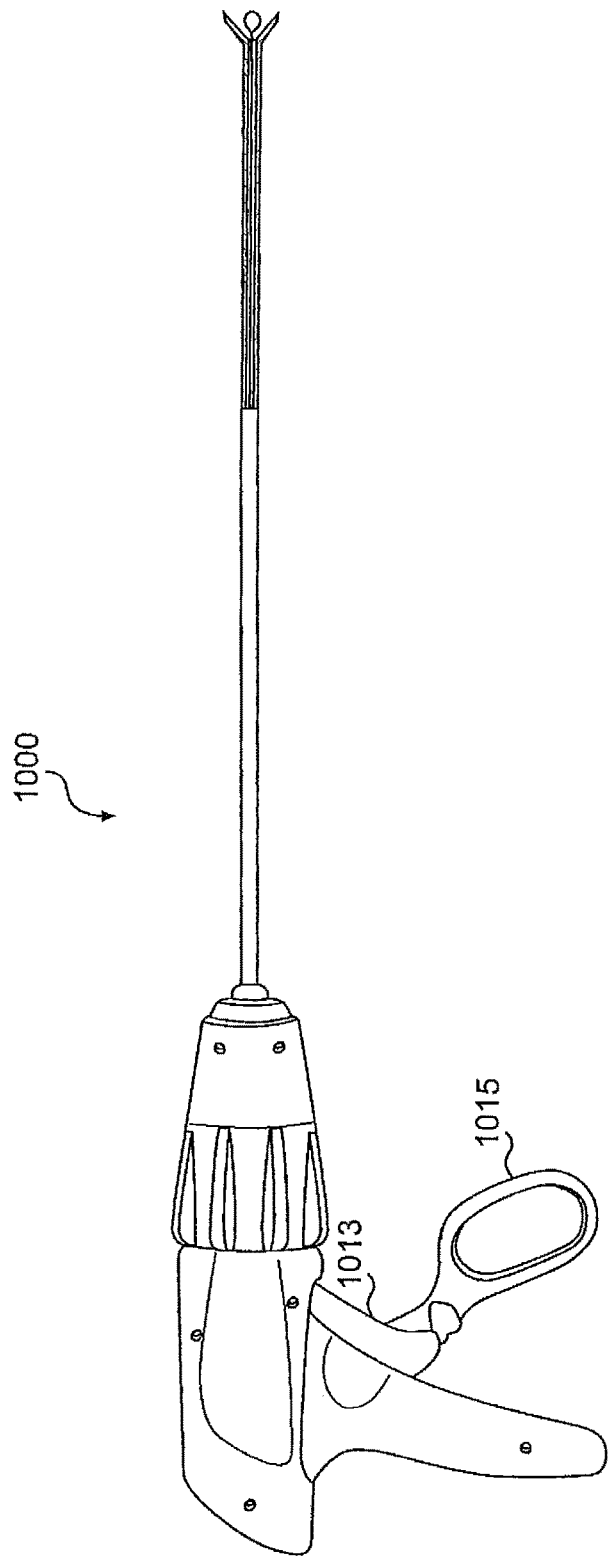
Figure 102:
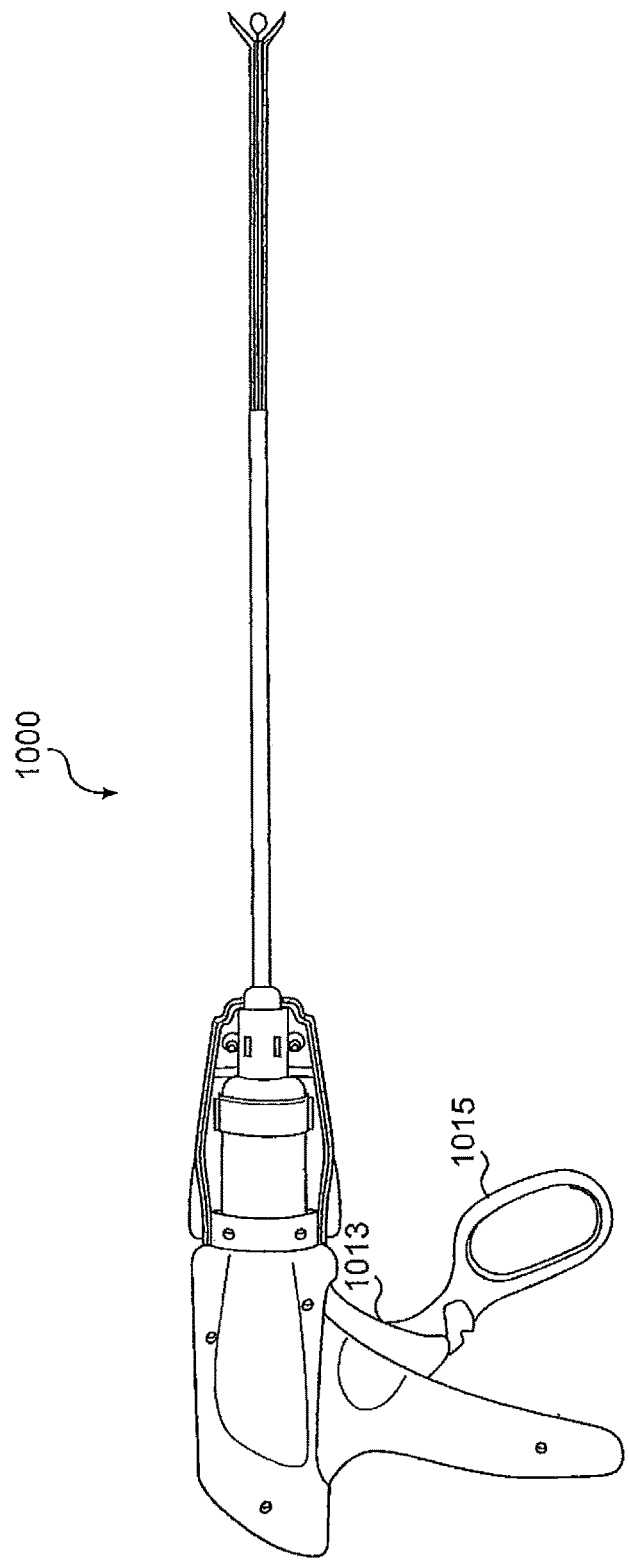
Figure 103:
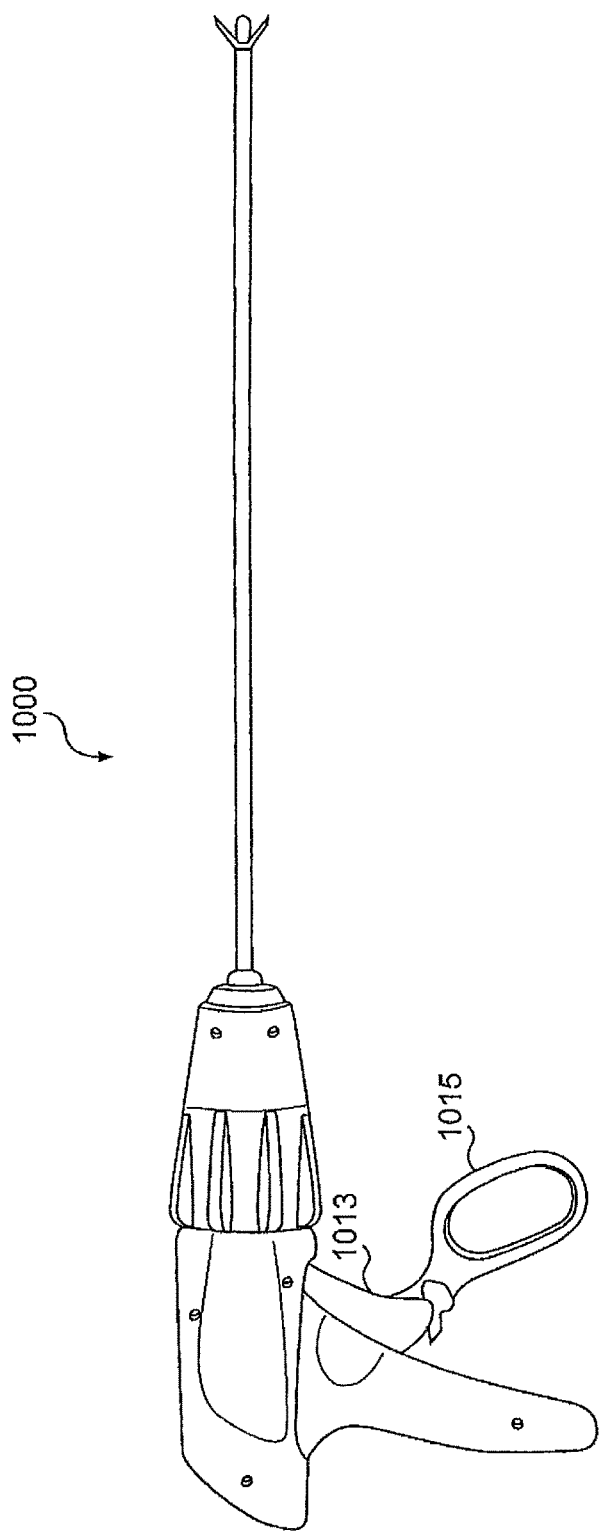
Figure 104:
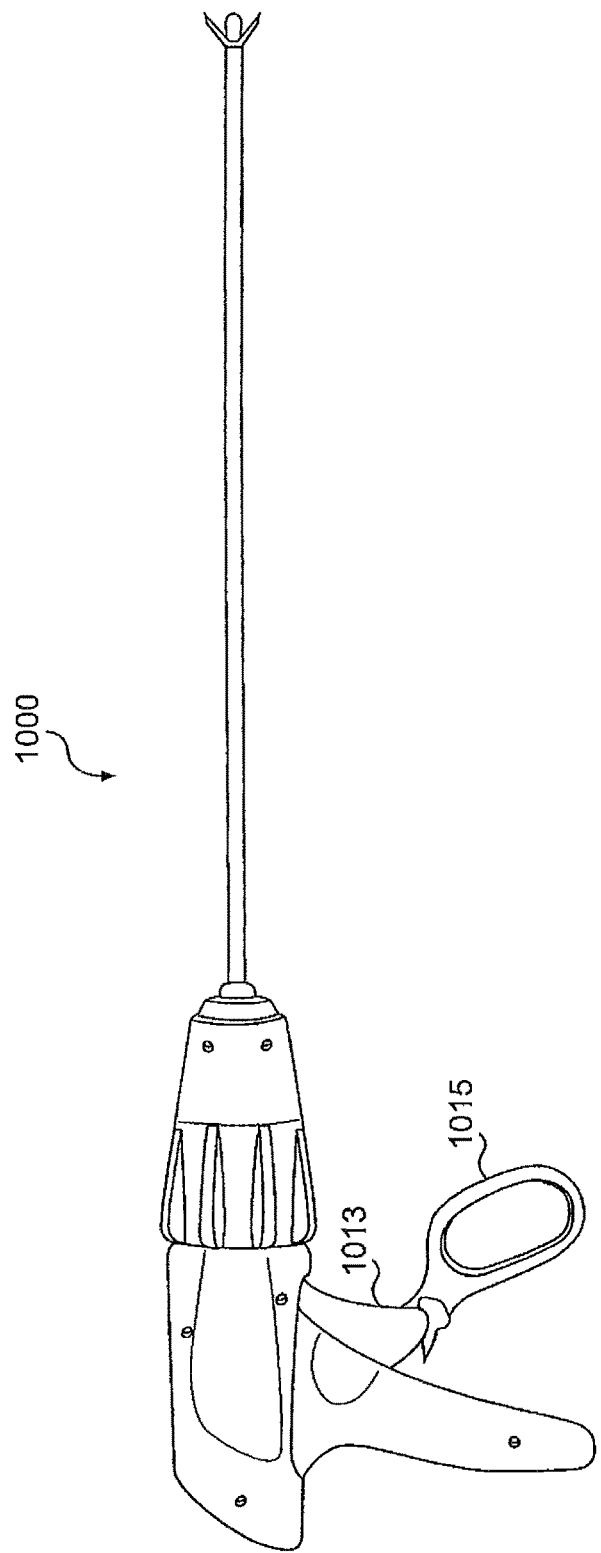
Figure 105:
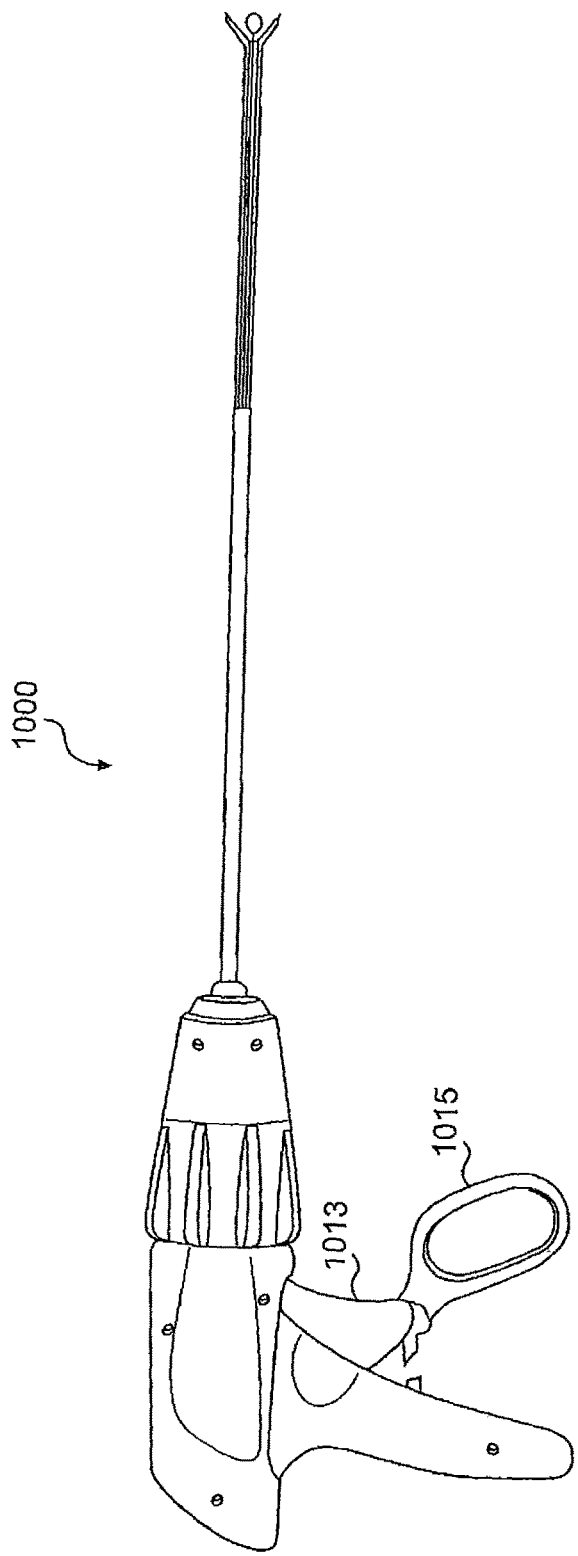
Figure 106:
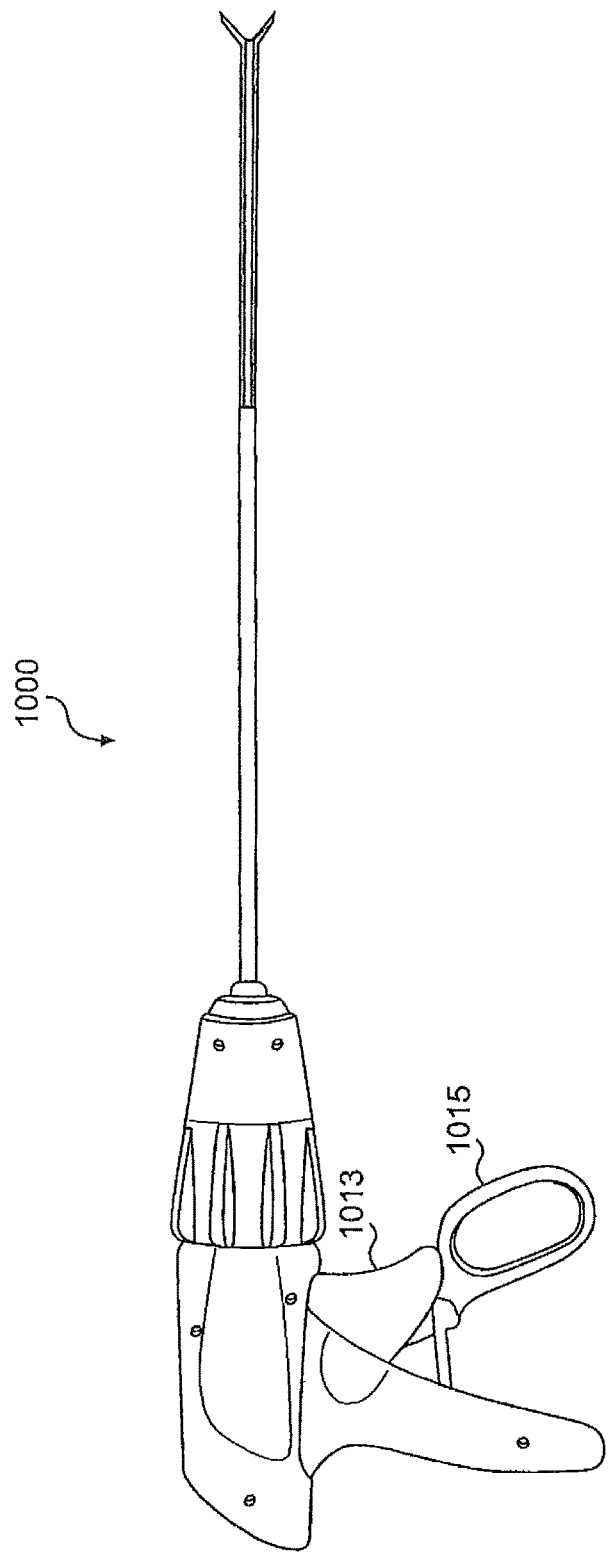
Figure 107:
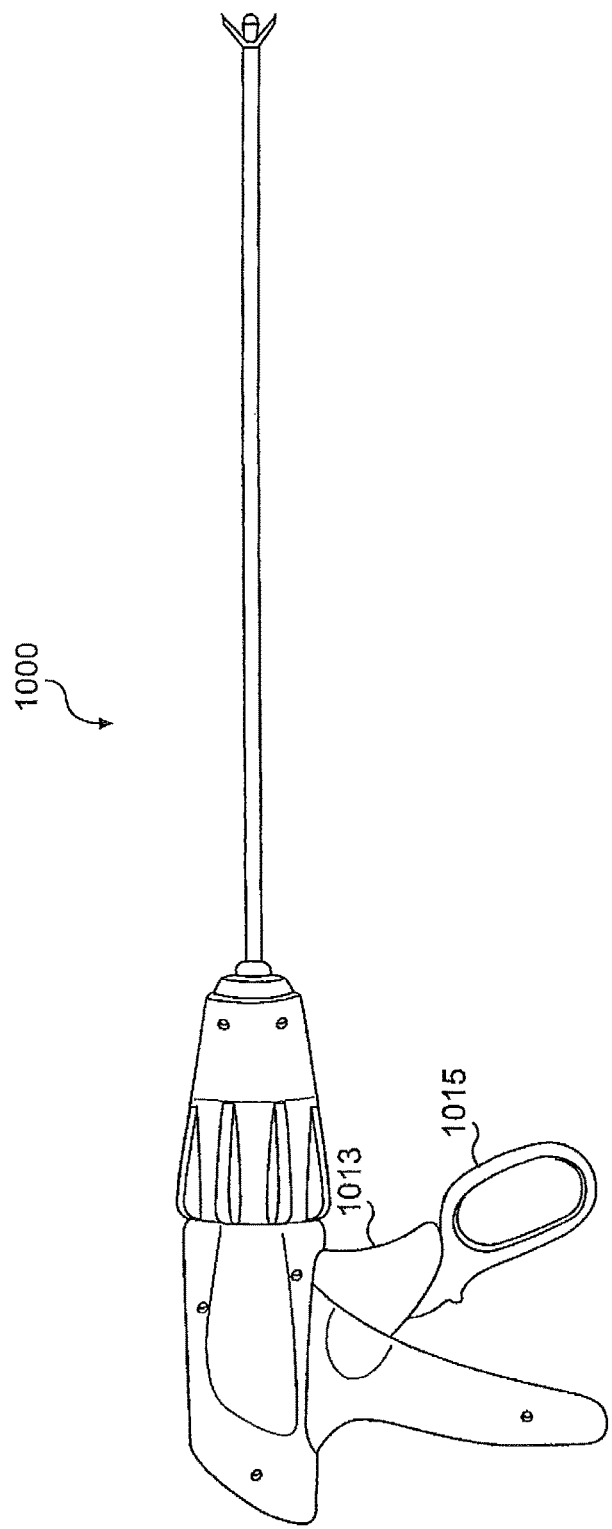
Figure 108:
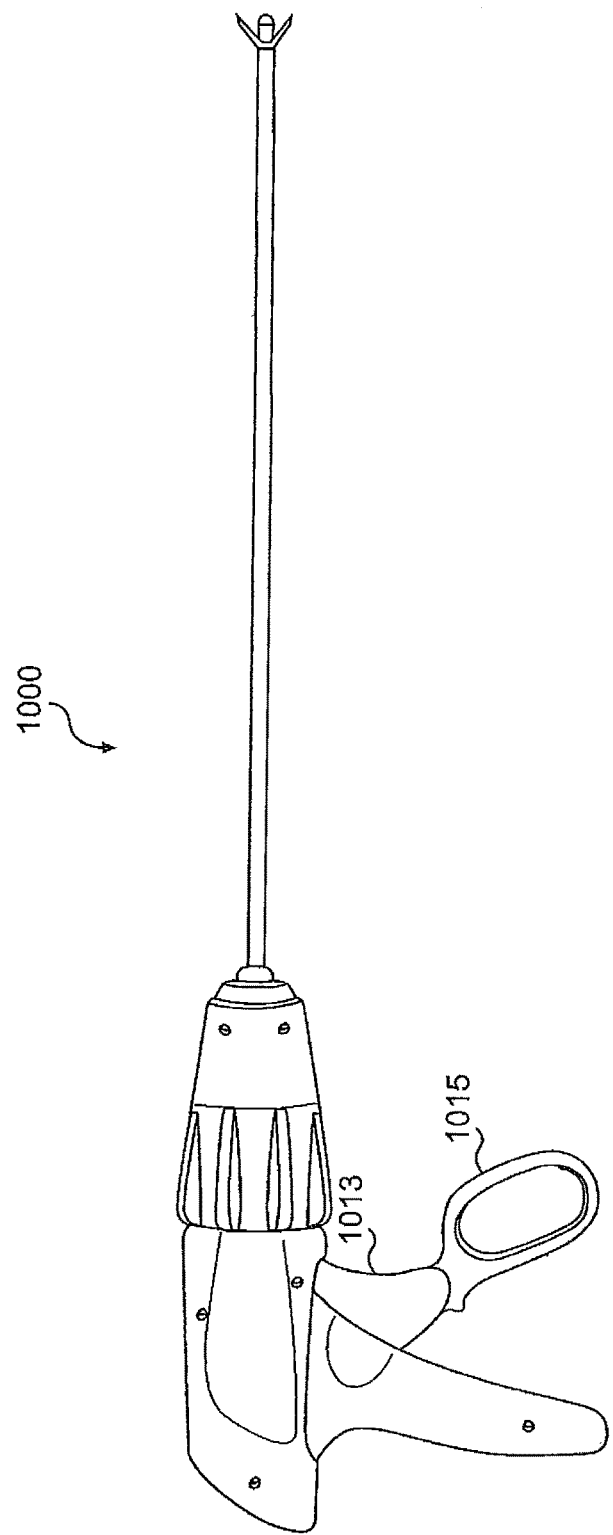

Another embodiment of the distal portion of the applier is made up of 10 parts. One outer tube, one inner tube, two jaws, one walking beam, see FIG. 77-79, one walking beam pusher, see FIGS. 80 and 81, one punch ring, see FIG. 82, two punch doors with door wedges, see FIGS. 83 & 84, and two clip advancers, see FIG. 85. When assembled the inner and outer tubes are concentric and both attach to the jaws. The outer tube has tabs with holes that the jaws fit into and rotate about. The inner tube connects to the jaws in a pocket that provides the cam surface to open and close the jaws. The inner tube acts as a push pull link to actuate the jaws. When assembled the walking beam pusher rides in grooves on the walking beam. The punch ring is permanently fixed to the distal end of the walking beam and provides the attachment point for the punch doors. The punch doors are attached to the punch ring via a rivet or tabs that allow the doors to rotate. The doors are forced closed by a torsion spring or may be a plastic part that has spring like characteristics that keep the doors closed. On the underside of the punch doors are wedges that force the clip to open when the clip is pushed through the doors. The clip is pushed forward by a pair of clip advancers that ride on the outside of the walking beam and walking beam pusher. For actuation of the parts and clip advance/lock, see FIG. 86-97. A cross-section of the distal end is shown in FIG. 98 for assembly reference.

The distal portion of the applier would be attached to a proximal handle with components that achieve the proper sequence to successfully apply a ligation clip. The following discussion refers to the FIGS. and specific reference characters.

Figure 16:
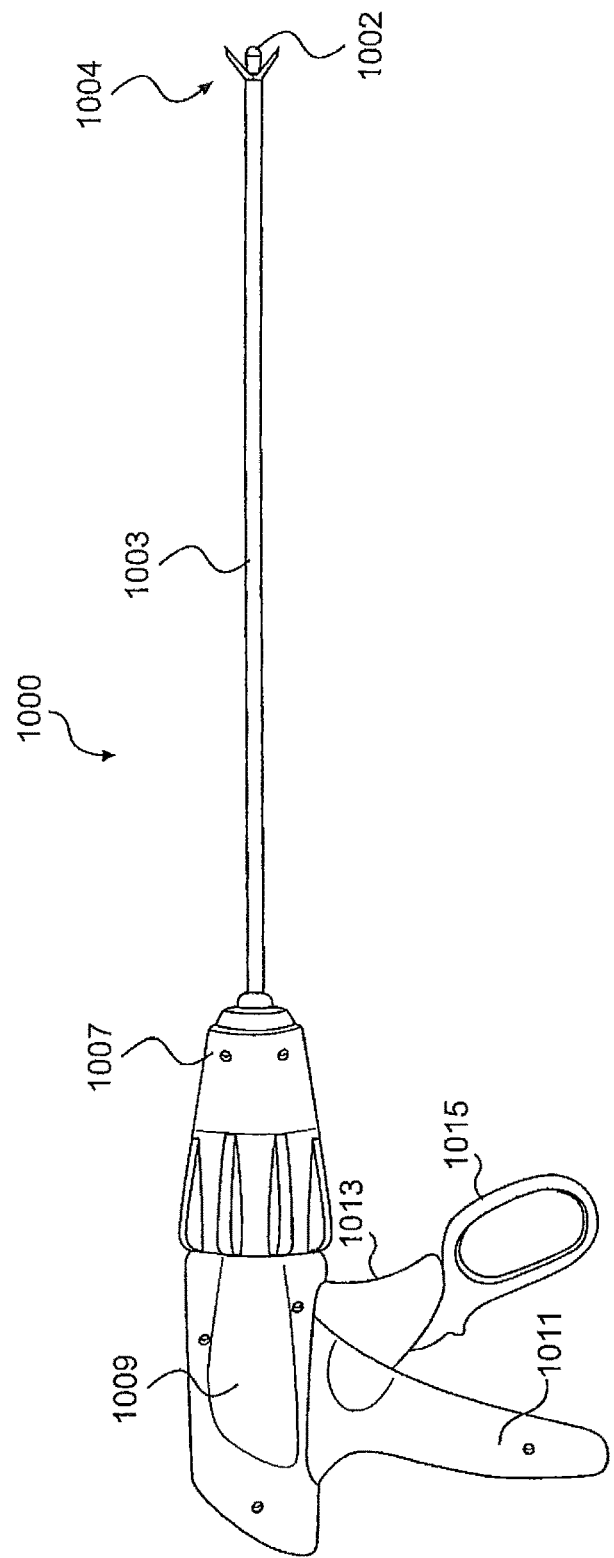
FIG. 16 shows a side view of an applier.

FIG. 16 shows an applier 1000 in accordance with an embodiment of the invention. The applier 1000 is shown about to clamp a blood vessel or tissue 1002. The applier 1000 includes jaws 1004, a shaft 1003, and a clamshell transmission housing 1007. The applier 1000 also includes a clamshell housing 1009, a handle 1011, a ligate trigger 1013, and a jaw actuating trigger 1015.

Figure 17:
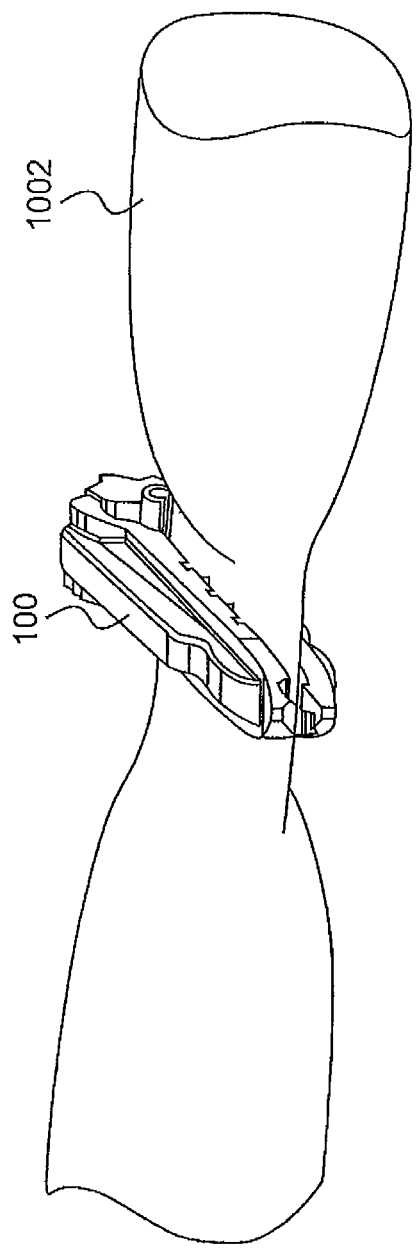
FIG. 17 shows a isometric view of clip latched on vessel.
Figure 18:
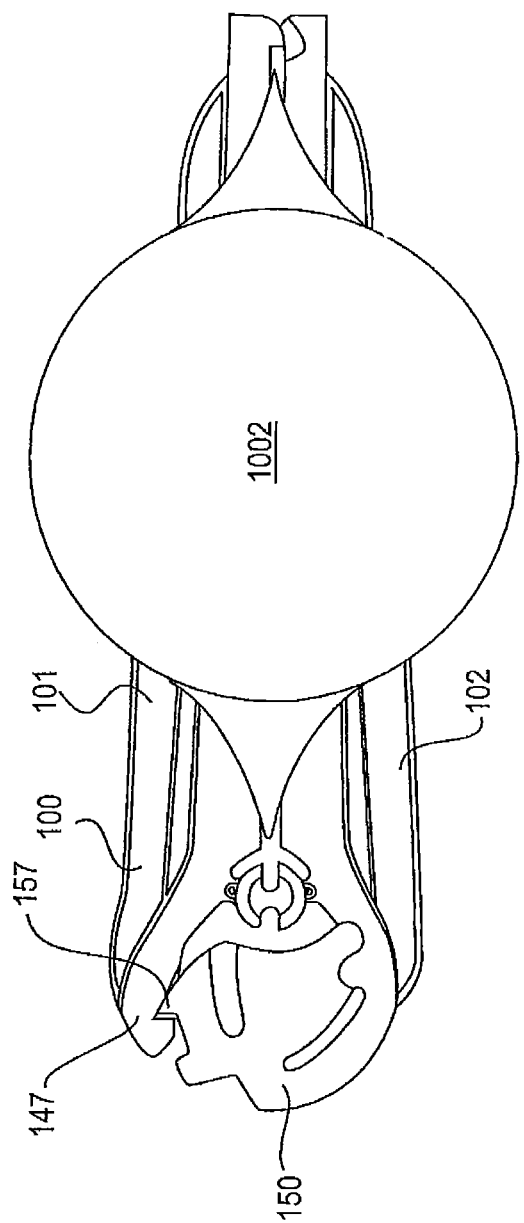
FIG. 18 shows a clip latched on vessel.

FIGS. 17 and 18 shows a clip 100 after it has clamped a vessel or tissue 1002 via the applier 1000. As shown in FIG. 18, the clip 100 has the first 101 and second legs 102 locked in a clamping position over the vessel or tissue 1002. The buttress body 150 on the clip 100 has moved forward and locked the legs 101 and 102 by interlocking the detent 157 into the notch 147.

FIG. 19 shows the applier 1000 about to clamp a vessel or tissue 1002. The upper jaw 1006 and the lower jaw 1008 are positioned to be above the vessel or tissue 1002. FIG. 20 shows the jaws 1004 of the applier 1000 shut and thereby clamping the vessel or tissue 1002 with the jaws 1004.

Figure 21:
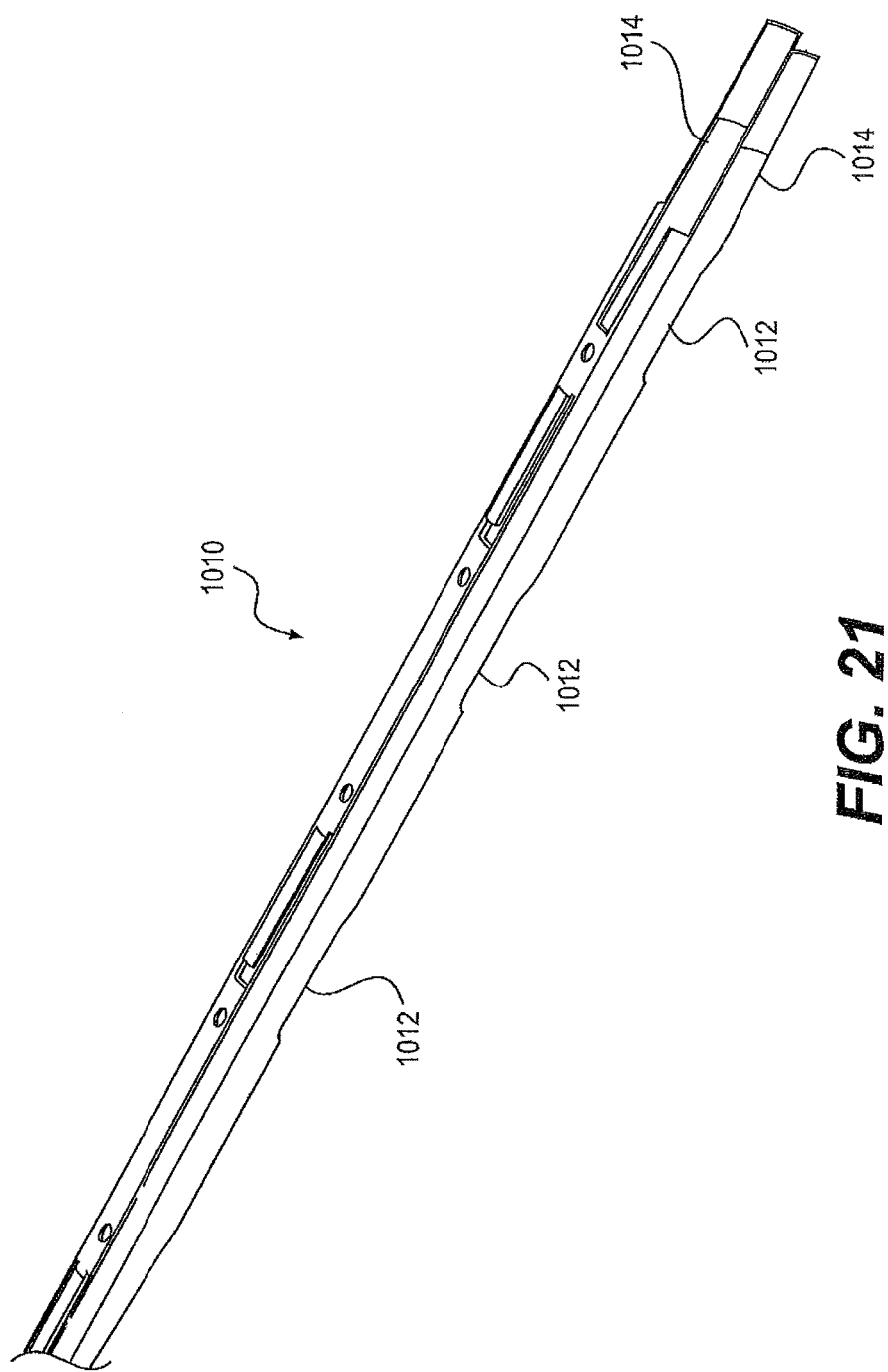
FIG. 21 shows a feed rail.
Figure 22:
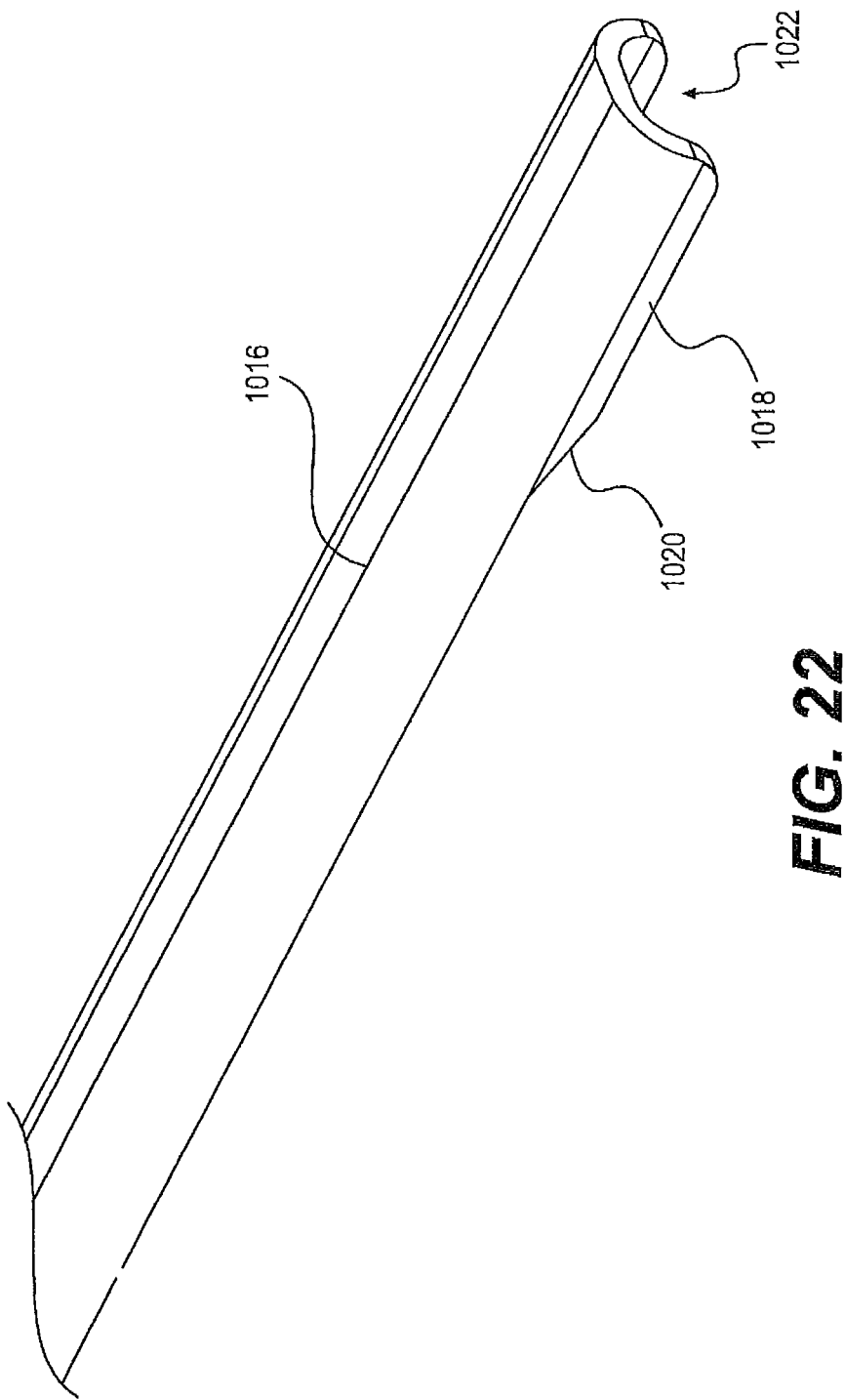
FIG. 22 shows a wedge.

FIGS. 21-31 show various parts of the applier 1000. FIG. 21 shows a feed rail 1010. The feed rail 1010 has end projections 1014 and cut out slots 1012. The cut out slots 1012 form slots that will be discussed in more detail later. FIG. 22 shows a wedge 1016. While only one is shown in FIG. 22 in the applier 1000, there are two wedges 1016 and they are identical or mirror images of each other. The wedges 1016 include a thicker portion 1018, a slanted surface 1020 and define a U-shaped channel 1022.

Figure 23:
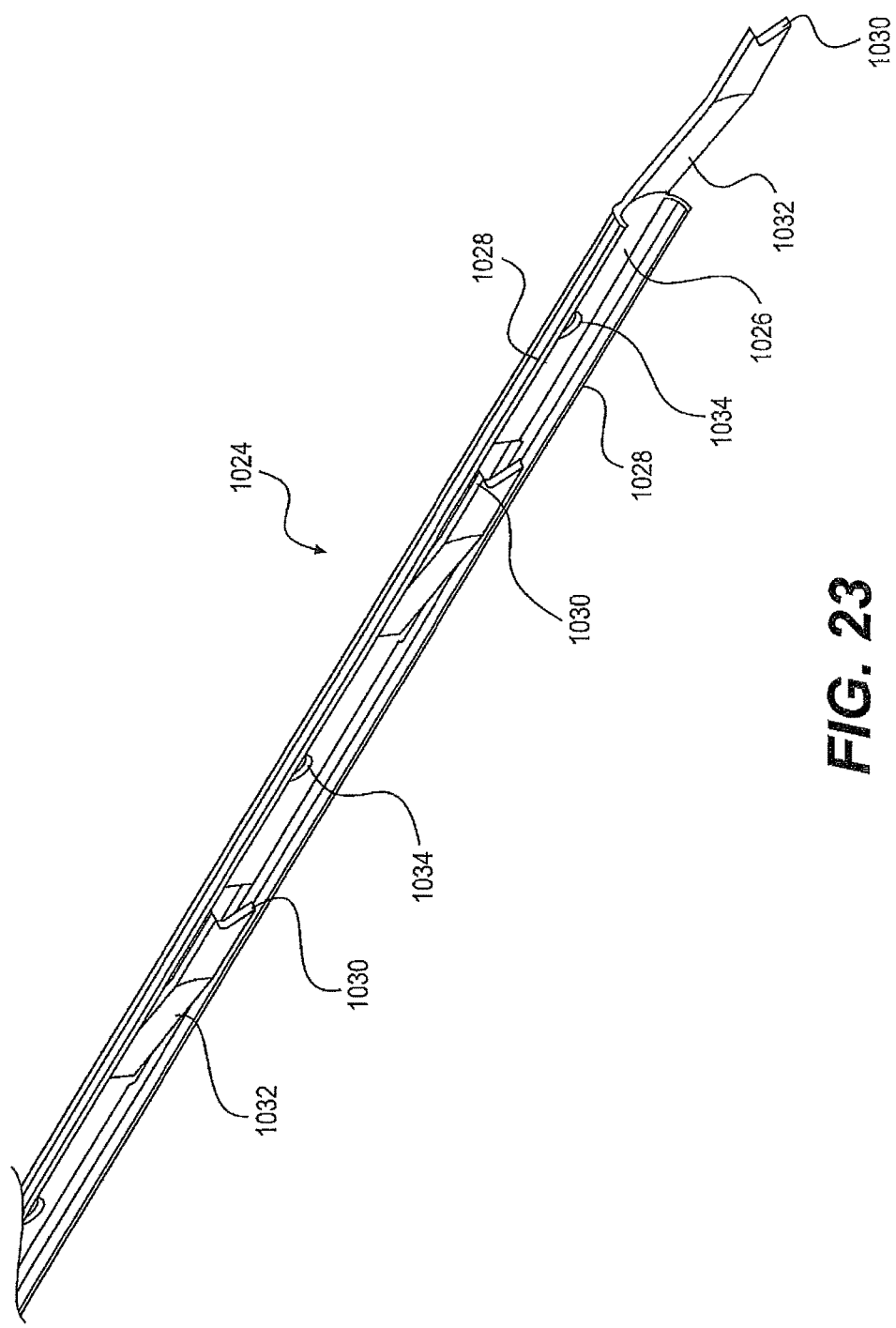
FIG. 23 shows a primary pusher.

FIG. 23 shows a primary pusher 1024. While only one primary pusher 1024 is shown in FIG. 23 there are two primary pusher 1024 that are identical or mirror images of each other in the applier 1000. The primary pusher 1024 includes a flat portion 1026, two rails 1028, and several forked engagers 1030. The forked engagers 1030 connect to the flat portion 1026 via a engager connector 1032. The number of forked engagers 1030 may vary depending upon the length of the shaft 1003 (See FIG. 16) and how many clips 100 are loaded in the applier 1000. The forked engagers 1030 are used to move the clips 100 forward and will be discussed further below.

Figure 24:
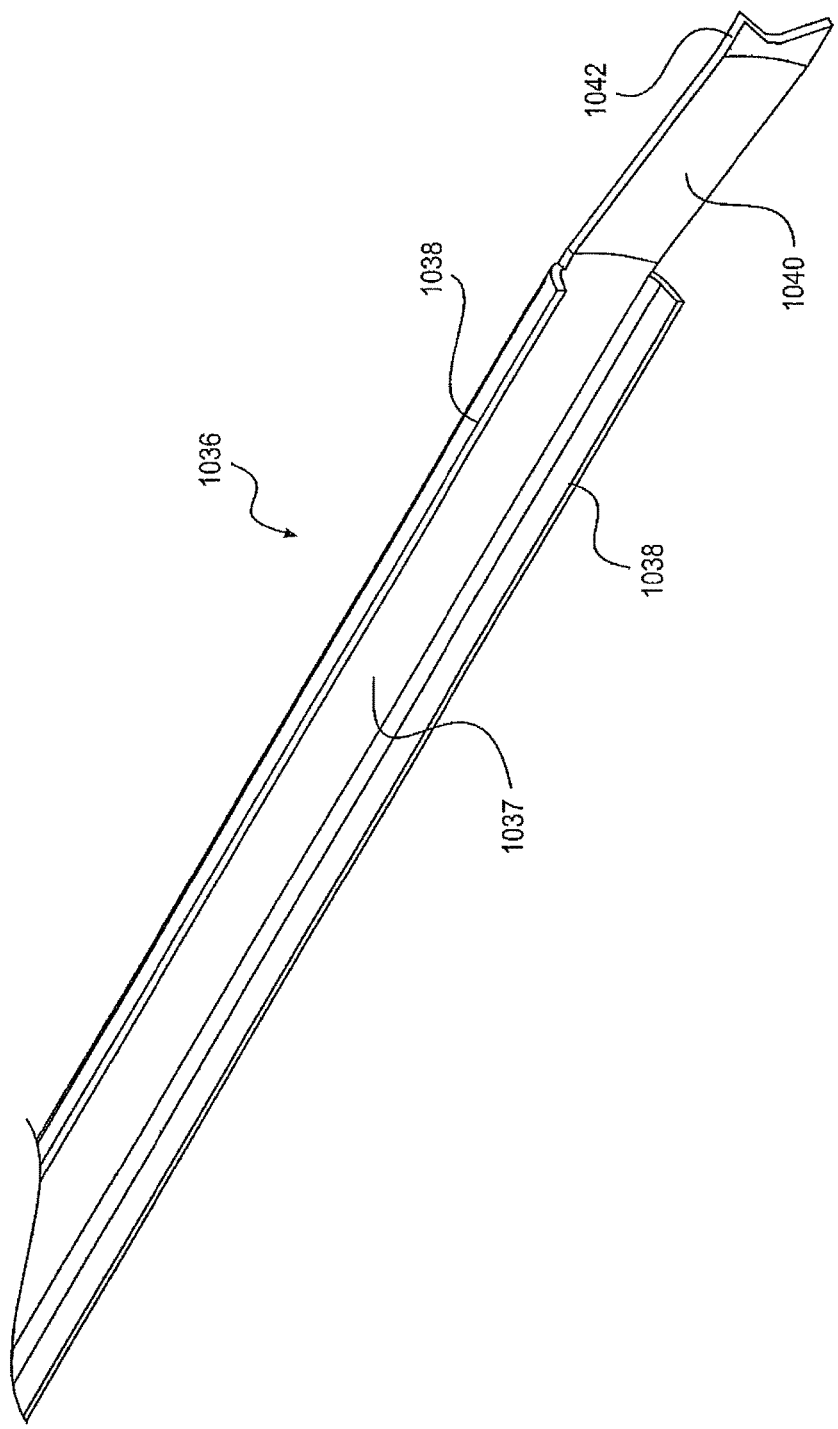
FIG. 24 shows a final pusher.

FIG. 24 shows a final pusher 1036. The final pusher 1036 includes a pusher backing 1037, two sets of pusher rails 1038, a pusher engager connector 1040 and a final pusher forked engager 1042. The final pusher forked engager 1042 will engage and push a clip 100 (not shown in FIG. 24) as will be discussed later.

Figure 25:
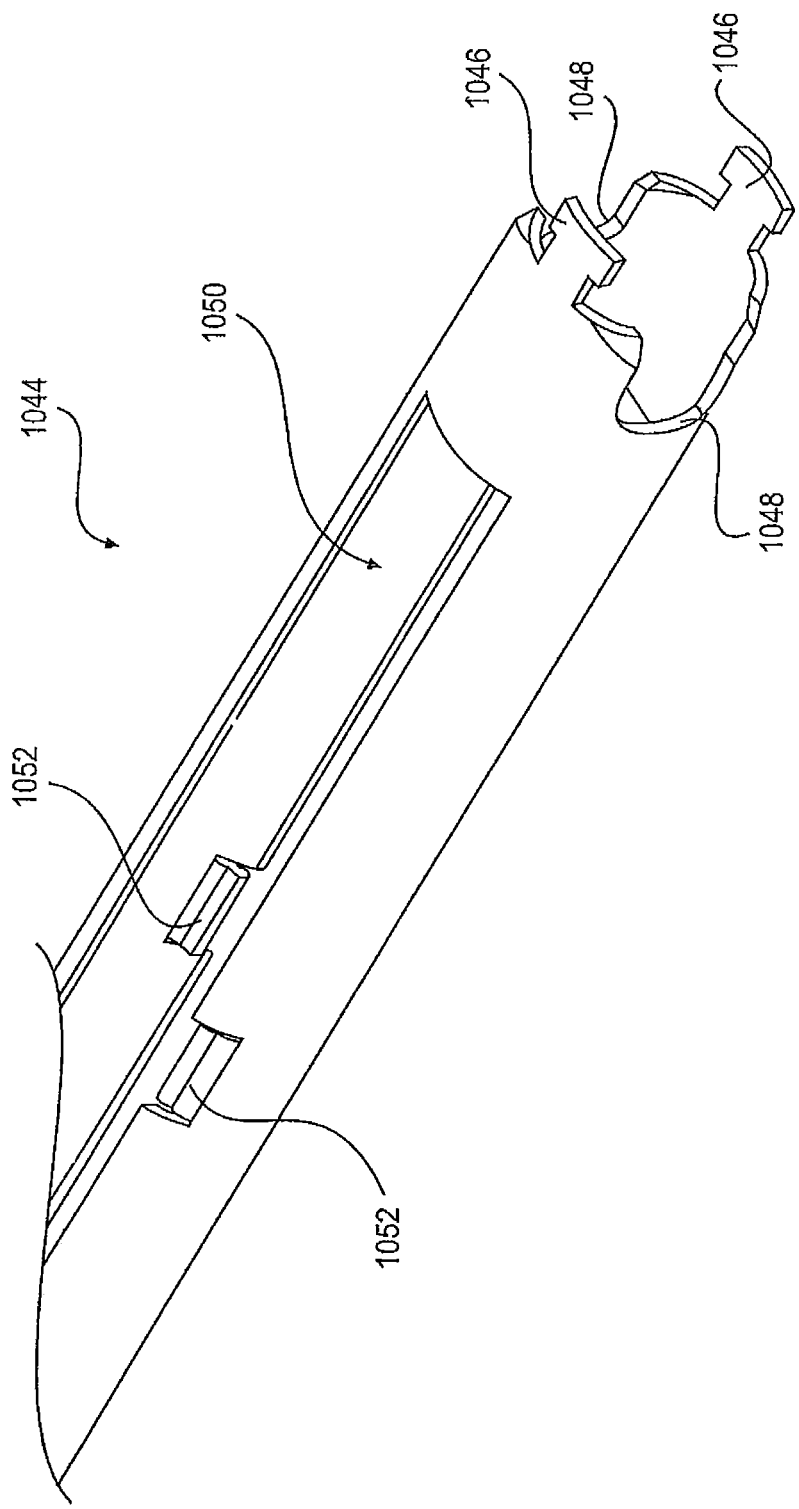
FIG. 25 shows an inner tube.
Figure 26:
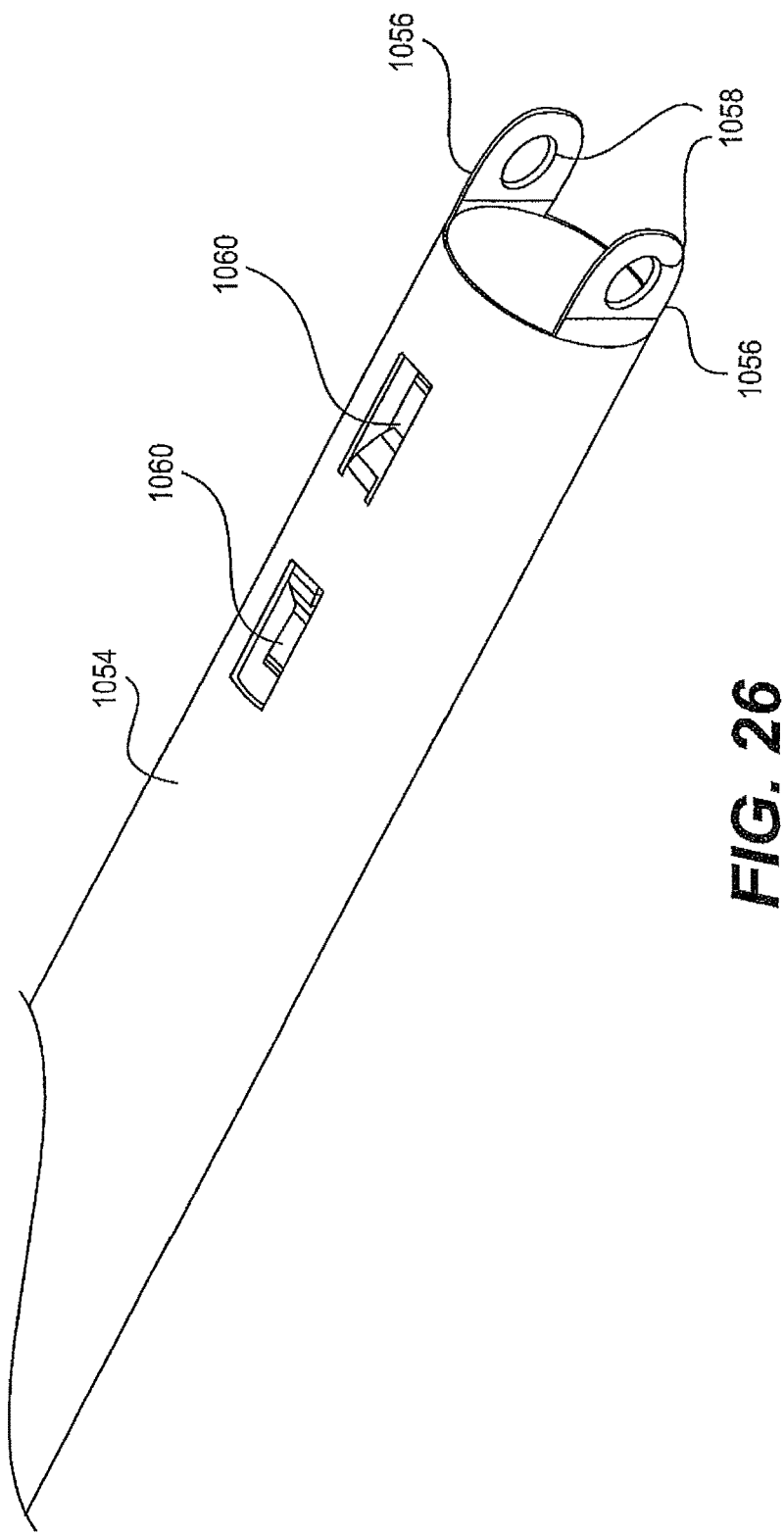
FIG. 26 shows an outer tube.

FIG. 25 shows an inner tube 1044. The inner tube 1044 has T-shaped connecting structure 1046, U-shaped channels 1048, a top slot 1050 and guides 1052 in the top slot 1050. FIG. 26 shows a outer tube 1054. The outer tube 1054 provides the outer housing for the shaft 1003. The outer tube 1054 has eye brackets 1056 defining holes 1058. The outer tube 1054 also has leaf spring limbs 1060. The leaf spring limbs 1060 extend into the interior of the outer tube 1054.

Figure 27:
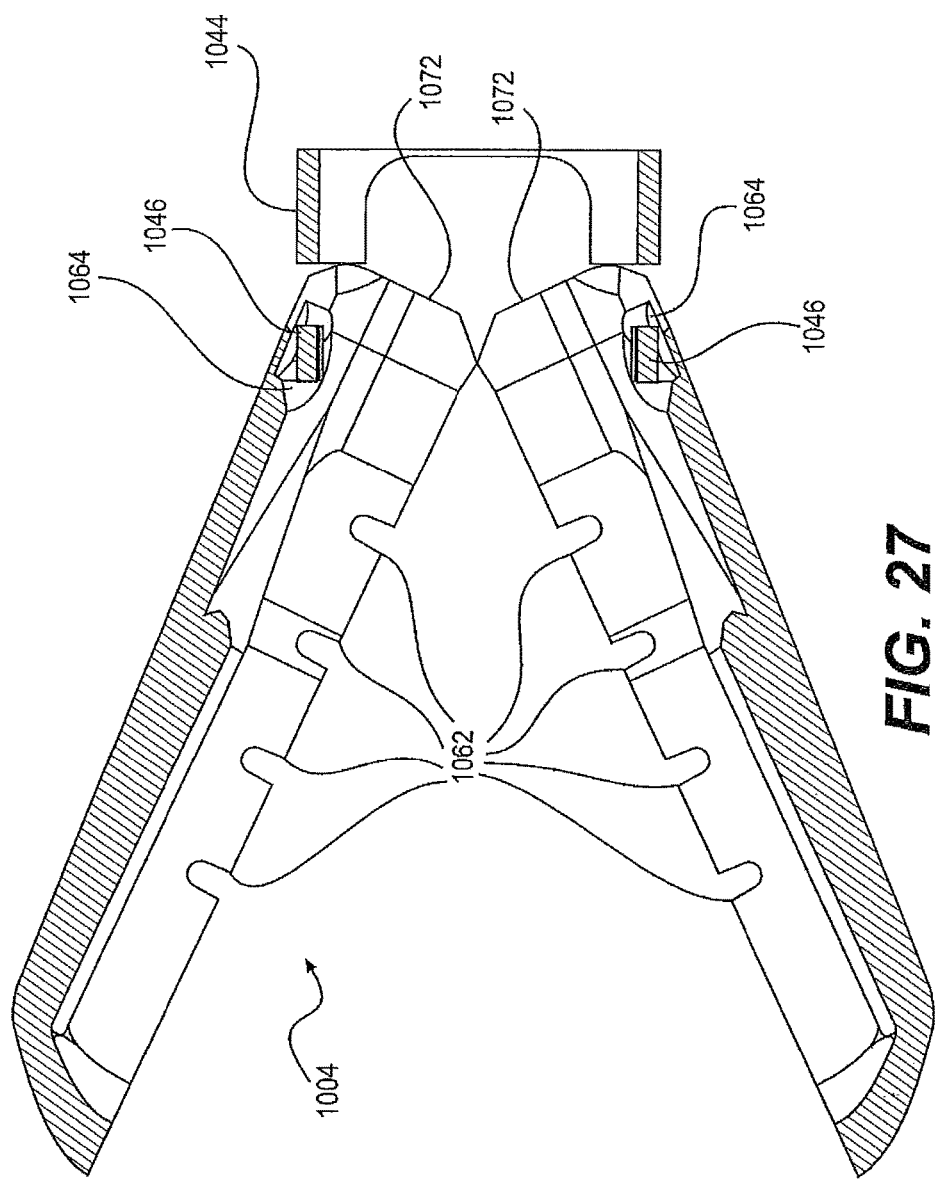
FIG. 27 shows a jaw/inner tube camming.
Figure 28:
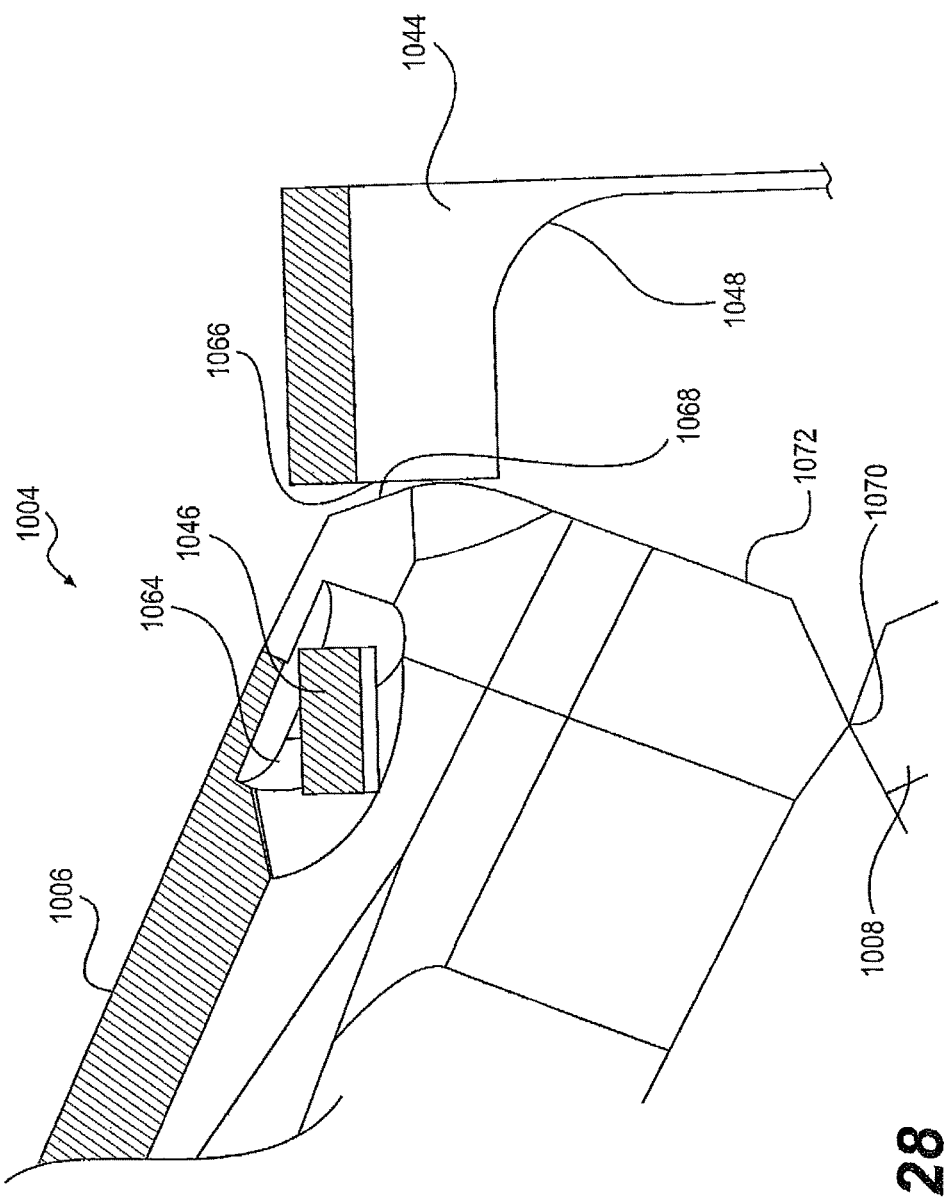
FIG. 28 shows a jaw/inner tube cam points.

FIG. 27 shows the jaws 1004 connected to the inner tube 1044. The jaws 1004 have T-shaped structure holes 1064. The T-shaped connecting structure 1046 of the inner tube 1044 fit into the T-shaped structure holes 1064 of the jaws 1004 and allow the jaws 1004 to pivot on the T-shaped structure 1046. The jaws 1004 have jaw grooves 1062 for assisting in the engagement of the jaws 1004 with a vessel or tissue 1002. The jaws 1004 also have pushing surfaces 1072. When an object pushes against the pushing surfaces 1072 the jaws 1004 will pivot on the T-shaped structure 1046 to an opened position. FIG. 28 is an enlarged partial view of the jaws 1004 and the inner tube 1044. The top jaw 1006 has a press point 1070 with the lower jaw 1008. The cam surface 1066 on the inner tube 1044 is seen as well as the cam surface 1068 on the jaw 1006. When an object presses on the press surface 1072 the cam surfaces 1066 and 1068 urge against each other as the jaws 1004 open. The cam surfaces 1066 and 1068 also urge against each other as the jaws 1004 close.

FIG. 29-31 show various views of the top jaw 1006. The top jaw 1006 is the same as or a mirror image of the low jaw 1008. The top jaw 1006 has T-shaped structure holes 1064, jaw hinge pins 1074 and hinge pin caps 1076. The hinge pin caps 1076 have been removed from one of the jaw hinge pins 1074 for clarity, usually there are hinge pin caps 1076 on each hinge pin 1074. The top 1078 and the bottom 1080 of the top jaw 1006 are shown.

Figure 32:
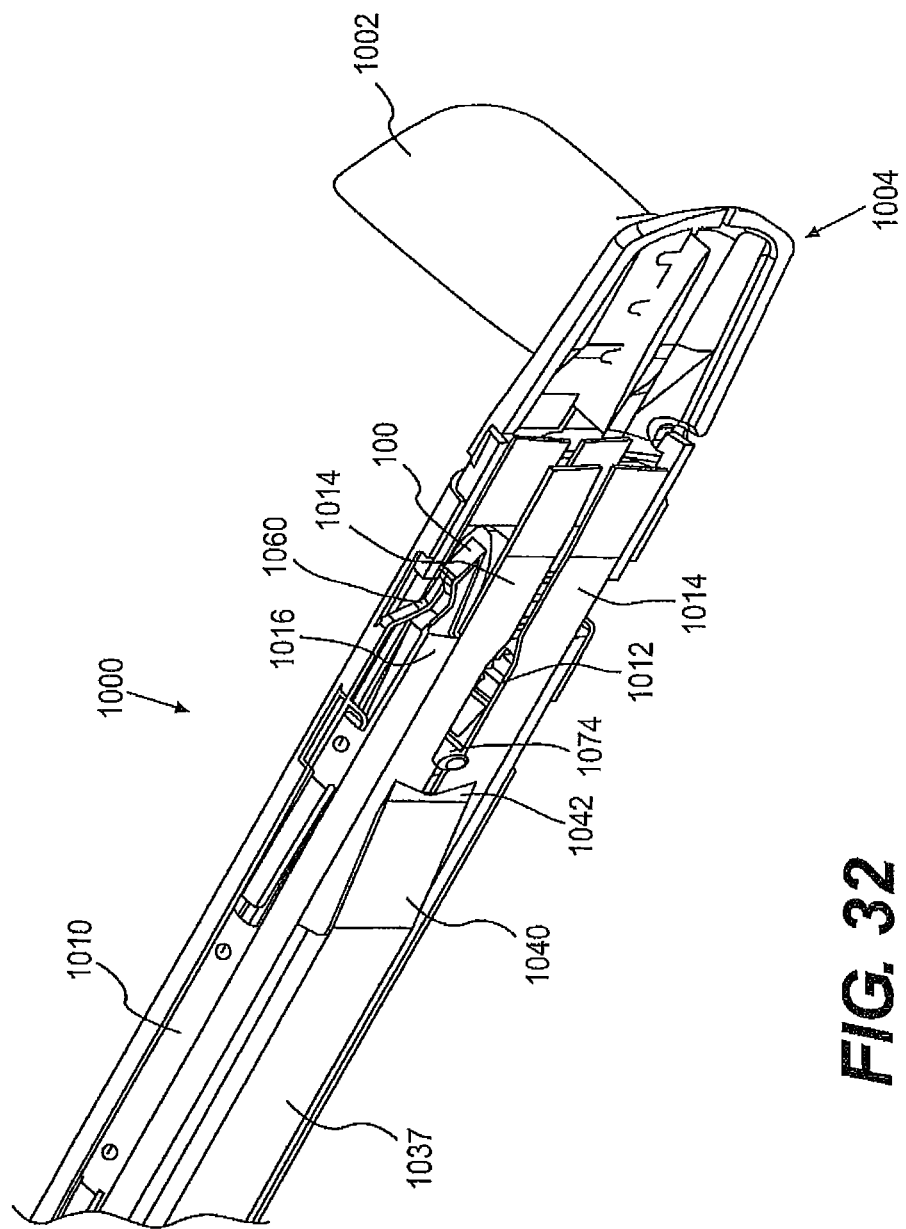
FIG. 32 shows inner and outer tubes cut away to see interior of distal end.

FIG. 32 is a side isometric view of a part of the applier 1000. The inner 1044 and outer tubes 1054 are cut away to better show interior parts. The jaws 1004 are clamped on a vessel or tissue 1002. The clip 100 has not yet moved forward into the jaws 1004 so that it can clamp the vessel or tissue 1002. The end projections 1014 of the feed rail 1010 are visible. The slot cut outs 1012 make a space for the jaw hinge pin 1074 to reside. In the position shown in FIG. 32 the final pusher forked engager 1042 is spaced from the hinge pin 1074 on the clip 100. The final pusher engager connector 1040 connects the final pusher forked engager 1042 to the final pusher back 1037. The clip 100 is in a somewhat open position and the leaf spring limbs 1060 are not engaging the clip 100. The wedges 1016 can also be seen.

Figure 33:
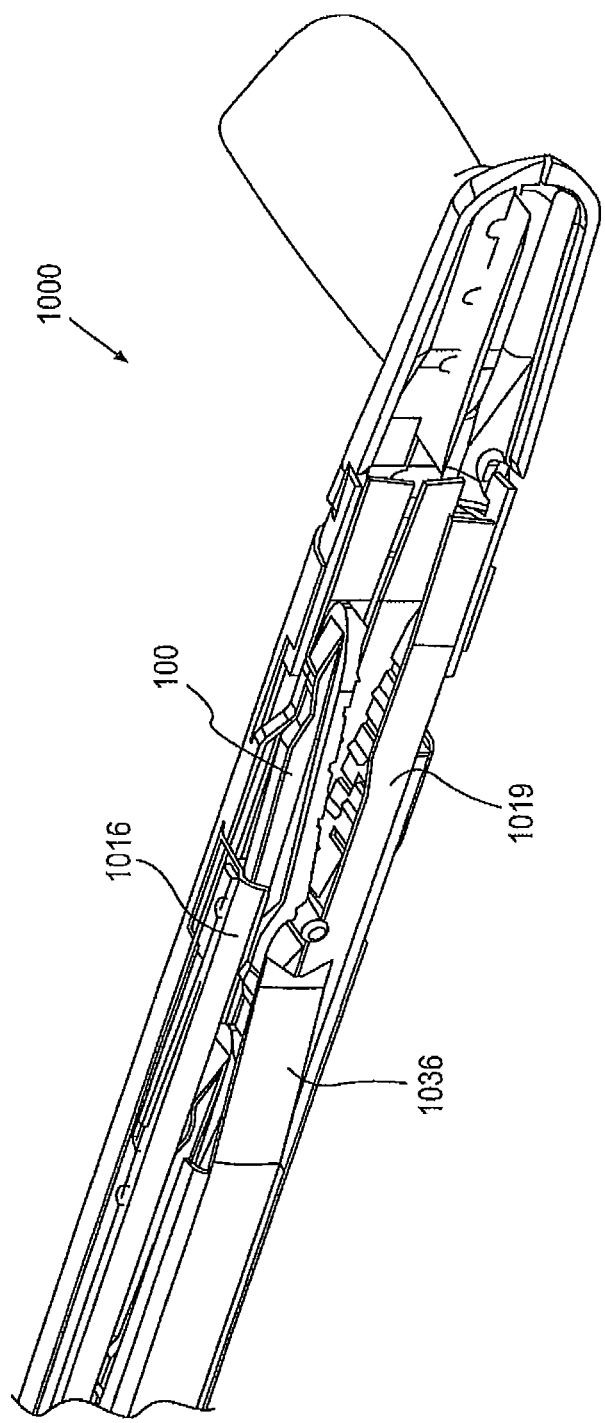
FIG. 33 shows a top feed rail cut away to see clip and wedge.
Figure 34:
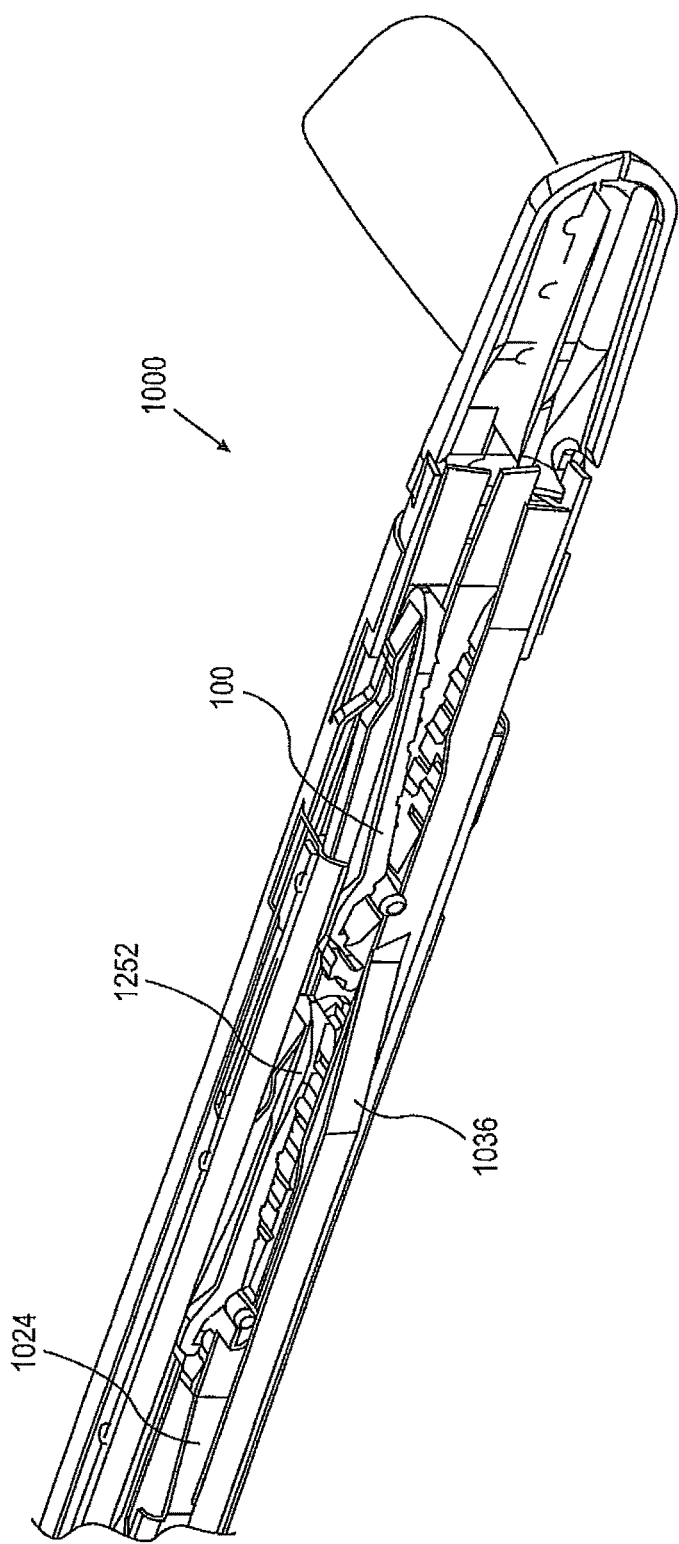
FIG. 34 shows a final pusher cut away to show primary pusher.

FIG. 33 is similar to FIG. 32 but shows the top feed rail 1010 cut away. The clip 100 and the top wedge 1016 can be seen along with the final pusher 1036. In FIG. 34, a similar view of the applier 1000 is shown but the top of the final pusher 1036 is cut away. The clip 100 can be seen. A second clip 1252 can be seen in position behind the first clip 100. The primary pusher 1024 can be seen. Once the first clip 100 is applied, the second clip 1084 will move forward and become the first clip 100 (from the point of view of position) as will be explained later.

FIGS. 35-44 will illustrate in cross section views the application sequence and forward movement of the clips 100, 1084 in the applier 1000. The jaws 1004 are clamped on the vessel or tissue 1002. The end projections 1014 are visible forward the clip 100. The top wedge 1016 is also visible. The final pusher 1036 is cut in half for clarity. A second clip 1084 may also be seen with the primary pusher 1024 behind the second clip 1084. FIG. 35 shows an initial condition of the various parts of the applier 1000 when the jaws 1004 are first clamped on the vessel or tissue 1002.

FIG. 36 shows the start of ligation. The wedges 1016, the primary pushers 1024 and the final pusher 1036 begin to move. The feeder rails 1010 spread apart to allow the boss 1082 on the clip 100 to pass through. The primary pusher 1024 engages the second clip 1084. In FIG. 37, the wedges 1016 open the clip 100 and by a camming action between the thicker portion 1018 of the wedge and the clip 100. The final pusher 1036 advances the open clip 100 into the jaws 1004 and over the vessel or tissue 1002. The primary pusher 1024 advances the second clip 1084 (and any other clips that may be located behind the initial clip 100). FIG. 38 shows the wedges 1084 advancing by action of the primary pusher 1024. The wedges 1016 advance to close the clip 100 onto the vessel or tissue 1002.

As shown in FIG. 39 the second clip 1084 advances by action of the primary pusher 1024 into buttress 150 of the first clip 100 (sometimes referred to as the initial clip 100). The buttress 150 is moved by the second clip 1084 to the point that the detent 157 fits into the notch 147 thereby locking the first clip 100 onto the vessel or tissue 1002. In FIG. 40, the wedges 1016 retract, however, the feeder rails 1010 (partially cut away in FIG. 40 and are better shown in FIG. 35) stay together and thus keep the second clip 1084 from retracting. The final pusher 1036 stays in place to keep the initial clip 100 in a forward position. In FIG. 41 the wedges 1016, the primary pusher 1024 and the second clip 1084 (and any other clips behind the initial clip retract).

Figure 43:
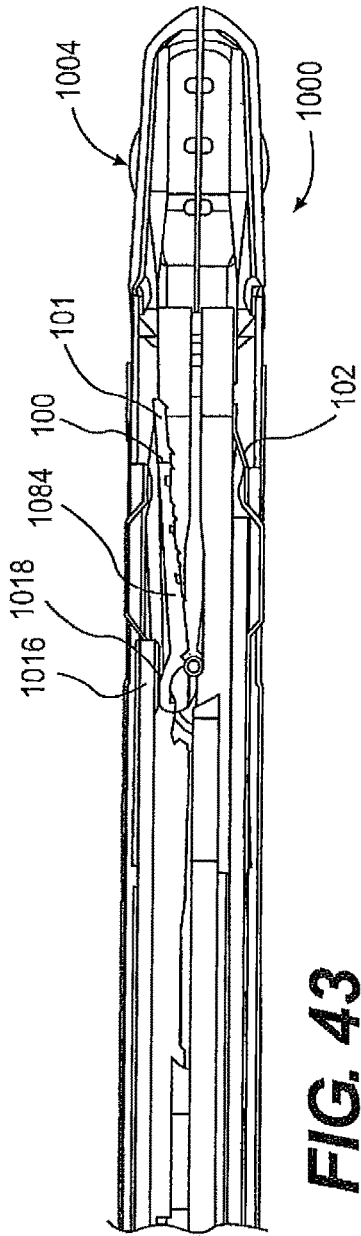
FIG. 43 shows all moving parts return to start position, first clip on vessel is released when jaws are opened.

As shown in FIG. 42 the second clip 1084 stops in the slot 1012 (best shown in FIG. 32) in the feeder rails 1010. The wedges 1016, primary pushers 1024 and the final pusher 1036 begin to retract. FIG. 43 shows the parts returning to an initial or start condition. The thicker portion 1018 of the wedges 1016 open top 101 and bottom 102 legs of the second clip 1084. The first clip 100 was released and exited the applier 1000 when the jaws 1004 were opened. The second clip 1084 now becomes the first clip 100 and the cycle starts over.

Figure 44:
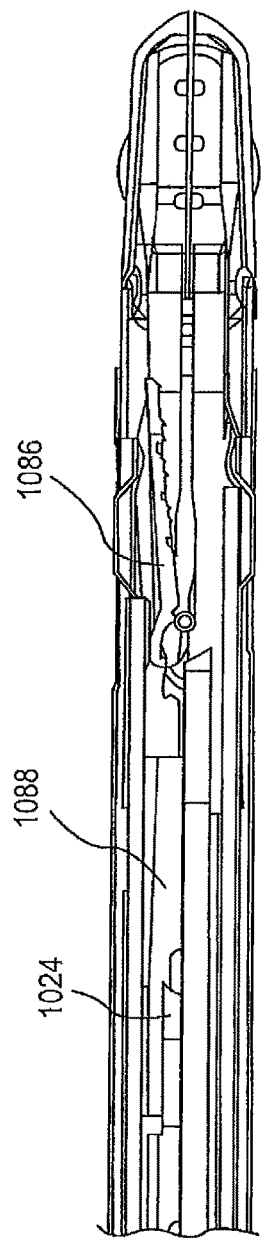
FIG. 44 shows a last clip in stack is locked with a false clip.
Figure 45:
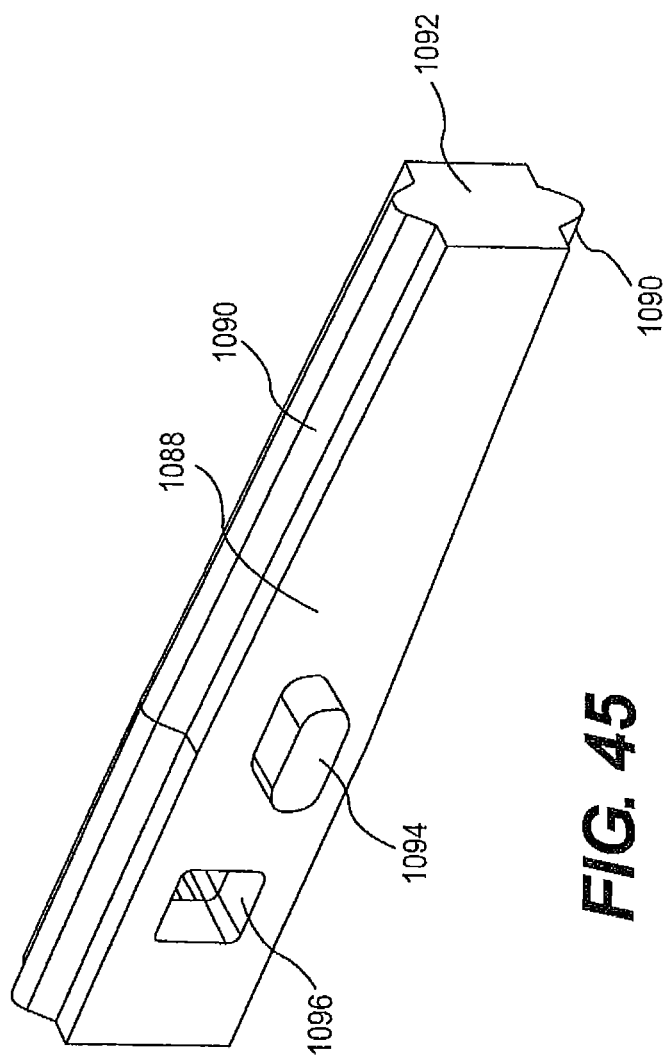
FIG. 45 shows a false clip.

FIG. 44 shows how that final clip 1086 is applied. The cycle is substantially the same as described above for applying a clip 100 but a false clip 1088 performs the function of locking the last clip 1086. FIG. 45 shows the false clip 1088. The false clip 1088 includes longitudinal ridges 1090, a butting face 1092, a boss 1094. These features perform similar functions as the similar features found on the actual clip 100. The false clip 1088 also has a hole 1096.

Figure 46:
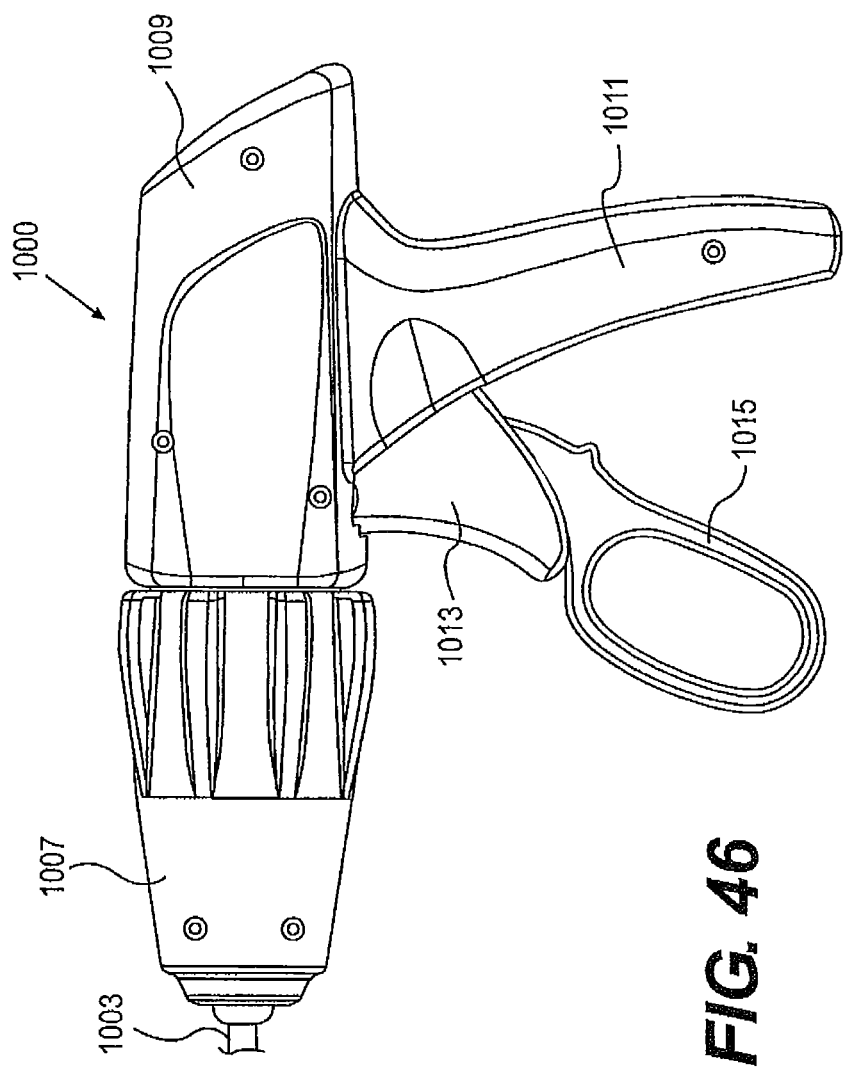
FIG. 46 shows a dual trigger handle.
Figure 47:
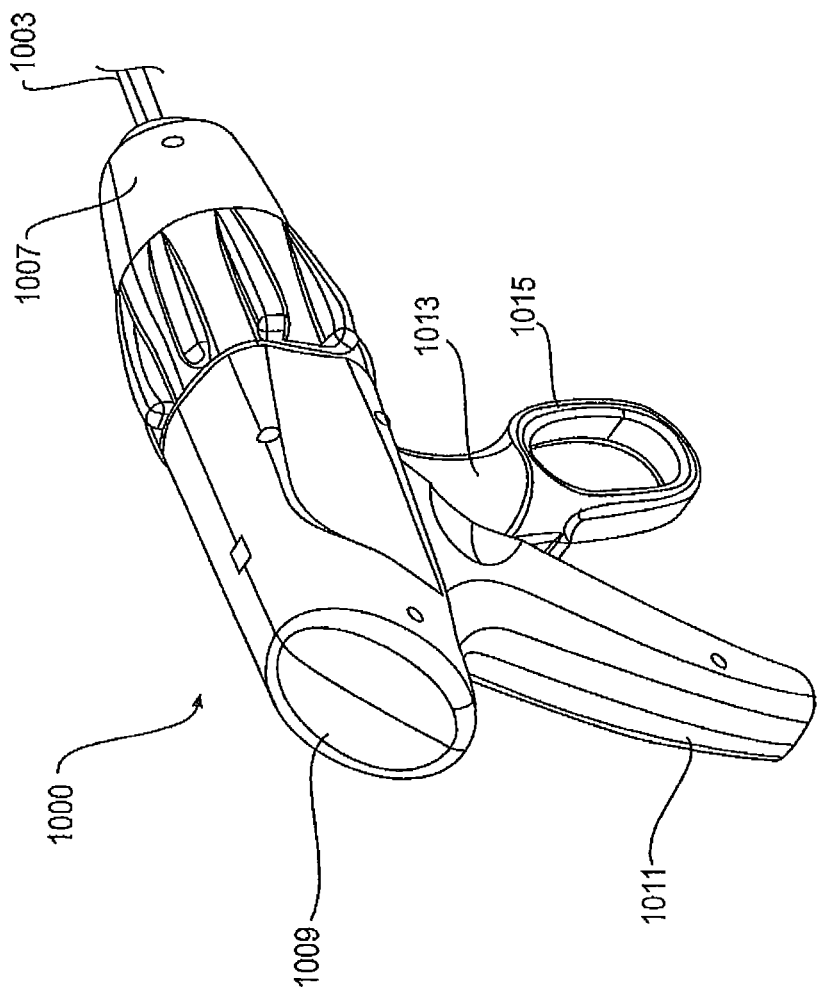
FIG. 47 show an isometric view of handle.

FIGS. 46-58 show and describe how the applier receives inputs from a user and provides those inputs to the transmission 1098. The transmission 1098 receives the inputs and converts them to motions to the parts that act on the clips 100, 1084, 1086. FIGS. 46 and 47 show a part of an applier 1000 having a shaft 1003, a transmission housing 1007, a clam shell housing 1009, and handle 1011, a ligate trigger 1013 and a jaw trigger 1015. While claim shell housings may be described herein, other types of housings may be used.

Figure 48:
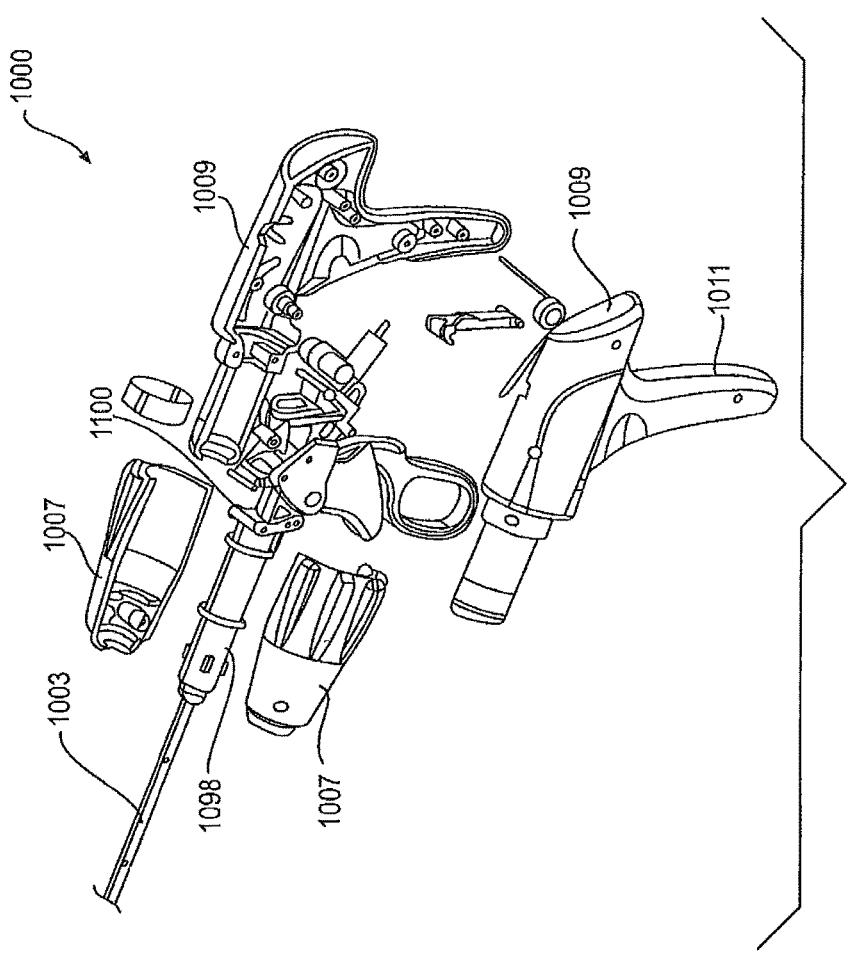
FIG. 48 shows a handle with shell and knobs exploded showing actuation mechanisms.

FIG. 48 shows and exploded view of part of the applier and some of the internal mechanisms. The clamshell housings 1009, the handle 1011, the transmission housing 1007, the shaft 1003 and the transmission 1098 as well as other parts that will be described in more detail can be seen. FIGS. 49 and 50 shows many of the internal components in more detail. The transmission 1098 has a jaw link input 1110 having a jaw link input groove 1112, a center spindle 1114 and a second input 1116 having a second input groove 1118. An upper grasper lever pin 1102 fits into the jaw link input groove 1112 and moves to provide an input to the transmission 1098. The upper grasper lever pin 1102 also fits into grasper lever holes 1106 and is controlled by the grasper levers 1100. The grasper levers 1100 have grasper lever slots 1108 in which the lower grasper lever pin 1104 rides. In some embodiments of the invention, the lower grasper lever pin 1104 fits into the jaw trigger pin holes 1154 on the jaw trigger 1015. The grasper levers 1100 and thus the input 1110 is controlled by the grasper/jaw trigger 1015.

The ligate lever 1120 has ligate lever slots 1122 in which the ratchet plate pin 1160 resides. The ratchet plate pin 1160 also fits in the ratchet plate pin holes 1162 on the ratchet plates 1158. Thus, the ligate lever 1120 is controlled by the ratchet plates 1158. The ligate lever 1120 has ligate lever trunnions 1124 which fit into the second input groove 1118 in the second input 1116. Thus, the ligate lever 1120 controls the second input 1116. The ratchet plates 1158 have ratchet teeth 1166 and disengaging cams 1168 that interact with forward 1126 and rearward 1128 facing pawls. The pawls 1126, 1128 ride on a pawl shaft 1130 that is connected by a pawl spring 1132 connected to a spring anchor 1134. It is noted that the inputs 1110 and 1116 are circular and the features (i.e. pins) that control the inputs may be rotated 360° about the inputs 1110 and 1116 so that a user can manipulate the triggers 1013 and 1015 from a rotated position with respect to the transmission 1098 and jaws 1004. FIGS. 51-58 show the pawl mechanism and its accompanying discussion will explain how the pawl mechanism works.

Springs 1146 and 1148 are used to bias the triggers 1013 and 1015 to a position against the handle 1011. The triggers 1013 and 1015 and the ratchet plates 1158 all pivot about the same hole 1156. A pivot pin may be provided or trunnion on the housing 1009 may provide a pivot. In some embodiments, a spring extension 1150 may be used to connect either or both of the springs 1148 and 1146 to a desired feature. In some embodiments the spring extension 1150 may attach to the pin 1152 which may fit in holes 1164 in the ratchet plates 1158. A low clip indicator spring 1136 may fit around a low clip indictor anchor 1138. The low clip indicator 1136 is connected to the low clip indicator 1140, which in turn is connected to the last clip lock out 1142 and grommets 1144. The low clip indicator 1140 may help a user to know that the amount of clips in the applier are low. The last clip lockout 1142 may prevent the user from using the applier 1000 when there are no more clips in the applier 1000. FIG. 50 shows a trigger lock 1170. The trigger lock 1170 has a trigger lock groove 1172. A trigger release 1178 has a detent 1174 that fits into the trigger lock groove 1172. A trigger lock spring 1176 urges the trigger release 1178 toward the trigger 1013.

Figure 51:
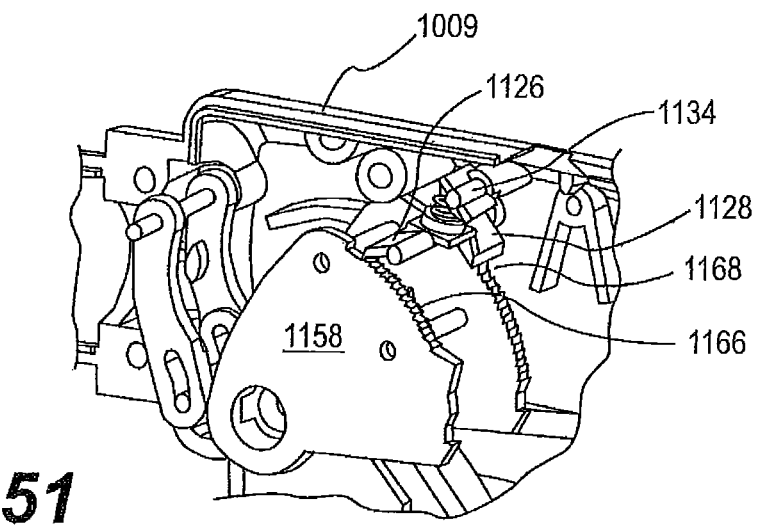
FIGS. 51-58 show a pawl mechanism.
Figure 52:
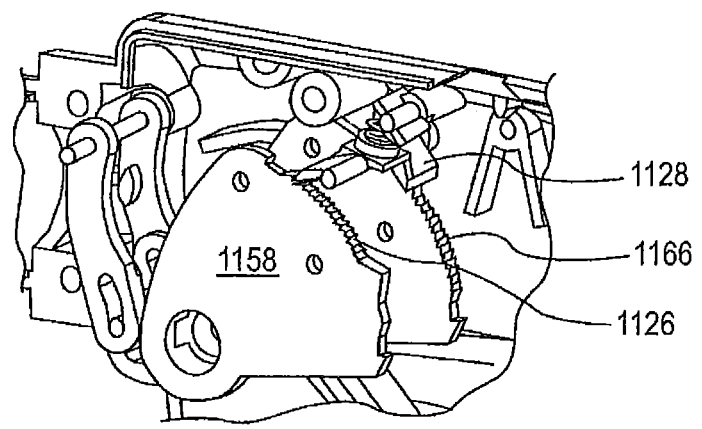
Figure 53:
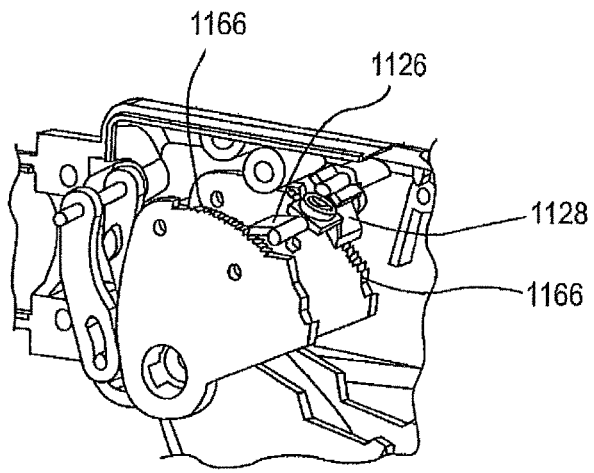
Figure 54:
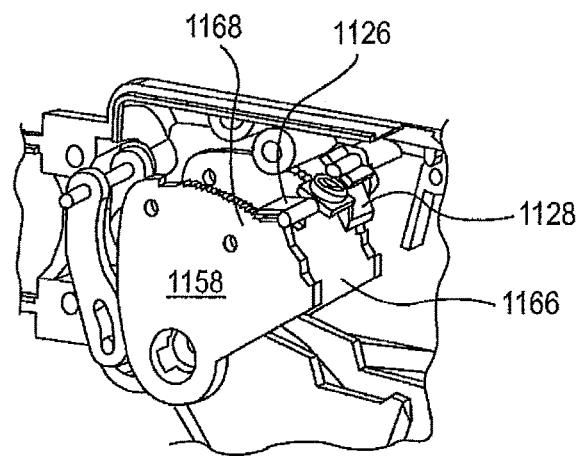
Figure 55:
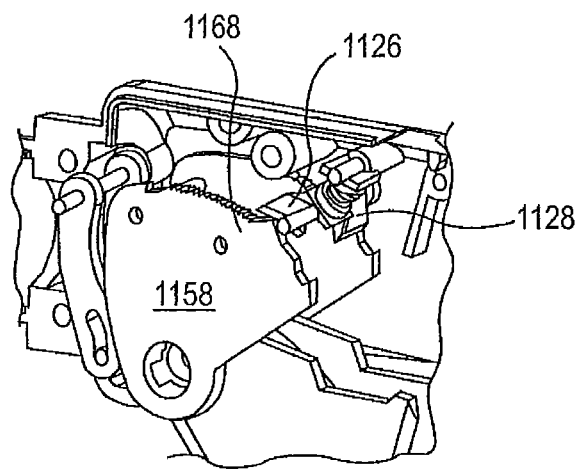
Figure 56:
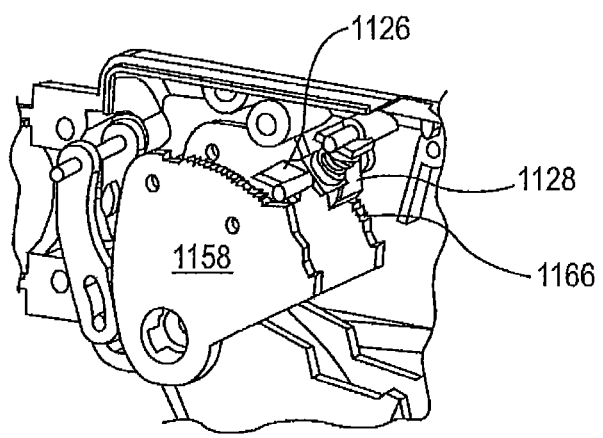
Figure 57:
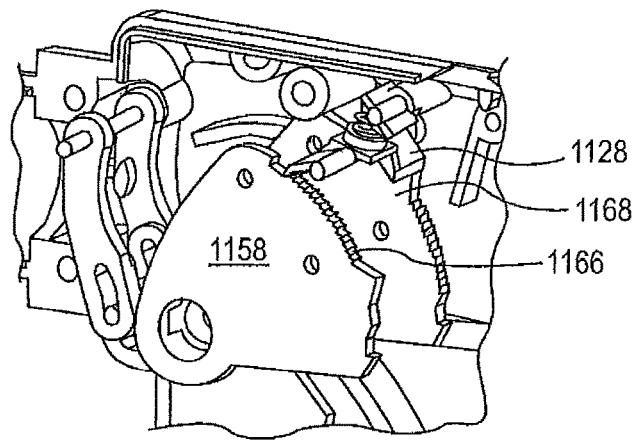
Figure 58:
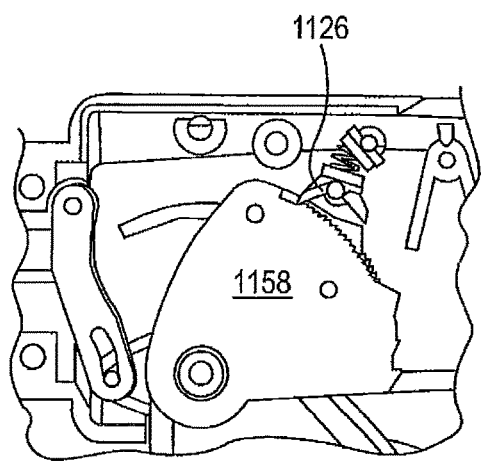

FIG. 51 shows an initial condition where the triggers 1013 and 1015 (not well shown in FIG. 51) are in a position against the handle 1011 (see FIG. 16) The triggers 1013 and 1015 and the ratchet plates 1158 will move as shown and described. The teeth 1166 on ratchet plates 1158 are not engaged with either the forward facing 1126 or the rearward facing 1128 pawl. The pawl anchor is attached to the housing 1009 (a front housing piece has been removed to the pawl mechanism may be seen). The disengaging cam 1168 has disengaged the reward facing pawl 1128 from the teeth 1166. FIG. 52 shows that the rearward facing pawl 1128 is disengaged with the teeth 1166 and the forward facing pawl 1126 is engaged with the teeth 1166 during the pull of the ligate trigger 1013. In FIG. 53, the forward facing pawl 1126 is engaged with the teeth 1166 the rearward facing pawl 1128 is engaged. In FIG. 54 the disengaging cam 1168 disengages the pawl 1126 and engages the pawl 1128 with the teeth 1166. FIG. 55 shows the pawl 1126 disengaged by the disengaging cam 1168 and the cam 1168 engaged. FIG. 56 shows that during the return of the trigger, the rearward facing pawl 1128 stays engaged with the teeth 1166 while the forward facing cam 1126 remains disengaged with the teeth 1166 on the ratchet plates 1158. FIG. 57 is similar to FIG. 51 as the triggers 1013 and 1015 return to the initial position proximate to the handle 1011. FIG. 58 is a side view of the pawl 1126 and ratchet plate 1158 in the position shown in FIGS. 51 and 57.

Figure 59:
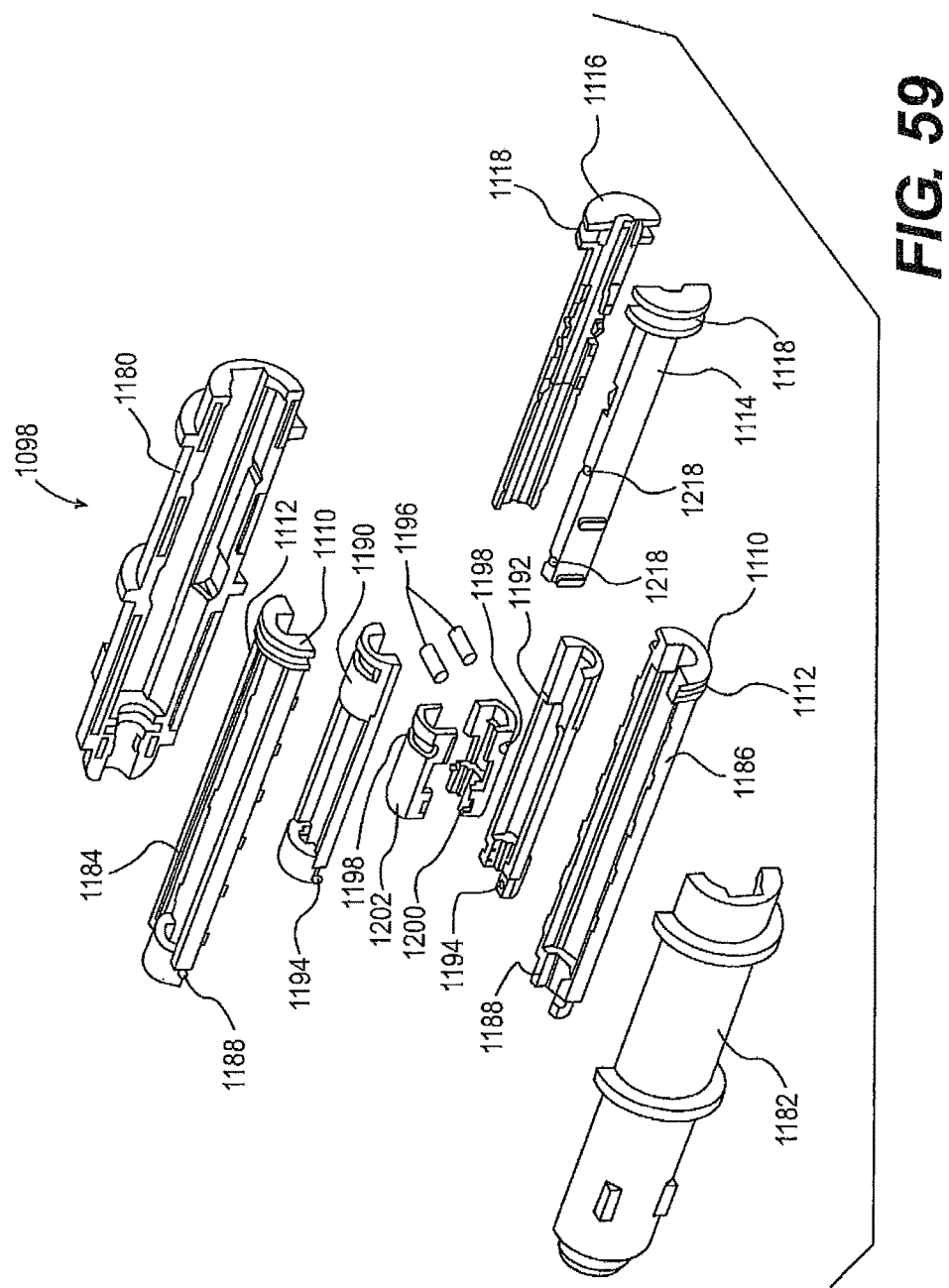
FIG. 59 shows transmission parts.

FIGS. 59-66 show the parts and the layout of the parts of the transmission 1098 various parts will be removed from the FIGS. to show interior parts. FIG. 59 is an exploded view of the transmission 1098. FIG. 59 shows the outer rotating housing 1180, 1182 of the transmission. The outer rotating housing 1180, 1182 may be a clamshell housing. Jaw link actuators 1184 and 1186 define the jaw link input 1110 and jaw link input groove 1112. The jaw link actuators 1184 and 1186 have attaching structure 1188 for attaching to parts that will be described later. Within the jaw link actuators 1184, 1186, are final pusher latches 1190, 1192. The final pusher latches 1190, 1192 also have attaching structure 1194 for attaching to other parts as will be described later.

A primary pusher latch 1202 (or latches, many of the parts may be referred to in the singular or plural form as many are made of two pieces. However multiple piece are not required to be referred to in the plural form) may have attaching structure 1200 for attaching to other parts as will be described later. The primary pusher latch 1202 may include attaching pin grooves 1198 for attaching pins 1196. The center spindle 1114 is attached to the second input 1116 which defines the second input groove 1118. The center spindle 1114 has pin grooves 1218.

Figure 60:
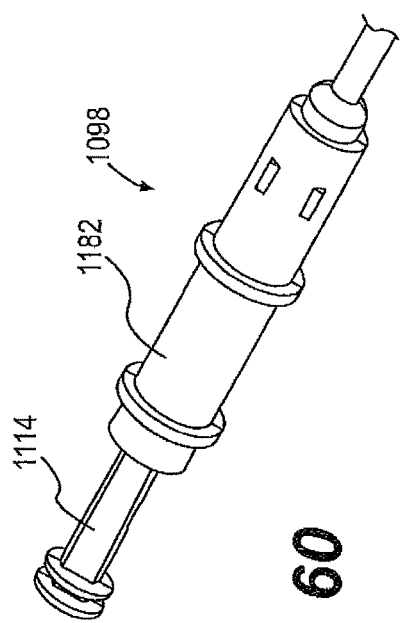
FIG. 60 shows a multi stage transmission.
Figure 61:
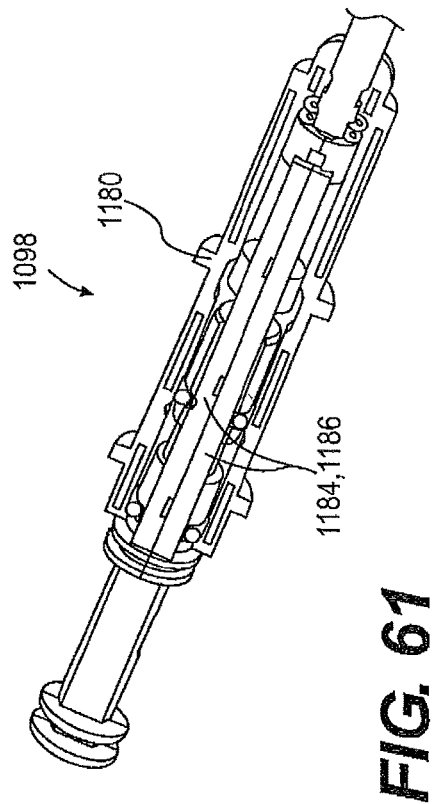
FIG. 61 shows a outer shell of transmission removed.

FIG. 60 shows the transmission 1098 with the outer rotation housing 1180 in place and the center spindle 1114 extending from the housing 1182. In FIG. 61, one of the housing members 1182 has been removed. The housing 1180 is still present. The jaw link actuators 1184, 1186 are visible. FIG. 62 shows the transmission 1098 with the jaw link actuators 1184, 1186 removed. The final pusher latches 1190, 1192 and the primary pusher latches 1202 are visible along with the attaching pins 1196. FIG. 63 has the housing 1180 removed. The final pusher latches 1190, 1192 and the primary pusher latches 1202 are visible along with the attaching pins 1196 in the attaching pin grooves 1198. FIG. 64 shows the transmission 1098 with the final pusher latches 1202 and pins 1196 removed. The primary pusher latch 1202 is visible. In the transmission 1098 shown in FIG. 65 the final pusher latch 1202 is removed.

Figure 66:
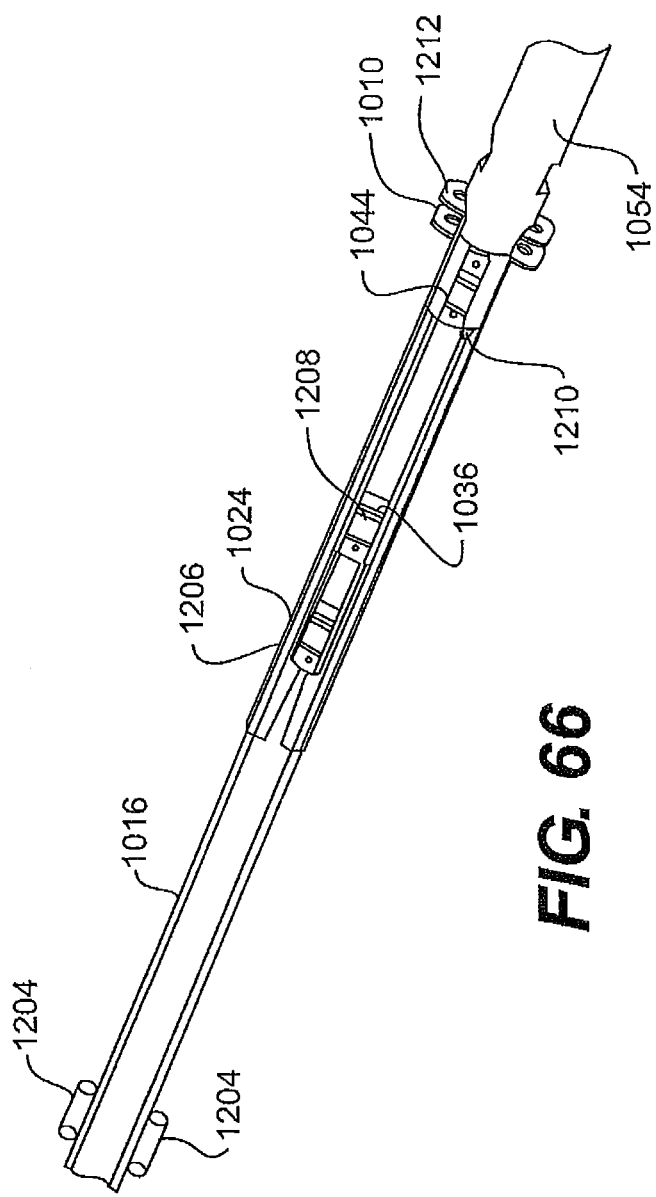
FIG. 66 shows center spindles removed distal end connection points shown.
Figure 67:
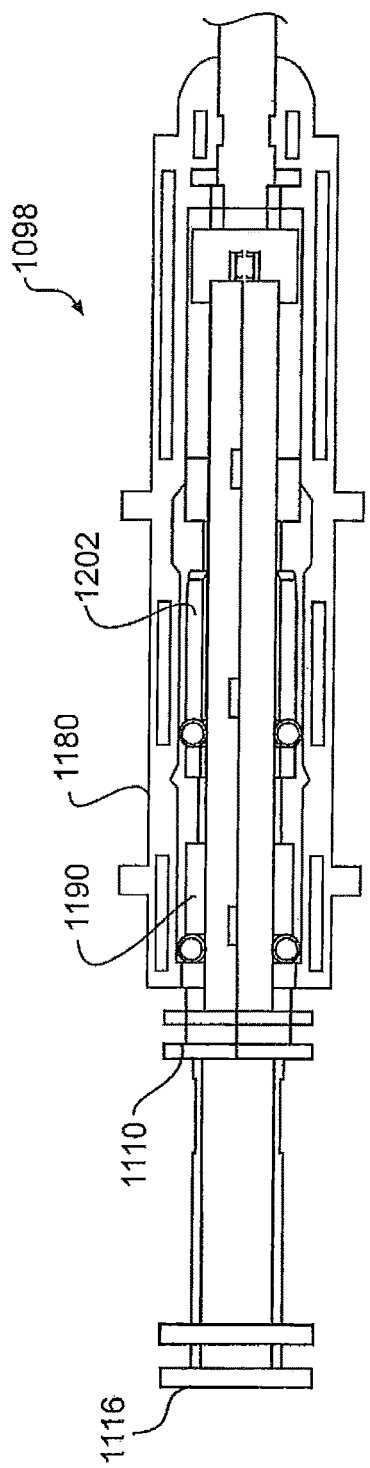
FIG. 67 shows input positions when the jaws are open.
Figure 68:
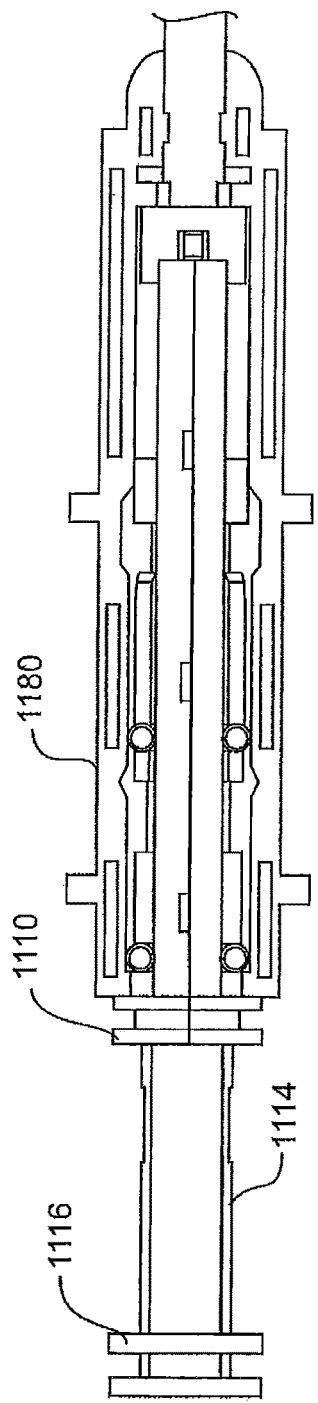
FIG. 68 shows input positions when the jaws are clamped on vessel.

FIG. 66 shows the transmission 1098 with the center spindle 1114 removed. The wedges 1016 are shown with wedge connection brackets 1204 where the wedges 1016 connect to the transmission 1098 via the center spindle 1114. The connection point 1206 where the primary pusher 1024 connects to the transmission 1098. The connection points 1208, 1210, and 1212 are shown for connecting the transmission 1098 to the final pusher 1036, the inner tube 1044, and the feed rail 1010 respectively are shown. The outer tube 1054 can also be shown. The connections between the transmission 1098 and the various elements are not limited to what is shown. Any suitable means may be used. One of ordinary skill in the art may, after reviewing this disclosure, conceive of various ways to connect these features to the transmission 1098.

Figure 69:
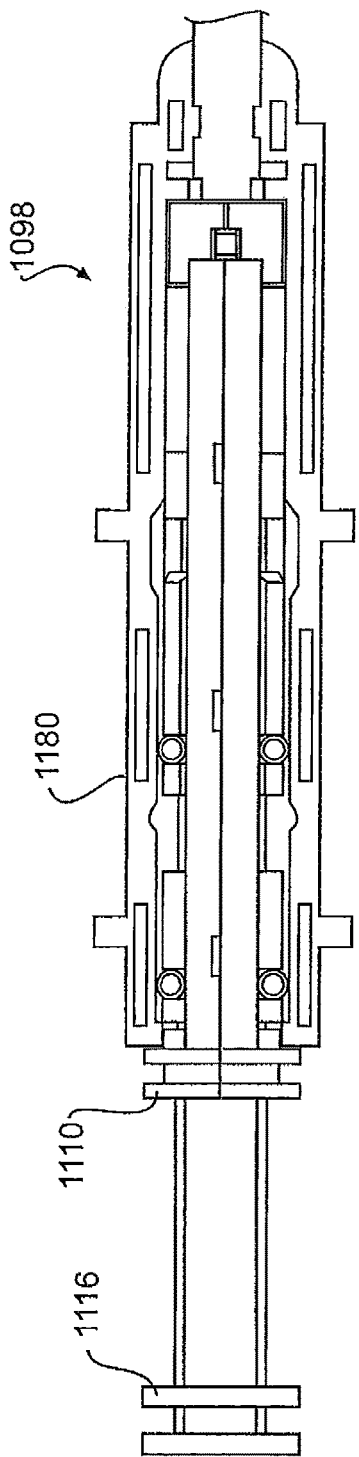
FIG. 69 shows input positions at a start of clip advance.

FIGS. 67-76 are cross sectional views of the transmission 1098 at various positions. The movement of the transmission components will cause the components they are connected to to move the clip 100 (not shown in these FIGS.) to various positions and/or orientations within the applier 1000. The components the transmission is manipulating are generally not shown in FIGS. 67-76 but they are shown and described with respect to other FIGS. At FIG. 67, transmission 1098 is in a position to cause the jaws 1004 to be in an open position. The second input 1116 is extended away from the transmission 1098. The jaw link input 1110 is spaced away from the outer housing 1180 of the transmission 1098. The final pusher latch 1190 and the primary pusher latch 1202 may be seen. At FIG. 68 the jaw link input 1110 has moved toward, and contacts the housing 1180. The jaws 1004 are in a clamped position. The center spindle 1114 and second input 1116 are still extended. In FIG. 69 the clip 100 is starting to advance. The second input 1116 is moved slightly toward the jaw link input 1110.

Figure 70:
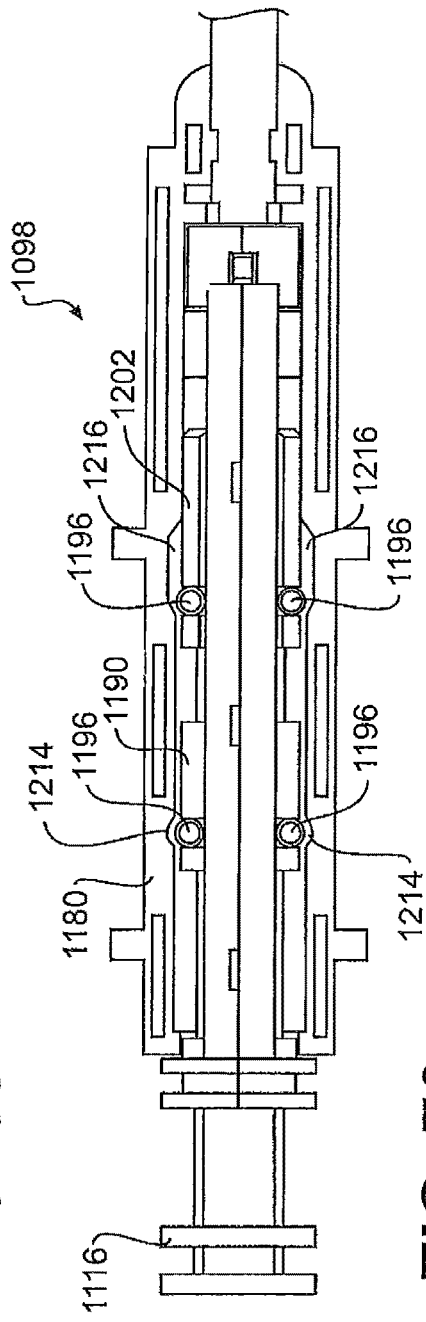
FIG. 70 shows input positions for a first clip advanced over vessel by final pushers and wedges advance second clip advances by primary pushers.

In FIG. 70, the first clip 100 is advanced to be over the vessel or tissue 1002 by the final pushers 1036 and the wedges 1016 advance. The second clip(s) 1084 are advanced by the primary pushers 1024. The final pusher latch 1190 has moved such that the attaching pins 1196 are aligned with pin notches 1214 in the outer housing 1180. The attaching pins 1196 can move out of the pin grooves 1218 in the center spindle 1114 (see FIG. 59) and into the into the pin notches 1214 and thus unlock the final pusher latch 1190 with the center spindle 1114. Likewise, the primary pusher latch 1202 has moved so that the attaching pins 1196 are aligned with the pin slot 1216 in the outer housing 1180. As a result, the pins 1196 can move out of the pin grooves 1218 in the center spindle 1114 and into the pin slot 1216 and thus unlock the primary pusher latch 1202 from the center spindle 1114. The primary pusher latch may move along the center spindle the length of the pin slot 1216.

Figure 73:
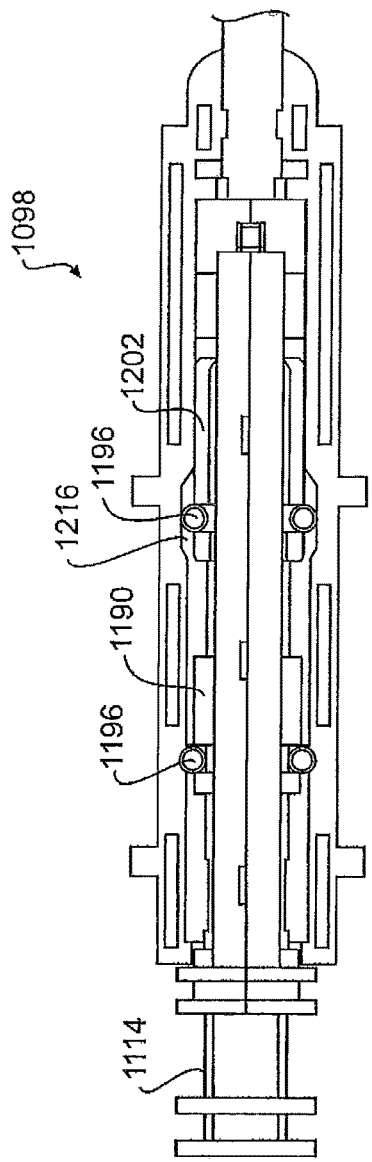
FIG. 73 shows input positions for wedges to begin to retract.
Figure 74:
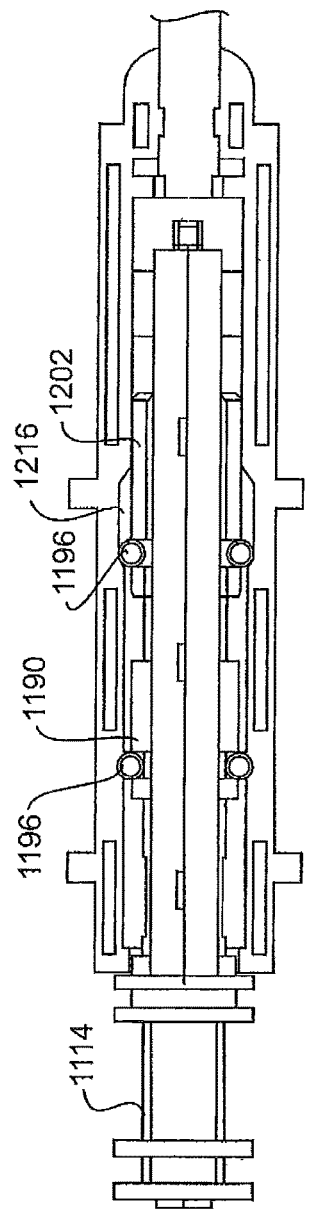
FIG. 74 shows input positions for primary pushers to retract and wedges continue to retract.

In FIG. 71 the transmission 1098 is shown where the wedges advance to close the first clip 100. The second input 1116 moves inward causing the center spindle 1114 to move inward. The pins 1196 are moved to the pin notches 1214 and pin slots 1216 in the housing 1180. In FIG. 72, the clip 100 is latched. The primary pushers 1036 advance the second clip 1084 (or false clip 1088) to lock the first clip 100. This is accomplished by moving the second input 1116/center spindle 1114 further into the transmission 1098. The pins 1196 stay in the pin notches 1214 and pin slot 1216. In FIG. 73 the transmission 1098 is shown where the wedges 1016 begin to retract. The center spindle 114 moves out of the transmission 1098. The pins 1196 are still in the pin notches 1214 and pin slots 1216. The final pusher latch 1190 and the primary pusher latch 1202 are unchanged from FIG. 72. In FIG. 74, the center spindle 1114 continues to move out of the transmission 1098. The pins 1196 still in the pin notches 1214 and slots 1216. The final pusher latch 1190 is unchanged from FIG. 72, but the primary pusher latch 1202 has moved back.

In FIG. 75 the position of the transmission 1098 is shown where the final pusher 1036 retracts and other parts also retract. The pins 1196 are once again aligned with the pin grooves 1218 and the final pusher latch 1190 and the primary pusher latch 1202 have moved back taking the pins 1196 out of alignment with the pin notches 1214 and pin slot 1216.

FIG. 76 shows the transmission 1098 back in the start position. The final pusher latch 1190 and the primary pusher latch 1202 are move back and the center spindle 1114 is full extracted. The transmission 1098 shown in FIG. 76 is similar to the transmission 1098 shown in FIG. 67.

A second embodiment is shown in FIGS. 77-98 this embodiment is similar to the applier 1000 described above, but it uses a slightly different system to move the clips 100, 1084 along. Where the description of the second embodiment is silent, as to specific parts, the second embodiment may be assumed to be similar to the first embodiment with respect to the not described features.

Figure 78:
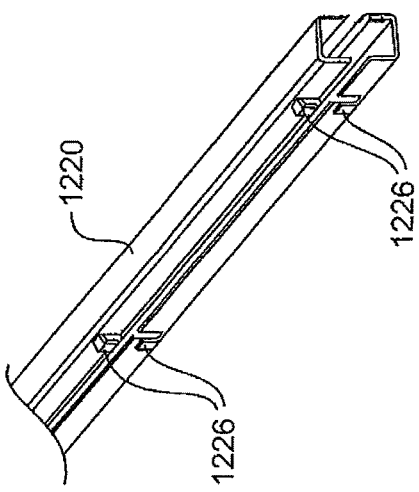
FIG. 78 shows a walking beam.
Figure 79:
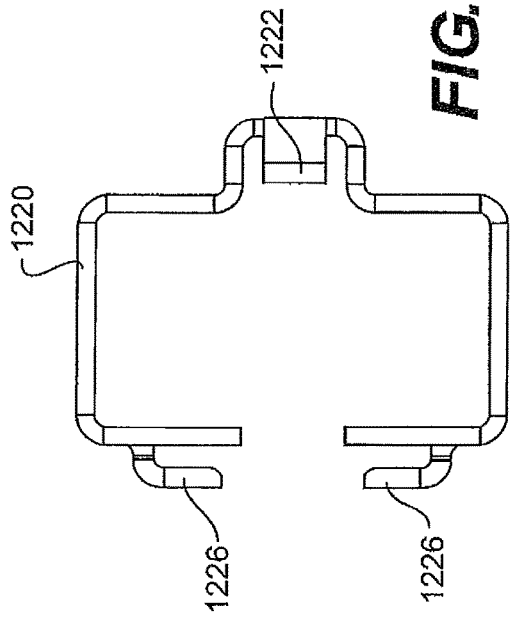
FIG. 79 shows a walking beam.
Figure 77:
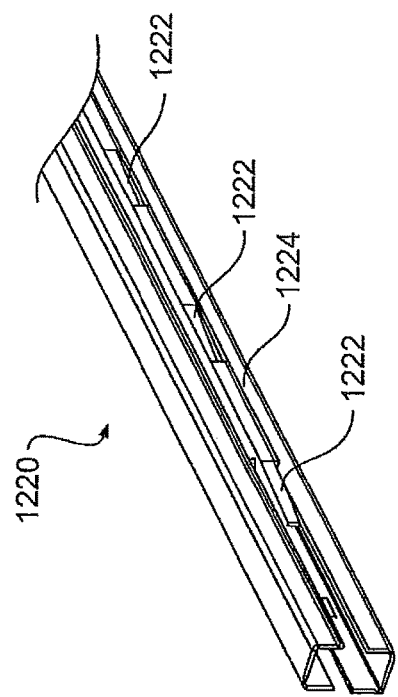
FIG. 77 shows a walking beam.

FIGS. 77-85 show individual elements. How these elements fit together and operate are shown and described with respect to FIGS. 86-98. FIGS. 77-79 show a walking beam 1220. The walking beam 1220 includes pusher arms 1222 mounted to a side 1224 of the walking beam 1220. The walking beam 1220 also has brackets 1226 mounted to one side. FIGS. 80-81 show a walking beam pusher 1228 which includes pusher arms 1230.

Figure 82:
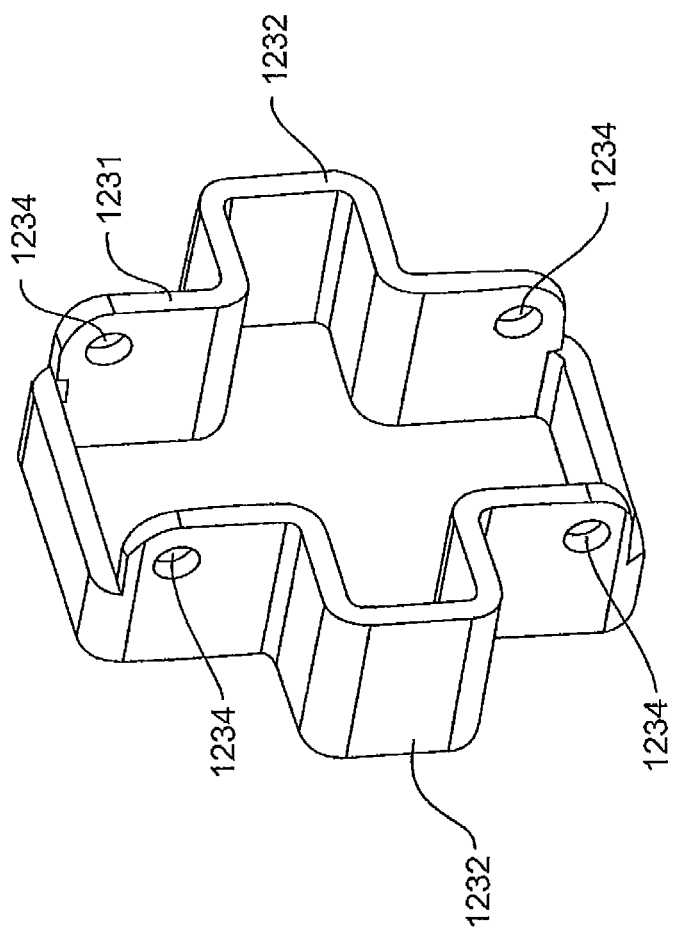
FIG. 82 shows a punch ring.
Figure 83:
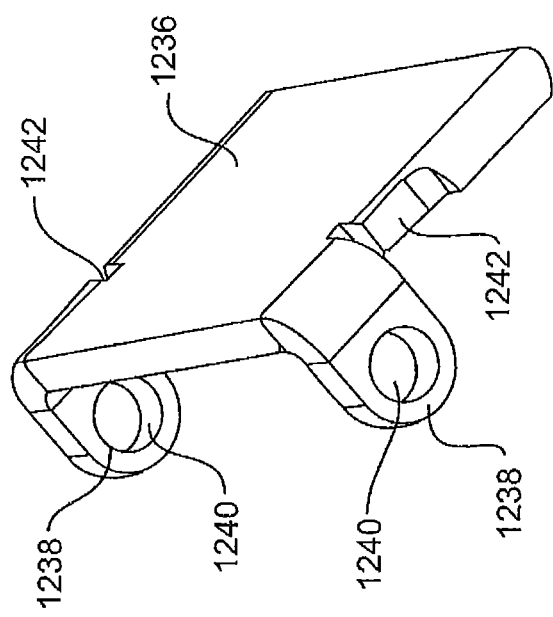
FIG. 83 shows a punch door.
Figure 84:
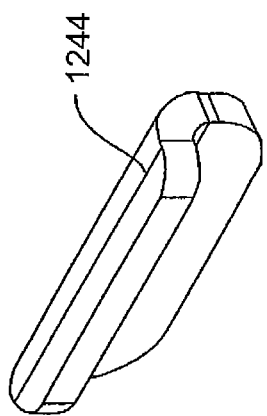
FIG. 84 shows a door wedge.

FIG. 82 shows a punch ring 1231. The punch ring 1231 includes U-shaped protrusions 1232 and connecting holes 1234. FIG. 83, shows a punch door 1236 that mounts to the punch ring 1231. The punch door 1236 includes eye brackets 1238, holes 1240 in the eye brackets 1238 and slots 1242. FIG. 84 shows a door wedge 1244. FIG. 85 shows a clip advancer 1246 having a pushing member 1248.

FIG. 86 shows the elements of the second embodiment fit in an outer tube 1054. The position of the element is an initial or start position. The jaws 1004 are fit onto the outer tube in a similar manner as described with respect to the first embodiment. Door pins 1250 are shown connecting the punch doors 1236 with the punch ring 1231. A clip 100 is shown behind the punch doors 1236.

FIG. 87 shows the clip advancer 1246 pushing the first clip 100 through the punch ring 1231 and punch doors 1236. The clip opens by virtue of a camming action between the wedges 1244 and the clip 100 passing by the wedges 1244.

Figure 90:
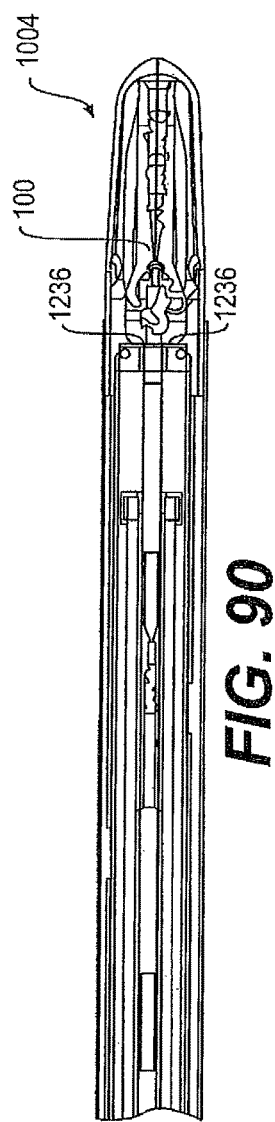
FIG. 90 shows punch doors fully closed against punch ring.
Figure 91:
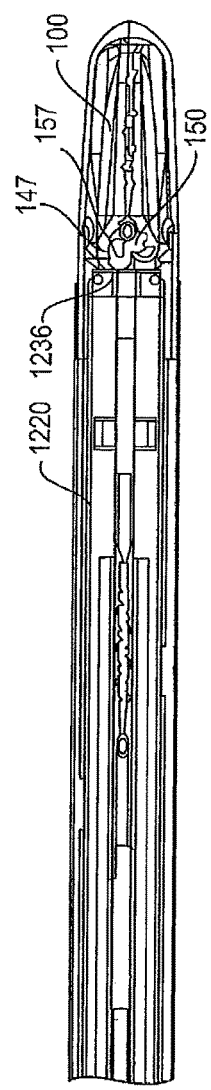
FIG. 91 shows once the doors are closed the walking beam advances again and latches the clip.
Figure 92:
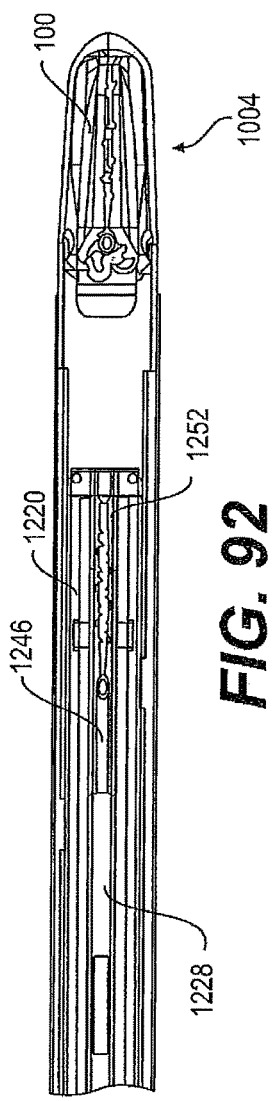
FIG. 92 shows the walking beam and clip advancers return to their start position.

FIG. 88 shows the walking beam 1220 and clip advancers 1246 moving forward toward the jaws 1004 to partially advance the clip 100 over the vessel or tissue 1002 (not shown in FIG. 87.). In FIG. 89 the walking beam 1229 has stopped. The clip advancers 1246 push the clip 100 the final distance into the jaws 1004. The clip 100 is pushed through the punch doors 1236 and wedges 1244. The punch doors 1236 closed as they are spring loaded to do so. In FIG. 90, the clip 100 is fully in the jaws 1004 and the punch doors 1236 are closed behind the clip 100. In FIG. 91, the walking beam 1220 advances to lock the clip 100. The walking beam 1220 has moved forward and presses the punch doors 1236 against the buttress body 150 of the clip 100 causing the detent 157 to fit and lock into the notch 147. In FIG. 92, the walking beam 1220, the clip advancers 1246 have returned to the start positions. The second clip 1084 and any other clips have advanced one position by the stationary walking beam pusher 1228. The clip 100 may be released when the jaws 1004 are opened.

Figure 93:
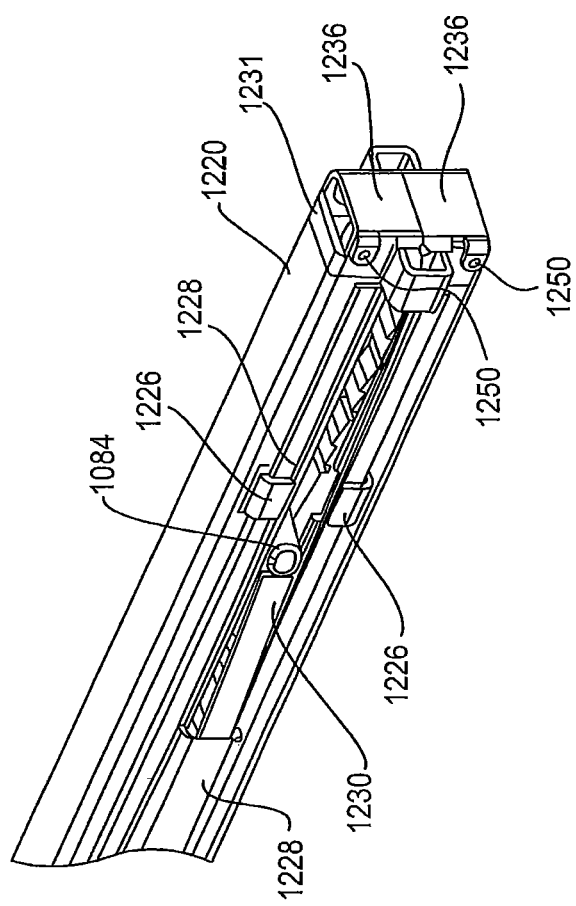
FIG. 93 shows a start of clip advance and latch.

FIGS. 93-97 illustrate the process described above but with some of the components removed for clarity. In FIG. 93, clip 100 starts to advance by the pusher arm 1230 of the walking beam pusher 1228 pushing against the second clip 1084. The brackets 1226 on the walking beam 1220 are shown. The brackets 1226 allow the walking beam pusher 1228 to slidably connect to the walking beam 1220. The punch ring 1231 is visible and the punch doors 1236 are shown on the punch ring 1231. In some embodiments of the invention, the punch doors 1236 connect to the punch ring 1231 by hinge pins 1250 in the holes 1234 in the punch ring 1231 and holes 1240 in the eye brackets 1238 on the punch doors 1236.

Figure 94:
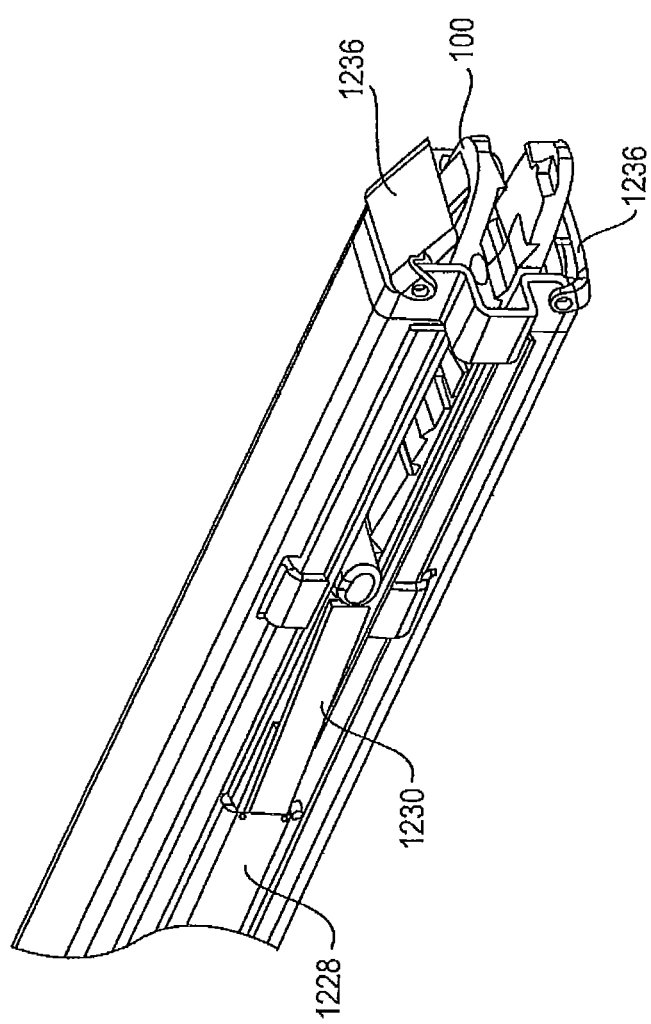
FIG. 94 shows a clip pushed through punch doors.
Figure 95:
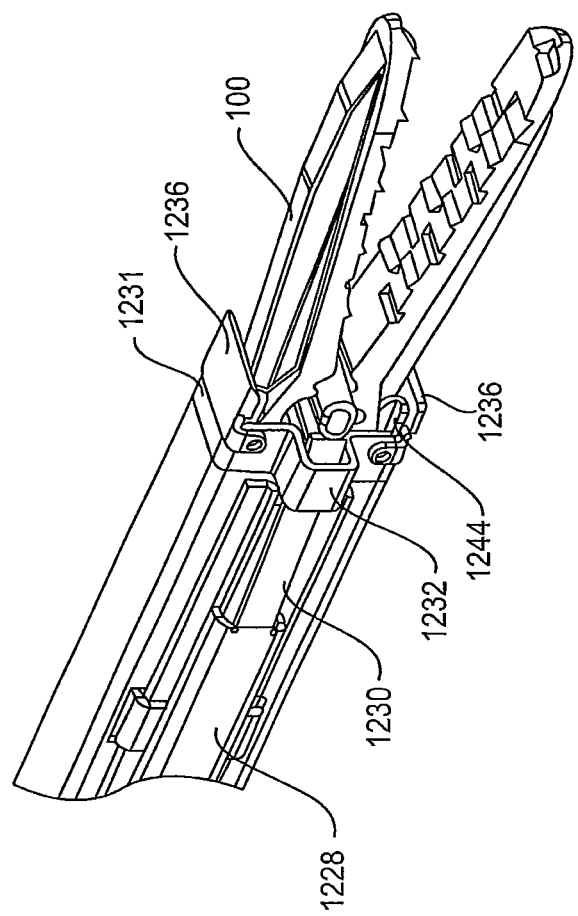
FIG. 95 shows a clip opened by wedges on punch doors.
Figure 96:
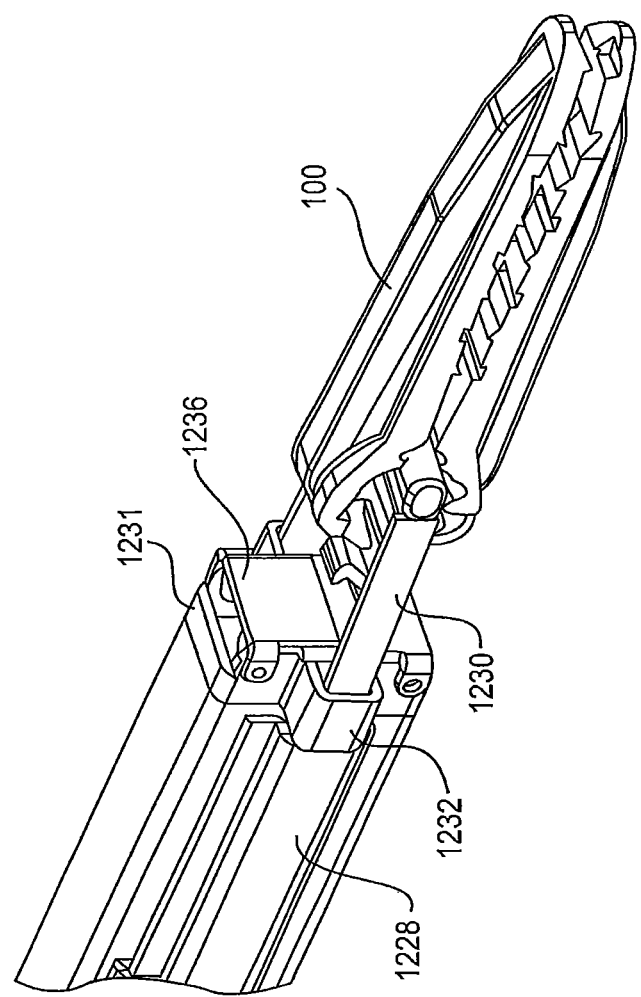
FIG. 96 shows a clip pushed out of wedge/punch doors.

FIG. 94 shows the clip 100 partially extending through the punch doors 1236. The pusher arm 1230 of the walking beam pusher 1228 is advancing the clip 100. In FIG. 95 the clip 100 is opened by the wedges 1244 as the clip 100 passes through the doors 1236. The pusher arm 1230 passes though the U-shaped protrusion 1232 of the punch ring 1231. In FIG. 96 The clip 100 has extended through the punch doors 1236. The pusher arm 1230 passes though the U-shaped protrusion 1232 of the punch ring 1231. In FIG. 97 the walking beam 1220 moves forward, but the walking beam pusher 1228 remains stationary. The forward movement of the walking beam 1220 causes the punch doors 1236 to press against the buttress body 150 and rotate the buttress body 150 to lock as the detent 157 interlocks with the notch 147. Thus, the clip 100 is locked in the closed position.

FIG. 98 is an end view of the applier 1000 where the punch doors 1236 are opened. The outer tube 1054 may be seen. The door wedges 1244 are shown in the punch ring 1231. The U-shaped protrusions 1232 are also visible. The brackets 1226 on the walking beam 1220 holding the walking beam pusher 1228 are also visible.

FIGS. 99-108 show various trigger 1013 and 1015 positions that may occur while the applier 1000 is performing various steps.

Figure 109:
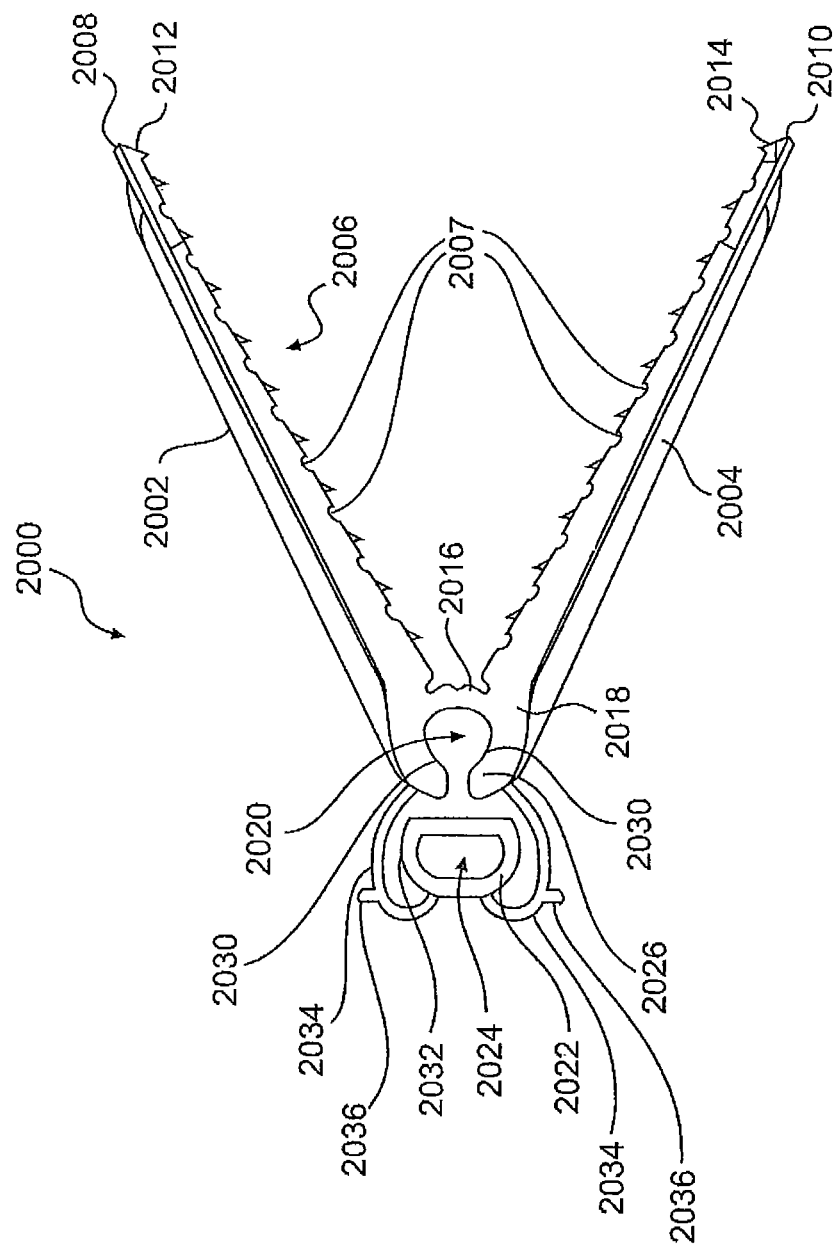
FIG. 109 illustrates a side view of the clip according to another embodiment

In another embodiment, a different clip 2000 and adapter 2040 is used. This clip 2000 and adapter 2040 is shown and described in FIGS. 109-113. FIG. 109 shows a side view of the clip 2000. The clip 2000 includes an upper leg 2002 and a lower leg 2004. Both legs 2002 and 2004 include teeth 2006 and grooves 2007. The upper leg 2002 includes an upper front end 2008 the lower leg 2004 includes a lower front end 2010. The upper front end 2008 includes an upper slanted edge 2012 and the lower front end 2010 includes a lower slanted edge 2014. The upper leg 2002 and the lower leg 2004 pivot about a hinge portion 2016 which is part of a body portion 2018.

The body portion 2018 includes a locking void 2020. The clip 2000 is locked by moving a buttress 2022 into the locking void 2020. The buttress 2022 includes a buttress void 2024. The body portion 2018 includes locking wings 2026. The locking wings 2026 help retain the buttress 2022 into the locking void 2020 when the clip 2000 is in a locking position. The buttress void 2024 includes locking interior surfaces 2030. The buttress 2022 includes locking exterior surfaces 2032. When the buttress 2022 is in the buttress void 2024, the locking interior surfaces 2030 and the locking exterior surfaces 2032 will be in contact with each other.

The buttress 2022 is attached to the body portion 2018 and the connectors 2034. The connectors 2034 are resilient and will flex to permit the movement of the buttress 2022 with respect to the body portion 2018. The connectors 2034 are equipped with projections 2036. The projections 2036 are useful when the clips 2000 are arranged in an automatic applier in a nose to tail fashion. In such an instance, the upper front end 2008 and lower front end 2010 of a clip 2000 behind a first clip 2000 will engage the projections 2036 of the clip 2000 in front.

Figure 110:
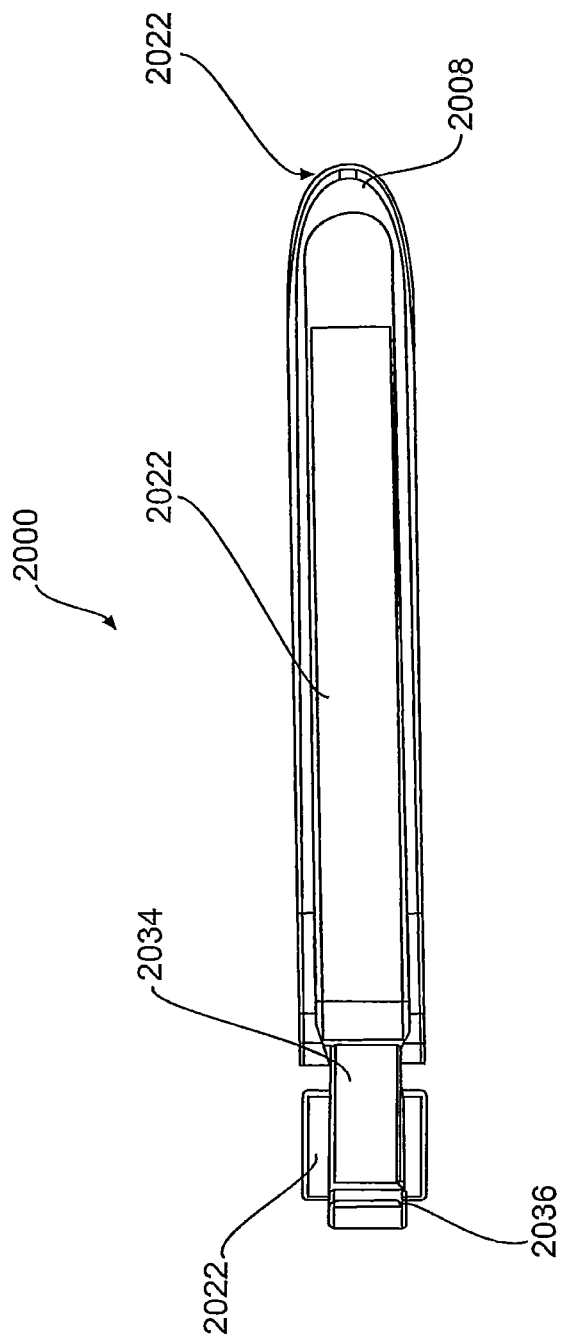
FIG. 110 illustrates a top view of the clip shown in FIG. 109.

FIG. 110 illustrates a top view of the clip 2000. The upper leg 2002 and the upper front end 2008 are visible. The connector 2034 connecting the buttress 2022 and having the projection 2036 is also shown in FIG. 110.

Figure 111:
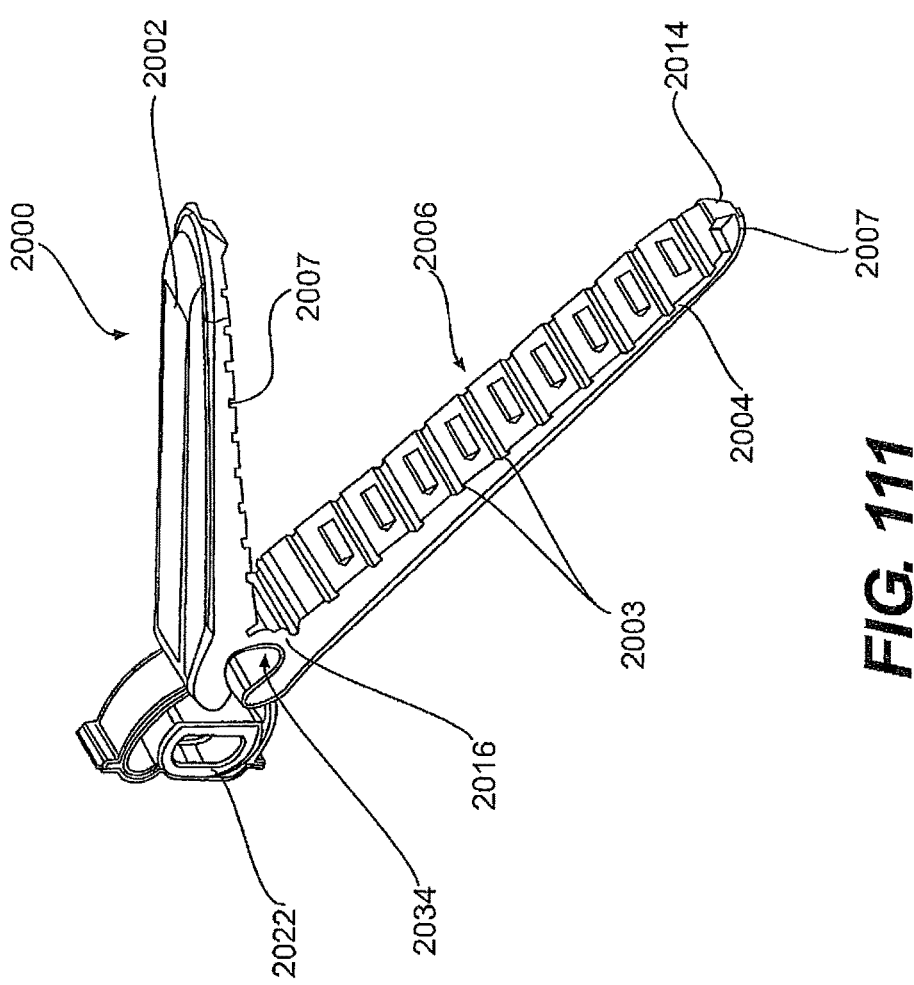
FIG. 111 illustrates an isometric view of the clip shown in FIG. 109.

FIG. 111 illustrates an isometric view of the clip 2000. The upper leg 2002, the lower leg 2004, the grooves 2007, and teeth 2006 are visible. The lower slanted edge 2014 can also be seen. The hinge portion 2016, the buttress void 2024, and the buttress 2022 are also visible in the isometric view shown in FIG. 111.

Figure 112:
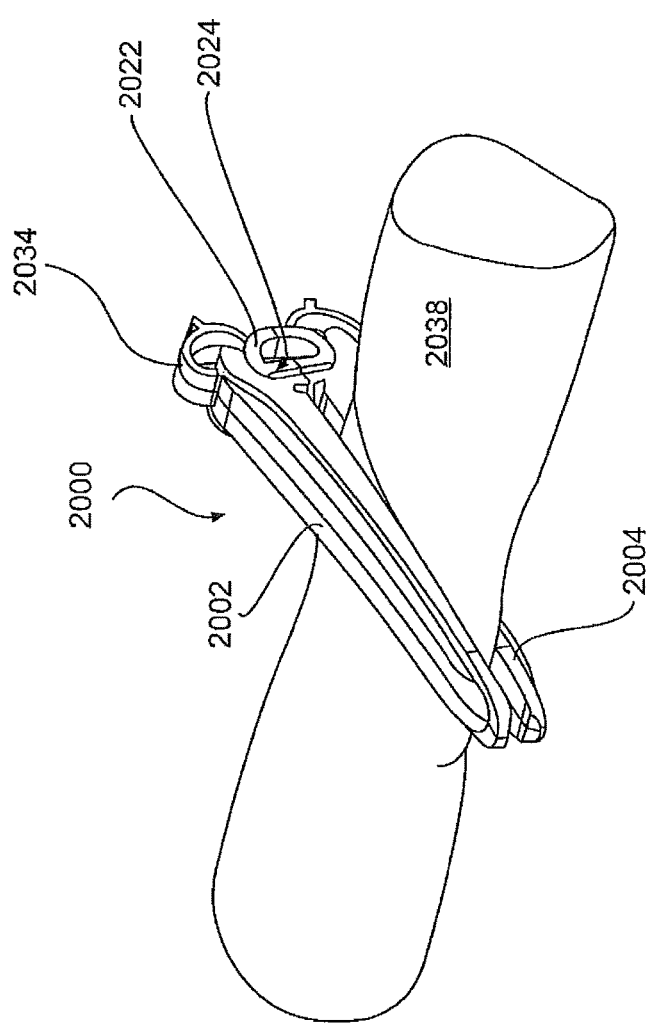
FIG. 112 illustrates an isometric view of a clip engaging a blood vessel.
Figure 113:
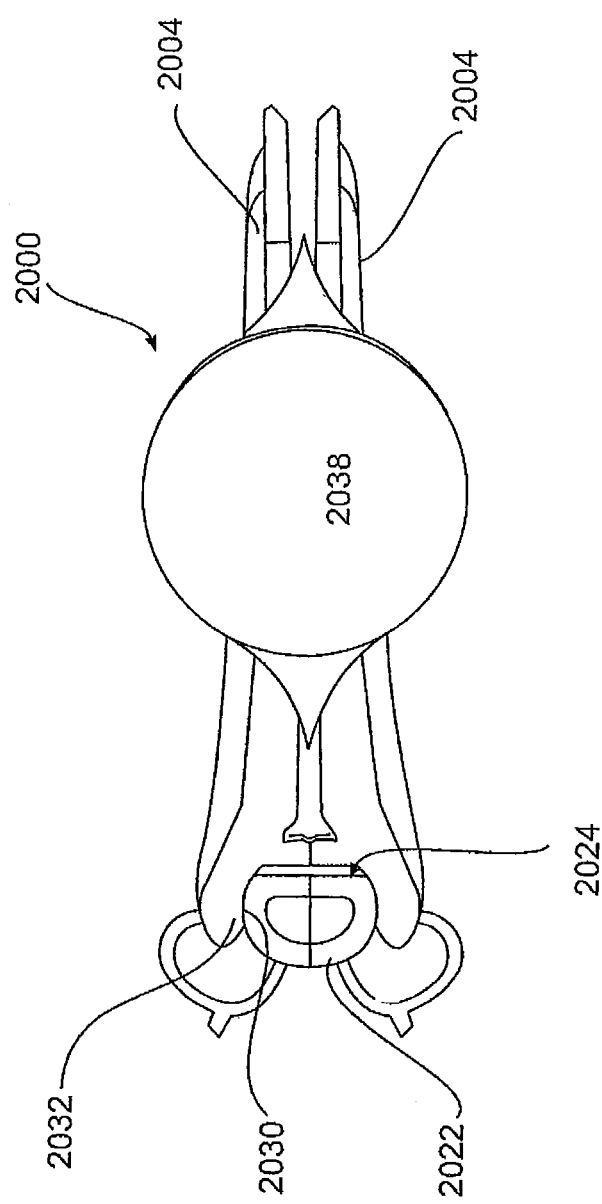
FIG. 113 illustrates a side view of a clip engaging a blood vessel.

FIGS. 112 and 113 illustrate the clip 2000 clamping onto a vessel 2038. The grooves and teeth are not shown and are removed for clarity in FIGS. 112 and 113. The vessel 2038 is clamped between the upper leg 2002 and the lower leg 2004. The buttress 2022 has been moved into the buttress avoid 2024 causing the locking interior surfaces 2030 and a locking exterior surfaces 2032 to be in contact with each other. Movement of the buttress 2022 into the buttress avoid 2024 has caused the upper leg 2002 and the lower leg 2004 to be locked in a closed position. It will be appreciated that closing of the clip 2000 will cause the hinge portion 2016 to rotate thereby enlarging the buttress avoid 2024 and allowing the buttress 2022 to be pushed or moved into the buttress void 2024 thereby locking the clip 2000 in the closed position. Once the clip 2000 is in the closed position the vessel 2028 is clamped.

Figure 114:
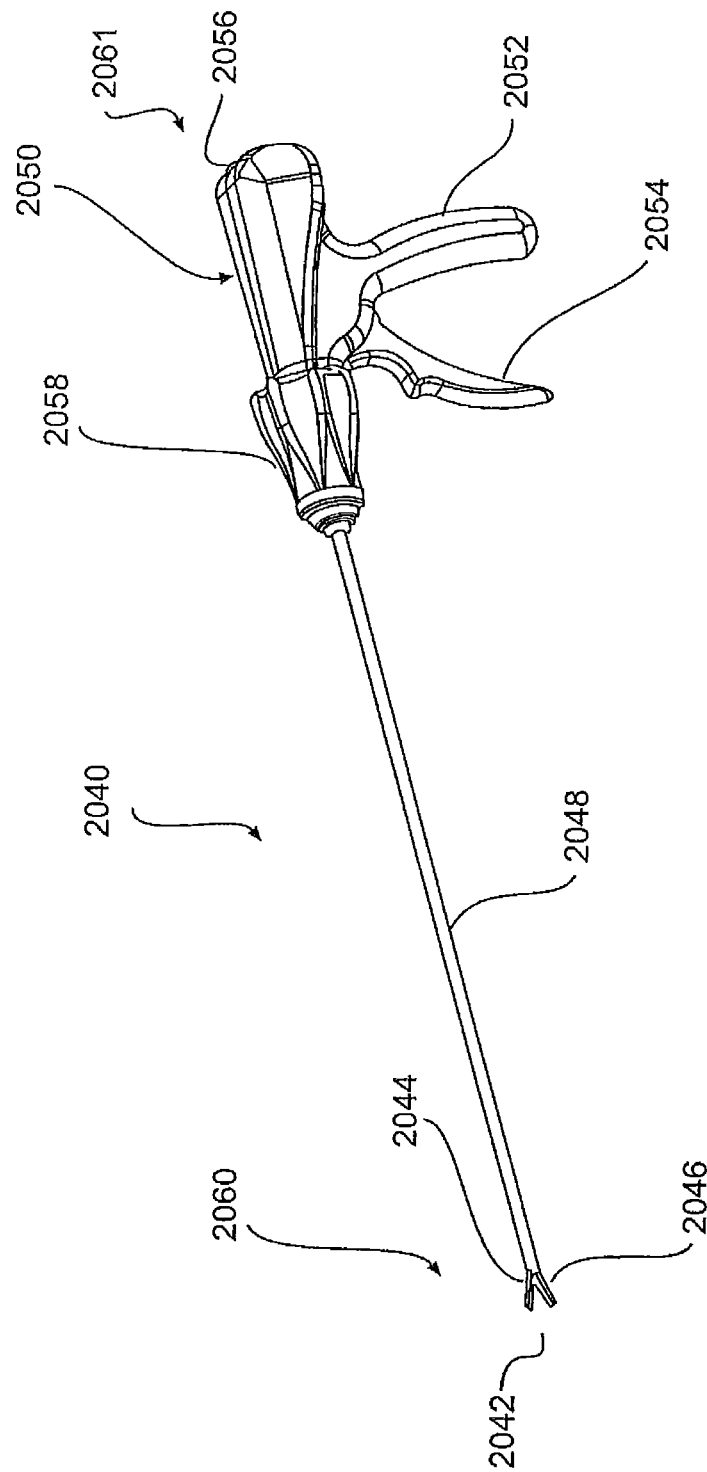
FIG. 114 is an isometric view of an applier records of in accordance with an embodiment of the invention.

FIG. 114 illustrates an automatic applier 2040. The automatic applier 2040 includes jaws 2042. The jaws 2042 including upper jaw 2044 and a lower jaw 2046 an outer tube assembly 2048 is located between the jaws 2042 and a handle assembly 2050. The handle assembly 2050 includes a handle 2052 and actuator 2054. The actuator 2054 functions and acts similar to a trigger and is pivotally connected to the handle assembly 2050. The handle assembly 2050 also includes a body 2056 and a rotator 2058. The rotator 2058 is configured to allow a user to rotate the rotator 2058 which will thereby rotate the outer tube assembly 2048 and the jaws 2042. Therefore the jaws 2042 can be oriented or rotated 360° to any orientation desired by a user. The automatic applier 2040 includes a distal end 2060 which includes the jaws 2042 and a proximal end 2061 which includes the handle assembly 2050.

Figure 115:
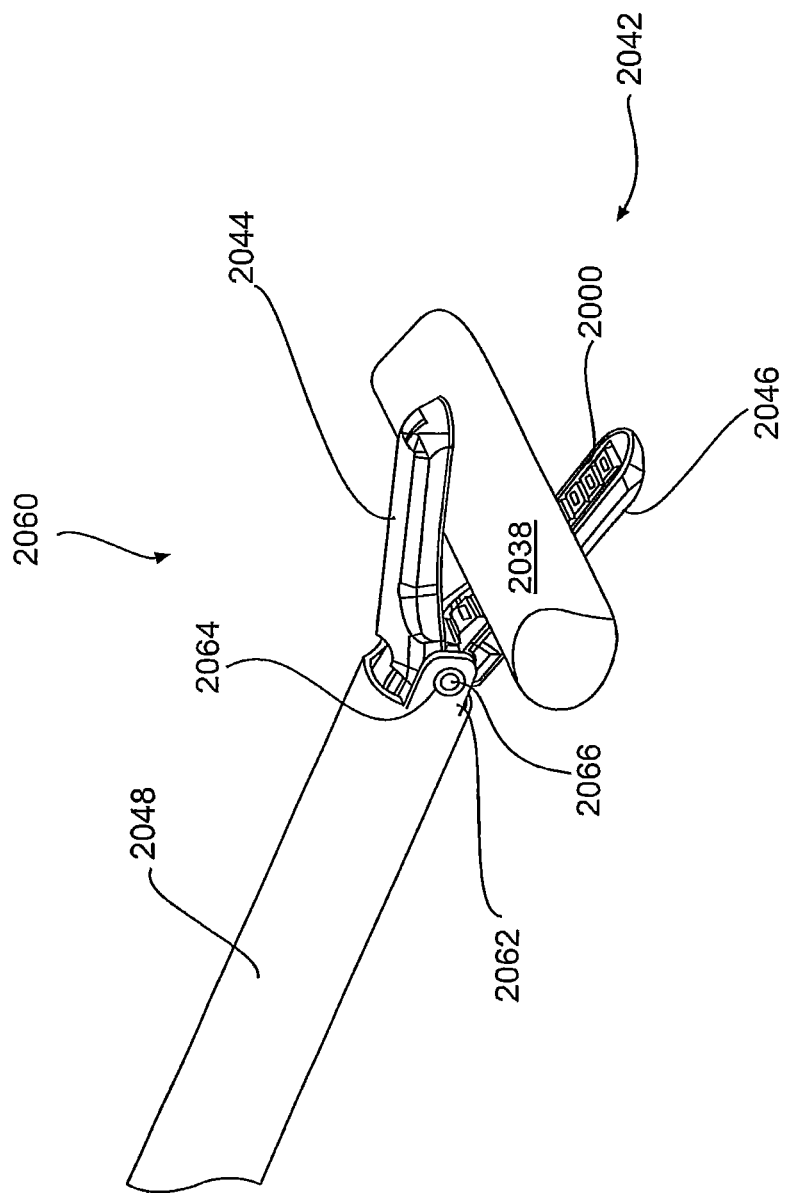
FIG. 115 is a partial isometric view of a distal end of an applier.

FIG. 115 illustrates a portion of the distal end 2060. The outer tube assembly 2048 includes bosses 2062. The bosses 2062 define holes 2064. Jaw projections 2066 extend from the jaws 2044 and 2046 outwardly through the holes 2064. The jaws 2044 and 2046 pivot about the jaw projections 2066 which pivotally connected jaws 2044 and 2046 to the outer tube assembly 2048. The jaws 2042 are shown in an open condition and contain a clip 2000. The jaws 2042 have approached flesh or a blood vessel 2038 but have not yet contacted it.

Figure 116:
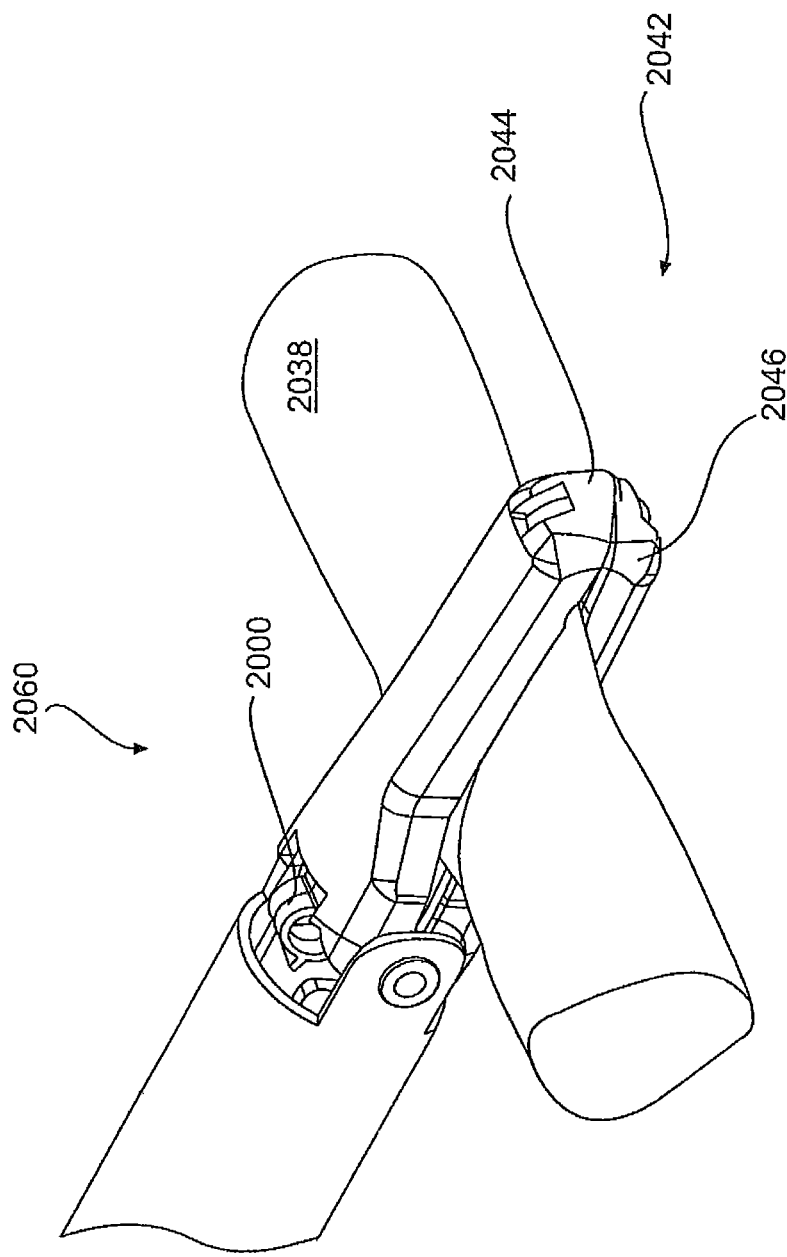
FIG. 116 is a partial isometric view of the jaws on applier engaging a blood vessel.

FIG. 116 illustrates the distal end 2060 and shows the jaws 2042, 2044, 2046 clamped on the flesh or vessel 2038. A portion of the clip 2000 can be seen within the jaws 2042. Closing the jaws 2042 is caused the clip 2000 to also be closed.

Figure 117:
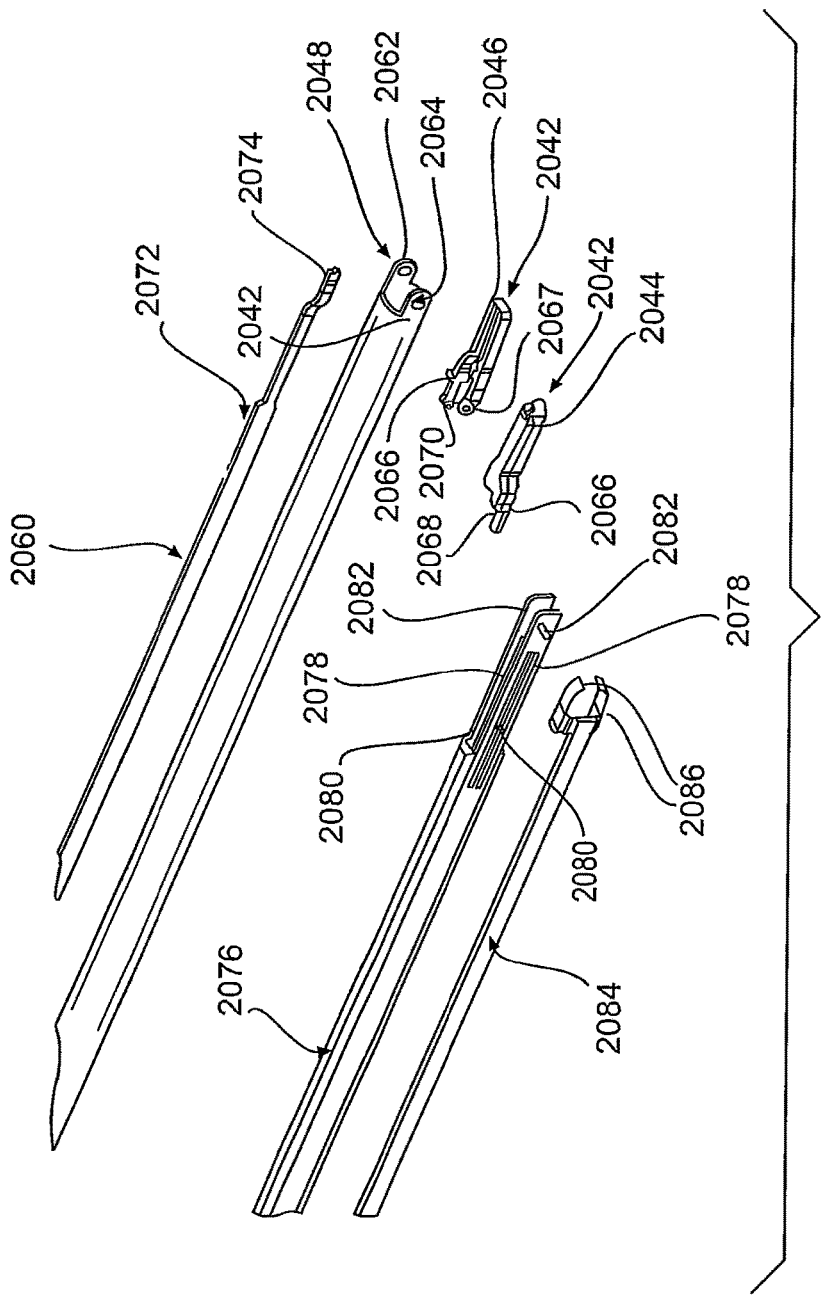
FIG. 117 is a isometric, partial, exploded view of a distal end of an applier.

FIG. 117 is an exploded isometric view of the distal end 2060. The outer tube assembly 2048 is shown along with the top jaw 2044 and lower jaw 2046. Both of the jaws 2042 are identical parts and some embodiments of the invention. In other embodiments they can be slightly different or mirror images of each other. Each jaw 2044 and 2046 includes a jaw projection 2066 that extends outward and away from the jaws 2044 and 2046. The jaw projections 2066 extend into the holes 2064 defined by the bosses 2062 and the outer tube assembly 2048. The jaws 2044 and 2046 also include a jaw arm 2068. The jaw arm 2068 defines an inward projecting a projection 2070. It is the inward pointing projection 2070 that fits within the actuation slots 2082 found on the feed tube 2076. By moving the feed tube 2076 in a distal or proximal direction, the inward projections 2070 on the jaws 2046 and 2044 pivot and cam within the slots 2082 to open and close the jaws 2042.

The feed tube 2076 further contain slots 2078 and spring fingers 2080 fit within the slots 2078. The spring fingers 2080 are useful in preventing clips 2000 (not shown in FIG. 117) from moving in a proximal direction at undesired times. The feed tube 2076 stores a stack of clips 2000 which will be discussed further below. The clip lock arm 2072 includes a clip engaging portion 2074. The clip engaging portion 2074 fits through one of the slots 2078 in the feed tube 2076. The clip engaging portion 2074 is configured to move axially so that the clip engaging portion 2074 will engage and lock a clip 2000 as will be discussed further below.

A clip advance arm 2084 is equipped with pinchers 2086. The clip advance arm 2084 also is configured to move axially and performs several functions. For example, it moves a clip 2000 forward into the jaws 2042 and also opens and closes the clip 2000 by action of the pinchers 2086 acting upon either the legs 2002, 2004 (to close the clip 2000) or on the locking wings 2026 and/or connectors 2034 to open the clip 2000. When assembled, the feed tube 2076, the clip locked arm 2072, and the clip advance arm 2084 are all fit with in the outer tube assembly 2048.

Figure 118:
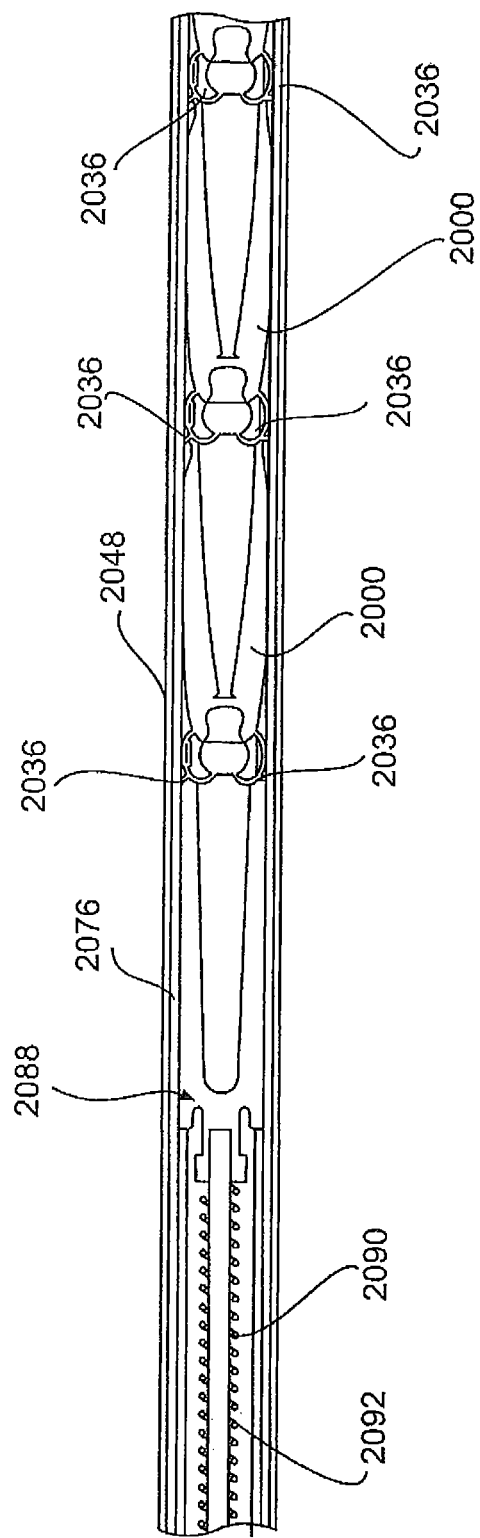
FIG. 118 is a partial cross-sectional view of a midsection of an applier.

FIG. 118 is a partial cutaway view of the outer tube assembly 2048 and feed tube 2076 containing a stack of clips 2000. Each clip 2000 has its upper and lower legs 2002, 2004 pushing on the projections 2036 of the clip 2000 in front of it. A clip stack pusher 2088 pushes on the projections 2036 of the last clip 2000 of the clip stack. This clip stack pusher 2088 is spring-loaded and has a clip advance rod 2090 surrounded by a spring 2092. The spring 2092 urges the clip stack pusher 2088 in a distal direction thus urging the clips 2000 also in a distal direction. Spring 2092 may urge against an internal portion of the handle assembly 2050 as can be appreciated by one of ordinary skill the art after viewing this disclosure.

Figure 119:
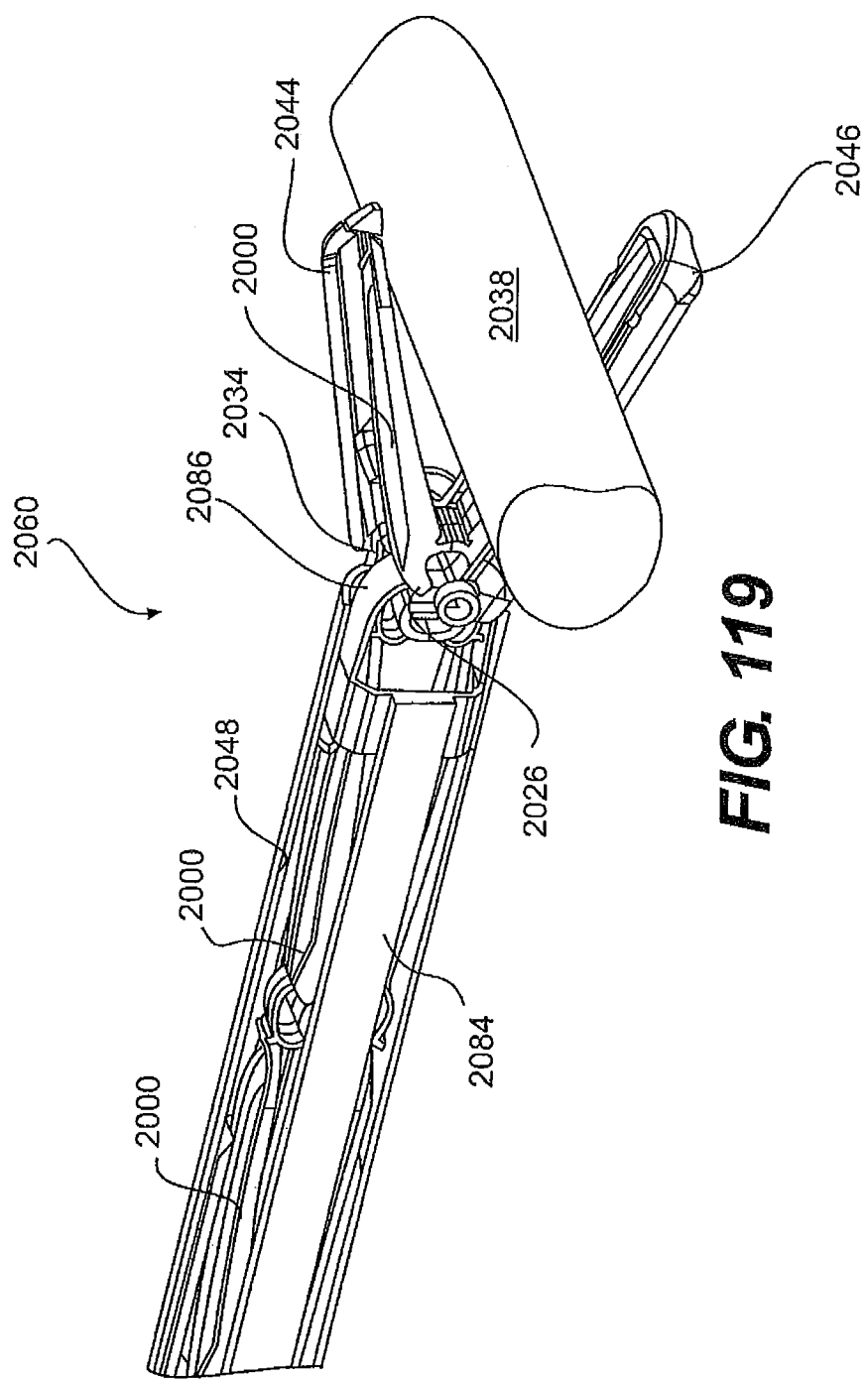
FIGS. 119-126 are isometric, cutaway views of the distal end of an applier.

FIG. 119 shows the distal portion 2060 including the upper jaw 2044 and the lower jaw 2046. The jaws 2044 and 2046 are open and about to close over a tissue or blood vessel 2038. A clip 2000 is shown to be in the jaws 2044 and 2046 and is also in the open position. The pinchers 2086 of the clip advance arm 2084 have moved forward and are contacting the locking wings 2026 and connectors 2034 of the clip 2000. The pinching pressure placed on the connectors 2034 biases the jaws 2044 and 2046 to be open. The outer tube assembly 2048 is partially cutaway to expose internal components. The clips 2000 contained within the outer tube assembly 2048 are also shown.

Figure 120:
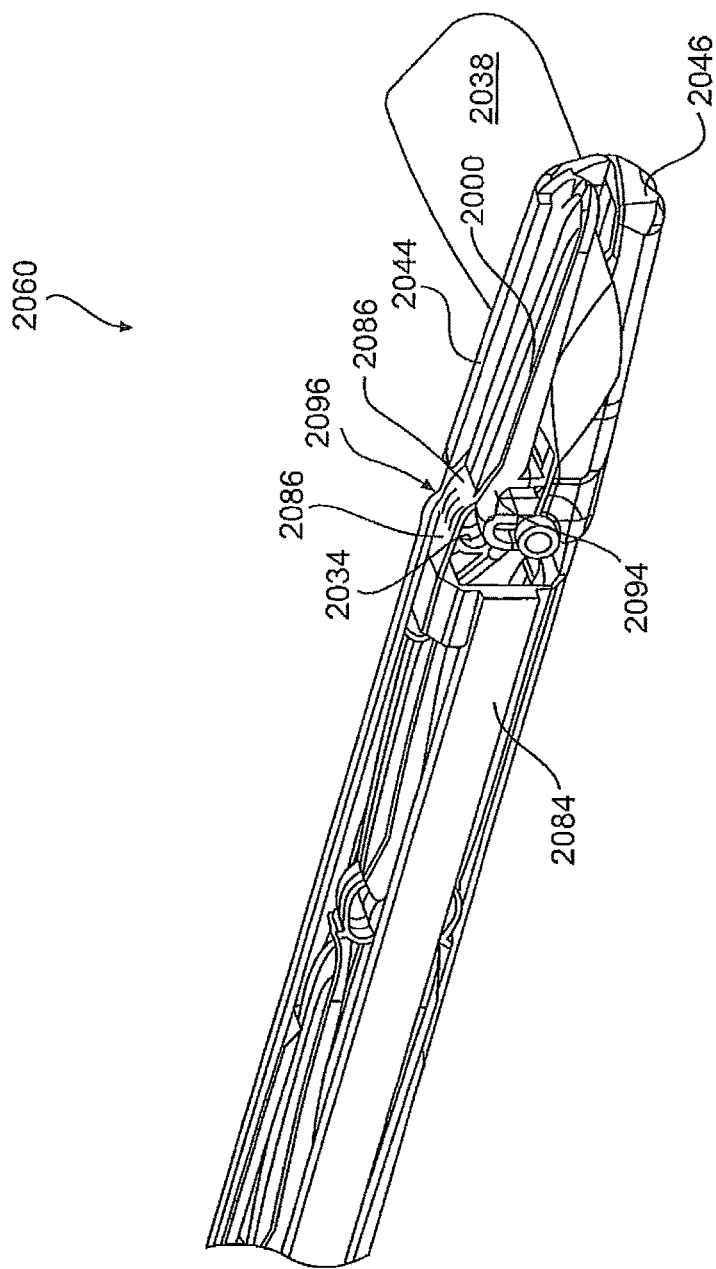

In FIG. 120 the distal portion 2060 is illustrated again in a cutaway view. The jaws 2044 and 2046 are now in a closed position clamping the tissue or blood vessel 2038. In order for the jaws 2044 and 2046 to close, the feed tube 2076 has moved to a proximate position. However the feed tube 2076 is not shown in FIG. 120. The clip 2000 and is also in the clamp position and the connectors 2034 of the clamp are flexing the pinchers 2086 of the clip advance arm 2084. The flex marks 2096 on the pinchers 2086 illustrates this. The broken line region 2094 of the pinchers 2086 also illustrates the interference between the clip 2000 and the pinchers 2086. As a result of this interference, the clip 2000 and the pinchers 2086 will flex.

Figure 121:
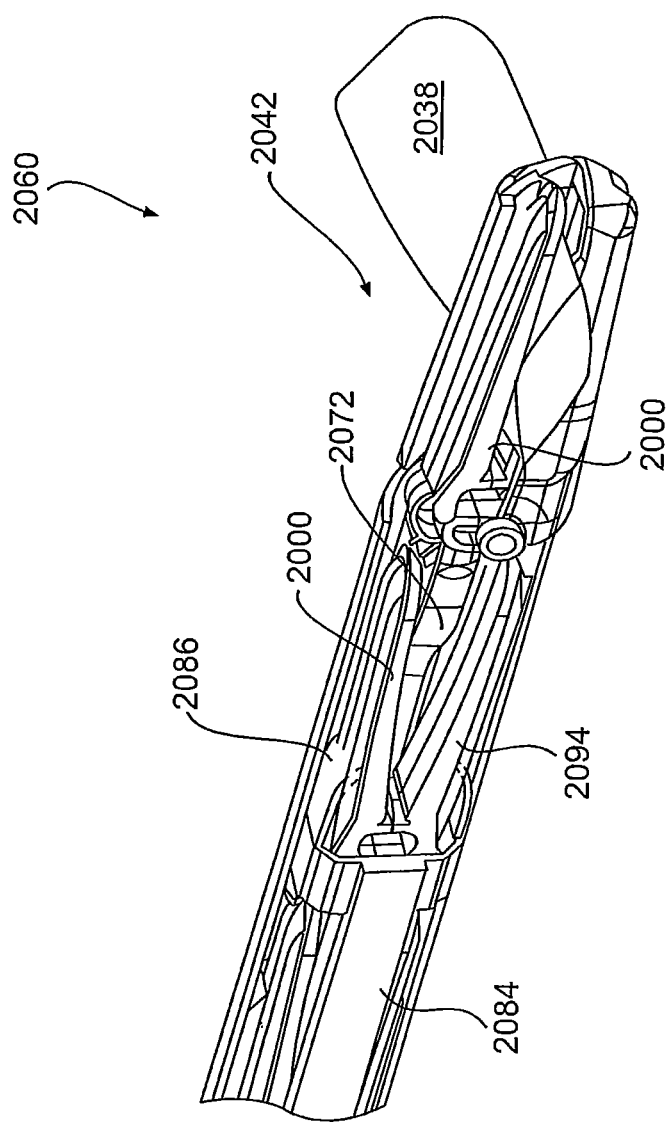

FIG. 121 shows the advance arm 2084 moving back to a proximal position to engage a second clip 2000. Again, the broken line region 2094 represents the interference fit between the clip 2000 and the pinchers 2086 of the clip advance arm 2084. Both the clip 2000 and the pinchers 2086 will flex to accommodate the interference. The second clip 2000 is prevented from moving back in a proximal direction by the rearward movement of the pinchers 2086 by the spring fingers 2080 (best shown in FIG. 117) on the feed tube 2076. The clip locked arm 2072 starts to advance toward the clip 2000 in the jaws 2042. The clip 2000 and the jaws 2042 are clamped onto the vessel 2038, however the clip 2000 is not yet locked in the clamping or closed position.

Figure 122:
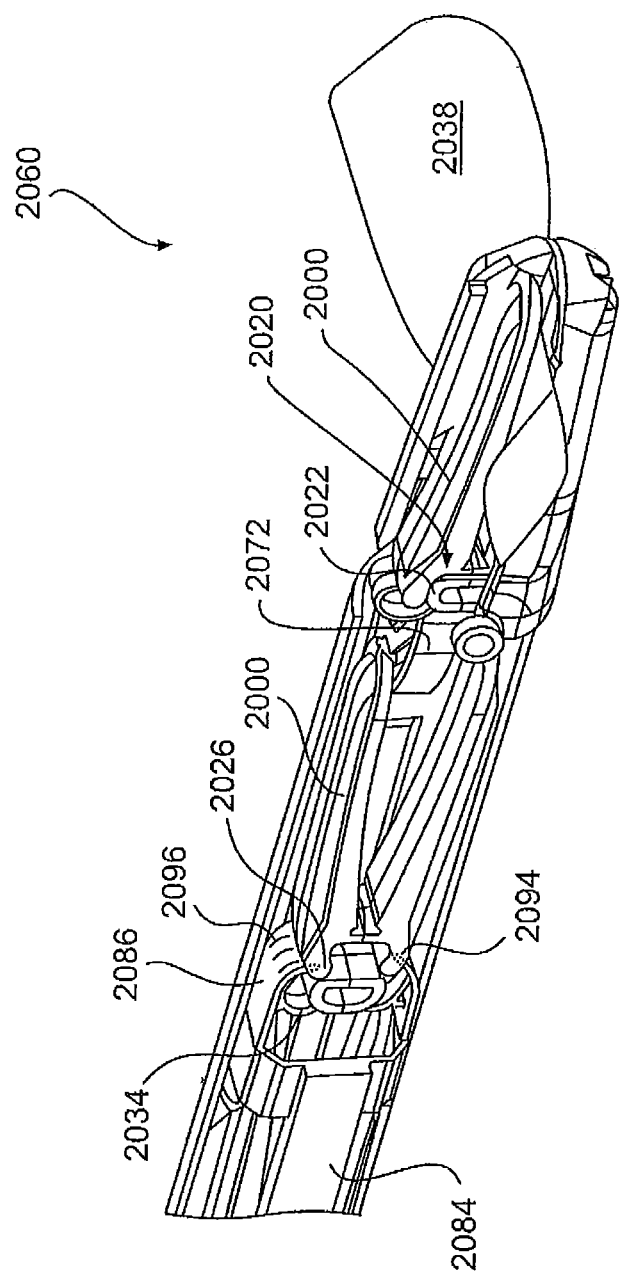

FIG. 122 illustrates the distal end 2060 cutaway view. The clip advance arm 2084 has moved fully back or in the full proximal position and is now pinching the connectors 2034 and/or locking wings 2026 thereby urging the clip 2002 to move to an open position. Broken line region 2094 on the pinchers 2086 illustrates interference fit between the pinchers 2086 and the clip 2000 and the flex portion 2096 of the pinchers 2086 also illustrates stress on the pinchers 2086 to open. Thus the pinchers 2086 and the clip 2000 will flex to accommodate this interference fit. The clip lock arm 2072 has moved distally forward and has engaged and moved the buttress 2022 to push the buttress 2022 into the locking void 2020 to lock the clip 2000 onto the vessel 2038.

Figure 123:
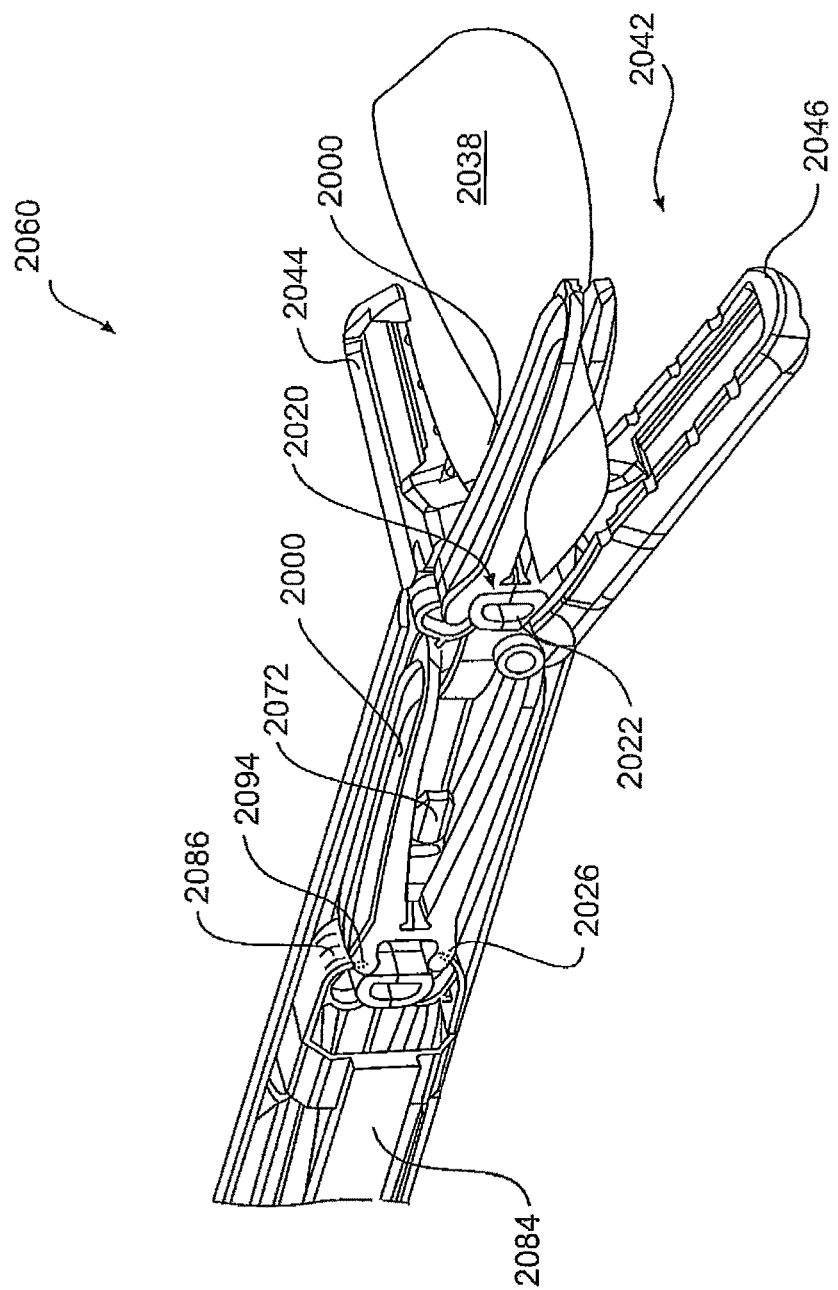

FIG. 123 illustrates the distal portion 2060 in a cutaway view. The feed tube 2076 pushes forward or distally thereby opening the jaws 2042, 2044, 2046 to release the locked clip 2000 and vessel 2038. The clip lock arm 2072 returns to its initial position. The clip advance arm 2084 remains in its pulled back or proximal position. The pinchers 2086 and the locking wings 2026 of the second clip 2000 are in an interference fit as indicated by the broken line section 2094. Thus the clip 20 and the pinchers 2086 will flex to accommodate this fit. The buttress 2022 is still in the locking void 2020 causing the clip 2000 now exiting the jaws 2042 to remain locked on the vessel 2038.

Figure 124:
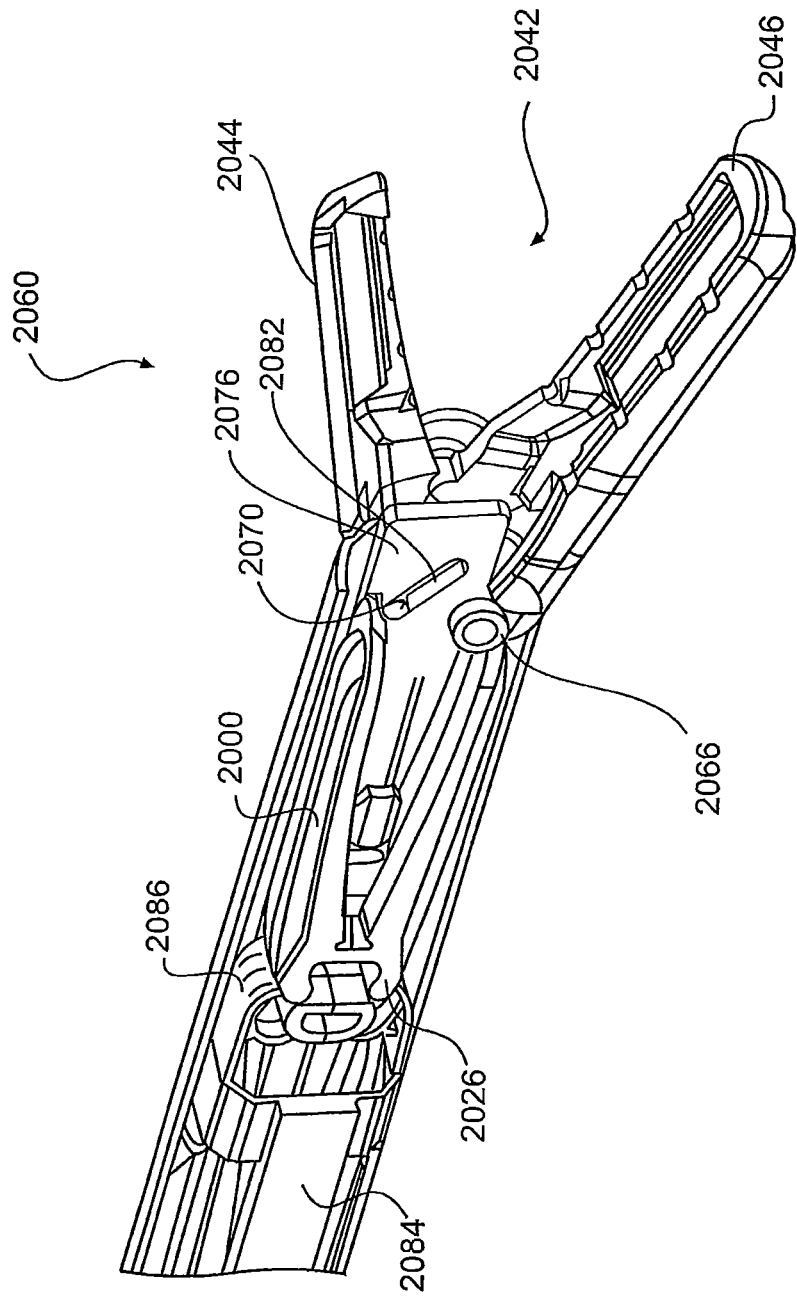

FIG. 124 illustrates the distal portion 2060 in a cutaway view. The clip 2000 and vessel 2038 are now clear of the jaws 2042 and are therefore not shown in FIG. 124. The clip advance arm 2084 now pushes the next clip 2000 distally or forward into the jaws 2042. The jaw projection 2066 of jaw 2046 is shown, as well as part of the feed tube 2076 and the actuation slots 2082 containing the actuation projection 2070 attached to jaw 2044.

Figure 125:
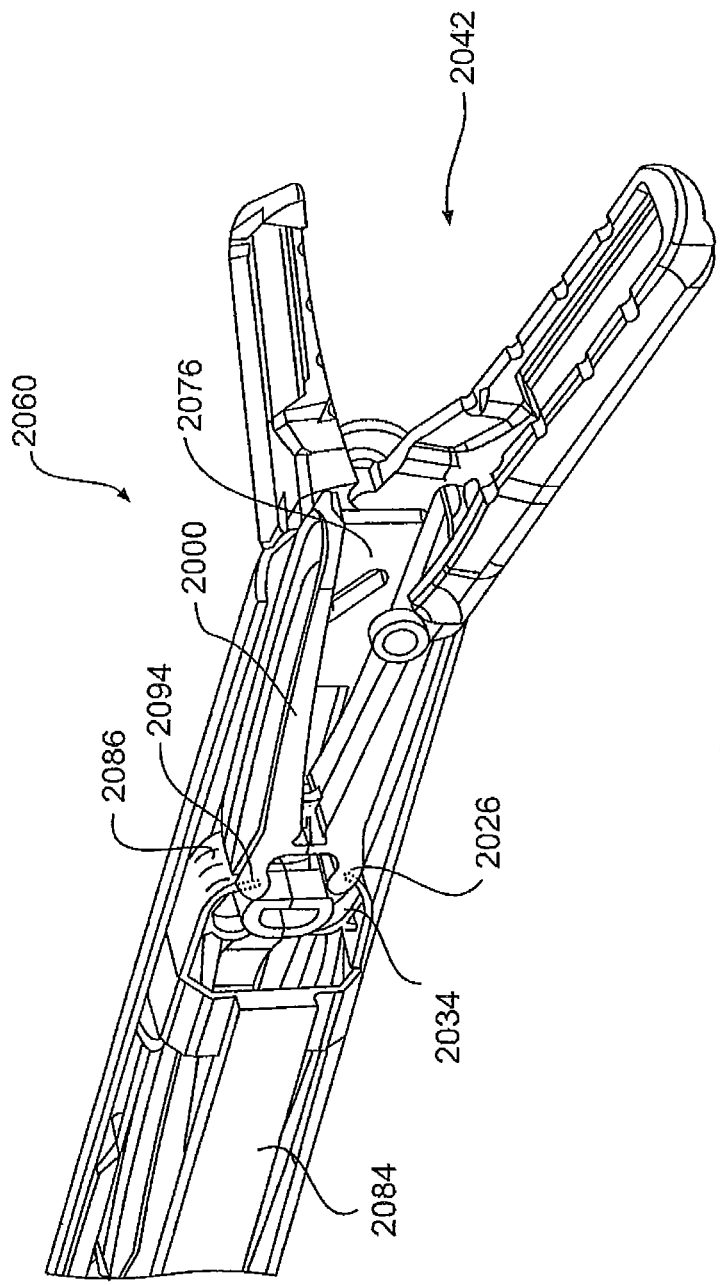

FIG. 125 illustrates the distal portion 2060 in a cutaway view. The clip advance arm 2084 moves forward or distally to push the clip 2000 into the jaws 2042. At the same time, the pinchers 2086 apply force on to the locking wings 2026 and connectors 2034 to cause the clip 2000 to open as it enters the jaws 2042. As the clip advance arm 2084 moves forward or distally, the clips 2000 and the clip stack move forward under the spring tension from the clip stack pusher 2088 (best shown in FIG. 118).

Figure 126:
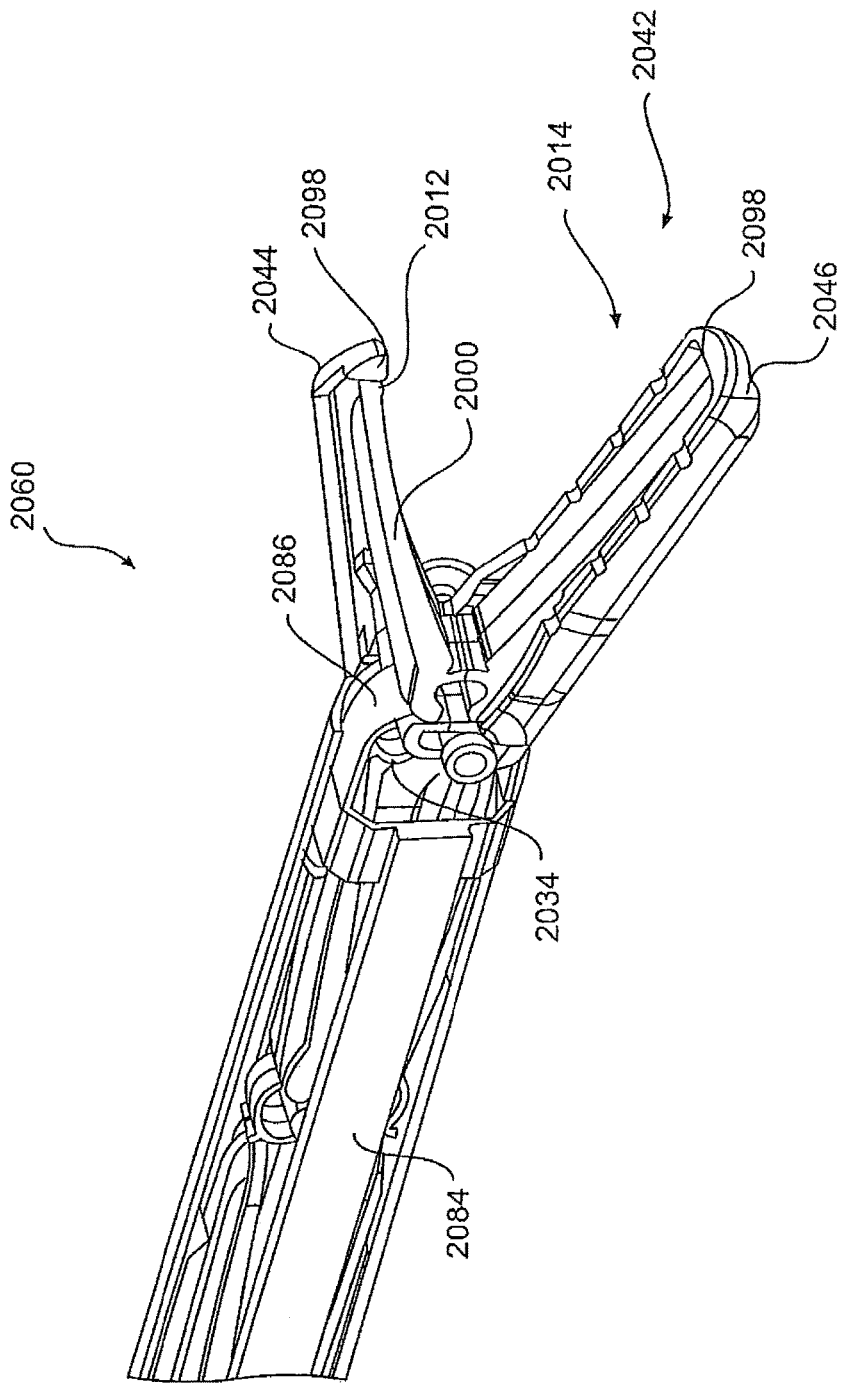

FIG. 126 illustrates the distal portion 2060 in a cutaway view. The second clip 2000 and is fully advanced into the jaws 2042 by the pinchers 2086 of the clip advance arm 2084. The connectors 2034 are under pinching pressure from the pinchers 2086 causing the clip 2000 to be an open position. The upper slanted edge 2012 of the clip 2000 is fit into a void or pocket that is defined at least in part by the slanted edge 2098 of the upper jaw 2044. Similarly the lower slanted edge 2014 of the clip 2000 has fit into a void or pocket defined at least in part by the slanted edge 2098 of lower jaw 2046. By retaining the clip 2000 in this way, the clip 2000 can be manipulated without coming out of the jaws 2042 at undesired times.

Figure 127:
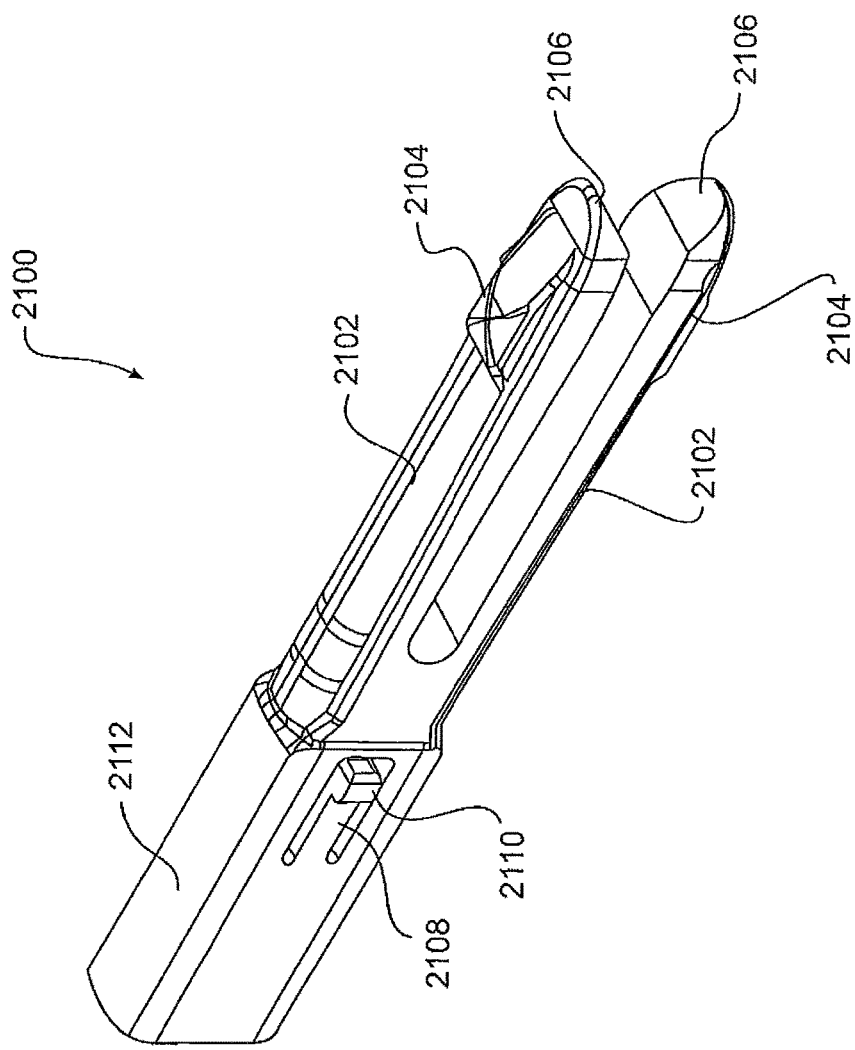
FIG. 127 is an isometric view of a clip stick pusher.
Figure 128:
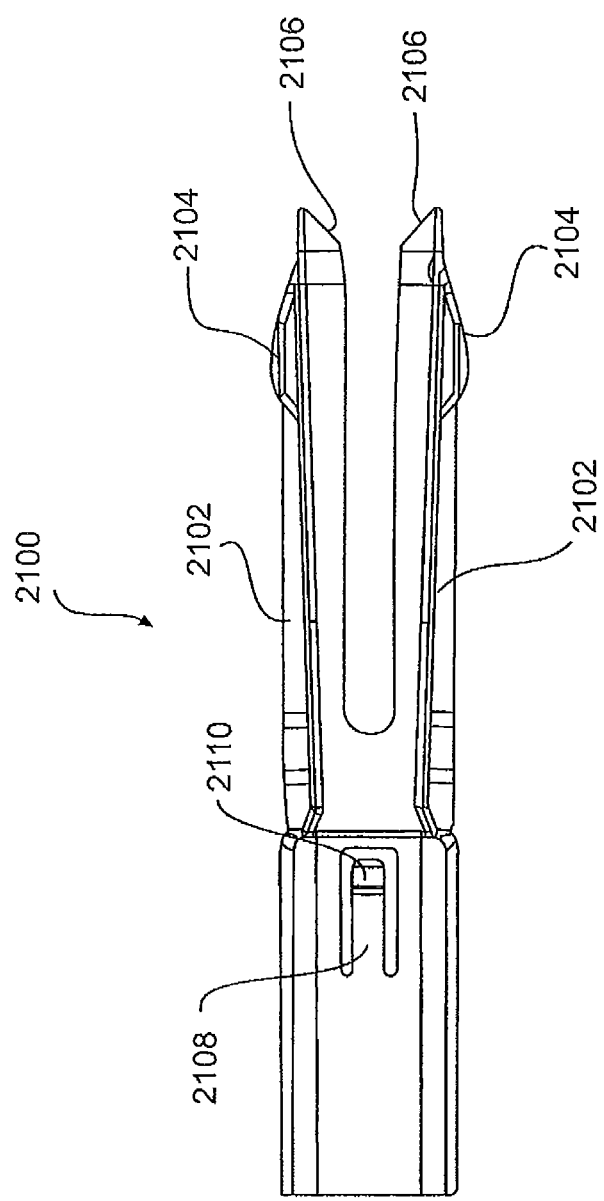
FIG. 128 is a side view of a clip stack pusher.
Figure 129B:
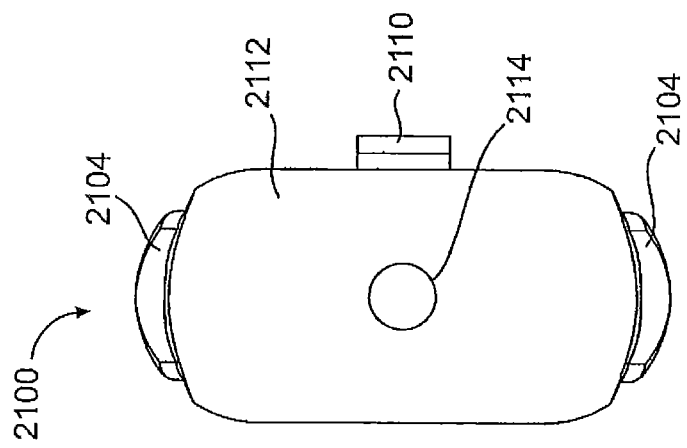
FIGS. 129A and 129B are front and rear views of a clip stick pusher.
Figure 129A:
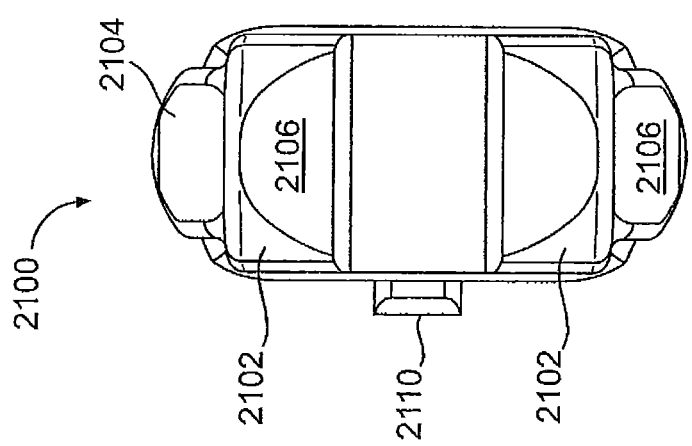

FIG. 127 is an isometric view, FIG. 128 is a side view, FIGS. 129A and 129B are front and rear views of a clip pusher 2100 in accordance with another embodiment of the invention. FIGS. 127-138 illustrate a variation of the embodiments described above. The embodiment shown in FIGS. 127-138 is very similar to the embodiments described above and differ in geometry and in operation as described below. Where features are not described it may be assumed that the embodiment operates in a manner similar to that described above unless the FIGS. show otherwise.

The clip pusher 2100 includes a spring arms 2102 and projections 2104 which may aid in moving the clip pusher 2100 through the feed tube 2076. The projections 2104 may include pushing surfaces 2106, which may be configured to push a clip 2000 forward. The clip pusher 2100 includes spring fingers 2108 terminated with projections 2110. In some embodiments of the invention, the projections 2110 aid in limiting the movement of the clip pusher 2100 when it is desired for the clip pusher 2100 to remain stationary. In some embodiments of the invention, at certain times, the projections 2110 will be moved inward by flexing the spring fingers 2108 when it is desired to move the clip pusher 2100. In some embodiments, the body 2112, the projections 2110, the spring fingers 2108, the projections 2104, and the spring arms 2102 may be made of a single material and are unified. In other embodiments, they may be made of separate parts. FIG. 129B illustrates a hole 2114 located in the body 2112 for receiving a clip advance rod 2090 (best shown in FIG. 118).

Figure 130:
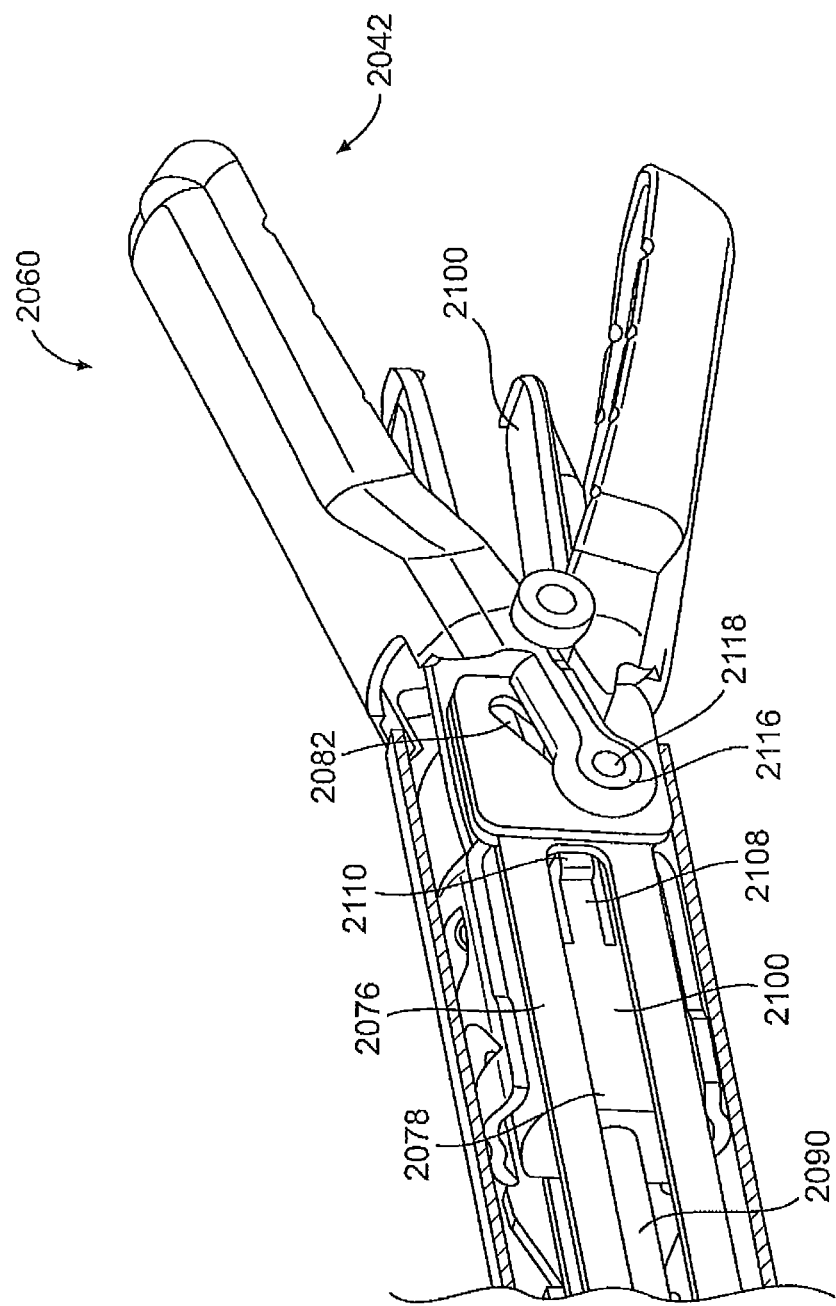
FIG. 130 is a partial cutaway distal view of an applier.

FIG. 130 is an isometric, cutaway view of the distal end 2060 according to another embodiment. The feed tube 2076 is shown having slots 2078. The projection 2110 on the spring finger 2108 has stopped the clip pusher 2100 from further moving distally or forward. Thus, when there are no clips 2000 in the feed tube 2076, the clip pusher 2100 will move partially into the jaws 2042 but will be stopped by the projections 2110 (one on each side). The clip advance rod 2090 can be seen attached to the clip pusher 2100. The spring is not shown in order to avoid overcrowding figure. The jaw boss 2116 is shown with the jaw projection 2118 in the jaw boss 2116 providing a camming projection for the jaws 2042 when the projection 2118 moves through the actuation slot 2082.

Figure 131:
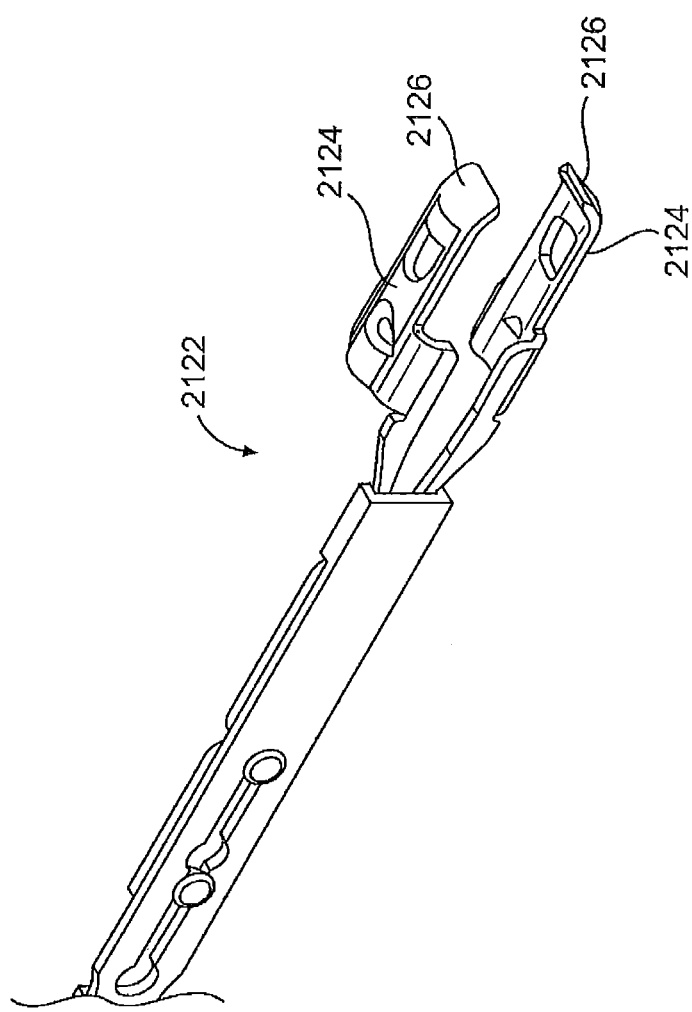
FIG. 131 is a partial, perspective view of the distal end of a cam finger assembly.

FIG. 131 is a perspective view of a cam finger assembly 2122. The cam finger assembly 2122 includes cam fingers 2124 and cam surfaces 2126. The cam surfaces contact the clip 2000 to push it forward.

Figure 132:
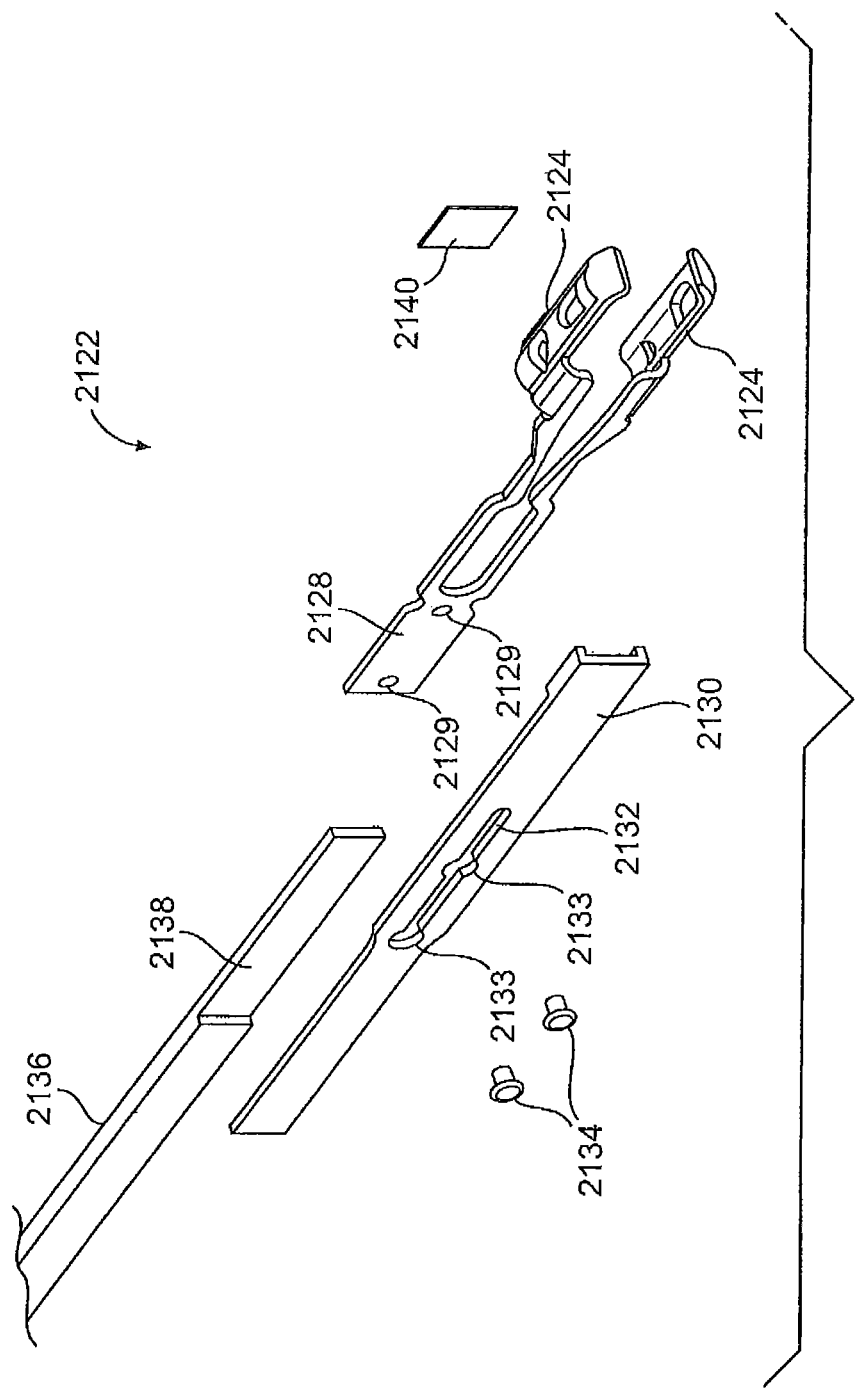
FIG. 132 is a partial, exploded view of a cam finger assembly.

FIG. 132 is an isometric, exploded view of the cam finger assembly 2122. The cam finger assembly 2122 includes the cam fingers 2124, and the unified portion 2128. The unified portion 2128 has holes 2129 to accept fasteners 2134. A cam finger base 2130 attaches to the unified portion 2128 and contacts the clip advance arm 2136. The clip advance arm 2136 has a notch 2138 for interfacing with the cam finger base 2130. The cam finger base 2130 has a slot 2132 including to larger diameter portions 2133. The fasteners 2134 attach the cam finger base 2130 to the unified portion 2128 while still being able to slide within the slot 2132. The larger diameter portions 2133 may align with the holes 2129 in the unified portion 2128. A cam finger shim 2140 is also shown.

Figure 133:
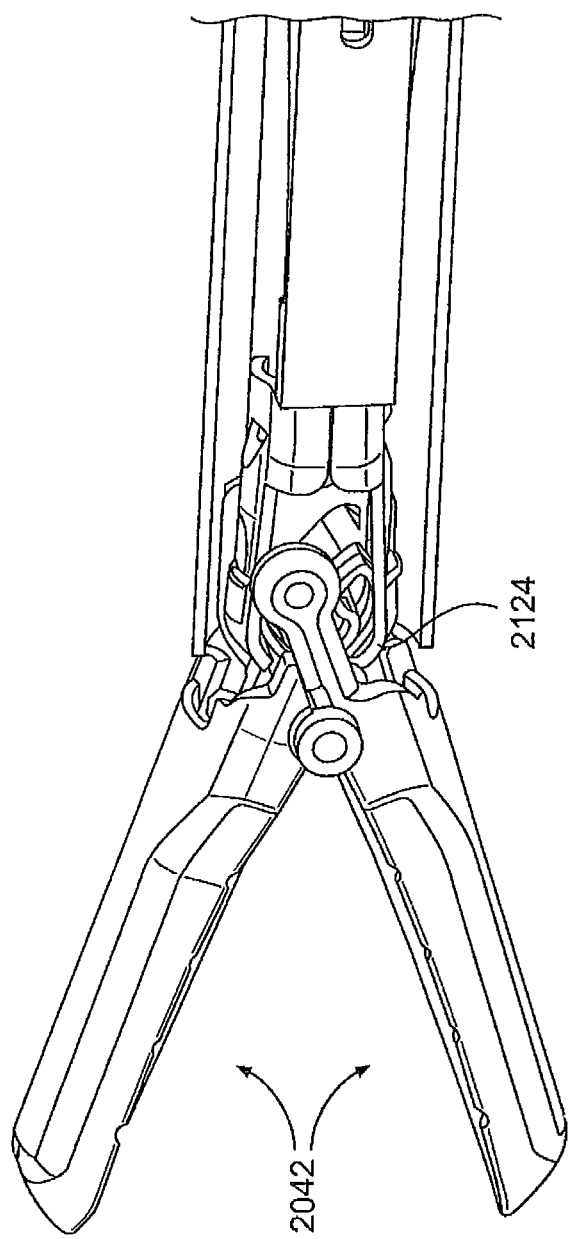
FIGS. 133-138 are partial cutaway isometric views of the distal end of an applier.
Figure 134:
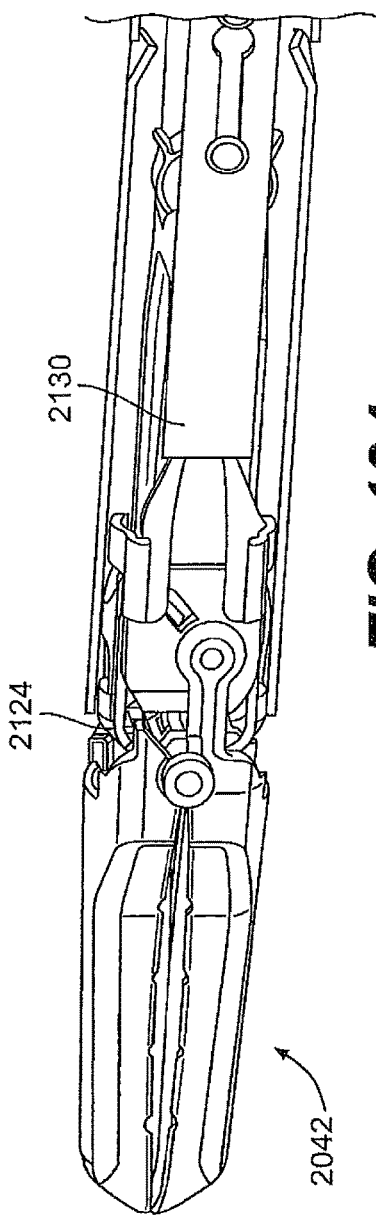

FIG. 133 illustrates the jaws 2042 in an open position. The cam fingers 2124 have moved forward and would engage a clip 2000 just behind the hinge portion 2016 and in front of the connectors 2034 to bias the clip 2000 and an open position. However, the majority of the clip 2000 itself is not visible from the view shown in FIG. 133. FIG. 134 illustrates the jaws 2042 and a closed position. The cam finger base 2130 has moved back or proximately as the jaws 2042 closed releasing the cam fingers 2124 from the clip 2000 thereby releasing the clip 2000 in the jaws 2042.

Figure 135:
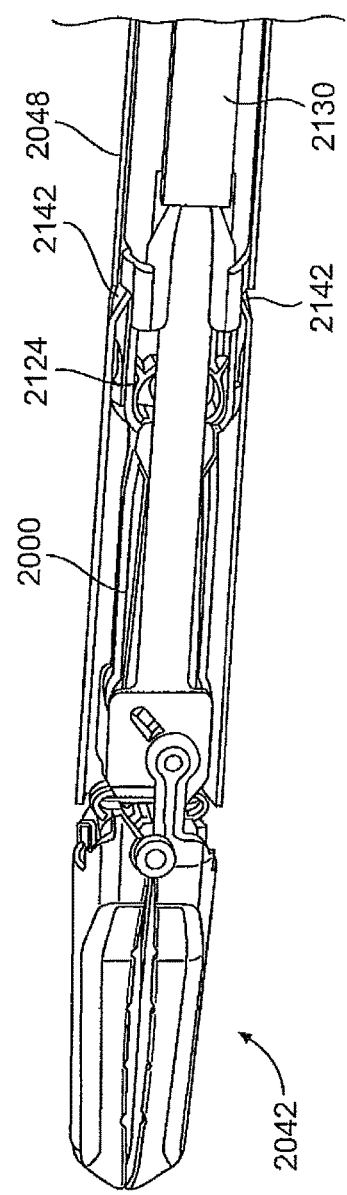
Figure 136:
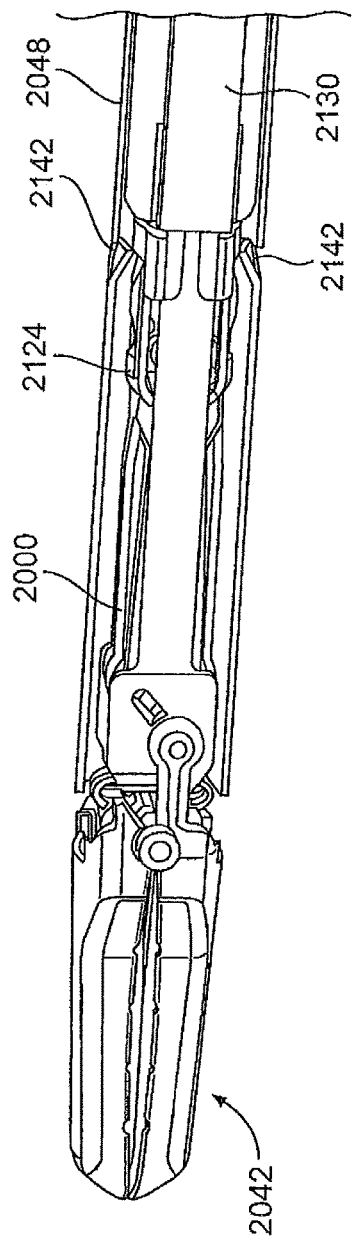

FIG. 135 shows the jaws 2042 in a closed position. The cam finger base 2130 has moved back pulling the cam fingers 2124 over the clip 2000 just inside the outer tube 2048 and sets into the tabs 2142 in the outer tube 2048. FIG. 136 illustrates the jaws 2042 just beginning to open as the cam finger base 2130 moves forward camming the cam fingers 2124 to pinch the clip 2000 open. The cam fingers 2124 are held in place by the tabs 2142 in the outer tube assembly 2048 until the clip 2000 is fully pinched.

Figure 137:
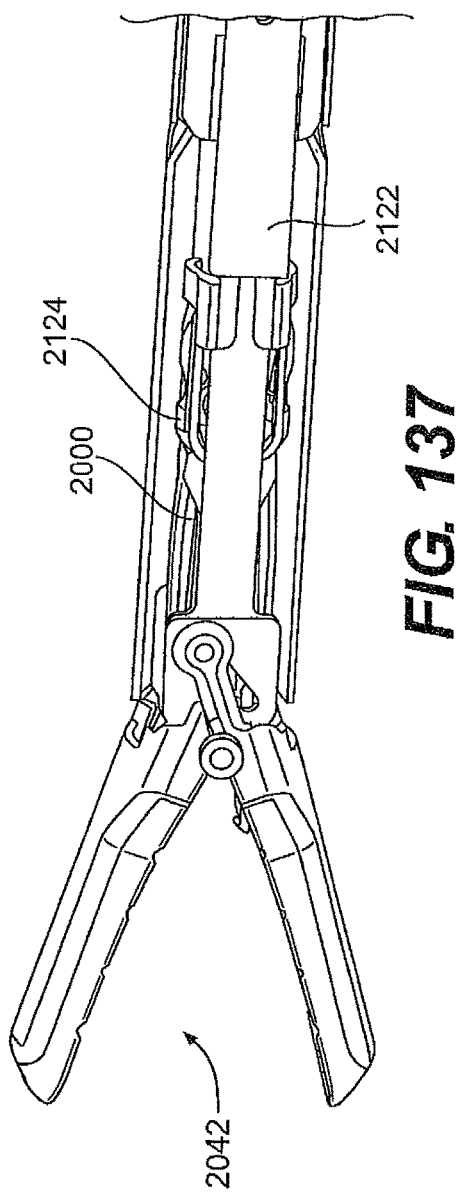

The jaws 2042 are in an open position that shown in FIG. 137. Once the jaws 2042 have opened, the cam finger assembly 2122 moves forward. The cam fingers 2124 push the clip 2000 forward or distally. At the same time the clip 2000 is pushed into the jaws 2042 and opens as it advances into the jaws 2042 and out of the outer tube assembly 2048.

Figure 138:
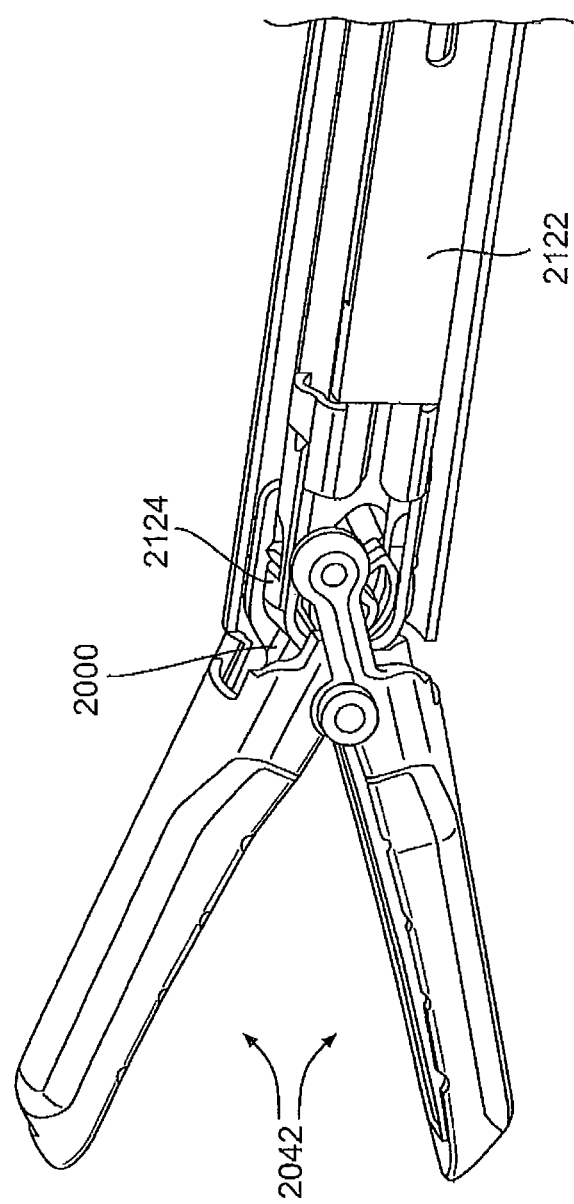

As shown in FIG. 138, the clip 2000 is fully advanced into the jaws 2042 by the forward or distal movement of the cam fingers 2124 of the cam finger assembly 2122.

FIGS. 139 through 144 illustrate a handle assembly 2050 that may be used in accordance with some embodiments of the invention. The handle assembly 2050 is meant to be exemplary only and is in no way limiting. The distal end 2060 (See FIG. 114) of the applier 2040 can be used with a variety of different handle assemblies are not limited to those shown herein. Furthermore, one of ordinary skill the art can appreciate after reviewing this disclosure that there are many other ways to manipulate the movements of the distal end 2060. For example, a manually operated handle may be used as well as electro/mechanically operated handles, robotically controlled interfaces and other suitable interfaces may also be used. Mechanical handles that may be used include not only the various mechanical handles illustrated and described in the various embodiments described herein but other mechanical handles may also be used. While the specific attachments between the handle assemblies 2050 in various features of the distal end 2060 are not shown with respect to the embodiments described FIGS. 139 through 145, these types of connections are shown with respect to other embodiments described herein. Furthermore, other types of these connections may be well known in the art and may be used in accordance with some embodiments of the invention. After reviewing the disclosure made herein, one of ordinary skill the art will understand how to operatively connect the handle assembly 2050 of FIGS. 139-145 to various distal features of the applier 2040. FIGS. 139 through 145 show the handle assembly 2050 with one of the clamshell housings 2144 removed in order to better show internal parts.

Figure 139:
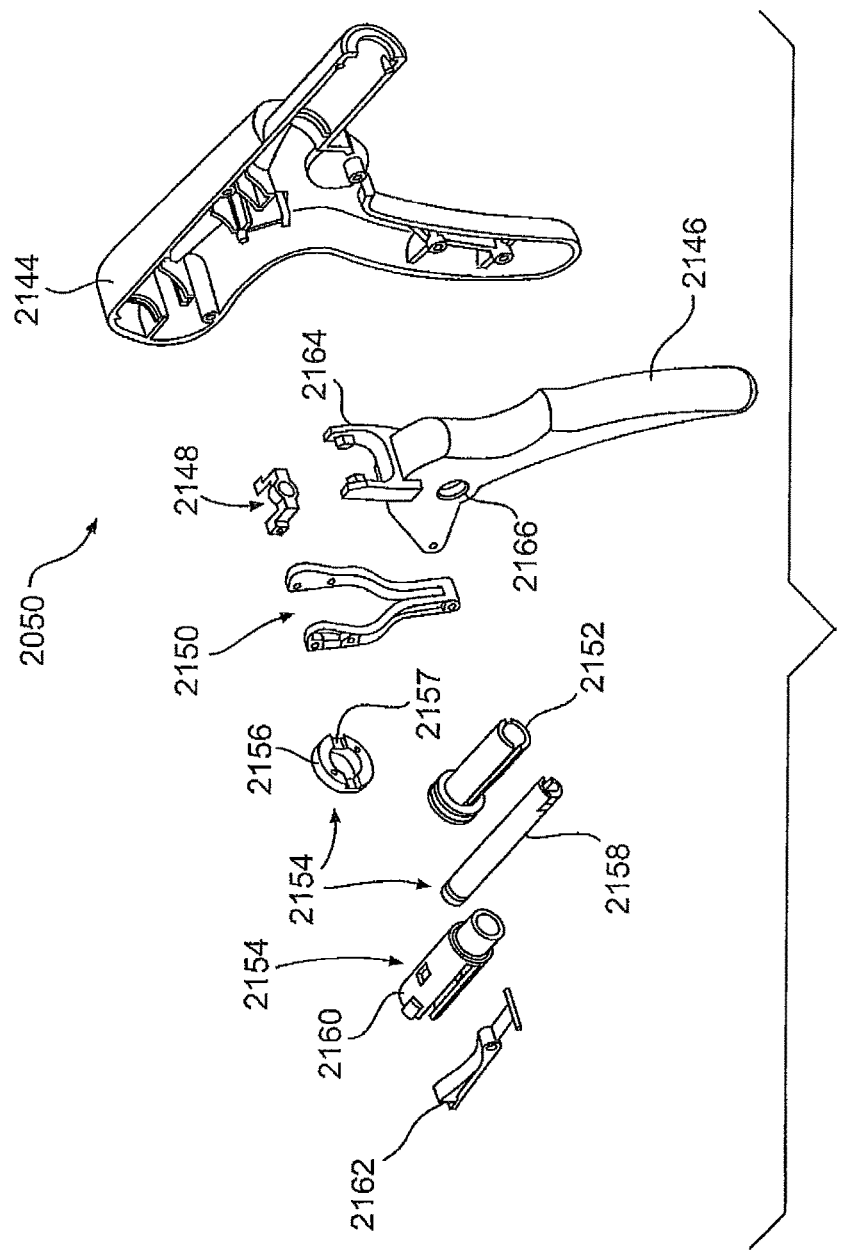
FIG. 139 is an exploded view of a handle portion of an applier.

FIG. 139 is an exploded view of a handle assembly 2050. The handle assembly 2050 includes a handle clamshell 2144. It will be appreciated that although only one handle clamshell 2144 is illustrated, two handle clamshells are used and are substantially mirror images of each other with minor variations to facilitate attaching the two handle shells 2144 together or to accommodate interior parts contained in the handle shells 2144. The handle assembly 2050 also includes a pivotal trigger 2146. The pivotal trigger 2146 may include a pivot hole 2166 and connecting ears 2164. The handle assembly 2050 may also include a jaw link 2148 and the trigger link 2150. The handle assembly 2050 may also include a clip lock arm connector 2152 and an advance arm connector 2154. The advance arm connector 2154 may be made of several parts including an arm cap 2156, and arm shaft 2158 and a connector arm housing 2160. The arm cap 2156 may include a slot 2157 into which the jaw link 2148 may fit. The arm shaft 2158 is fit into the connector arm housing 2160 and both are capped by the arm cap 2156. The handle assembly 2050 may also include a pawl 2162.

Figure 140:
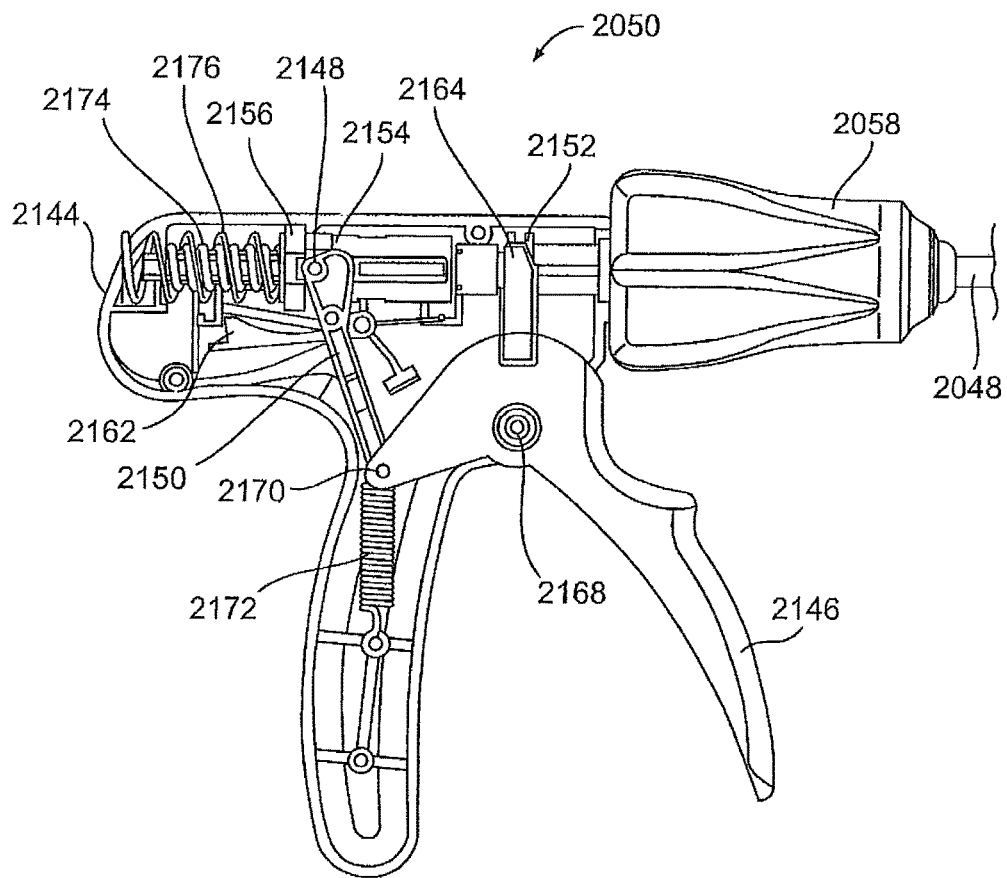
FIGS. 140-145 are partial cutaway views of the handle portion of the applier

FIG. 140 illustrates the start or default position of the components in the handle assembly 2050. The rotator 2058 allows a user to rotate the outer tube assembly 2048 and thereby the jaws to a desired angular rotation by merely twisting the rotator 2058. The trigger 2146 is shown along with its pivot point 2168. The trigger 2146 is equipped with connecting ears 2164 which connect to a clip lock arm connector 2152 which is operatively connected to the clip lock arm 2072 (not shown in FIG. 140). The trigger 2146 has a second pivot point 2170. The second pivot point 2170 is connected to a spring 2172 for biasing the trigger 2146 and a trigger link 2150. The trigger link 2150 is connected to the jaw link 2148 within the advance arm connector 2154. The advance arm connector 2154 is operatively connected to the feed tube 2076 (not shown in FIG. 140). The advance arm connector 2154 is capped by the arm cap 2156. The spring 2172 urges against the handle shell 2144 on one end and the advance arm connector 2154 and the clip lock arm connector 2152 at the other end. The spring 2174 urges against the feed tube 2076 on one end and the jaw link 2148 on the other end. The springs 2174 and 2176 bias the components of the handle assembly 2054 to the position shown in FIG. 140. The pawl 2162 is shown in a disengaged position.

Figure 141:
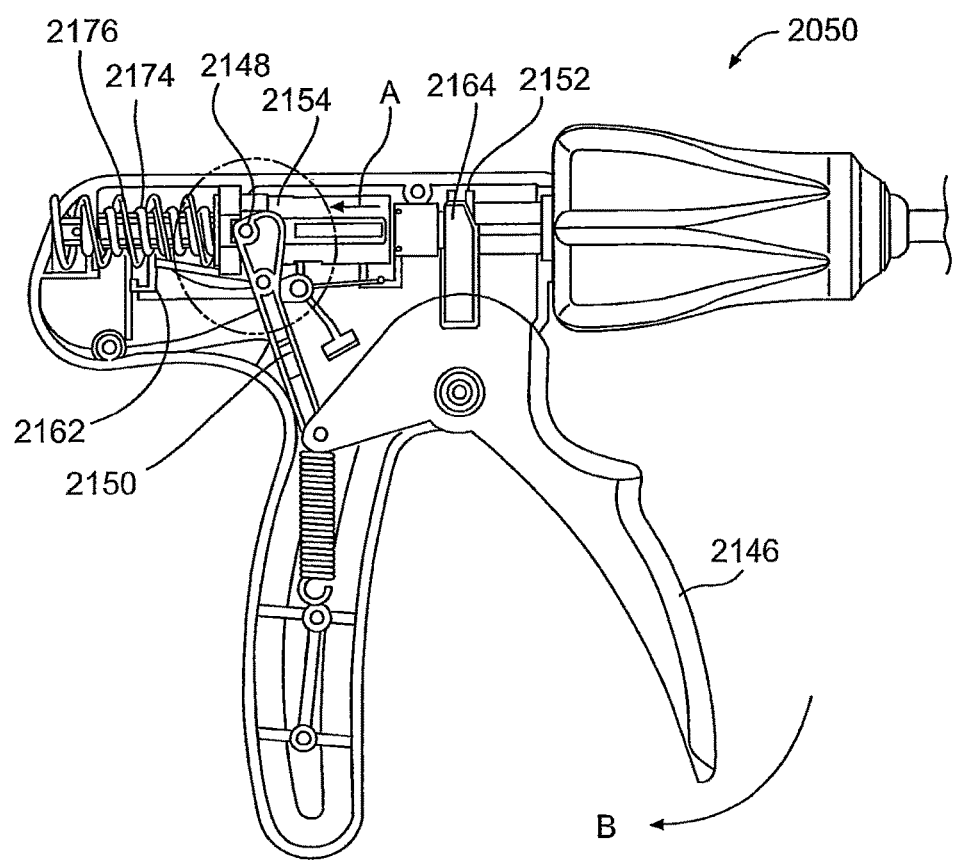

FIG. 141 illustrates the handle assembly where the trigger 2146 is moved slightly the direction indicated by arrow B. The movement of the trigger 2146 has caused the jaws 2042 (not shown in FIG. 141) to close. The jaw link 2148 has moved back in the direction illustrated by arrow A to advance the clip advance arm connectors 2152. The jaw link 2148 pulls back the feed tube (not shown in FIG. 141) through a spring.

Figure 142:
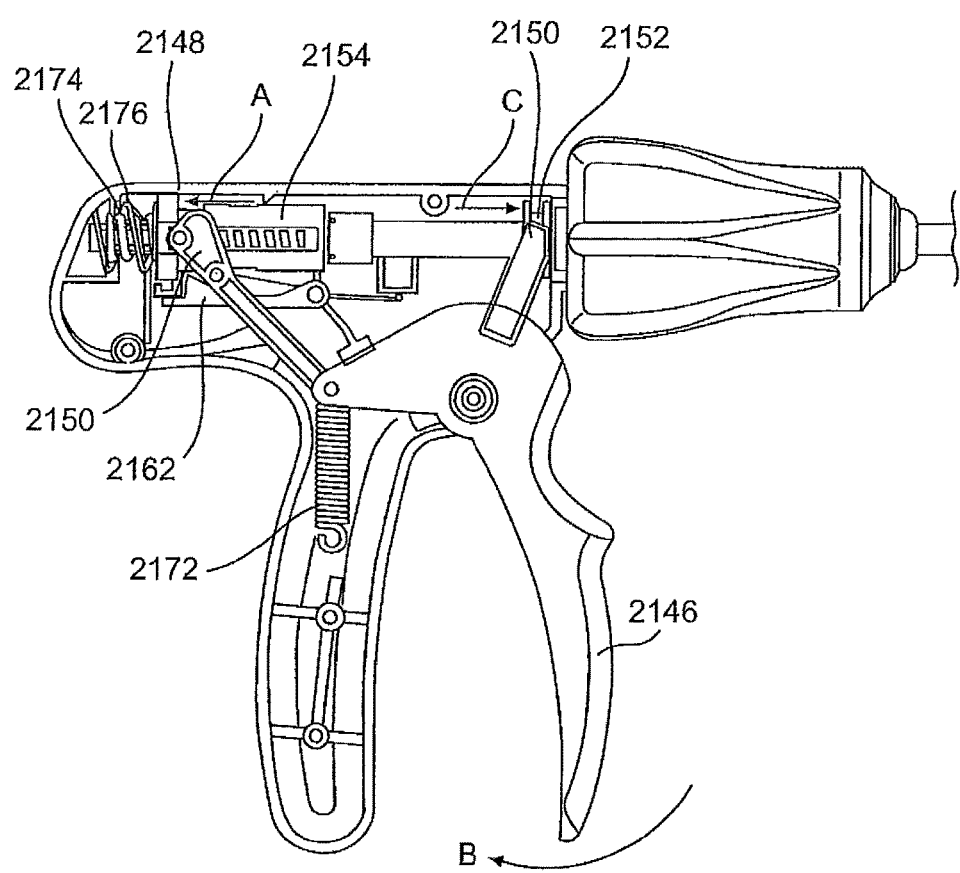

As shown in FIG. 142, continued movement of the trigger 2146 in the direction of arrow B causes the clip advance arm connector 2154 to move over the pawl 2162 in the direction of arrow A. The trigger link 2150 pushes the clip lock arm connector 2152 forward causing the clip lock arm 2072 (not shown in FIG. 142). To move forward and lock the clip 2000 contained within the jaws 2042. Continued movement of the trigger 2146 in the direction of arrow B the causes the jaw link 2148 within the advance arm connector 2154 to further compress the spring 2174 thereby limiting the amount of jaw 2042 clamping force. In other words, the spring 2174 is part of an overdrive which limits the amount of closing or clamping force the jaws 2042 can exert. Thus, once the trigger 2146 has achieved a particular position, any additional force on the trigger 2146 to continue moving in the direction of arrow B will not cause increased clamping force on the jaws but rather will simply compress the spring 2174.

Figure 143:
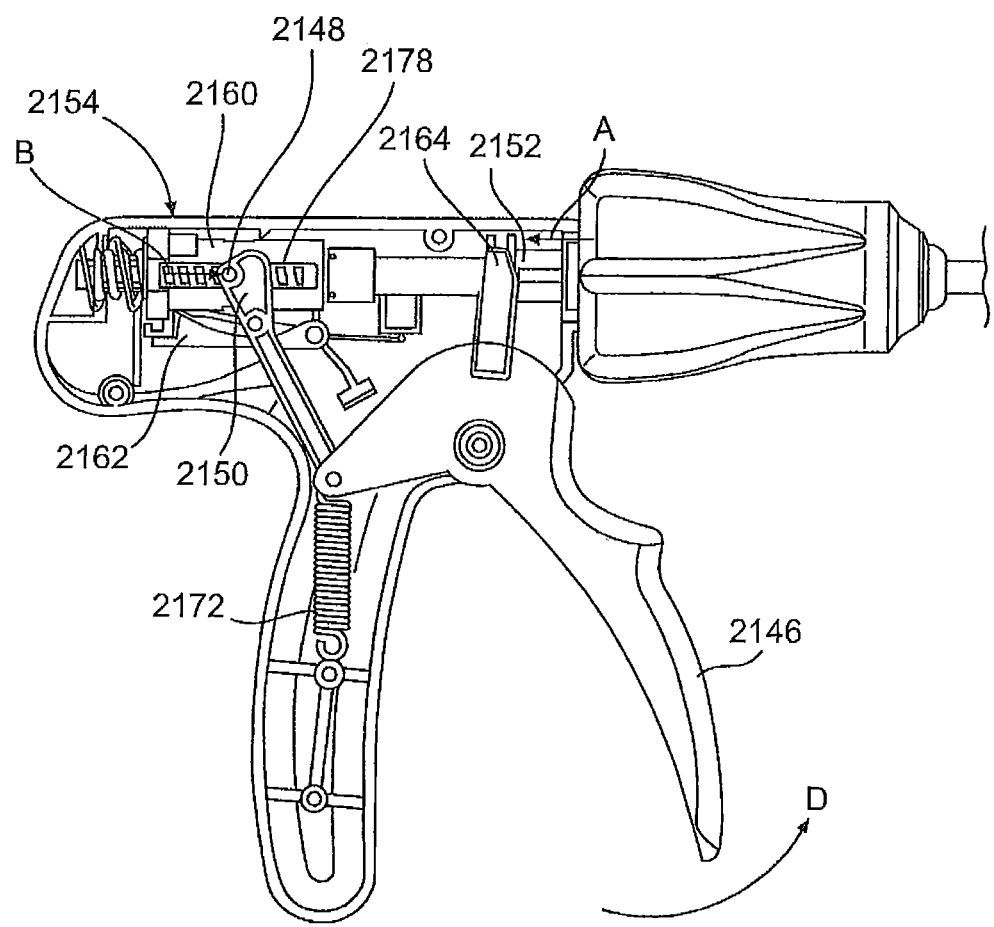
Figure 144:
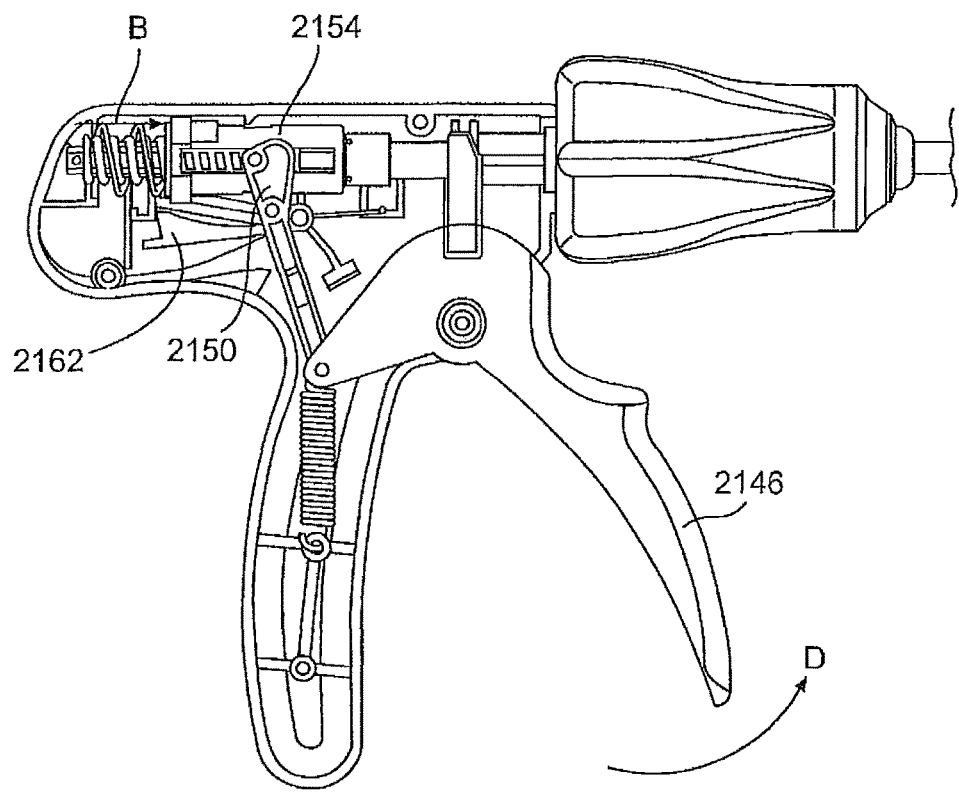

FIG. 143 shows the trigger 2146 returning to its initial position in the direction of arrow D. The trigger 2146 returns as result of the biasing from spring 2172. While FIG. 143 does not show the lower end of the spring 2172 to anchored, one of ordinary skill the art will understand when the second clamshell housing 2244 is installed, the spring 2172 will be anchored similar to that shown in FIGS. 144 and 145. The return movement of the trigger 2146 causes connecting ears 2164 to move the clip lock arm 2152 in the direction of arrow A. The clip advance arm 2154 is locked in place by the pawl 2162. The jaw link 2148 and trigger link 2150 are moved in the direction of arrow B through the slot 2178 in the connector housing 2160.

As the trigger 2146 continues to move to its initial condition in the direction of arrow D, the jaws 2042 (not shown in FIG. 144) open, the pawl 2162 is tripped and the advance arm 2154 moves forward as illustrated by arrow B.

Figure 145:
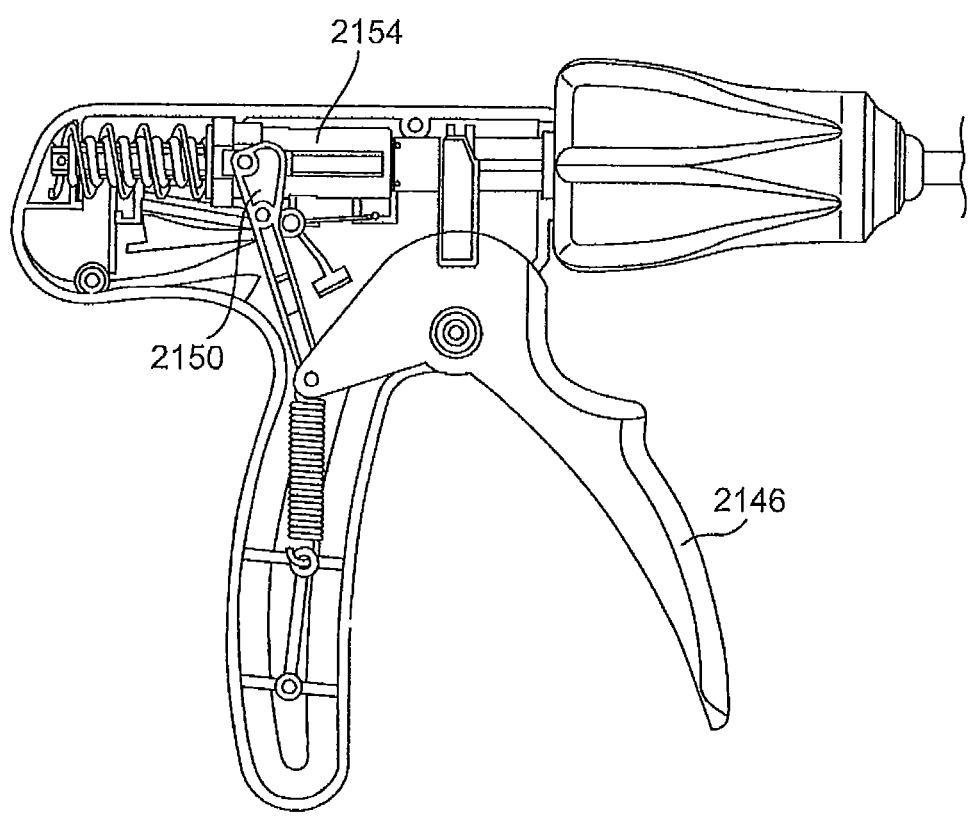

FIG. 145 shows the components at their initial conditions. The trigger 2146 is at its full forward position the clip 2000 and loaded into the jaws 2042 (not shown in FIG. 145) the advance arm connector 2154 is in its initial condition along with the trigger link 2150.

Figure 146:
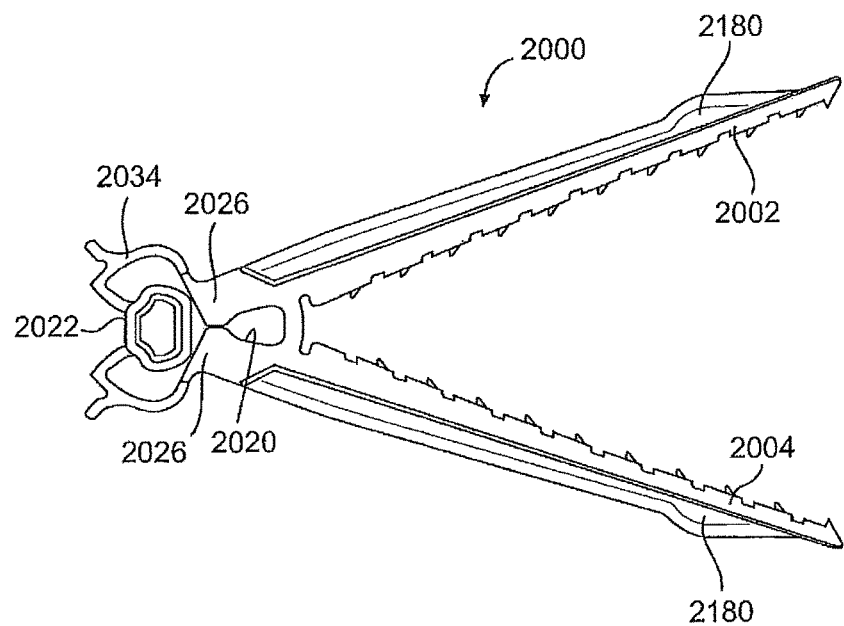
FIG. 146 is a side view of another clip that may be used in accordance with invention.
Figure 147:
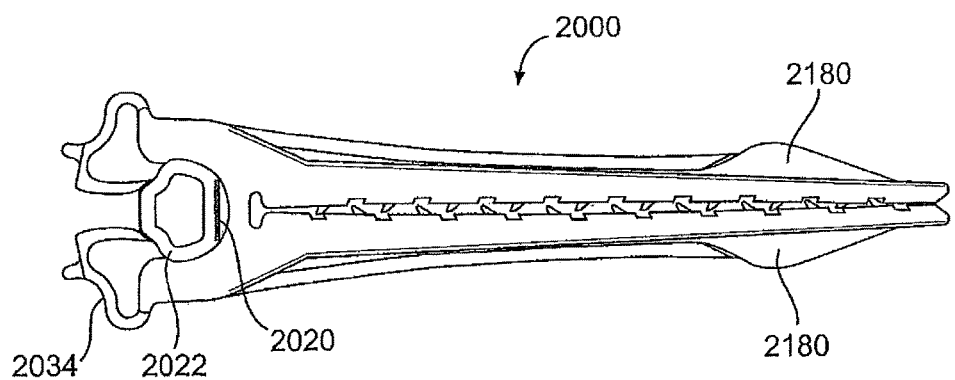
FIG. 147 is a side view of the clip shown FIG. 146 and a closed position.
Figure 148:
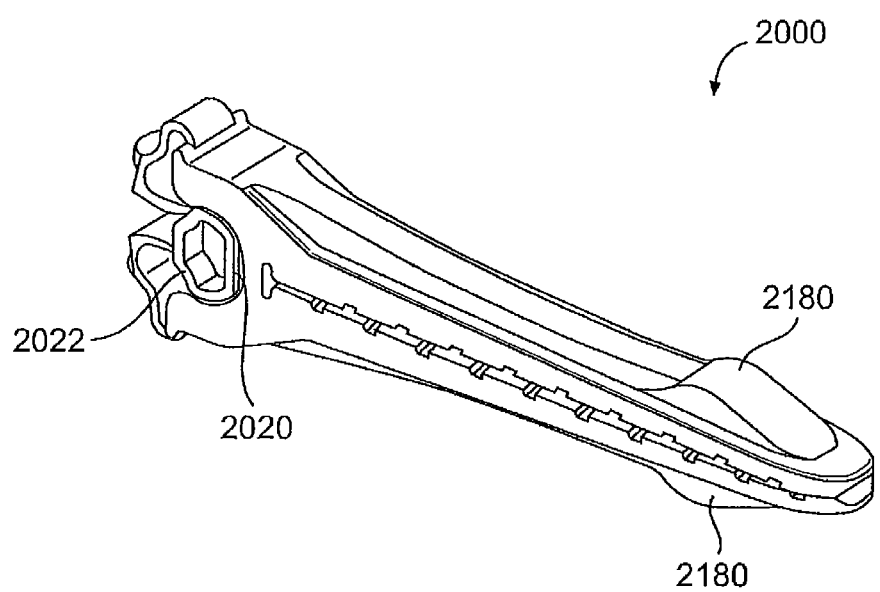
FIG. 148 is a isometric view of the clip illustrated in FIG. 146.

FIGS. 146-148 illustrate another clip 2000 that may be used in some embodiments of the invention. The clip 2000 shown in FIGS. 146-148 is similar to the clip illustrated in FIGS. 108-113. Differences between the clip 2000 shown in FIGS. 146-148 include the buttress 2022 having a different exterior geometry. The buttress 2022 is attached the connectors 2034 which, in turn, are connected to the locking wings 2026 of the clip 2000. The locking wings 2026 have a slightly different geometry as the clips 2000 shown earlier figures but is shaped to correspond to the exterior geometry of the buttress 2022. The different exterior geometry of the buttress 2022 provides desired locking and unlocking characteristics for facilitating insertion or removal of the buttress 2022 from the locking void 2020. The clip 2000 also has bulges 2180 mounted on the upper leg 2002 and the rear bottom leg 2004. In some embodiments, the bulges 2180 assist in the retention and removal of the clip 2000 in the jaws 2042 of the applier 2040. In other embodiments of the invention appliers 2040 can be used with various shaped clips and are not limited to the various clips described herein. For example, other clips are shown and described in the application titled "Narrow Profile Surgical Ligation Clip" filed Sep. 14, 2012 and identified as U.S. patent application Ser. No. 13/616,120 which is incorporated by reference in its entirety herein.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention. All ranges cited herein specifically incorporate all values and sub-ranges within the cited range.

What is claimed is:

1. A method of applying a ligation clip with an applier having a pair of jaws, the method comprising:
   sliding a feed tube forward thereby camming a projection on the jaws to move the jaws to an open position;
   sliding a clip advance arm forward thereby pushing a clip into the jaws;
   sliding the feed tube rearward thereby camming the projection on the jaws to move the jaws to a closed position; and
   advancing a clip lock arm to a forward position to push a buttress on the clip into a buttress locking void thereby locking the clip into a closed position.

2. The method of claim 1, further comprising storing a stack of clips in the feed tube wherein the clips are in a semi-closed state.

3. The method of claim 1, further comprising:
   actuating the feed tube with a lever; and
   once the feed tube has moved rearward to close the jaws, diverting any additional force applied on the lever to a spring thereby limiting a closing force of the jaws.

4. The method of claim 1, further comprising opening the clip as it enters the jaws.

5. The method of claim 1, further comprising advancing a clip stack pusher into the jaws once there are no more clips in the feed tube.

6. The method of claim 1, wherein the applier comprises:
   an outer tube having mounting bosses, the mounting bosses defining holes;
   the pair of jaws pivotally connected to the mounting bosses, the jaws having outwardly extending projections that extend through the holes in the bosses and inwardly extending actuating projections;
   the feed tube located in the outer tube and configured to move axially within the outer tube, the feed tube having actuating slots into which the actuating projections extend;
   the clip lock arm located in the outer tube and being configured to move axially within the outer tube; and
   the clip advance arm located in the outer tube and configured to move axially within the outer tube, the clip advance arm having flexible pinchers at one end of the clip advance arm.

7. The method of claim 6, wherein the applier further comprises a trigger configured to actuate the applier.

8. The method of claim 1, further comprising securing the clip in the jaws with a feature located in a distal end of the jaws.

9. The method of claim 8, wherein the feature is a recess.

10. The method of claim 1, further comprising positing the jaws and the clip over tissue to be ligated.

11. The method of claim 10, further comprising closing the jaws and clip over the tissue to be ligated.

12. A method of closing a clip with an actuator, the method comprising:
   storing a clip in a tube;
   biasing the clip to a distal end of the actuator having a pair of jaws;
   moving the tube forward and thereby open the jaws;
   moving the clip into the jaws;
   closing the jaws; and moving a buttress portion of the clip into a buttress locking void thereby locking the clip in a closed position.

13. The method of claim 12, further comprising securing the clip in the tube with a spring finger on the tube.

14. The method of claim 12, further comprising closing the clip with flexible pinchers on the actuator.

15. The method of claim 12, further comprising pivotally connecting the jaws to an outer boss of the actuator with a pivot pin.

16. The method of claim 12, wherein the tube storing the clip is an inner tube contained within an outer tube.

17. The method of claim 16, wherein the inner tube is configured to move with respect to the outer tube.

18. The method of claim 12, further comprising moving the buttress portion with a clip lock arm.

19. The method of claim 12, further comprising opening the clip when it moves into the jaws.

\* \* \* \* \*